United States Patent
Chobanian et al.

(10) Patent No.: US 10,662,171 B2
(45) Date of Patent: May 26, 2020

(54) ANTIDIABETIC BICYCLIC COMPOUNDS

(71) Applicant: Merck Sharp & Dohme Corp., Rahway, NJ (US)

(72) Inventors: Harry Chobanian, Aberdeen, NJ (US); Duane DeMong, Hanover, MA (US); Yan Guo, Westfield, NJ (US); Barbara Pio, West Orange, NJ (US); Christopher W. Plummer, Hoboken, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 38 days.

(21) Appl. No.: 15/328,908

(22) PCT Filed: Aug. 3, 2015

(86) PCT No.: PCT/US2015/043360
§ 371 (c)(1),
(2) Date: Jan. 25, 2017

(87) PCT Pub. No.: WO2016/022448
PCT Pub. Date: Feb. 11, 2016

(65) Prior Publication Data
US 2017/0217920 A1    Aug. 3, 2017

Related U.S. Application Data

(60) Provisional application No. 62/034,854, filed on Aug. 8, 2014.

(51) Int. Cl.
| | | |
|---|---|---|
| C07D 335/06 | (2006.01) | |
| C07D 213/64 | (2006.01) | |
| C07D 311/04 | (2006.01) | |
| A61K 45/06 | (2006.01) | |
| A61K 31/453 | (2006.01) | |
| A61K 31/44 | (2006.01) | |
| A61K 31/353 | (2006.01) | |
| A61K 31/192 | (2006.01) | |
| A61K 31/352 | (2006.01) | |
| C07D 311/20 | (2006.01) | |
| A61K 31/366 | (2006.01) | |
| A61K 31/382 | (2006.01) | |
| C07D 405/04 | (2006.01) | |
| A61K 31/444 | (2006.01) | |
| C07D 405/10 | (2006.01) | |

(52) U.S. Cl.
CPC ........ *C07D 335/06* (2013.01); *A61K 31/192* (2013.01); *A61K 31/352* (2013.01); *A61K 31/353* (2013.01); *A61K 31/366* (2013.01); *A61K 31/382* (2013.01); *A61K 31/44* (2013.01); *A61K 31/444* (2013.01); *A61K 31/453* (2013.01); *A61K 45/06* (2013.01); *C07D 213/64* (2013.01); *C07D 311/04* (2013.01); *C07D 311/20* (2013.01); *C07D 405/04* (2013.01); *C07D 405/10* (2013.01)

(58) Field of Classification Search
None
See application file for complete search history.

(56) References Cited

U.S. PATENT DOCUMENTS

| | | | |
|---|---|---|---|
| 3,288,804 A | 11/1966 | Fleck et al. | |
| 4,602,022 A * | 7/1986 | Cozzi | C07D 231/12 514/337 |
| 8,030,354 B2 | 10/2011 | Brown et al. | |
| 8,450,522 B2 | 5/2013 | Brown et al. | |
| 2006/0258722 A1 | 11/2006 | Yasuma et al. | |
| 2007/0244155 A1 | 10/2007 | Sharma et al. | |

FOREIGN PATENT DOCUMENTS

| | | |
|---|---|---|
| GB | 2498976 A | 7/2013 |
| WO | WO2004022551 A1 | 3/2004 |
| WO | WO2004041266 A1 | 5/2004 |

(Continued)

OTHER PUBLICATIONS

Federal Register, vol. 76, No. 27, Feb. 9, 2011, 7162-7175, 7166.*

(Continued)

*Primary Examiner* — Po-Chih Chen
(74) *Attorney, Agent, or Firm* — Baerbel R. Brown; Catherine D. Fitch

(57) ABSTRACT

Novel compounds of the structural formula (I), and the pharmaceutically acceptable salts thereof, are agonists of G-protein coupled receptor 40 (GPR40) and may be useful in the treatment, prevention and suppression of diseases mediated by the G-protein-coupled receptor 40. The compounds of the present invention may be useful in the treatment of Type 2 diabetes mellitus, and of conditions that are often associated with this disease, including obesity and lipid disorders, such as mixed or diabetic dyslipidemia, hyperlipidemia, hypercholesterolemia, and hypertriglyceridemia.

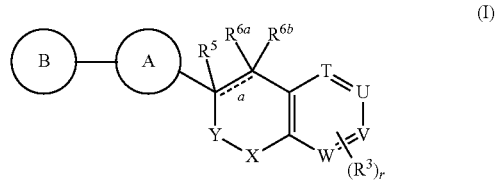

15 Claims, No Drawings

(56) References Cited

FOREIGN PATENT DOCUMENTS

| WO | WO2005051373 A1 | 6/2005 |
|---|---|---|
| WO | WO2005051890 A1 | 6/2005 |
| WO | WO2005063729 A1 | 7/2005 |
| WO | WO2005086661 A2 | 9/2005 |
| WO | WO2005087710 A1 | 9/2005 |
| WO | WO2006038738 A1 | 4/2006 |
| WO | WO2006083612 A1 | 8/2006 |
| WO | WO2006083781 A1 | 8/2006 |
| WO | WO2006127503 A2 | 11/2006 |
| WO | WO2007013689 A1 | 2/2007 |
| WO | WO2007033002 A1 | 3/2007 |
| WO | WO2007106469 A2 | 9/2007 |
| WO | WO2007123225 A1 | 11/2007 |
| WO | WO2007136572 A2 | 11/2007 |
| WO | WO2007136573 A2 | 11/2007 |
| WO | WO2008001931 A2 | 1/2008 |
| WO | WO2008030520 A1 | 3/2008 |
| WO | WO2008030618 A1 | 3/2008 |
| WO | WO2008054674 A2 | 5/2008 |
| WO | WO2008054675 A2 | 5/2008 |
| WO | WO2008066097 A1 | 6/2008 |
| WO | WO2008130514 A1 | 10/2008 |
| WO | WO2009048527 A1 | 4/2009 |
| WO | WO2009058237 A1 | 5/2009 |
| WO | WO2009079011 A1 | 6/2009 |
| WO | WO2009111056 A1 | 9/2009 |
| WO | WO2010004347 A1 | 1/2010 |
| WO | WO2010024903 A1 | 3/2010 |
| WO | WO2010085522 A1 | 7/2010 |
| WO | WO2010085525 A1 | 7/2010 |
| WO | WO2010085528 A1 | 7/2010 |
| WO | WO2010091176 A1 | 8/2010 |
| WO | WO2010143733 A1 | 12/2010 |
| WO | WO2012011125 A1 | 1/2012 |
| WO | WO2012072691 A1 | 6/2012 |
| WO | WO2013104257 A1 | 7/2013 |
| WO | WO2013122028 A1 | 8/2013 |
| WO | WO2013122029 A1 | 8/2013 |
| WO | WO2013128378 A1 | 9/2013 |
| WO | WO2013178575 A1 | 12/2013 |
| WO | WO2014073904 A1 | 5/2014 |
| WO | WO2014078608 A1 | 5/2014 |
| WO | WO2014078609 A1 | 5/2014 |
| WO | WO2014078610 A1 | 5/2014 |
| WO | WO2014078611 A1 | 5/2014 |
| WO | WO2014130608 A1 | 8/2014 |
| WO | WO2016019587 A1 | 2/2016 |
| WO | WO2016019863 A1 | 2/2016 |
| WO | WO2016022446 A1 | 2/2016 |
| WO | WO2016022448 A1 | 2/2016 |
| WO | WO2016022742 A1 | 2/2016 |

OTHER PUBLICATIONS

Chemical Abstract Registry No. 1082390-77-9, indexed in the Registry File on STN CAS Online Dec. 9, 2008.*
Chemical Abstract Registry No. 1082529-21-2, indexed in the Registry File on STN CAS Online Dec. 9, 2008.*
Sabatier et al., Type 1 and Type 2 Diabetic Patients Display Different Patterns of Cellular Microparticles. Diabetes, 2002, 51, 2840-2845.*
Ito et al., A medium-term rat livery bioassay for rapid in vivo detection of carcinogenic potential of chemicals. Cancer Science, 2003, 94, 3-8.*
Sessions, E. H. et al., Benzimidazole- and benzoxazole-based inhibitors of Rho kinase, Bioorganic & Medicinal Chemistry Letters, 2008, p. 6390-6393, vol. 18.
Sessions, E. H. et al., The development of benzimidazoles as selective rho kinase inhibitors, Bioorganic & Medicinal Chemistry Letters, 2010, p. 1939-1943, vol. 20.
Yin, Yan, et al., Benzothiazoles as Rho-associated kinase (ROCK-II) inhibitors, Bioorganic & Medicinal Chemistry Letters, 2009, p. 6686-6690, vol. 19.
Briscoe, C. P. et al., The Orphan G Protein-coupled Receptor GPR40 is Activated by Medium and Long Chain Fatty Acids, The Journal of Biological Chemistry, 2003, 11303-11311, No. 13, 278.
Brown, S. P. et al., Discovery of AM-1638: A Potent and Orally Bioavailable GPR40/FFA1 Full Agonist, American Chemical Society, 2012, p. 726-730, vol. 3.
Du, Xiaohui, et al., Improving the Pharmacokinetics of GPR40/FFA1 Full Agonists, ACS Medicinal Chemistry Letters, 2014, p. 384-389, vol. 5, No. 4.
Houze, J. B. et al., 265—AMG 837: A potent, orally bioavailable, partial allosteric agonist of GPR40, MEDI, 2012, p. 1, Abstracts of Papers, 243rd ACS National Meeting & Exposition, San Diego, CA, Mar. 25-29, 2012.
Houze, J. B. et al, AMG 837: A potent, orally bioavailable GPR40 agonist, Bioorganic & Medicinal Chemistry Letters, 2012, p. 1267-1270, vol. 22.
Itoh, Y. et al., Free fatty acids regulate insulin secretion from pancreatic B cells through GPR40, Nature, 2003, 173-176, 422.
Kotarsky, K. et al., A human cell surface receptor activated by free fatty acids and thiazolidinedione drugs, Biochemical and Biophysical Research Communications, 2003, 406-410, 301.
Lin, D. C. H. et al, Identification and Pharmacological Characterization of Multiple Allosteric Binding Sites on the Free Fatty Acid 1 Receptor, Molecular Pharmacology, 2012, p. 843-859, vol. 82, No. 5.
Lin, D. D. H. et al., AMG 837: A Novel GPR40/FFA1 Agonist that Enhances Insulin Secretion and Lowers Glucose Levels in Rodents, PLoS One, 2011, p. 1-10, vol. 6, No. 11.
Lou, J. et al., A Potent Class of GPR40 Full Agonist Engages the Enterolnsular Axis to Promote Glucose Control in Rodents, Plos One, 2012, p. 6-12, vol. 7, Issue 10.
Lu, H. et al., Discovery of novel orally bioavailable GPR40 agonists, Bioorganic & Medicinal Chemistry Letters, 2013, p. 2920-2924, vol. 23.
Negoro, Nobuyuki, et al., Discovery of TAK-875: A Potent, Selective, and Orally Bioavailable GPR40 Agonist, ACS Medicinal Chemistry Letters, 2010, p. 290-294, vol. 1, No. 6.
Takano, Rieko, et al., Discovery of 3-aryl-3-ethoxypropanoic acids as orally acitve GPR40 Agonists, Bioorganic & Medicinal Chemistry Letters, 2014, p. 2949-2953, vol. 24.
Tan, C. P. et al., Selective Small-Molecule Agonists of G Protein-Coupled Receptor 40 Promote Glucose-Dependent Insulin Secretion and Reduce Blood Glucose in Mice, Diabetes, 2008, p. 2211-2219, vol. 57.
Walsh, S. P. et al., 3-Substituted 3-(4-aryloxyaryl)-propanoic acids as GPR40 agonists, Bioorganic & Medicinal Chemistry Letters, 2011, p. 3390-3394, vol. 21.
Wang, Y. et al., Discoveryand Optimization of Potent GPR40 Full Agonists Containing Tricyclic Spirocycles, ACS Medicinal Chemistry Letters, 2013, p. 551-555, vol. 4.
Yang, L., 313—Discovery of selective small molecule GPR40 agonists as antidiabetic compounds, MEDI, 2010, p. 1, Abstracts of Papers, 239th ACS Meeting, San Francisco, CA, Mar. 21-25.
Zhou, C. et al., Discovery of 5-aryloxy-2,4-thiazolidinediones as potent GPR40 agonists, Bioorganic & Medicinal Chemistry Letters, 2010, p. 1298-1301, vol. 20.

* cited by examiner

ANTIDIABETIC BICYCLIC COMPOUNDS

CROSS-REFERENCE TO RELATED APPLICATIONS

This application is a U.S. National Phase application under 35 U.S.C. § 371 of PCT Application No. PCT/US15/043360, filed on Aug. 3, 2015, which claims priority from and the benefit of U.S. Patent Application Ser. No. 62/034,854, filed Aug. 8, 2014.

BACKGROUND OF THE INVENTION

Diabetes mellitus is a disease derived from multiple causative factors and characterized by elevated levels of plasma glucose (hyperglycemia) in the fasting state or after administration of glucose during an oral glucose tolerance test. There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin-dependent diabetes mellitus (NIDDM), insulin is still produced in the body, however patients have a resistance to the effects of insulin in stimulating glucose and lipid metabolism in the insulin-sensitive muscle, liver and adipose tissues. Type 2 diabetes patients often have normal levels of insulin, and may have hyperinsulinemia (elevated plasma insulin levels), as they compensate for the reduced effectiveness of insulin by secreting increased amounts of insulin. This lack of responsiveness to insulin results in insufficient insulin-mediated activation of uptake, oxidation and storage of glucose in muscle, and inadequate insulin-mediated repression of lipolysis in adipose tissue and of glucose production and secretion in the liver.

Persistent or uncontrolled hyperglycemia is associated with increased and premature morbidity and mortality. Abnormal glucose homeostasis is associated both directly and indirectly with obesity, hypertension, and alterations of the lipid, lipoprotein and apolipoprotein metabolism, as well as other metabolic and hemodynamic disease. Patients with Type 2 diabetes mellitus have a significantly increased risk of macrovascular and microvascular complications, including atherosclerosis, coronary heart disease, stroke, peripheral vascular disease, hypertension, nephropathy, neuropathy, and retinopathy. Therefore, therapeutic control of glucose homeostasis, lipid metabolism, obesity, and hypertension are critically important in the clinical management and treatment of diabetes mellitus.

Patients who have insulin resistance often have Metabolic Syndrome (as defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670). Patients with Metabolic Syndrome have an increased risk of developing the macrovascular and microvascular complications that occur with Type 2 diabetes, such as atherosclerosis and coronary heart disease.

There are several available treatments for Type 2 diabetes. Physical exercise and a reduction in dietary intake of calories are the recommended first-line treatment of Type 2 diabetes and of pre-diabetic conditions associated with insulin resistance, however compliance is generally poor.

Pharmacologic treatments for diabetes have largely focused on three areas of pathophysiology: (1) hepatic glucose production (biguanides, such as phenformin and metformin), (2) insulin resistance (PPAR agonists, such as rosiglitazone, troglitazone, engliazone, balaglitazone, and pioglitazone), (3) insulin secretion (sulfonylureas, such as tolbutamide, glipizide and glimipiride); (4) incretin hormone mimetics (GLP-1 derivatives and analogs, such as exenatide, liraglutide, dulaglutide, semaglutide, lixisenatide, albiglutide and taspoglutide); and (5) inhibitors of incretin hormone degradation (DPP-4 inhibitors, such as sitagliptin, alogliptin, vildagliptin, linagliptin, denagliptin and saxagliptin).

The two best known biguanides, phenformin and metformin, cause some correction of hyperglycemia, but can also induce lactic acidosis and nausea/diarrhea. PPAR gamma agonists, such as rosiglitazone and pioglitazone, are modestly effective in reducing plasma glucose and Hemoglobin A1C. However, the currently marketed glitazones do not greatly improve lipid metabolism and may negatively effect on the lipid profile. The administration of insulin secretagogues, such as the sulfonylureas (e.g. tolbutamide, glipizide, and glimepiride) can result in hypoglycemia; their administration must therefore be carefully controlled.

There has been a renewed focus on pancreatic islet-based insulin secretion that is controlled by glucose-dependent insulin secretion. This approach has the potential for stabilization and restoration of β-cell function. Several orphan G-protein coupled receptors (GPCR's) have been identified that are preferentially expressed in the β-cell and that are implicated in glucose stimulated insulin secretion (GSIS). GPR40 is a cell-surface GPCR that is highly expressed in human (and rodent) islets as well as in insulin-secreting cell lines. Several naturally-occurring medium to long-chain fatty acids (FA's) as well as synthetic compounds, including several members of the thiazolidinedione class of PPARγ agonists, have recently been identified as ligands for GPR40 [Itoh, Y. et al., *Nature*, 422: 173 (2003); Briscoe, C. P. et al., *J. Biol. Chem.*, 278: 11303 (2003); Kotarsky, K. et al., *Biochem. Biophys. Res. Comm.*, 301: 406 (2003)]. Under hyperglycemic conditions, GPR40 agonists are capable of augmenting the release of insulin from islet cells. The specificity of this response is suggested by results showing that the inhibition of GPR40 activity by siRNA attenuates FA-induced amplification of GSIS. These findings indicate that, in addition to the intracellular generation of lipid-derivatives of FA's that are thought to promote insulin release, FA's (and other synthetic GPR40 agonists) may also act as extracellular ligands that bind to GPR40 in mediating FA-induced insulin secretion. There are several potential advantages of GPR40 as a target for the treatment of Type 2 diabetes. First, since GPR40-mediated insulin secretion is glucose dependent, there is little or no risk of hypoglycemia. Second, the limited tissue distribution of GPR40 (mainly in islets) suggests that there would be less chance for side effects associated with GPR40 activity in other tissues. Third, GPR40 agonists that are active in the islets may have the potential to restore or preserve islet function. This would be advantageous, because long term diabetes therapy often leads to the gradual diminution of islet activity; after extended periods of treatment, it is often necessary to treat Type 2 diabetic patients with daily insulin injections. By restoring or preserving islet function, GPR40 agonists may delay or prevent the diminution and loss of islet function in a Type 2 diabetic patient.

Compounds that are agonists of G-protein-coupled receptor 40 (GPR40) may be useful to treat type 2 diabetes mellitus, obesity, hypertension, dyslipidemia, cancer, and metabolic syndrome, as well as cardiovascular diseases, such as myocardial infarction and stroke, by improving glucose and lipid metabolism and by reducing body weight.

There is a need for potent GPR40 agonists that have pharmacokinetic and pharmacodynamic properties suitable for use as human pharmaceuticals.

G-protein-coupled receptor 40 (GPR40) agonists are disclosed in WO 2007/136572, WO 2007/136573, WO 2009/058237, WO 2006/083612, WO 2006/083781, WO 2010/085522, WO 2010/085525, WO 2010/085528, WO 2010/091176, WO 2004/041266, EP 2004/1630152, WO 2004/022551, WO 2005/051890, WO 2005/051373, EP 2004/1698624, WO 2005/086661, WO 2007/213364, WO 2005/063729, WO 2005/087710, WO 2006/127503, WO 2007/1013689, WO 2006/038738, WO 2007/033002, WO 2007/106469, WO 2007/123225, WO 2008/001931, WO 2008/030520, WO 2008/030618, WO 2008/054674, WO 2008/054675, WO 2008/066097, WO 2008/130514, WO 2009/048527, WO 2009/058237, WO 2009/111056, WO 2010/004347, WO 2010/045258, WO 2010/085522, WO 2010/085525, WO 2010/085528, WO 2010/091176, WO 2010/143733, WO 2012/0004187, WO 2012/011125, WO 2012/072691, WO2013/104257, WO 2013/122028, WO 2013/122029, WO 2013/128378, WO 2013/178575, WO 2014/073904, WO 2014/078608, WO 2014/078609, WO 2014/078610, WO 2014/078611, U.S. Pat. Nos. 8,030,354, 8,450,522, CN 103030646, CN 103012343, and GB 2498976.

GPR40 agonists are also disclosed in Negoro et al., ACS Medicinal Chemistry Letters (2010), 1(6), 290-294; Walsh et al., Bioorganic & Medicinal Chemistry Letters (2011), 21(11), 3390-3394; Zhou et al., Bioorganic & Medicinal Chemistry Letters (2010), 20(3), 1298-1301; Houze et al., Bioorganic & Medicinal Chemistry Letters (2012), 22(2), 1267-1270; Lu et al., Bioorganic & Medicinal Chemistry Letters (2013), 23(10), 2920-2924; Takano et al., Bioorganic & Medicinal Chemistry Letters (2014), 24(13), 2949-2953; Tan et al., Diabetes (2008), 57(8), 2211-2219; Brown et al., ACS Medicinal Chemistry Letters (2012), 3(9), 726-730; Lin et al., PloS One (2011), 6(11), e27270; Lou et al., PloS One (2012), 7(10), e46300; Lin et al., Molecular Pharmacology (2012), 82(5), 843-859; Yang, Lihu, Abstracts of Papers, 239th ACS Meeting, San Francisco, Calif., USA Mar. 21-25, 2010 MEDI-313; Houze et al., Abstracts of Papers, 243rd ACS National Meeting & Exposition, San Diego, Calif., USA Mar. 25-29, 2012, MEDI-265; Wang et al., ACS Medicinal Chemistry Letters (2013), 4(6), 551-555; and Du et al., ACS Medicinal Chemistry Letters (2014), 5(4), 384-389.

SUMMARY OF THE INVENTION

The present invention relates to novel substituted compounds of structural formula I:

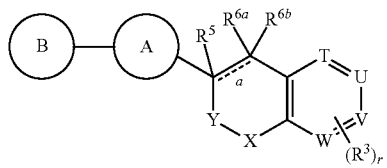

and pharmaceutically acceptable salts thereof. The compounds of structural formula I, and embodiments thereof, are agonists of G-protein-coupled receptor 40 (GPR40) and may be useful in the treatment and suppression of prevention of diseases, disorders and conditions mediated by agonism of the G-protein-coupled receptor 40, such as Type 2 diabetes mellitus, insulin resistance, hyperglycemia, dyslipidemia, lipid disorders, obesity, hypertension, Metabolic Syndrome and atherosclerosis.

The present invention also relates to pharmaceutical compositions comprising the compounds of the present invention and a pharmaceutically acceptable carrier. The present invention also relates to methods for the treatment, control or prevention of disorders, diseases, and conditions that may be responsive to agonism of the G-protein-coupled receptor 40 in a subject in need thereof by administering the compounds and pharmaceutical compositions of the present invention. The present invention also relates to the use of compounds of the present invention for manufacture of a medicament useful in treating diseases, disorders and conditions that may be responsive to the agonism of the G-protein-coupled receptor 40. The present invention is also concerned with treatment of these diseases, disorders and conditions by administering the compounds of the present invention in combination with a therapeutically effective amount of another agent that may be useful to treat the disease, disorder and condition. The invention is further concerned with processes for preparing the compounds of this invention.

DETAILED DESCRIPTION OF THE INVENTION

The present invention is concerned with novel compounds of structural Formula I:

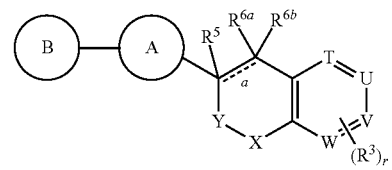

or a pharmaceutically acceptable salt thereof; wherein
"a" is a single bond or a double bond, provided that if "a" is a double bond, then $R^5$ and $R^{6b}$ are absent;
T is selected from the group consisting of:
  (1) CH,
  (2) N, and
  (3) N-oxide;
U is selected from the group consisting of:
  (1) $CR^1$,
  (2) N, and
  (3) N-oxide;
V is selected from the group consisting of:
  (1) $CR^2$,
  (2) N, and
  (3) N-oxide;
W is selected from the group consisting of:
  (1) CH,
  (2) N, and
  (3) N-oxide,
provided that no more than two of T, U, V and W are selected from N and N-oxide, further provided that if both T and W are N or N-oxide, then $R^3$ is absent, and further provided that both U and V are not N or N-oxide;
X is selected from the group consisting of:
  (1) oxygen,
  (2) sulfur,
  (3) $S(O)_2$, (4) —CR$^g$R$^g$,
(5) C=O,
(6) —C(R$^g$)OC$_{1-6}$alkyl,
(7) —CF$_2$, and
(8) —NR$^c$;
Y is selected from the group consisting of:
 (1) oxygen,
 (2) sulfur,
 (3) S(O)$_2$,
 (4) C=O,
 (5) —C(R$^g$)OC$_{1-6}$alkyl,
 (6) —CF$_2$,
 (7) —NR$^c$; and
 (8) —CR$^{4a}$R$^{4b}$,
provided that if X is oxygen, sulfur or —NR$^c$, then Y is not oxygen, sulfur or —NR$^c$, further provided that if X is C=O, then Y is not C=O or S(O)$_2$, and further provided that if X is S(O)$_2$, then Y is not S(O)$_2$, C=O, oxygen or sulfur;
A is selected from the group consisting of:
 (1) aryl,
 (2) heteroaryl,
 (3) C$_{3-6}$cycloalkyl, and
 (4) C$_{3-5}$ cycloheteroalkyl,
wherein A is unsubstituted or substituted with one to five substituents independently selected from R$^a$;
B is selected from the group consisting of:
 (1) hydrogen,
 (2) aryl,
 (3) aryl-O—,
 (4) aryl-C$_{1-10}$ alkyl-,
 (5) aryl-C$_{1-10}$ alkyl-O—,
 (6) C$_{3-6}$cycloalkyl,
 (7) C$_{3-6}$cycloalkyl-C$_{1-10}$alkyl-,
 (8) C$_{3-6}$cycloalkyl-C$_{1-10}$alkyl-O—,
 (9) C$_{3-6}$cycloalkenyl,
 (10) C$_{3-6}$cycloalkenyl-C$_{1-10}$alkyl-,
 (11) C$_{3-6}$cycloalkenyl-C$_{1-10}$alkyl-O—,
 (12) C$_{2-5}$ cycloheteroalkyl,
 (13) C$_{3-6}$cycloheteroalkyl-C$_{1-10}$alkyl-,
 (14) C$_{3-6}$cycloheteroalkyl-C$_{1-10}$alkyl-O—,
 (15) heteroaryl,
 (16) heteroaryl-O—,
 (17) heteroaryl-C$_{1-10}$ alkyl-, and
 (18) heteroaryl-C$_{1-10}$ alkyl-O—,
wherein B is unsubstituted or substituted with one to five substituents independently selected from R$^b$;
R$^1$ and R$^2$ are each independently selected from:
 (1) a bond,
 (2) hydrogen,
 (3) halogen,
 (4) —OR$^k$,
 (5) —CN,
 (6) —C$_{1-6}$alkyl,
 (7) —C$_{3-6}$cycloalkyl,
 (8) C$_{3-6}$cycloalkyl-C$_{1-3}$alkyl-,
 (9) —C$_{2-6}$cycloheteroalkyl, and
 (10) C$_{2-6}$cycloheteroalkyl-C$_{1-3}$ alkyl-,
wherein each alkyl, cycloalkyl and cycloheteroalkyl is unsubstituted or substituted with one to three substituents independently selected from R$^L$, and wherein one of R$^1$ and R$^2$ is substituted with R$^7$, or R$^1$ and R$^2$ together with the atom(s) to which they are attached form a C$_{3-6}$cycloalkyl ring or a C$_{2-5}$cycloheteroalkyl ring containing 0-2 additional heteroatoms independently selected from oxygen, sulfur and N—R$^g$, wherein each R$^1$ and R$^2$ is unsubstituted or substituted with one to three substituents independently selected from R$^L$, and wherein one of R$^1$ and R$^2$ is substituted with R$^7$; R$^3$ is absent or selected from the group consisting of:
 (1) hydrogen,
 (2) halogen,
 (3) —OR$^e$,
 (4) —CN,
 (5) —C$_{1-6}$alkyl,
 (6) —C$_{3-6}$cycloalkyl, and
 (7) C$_{3-6}$cycloalkyl-C$_{1-3}$alkyl-,
wherein each alkyl and cycloalkyl is unsubstituted or substituted with one to three substituents independently selected from R$^i$;
R$^{4a}$ is selected from the group consisting of:
 (1) hydrogen,
 (2) halogen,
 (3) OR$^e$,
 (4) CG-5alkylNR$^c$R$^d$,
 (5) C$_{1-6}$alkyl,
 (6) C$_{1-6}$alkyl-O—,
 (7) C$_{3-6}$cycloalkyl,
 (8) C$_{3-6}$cycloalkyl-O—,
 (9) C$_{3-6}$cycloalkyl-C$_{1-10}$alkyl-,
 (10) C$_{3-6}$cycloalkyl-C$_{1-10}$alkyl-O—,
 (11) C$_{2-5}$cycloheteroalkyl,
 (12) C$_{2-5}$ cycloheteroalkyl-O—,
 (13) C$_{2-5}$ cycloheteroalkyl-C$_{1-10}$alkyl-,
 (14) C$_{2-5}$ cycloheteroalkyl-C$_{1-10}$alkyl-O—,
 (15) aryl,
 (16) aryl-O—,
 (17) aryl-C$_{1-10}$alkyl-,
 (18) heteroaryl,
 (19) heteroaryl-O—, and
 (20) heteroaryl-C$_{1-10}$alkyl-,
wherein each alkyl, cycloalkyl, cycloheteroalkyl, aryl and heteroaryl is unsubstituted or substituted with one to three substituents selected from R$^j$,
provided that when R$^{4a}$ is selected from the group consisting of:
 (1) OR$^e$,
 (2) C$_{1-6}$alkyl-O—,
 (3) C$_{3-6}$cycloalkyl-O—,
 (4) C$_{3-6}$cycloalkyl-C$_{1-10}$alkyl-O—,
 (5) C$_{2-5}$ cycloheteroalkyl-O—,
 (6) C$_{2-5}$ cycloheteroalkyl-C$_{1-10}$alkyl-O—,
 (7) aryl-O—, and
 (8) heteroaryl-O—,
then X is selected from the group consisting of:
 (1) —CR$^g$R$^g$,
 (2) C=O,
 (3) —C(R$^g$)OC$_{1-6}$alkyl, and
 (4) —CF$_2$;
R$^{4b}$ is selected from the group consisting of:
 (1) hydrogen,
 (2) halogen,
 (3) C$_{1-6}$alkyl, and
 (4) C$_{3-6}$cycloalkyl,
wherein each alkyl and cycloalkyl is unsubstituted or substituted with one to three substituents independently selected from R$^j$;
R$^5$ is absent or selected from the group consisting of:
 (1) hydrogen,
 (2) —C$_{1-6}$alkyl, and
 (3) —C$_{3-6}$cycloalkyl,
wherein each alkyl and cycloalkyl is unsubstituted or substituted with one to three substituents independently selected from R$^j$;

$R^{6a}$ is selected from the group consisting of:
(1) hydrogen,
(2) halogen,
(3) $OR^e$,
(4) $C_{1-6}$alkyl,
(5) $C_{1-6}$alkyl-O—,
(6) $C_{3-6}$cycloalkyl,
(7) $C_{3-6}$cycloalkyl-O—,
(8) $C_{3-6}$cycloalkyl-$C_{1-10}$alkyl-,
(9) $C_{3-6}$cycloalkyl-$C_{1-10}$alkyl-O—,
(10) $C_{2-5}$ cycloheteroalkyl,
(11) $C_{2-5}$cycloheteroalkyl-O—,
(12) $C_{2-5}$ cycloheteroalkyl-$C_{1-10}$alkyl-,
(13) $C_{2-5}$ cycloheteroalkyl-$C_{1-10}$alkyl-O—,
(14) aryl,
(15) aryl-O—,
(16) aryl-$C_{1-10}$alkyl-,
(17) heteroaryl,
(18) heteroaryl-O—, and
(19) heteroaryl-$C_{1-10}$alkyl-,
wherein each alkyl, cycloalkyl, cycloheteroalkyl, aryl and heteroaryl is unsubstituted or substituted with one to three substituents independently selected from $R^j$;

$R^{6b}$ is absent or selected from the group consisting of:
(1) hydrogen,
(2) halogen, and
(3) —$C_{1-6}$alkyl;

$R^7$ is selected from the group consisting of:
(1) —$CO_2R^8$,
(2) —$C_{1-6}$alkyl-$CO_2R^8$,
(3) —$C_{1-6}$alkyl-$CONHSO_2R^m$,
(4) —$C_{1-6}$alkyl-$SO_2NHCOR^m$,
(5) —$C_{1-6}$alkyl-tetrazolyl, and
(6) a cycloheteroalkyl selected from the group consisting of:

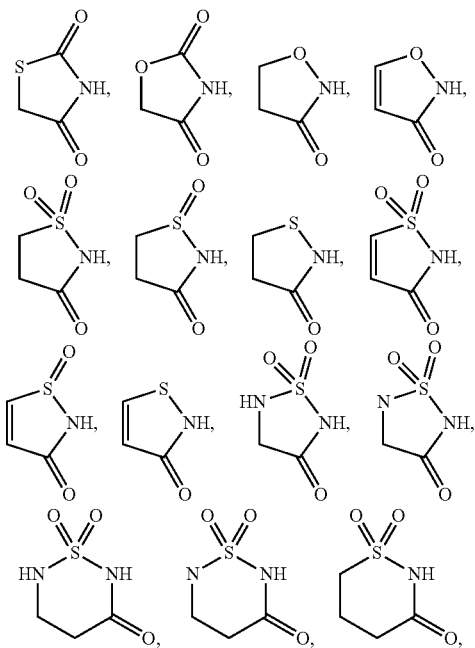

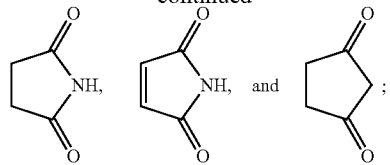

$R^8$ is selected from the group consisting of:
(1) hydrogen,
(2) —$C_{1-6}$alkyl,
(3) —$C_{3-6}$cycloalkyl, and
(4) aryl-$C_{1-6}$alkyl,
wherein each alkyl, cycloalkyl and aryl is unsubstituted or substituted with one to three independently substituents selected from $R^j$;

each $R^a$ is independently selected from the group consisting of:
(1) —$C_{1-6}$alkyl,
(2) halogen,
(3) —$C_{0-6}$alkyl-$OR^e$,
(4) —$C_{0-6}$alkyl-$NR^cS(O)_nR^e$,
(5) —$C_{0-6}$alkyl-$S(O)_nR^e$,
(6) —$C_{0-6}$alkyl-$S(O)_nNR^cR^d$,
(7) —$C_{0-6}$alkyl-$NR^cR^d$,
(8) —$C_{0-6}$alkyl-$C(O)R^e$,
(9) —$C_{0-6}$alkyl-$OC(O)R^e$,
(10) —$C_{0-6}$alkyl-$CO_2R^e$,
(11) —$C_{0-6}$alkyl-CN,
(12) —$C_{0-6}$alkyl-$C(O)NR^cR^d$,
(13) —$C_{0-6}$alkyl-$NR^cC(O)R^e$,
(14) —$C_{0-6}$alkyl-$NR^cC(O)OR^e$,
(15) —$C_{0-6}$alkyl-$NR^cC(O)NR^cR^d$,
(16) —$CF_3$,
(17) —$OCF_3$,
(18) —$OCHF_2$,
(19) —$C_{0-6}$alkyl-aryl,
(20) —$C_{0-5}$alkyl-heteroaryl,
(21) —$C_{0-6}$alkyl-$C_{3-10}$cycloalkyl,
(22) —$C_{0-6}$alkyl-$C_{3-10}$cycloalkenyl, and
(23) —$C_{0-6}$alkyl-$C_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alkyl, —CN, —$OCHF_2$, —$OCF_3$, —$CF_3$, and —$C_{0-6}$alkyl-$NR^cR^d$;

each $R^b$ is independently selected from the group consisting of:
(1) —$C_{1-10}$alkyl,
(2) —$C_{2-10}$alkenyl,
(3) —$CF_3$,
(4) halogen,
(5) —CN,
(6) —OH,
(7) —$OC_{1-10}$alkyl,
(8) —$OC_{2-10}$alkenyl,
(9) —$O(CH_2)_pOC_{1-10}$alkyl,
(10) —$O(CH_2)_pC_{3-6}$cycloalkyl,
(11) —$O(CH_2)_pC_{3-6}$ cycloalkyl-$C_{1-10}$alkyl,
(12) —$O(CH_2)_pC_{2-5}$cycloheteroalkyl,
(13) —$O(CH_2)_pC_{2-5}$cycloheteroalkyl-$C_{1-10}$alkyl,
(14) —O-aryl,
(15) —O-heteroaryl,
(16) —O-aryl-$C_{1-10}$alkyl,
(17) —O-heteroaryl-$C_{1-10}$alkyl,

(18) —O(CH$_2$)$_p$NR$^c$S(O)$_m$R$^e$,
(19) —O(CH$_2$)$_p$S(O)$_m$R$^e$,
(20) —O(CH$_2$)$_p$S(O)$_m$NR$^c$R$^d$,
(21) —O(CH$_2$)$_p$NR$^c$R$^d$,
(22) —C(O)R$^e$,
(23) —OC(O)R$^e$,
(24) —CO$_2$R$^e$,
(25) —C(O)NR$^c$R$^d$,
(26) —NR$^c$C(O)R$^e$,
(27) —NR$^c$C(O)OR$^e$,
(28) —NR$^c$C(O)NR$^c$R$^d$,
(29) —O(CH$_2$)$_p$O—C$_{3-6}$cycloalkyl,
(30) —O(CH$_2$)$_p$O—C$_{2-5}$ cycloheteroalkyl,
(31) —OCF$_3$,
(32) —OCHF$_2$,
(33) —(CH$_2$)$_p$C$_{3-6}$cycloalkyl,
(34) —(CH$_2$)$_p$C$_{2-5}$cycloheteroalkyl,
(35) aryl,
(36) heteroaryl,
(37) aryl-C$_{1-10}$alkyl-, and
(38) heteroaryl-C$_{1-10}$ alkyl-,
wherein each CH, CH$_2$, alkyl, alkenyl, cycloalkyl, cycloheteroalkyl, aryl and heteroaryl is unsubstituted or substituted with one to five substituents independently selected from: —C$_{1-6}$alkyl, halogen, OH, —O—C$_{1-6}$alkyl and —CF$_3$;
R$^c$ and R$^d$ are each independently selected from the group consisting of:
(1) hydrogen,
(2) C$_{1-10}$alkyl,
(3) C$_{2-10}$alkenyl,
(4) C$_{3-6}$cycloalkyl,
(5) C$_{3-6}$ cycloalkyl-C$_{1-10}$alkyl-,
(6) C$_{2-5}$ cycloheteroalkyl,
(7) C$_{2-5}$ cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents independently selected from R$^f$, or R$^c$ and R$^d$ together with the atom(s) to which they are attached form a C$_{2-10}$cycloheteroalkyl ring containing 0-2 additional heteroatoms independently selected from oxygen, sulfur and N—R$^g$,
wherein each R$^c$ and R$^d$ is unsubstituted or substituted with one to three substituents independently selected from R$^f$,
each R$^e$ is independently selected from the group consisting of:
(1) hydrogen,
(2) —C$_{1-10}$alkyl,
(3) —C$_{2-10}$ alkenyl,
(4) —C$_{3-6}$ cycloalkyl,
(5) C$_{3-6}$ cycloalkyl-C$_{1-10}$alkyl-,
(6) —C$_{2-5}$cycloheteroalkyl,
(7) C$_{2-5}$ cycloheteroalkyl-C$_{1-10}$alkyl-,
(8) aryl,
(9) aryl-C$_{1-10}$alkyl-,
(10) heteroaryl, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents independently selected from R$^h$;
each R$^f$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, C$_{1-6}$alkyl, cyano and S(O)$_2$C$_{1-6}$alkyl;
each R$^g$ is selected from the group consisting of:
(1) hydrogen,
(2) —C(O)R$^e$, and
(3) —C$_{1-10}$alkyl,
wherein each alkyl is unsubstituted or substituted with one to five halogens;
each R$^h$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, C$_{1-6}$alkyl, cyano and S(O)$_2$C$_{1-6}$alkyl;
each R$^i$ is independently selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —NR$^c$C(O)R$^e$,
(14) —NR$^c$C(O)OR$^e$,
(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$ cycloheteroalkyl;
each R$^j$ is independently selected from the group consisting of:
(1) —C$_{1-6}$alkyl,
(2) —OR$^e$,
(3) —NR$^c$S(O)$_m$R$^e$,
(4) halogen,
(5) —S(O)$_m$R$^e$,
(6) —S(O)$_m$NR$^c$R$^d$,
(7) —NR$^c$R$^d$,
(8) —C(O)R$^e$,
(9) —OC(O)R$^e$,
(10) —CO$_2$R$^e$,
(11) —CN,
(12) —C(O)NR$^c$R$^d$,
(13) —NR$^c$C(O)R$^e$,
(14) —NR$^c$C(O)OR$^e$,

(15) —NR$^c$C(O)NR$^c$R$^d$,
(16) —CF$_3$,
(17) —OCF$_3$,
(18) —OCHF$_2$,
(19) —C$_{3-6}$cycloalkyl, and
(20) —C$_{2-5}$ cycloheteroalkyl;

R$^k$ is selected from the group consisting of:
(1) hydrogen,
(2) —C$_{1-6}$ alkyl,
(3) —C$_{1-6}$alkyl-SO$_2$C$_{1-6}$alkyl,
(4) —CF$_3$, and
(5) —CHF$_2$, wherein each alkyl is unsubstituted or substituted with one to three substituents independently selected from: —OH, —OC$_{1-6}$alkyl, halogen, cyano, and —S(O)$_2$C$_{1-6}$alkyl;

each R$^L$ is independently selected from the group consisting of:
(1) —CO$_2$C$_{1-6}$alkyl,
(2) —C$_{1-10}$alkyl,
(3) —C$_{2-10}$ alkenyl,
(4) —C$_{2-10}$alkynyl,
(5) —C$_{3-6}$cycloalkyl,
(6) —C$_{2-6}$cycloheteroalkyl,
(7) aryl, and
(8) heteroaryl, wherein each alkyl, alkenyl, alkynyl, cycloalkyl, cycloheteroalkyl, aryl and heteroaryl is unsubstituted or substituted with one to four substituents independently selected from C$_{1-6}$alkyl, halogen, and —OC$_{1-6}$alkyl;

each R$^m$ is independently selected from the group consisting of:
(1) —C$_{1-10}$alkyl,
(2) —C$_{2-10}$ alkenyl,
(3) —C$_{3-6}$ cycloalkyl,
(4) C$_{3-6}$ cycloalkyl-C$_{1-10}$alkyl-,
(5) —C$_{2-5}$cycloheteroalkyl,
(6) C$_{2-5}$ cycloheteroalkyl-C$_{1-10}$alkyl-,
(7) aryl,
(8) heteroaryl,
(9) aryl-C$_{1-10}$alkyl-, and
(10) heteroaryl-C$_{1-10}$alkyl-;

each n is independently selected from: 0, 1 or 2;
each m is independently selected from: 0, 1 or 2;
each p is independently selected from: 0, 1, 2, 3, 4, 5 or 6; and
each r is independently selected from: 0, 1, 2 or 3.

The invention has numerous embodiments, which are summarized below. The invention includes the compounds as shown, and also includes individual diastereoisomers, enantiomers, and epimers of the compounds, and mixtures of diastereoisomers and/or enantiomers thereof including racemic mixtures.

In one embodiment, "a" is a single bond. In another embodiment, "a" is a single bond, and R$^5$ and R$^{6b}$ are present.

In another embodiment, "a" is a double bond. In another embodiment, "a" is a double bond, and R$^5$ and R$^{6b}$ are absent.

In another embodiment of the present invention, T is selected from the group consisting of: CH, N and N-oxide. In a class of this embodiment, T is selected from the group consisting of: CH and N. In another class of this embodiment, T is CH. In another class of this embodiment, T is N or N-oxide. In another class of this embodiment, T is N. In another class of this embodiment, T is N-oxide.

In another embodiment of the present invention, U is selected from the group consisting of: CR$^1$, N and N-oxide.

In a class of this embodiment, U is selected from the group consisting of: CR$^1$ and N. In another class of this embodiment, U is CR$^1$. In another class of this embodiment, U is N or N-oxide. In another class of this embodiment, U is N. In another class of this embodiment, U is N-oxide.

In another embodiment of the present invention, V is selected from the group consisting of: CR$^2$, N and N-oxide. In a class of this embodiment, V is selected from the group consisting of: CR$^2$ and N. In another class of this embodiment, V is CR$^2$. In another class of this embodiment, V is N or N-oxide. In another class of this embodiment, V is N. In another class of this embodiment, V is N-oxide.

In another embodiment of the present invention, W is selected from the group consisting of: CH, N and N-oxide, provided that no more than two of T, U, V and W are selected from N and N-oxide, further provided that if both T and W are N or N-oxide, then R$^3$ is absent, and further provided that both U and V are not N or N-oxide. In a class of this embodiment, W is selected from the group consisting of: CH and N, provided that no more than two of T, U, V and W are selected from N and N-oxide, further provided that if both T and W are N or N-oxide, then R$^3$ is absent, and further provided that both U and V are not N or N-oxide. In another class of this embodiment, W is CH, provided that no more than two of T, U, V and W are selected from N and N-oxide, further provided that if both T and W are N or N-oxide, then R$^3$ is absent, and further provided that both U and V are not N or N-oxide. In another class of this embodiment, W is N or N-oxide, provided that no more than two of T, U, V and W are selected from N and N-oxide, further provided that if both T and W are N or N-oxide, then R$^3$ is absent, and further provided that both U and V are not N or N-oxide. In another class of this embodiment, W is N, provided that no more than two of T, U, V and W are selected from N and N-oxide, further provided that if both T and W are N or N-oxide, then R$^3$ is absent, and further provided that both U and V are not N or N-oxide.

In another embodiment of the present invention, W is selected from the group consisting of: CH, N and N-oxide. In a class of this embodiment, W is selected from the group consisting of: CH and N. In another class of this embodiment, W is CH. In another class of this embodiment, W is N or N-oxide. In another class of this embodiment, W is N. In another class of this embodiment, W is N-oxide.

In another embodiment of the present invention, T is CH, U is CR$^1$, V is CR$^2$, and W is CH. In a class of this embodiment, T is CH, U is CR$^1$, V is CH, and W is CH. In another class of this embodiment, T is CH, U is CH, V is CR$^2$, and W is CH.

In another embodiment of the present invention, T is N or N-oxide, U is CR$^1$, V is CR$^2$, and W is CH. In a class of this embodiment, T is N, U is CR$^1$, V is CR$^2$, and W is CH. In another embodiment of the present invention, T is CH, U is N or N-oxide, and V is CR$^2$, and W is CH. In a class of this embodiment, T is CH, U is N, V is CR$^2$, and W is CH. In another embodiment of the present invention, T is CH, U is CR$^1$, V is N or N-oxide, and W is CH. In a class of this embodiment, T is CH, U is CR$^1$, and V is N or N-oxide, and W is CH. In another embodiment of the present invention, T is CH, U is CR$^1$, V is CR$^2$, and W is CH, N or N-oxide. In another embodiment of the present invention, T is CH, U is CR$^1$, V is CR$^2$, and W is N or N-oxide. In a class of this embodiment, T is CH, U is CR$^1$, V is CR$^2$, and W is N.

In another embodiment of the present invention, T is N or N-oxide, U is N or N-oxide, V is CR$^2$, and W is CH. In a class of this embodiment, T is N, U is N, V is CR$^2$, and W is CH.

In another embodiment of the present invention, T is N or N-oxide, U is $CR^1$, V is N or N-oxide, and W is CH. In a class of this embodiment, T is N, U is $CR^1$, V is N, and W is CH.

In another embodiment of the present invention, T is N or N-oxide, U is $CR^1$, V is $CR^2$, and W is N or N-oxide. In a class of this embodiment, T is N, U is $CR^1$, V is $CR^2$, and W is N. In another embodiment of the present invention, T is N or N-oxide, U is $CR^1$, V is $CR^2$, and W is N or N-oxide; and $R^3$ is absent. In a class of this embodiment, T is N, U is $CR^1$, V is $CR^2$, and W is N; and $R^3$ is absent.

In another embodiment of the present invention, T is CH, U is N or N-oxide, V is $CR^2$, and W is N or N-oxide. In a class of this embodiment, T is CH, U is N, V is $CR^2$, and W is N.

In another embodiment of the present invention, T is CH, U is $CR^1$, V is N or N-oxide, and W is N or N-oxide. In a class of this embodiment, T is CH, U is $CR^1$, V is N, and W is N.

In another embodiment of the present invention, X is selected from the group consisting of: oxygen, sulfur, $S(O)_2$, $-CR^gR^g$, $C=O$, $-CF_2$, and $-NR^c$. In another embodiment of the present invention, X is selected from the group consisting of: oxygen, sulfur, $S(O)_2$, $-CR^gR^g$, and $C=O$. In a class of this embodiment, X is selected from the group consisting of: oxygen, sulfur, $S(O)_2$, $-CH_2$, and $C=O$. In another embodiment of the present invention, X is selected from the group consisting of: oxygen, sulfur, and $-CR^gR^g$. In a class of this embodiment, X is selected from the group consisting of: oxygen, sulfur, and $-CH_2$.

In another embodiment of the present invention, Y is selected from the group consisting of: oxygen, sulfur, $S(O)_2$, $C=O$, $-CF_2$, $-NR^c$; and $-CR^{4a}R^{4b}$, provided that if X is oxygen, sulfur or $-NR^c$, then Y is not oxygen, sulfur or $-NR^c$, further provided that if X is $C=O$, then Y is not $C=O$ or $S(O)_2$, and further provided that if X is $S(O)_2$, then Y is not $S(O)_2$, $C=O$, oxygen or sulfur. In a class of this embodiment, Y is selected from the group consisting of: oxygen, sulfur, $S(O)_2$, $C=O$, $-CF_2$, $-NR^c$; and $-CH_2$, provided that if X is oxygen, sulfur or $-NR^c$, then Y is not oxygen, sulfur or $-NR^c$, further provided that if X is $C=O$, then Y is not $C=O$ or $S(O)_2$, and further provided that if X is $S(O)_2$, then Y is not $S(O)_2$, $C=O$, oxygen or sulfur.

In another embodiment of the present invention, Y is selected from the group consisting of: oxygen, $S(O)_2$, $C=O$, $-NR^c$; and $-CR^{4a}R^{4b}$, provided that if X is oxygen, sulfur or $-NR^c$, then Y is not oxygen or $-NR^c$, further provided that if X is $C=O$, then Y is not $C=O$ or $S(O)_2$, and further provided that if X is $S(O)_2$, then Y is not $S(O)_2$, $C=O$, or oxygen. In a class of this embodiment, Y is selected from the group consisting of: oxygen, $S(O)_2$, $C=O$, $-NR^c$; and $-CH_2$, provided that if X is oxygen, sulfur or $-NR^c$, then Y is not oxygen or $-NR^c$, further provided that if X is $C=O$, then Y is not $C=O$ or $S(O)_2$, and further provided that if X is $S(O)_2$, then Y is not $S(O)_2$, $C=O$, or oxygen.

In another embodiment of the present invention, Y is selected from the group consisting of: oxygen, and $-CR^{4a}R^{4b}$, provided that if X is oxygen, sulfur or $-NR^c$, then Y is not oxygen, and further provided that if X is $S(O)_2$, then Y is not oxygen. In a class of this embodiment, Y is selected from the group consisting of: oxygen, and $-CH_2$, provided that if X is oxygen, sulfur or $-NR^c$, then Y is not oxygen, and further provided that if X is $S(O)_2$, then Y is not oxygen.

In another embodiment of the present invention, Y is selected from the group consisting of: oxygen, and $-CR^{4a}R^{4b}$, provided that if X is oxygen or sulfur, then Y is not oxygen, and further provided that if X is $S(O)_2$, then Y is not oxygen. In another embodiment of the present invention, Y is selected from the group consisting of: oxygen, and $-CH_2$, provided that if X is oxygen or sulfur, then Y is not oxygen.

In another embodiment of the present invention, A is selected from the group consisting of: aryl, and $C_{3-5}$cycloheteroalkyl, wherein each aryl and cycloheteroalkyl is unsubstituted or substituted with one to five substituents independently selected from $R^a$. In a class of this embodiment, A is selected from the group consisting of: phenyl, and piperidine, wherein each phenyl and piperidine is unsubstituted or substituted with one to four substituents independently selected from $R^a$.

In another embodiment of the present invention, A is aryl, wherein aryl is unsubstituted or substituted with one to five substituents independently selected from $R^a$. In a class of this embodiment, A is phenyl, wherein phenyl is unsubstituted or substituted with one to four substituents independently selected from $R^a$.

In another embodiment of the present invention, A is $-C_{3-5}$cycloheteroalkyl, wherein cycloheteroalkyl is unsubstituted or substituted with one to five substituents independently selected from $R^a$. In a class of this embodiment, A is piperidine, wherein piperidine is unsubstituted or substituted with one to four substituents independently selected from $R^a$.

In another embodiment of the present invention, B is selected from the group consisting of: aryl, aryl-O—, aryl-$C_{1-10}$ alkyl-, aryl-$C_{1-10}$ alkyl-O—, $C_{3-6}$cycloalkyl, $C_{3-6}$cycloalkyl-$C_{1-10}$alkyl-, $C_{3-6}$cycloalkyl-$C_{1-10}$alkyl-O—, $C_{3-6}$cycloalkenyl, $C_{3-6}$cycloalkenyl-$C_{1-10}$alkyl-, $C_{3-6}$cycloalkenyl-$C_{1-10}$alkyl-O—, $C_{2-5}$cycloheteroalkyl, $C_{3-6}$cycloheteroalkyl-$C_{1-10}$alkyl-, $C_{3-6}$cycloheteroalkyl-$C_{1-10}$ alkyl-O—, heteroaryl, heteroaryl-O—, heteroaryl-$C_{1-10}$ alkyl-, and heteroaryl-$C_{1-10}$ alkyl-O—, wherein B is unsubstituted or substituted with one to five substituents independently selected from $R^b$.

In another embodiment of the present invention, B is selected from the group consisting of: aryl, aryl-O—, aryl-$C_{1-10}$ alkyl-, aryl-$C_{1-10}$ alkyl-O—, heteroaryl, heteroaryl-O—, heteroaryl-$C_{1-10}$ alkyl-, and heteroaryl-$C_{1-10}$ alkyl-O—, wherein B is unsubstituted or substituted with one to five substituents independently selected from $R^b$.

In another embodiment of the present invention, B is selected from the group consisting of: aryl, aryl-$C_{1-10}$ alkyl-, and heteroaryl, wherein each alkyl, aryl and heteroaryl is unsubstituted or substituted with one to five substituents independently selected from $R^b$. In a class of this embodiment, B is selected from the group consisting of: phenyl, phenyl-$CH_2$—, and pyridyl, wherein each $CH_2$, phenyl and pyridyl is unsubstituted or substituted with one to five substituents independently selected from $R^b$.

In another embodiment of the present invention, B is selected from the group consisting of: aryl, and heteroaryl, wherein each aryl and heteroaryl is unsubstituted or substituted with one to five substituents independently selected from $R^b$. In a class of this embodiment, B is selected from the group consisting of: phenyl, and pyridyl, wherein each phenyl and pyridyl is unsubstituted or substituted with one to five substituents independently selected from $R^b$.

In another embodiment of the present invention, $R^1$ and $R^2$ are each independently selected from: a bond, hydrogen, halogen, $-OR^k$, $-CN$, $-C_{1-6}$alkyl, $-C_{3-6}$cycloalkyl, $C_{3-6}$cycloalkyl-$C_{1-3}$alkyl-, $-C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents independently selected from $R^L$, and wherein one of $R^1$ and $R^2$ is substituted with $R^7$. In a class of this embodiment, each alkyl, cycloalkyl and cycloheteroalkyl is unsubstituted or substituted with one or two substituents independently selected from $R^L$.

In another embodiment of the present invention, $R^1$ and $R^2$ are each independently selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents independently selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents independently selected from $R^L$, and wherein one of $R^1$ and $R^2$ is substituted with $R^7$. In a class of this embodiment, each alkyl, cycloalkyl and cycloheteroalkyl is unsubstituted or substituted with one or two substituents independently selected from $R^L$. In another embodiment of the present invention, $R^1$ and $R^2$ are each independently selected from: hydrogen, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents independently selected from $R^L$, and wherein one of $R^1$ and $R^2$ is substituted with $R^7$. In a class of this embodiment, each alkyl, cycloalkyl and cycloheteroalkyl is unsubstituted or substituted with one or two substituents independently selected from $R^L$.

In another embodiment of the present invention, $R^1$ and $R^2$ are each independently selected from: hydrogen, halogen, —$OR^k$, —CN, and —$C_{1-6}$alkyl, wherein alkyl is unsubstituted or substituted with one to three substituents independently selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents independently selected from $R^L$, and wherein one of $R^1$ and $R^2$ is substituted with $R^7$. In a class of this embodiment, alkyl is unsubstituted or substituted with one or two substituents independently selected from $R^L$. In another embodiment of the present invention, $R^1$ and $R^2$ are each independently selected from: hydrogen, halogen, —$OR^k$, —CN, and —$C_{1-6}$alkyl, wherein alkyl is unsubstituted or substituted with one to three substituents independently selected from $R^L$, and wherein one of $R^1$ and $R^2$ is substituted with $R^7$. In a class of this embodiment, alkyl is unsubstituted or substituted with one or two substituents independently selected from $R^L$.

In another embodiment of the present invention, $R^1$ and $R^2$ are each independently selected from: hydrogen, halogen, and —$C_{1-6}$alkyl, wherein alkyl is unsubstituted or substituted with one to three substituents independently selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents independently selected from $R^L$, and wherein one of $R^1$ and $R^2$ is substituted with $R^7$. In a class of this embodiment, alkyl is unsubstituted or substituted with one or two substituents independently selected from $R^L$. In another embodiment of the present invention, $R^1$ and $R^2$ are each independently selected from: hydrogen, halogen, and —$C_{1-6}$alkyl, wherein alkyl is unsubstituted or substituted with one to three substituents independently selected from $R^L$, and wherein one of $R^1$ and $R^2$ is substituted with $R^7$. In a class of this embodiment, alkyl is unsubstituted or substituted with one or two substituents independently selected from $R^L$.

In another embodiment of the present invention, $R^1$ and $R^2$ are each independently selected from: hydrogen, and —$C_{1-6}$alkyl, wherein alkyl is unsubstituted or substituted with one to three substituents independently selected from $R^L$, and wherein one of $R^1$ and $R^2$ is substituted with $R^7$, or $R^1$ and $R^2$ together with the atom(s) to which they are attached form a $C_{3-6}$cycloalkyl ring or a $C_{2-5}$cycloheteroalkyl ring containing 0-2 additional heteroatoms independently selected from oxygen, sulfur and N—$R^g$, wherein each $R^1$ and $R^2$ is unsubstituted or substituted with one to three substituents independently selected from $R^L$, and wherein one of $R^1$ and $R^2$ is substituted with $R^7$. In a class of this embodiment, alkyl is unsubstituted or substituted with one or two substituents independently selected from $R^L$.

In another embodiment of the present invention, $R^1$ and $R^2$ are each independently selected from: hydrogen and —$C_{1-6}$alkyl, wherein alkyl is unsubstituted or substituted with one to three substituents independently selected from $R^L$, and wherein one of $R^1$ and $R^2$ is substituted with $R^7$. In a class of this embodiment, alkyl is unsubstituted or substituted with one or two substituents independently selected from $R^L$.

In another embodiment of the present invention, $R^1$ and $R^2$ are each independently selected from: hydrogen, and ethyl, wherein ethyl is unsubstituted or substituted with one to three substituents independently selected from $R^L$, and wherein one of $R^1$ and $R^2$ is substituted with $R^7$. In a class of this embodiment, alkyl is unsubstituted or substituted with one or two substituents independently selected from $R^L$.

In another embodiment of the present invention, $R^1$ and $R^2$ are each independently selected from: hydrogen, and —$C_{1-6}$alkyl, wherein one of $R^1$ and $R^2$ is —$C_{1-6}$alkyl substituted with $R^7$, and wherein alkyl is unsubstituted or substituted with one to three substituents independently selected from $R^L$; or a pharmaceutically acceptable salt thereof. In another embodiment of the present invention, $R^1$ and $R^2$ are each independently selected from: hydrogen, and ethyl, wherein one of $R^1$ and $R^2$ is ethyl substituted with $R^7$, and wherein ethyl is unsubstituted or substituted with one to three substituents independently selected from $R^L$; or a pharmaceutically acceptable salt thereof.

In another embodiment of the present invention, $R^1$ is —CH(cyclopropyl)-CH($CH_3$)—$CO_2H$. In another embodiment of the present invention, $R^1$ is —CH(cyclopropyl)-CH($CH_3$)—$CO_2H$, and $R^2$ is hydrogen. In another embodiment of the present invention, $R^2$ is —CH(cyclopropyl)-CH($CH_3$)—$CO_2H$. In another embodiment of the present invention, $R^2$ is —CH(cyclopropyl)-CH($CH_3$)—$CO_2H$, and $R^1$ is hydrogen.

In another embodiment of the present invention, $R^1$ is —CH(cyclopropyl)-$CH_2$—$CO_2H$. In another embodiment of the present invention, $R^1$ is —CH(cyclopropyl)-$CH_2$—$CO_2H$, and $R^2$ is hydrogen. In another embodiment of the present invention, $R^2$ is —CH(cyclopropyl)-$CH_2$—$CO_2H$.

In another embodiment of the present invention, $R^2$ is —CH(cyclopropyl)-$CH_2$—$CO_2H$, and $R^1$ is hydrogen.

In another embodiment, $R^1$ is selected from: halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$; and $R^2$ is hydrogen. In another embodiment of the present invention, $R^1$ is —$C_{1-6}$alkyl, wherein alkyl is unsubstituted or substituted with one to three substituents independently selected from $R^L$, and wherein $R^1$ is substituted with $R^7$; and $R^2$ is hydrogen. In another embodiment of the present invention, $R^1$ is -ethyl, wherein ethyl is unsubstituted or substituted with one to three substituents independently selected from $R^L$, and wherein $R^1$ is substituted with $R^7$; and $R^2$ is hydrogen. In another embodiment of the present invention, $R^1$ is ethyl, wherein ethyl is substituted with one or two substituents independently selected from $R^L$, and wherein $R^1$ is substituted with $R^7$; and $R^2$ is hydrogen. In another embodiment of the present invention, $R^1$ is ethyl, wherein ethyl is substituted with one substituent independently selected from $R^L$, and wherein $R^1$ is substituted with $R^7$; and $R^2$ is hydrogen. In another embodiment of the present invention, $R^1$ is ethyl, wherein ethyl is substituted with two substituents independently selected from $R^L$, and wherein $R^1$ is substituted with $R^7$; and $R^2$ is hydrogen.

In another embodiment, $R^2$ is selected from: halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$; and $R^1$ is hydrogen.

In another embodiment of the present invention, $R^2$ is —$C_{1-6}$alkyl, wherein alkyl is unsubstituted or substituted with one to three substituents independently selected from $R^L$, and wherein $R^2$ is substituted with $R^7$; and $R^1$ is hydrogen. In another embodiment of the present invention, $R^2$ is ethyl, wherein ethyl is unsubstituted or substituted with one to three substituents independently selected from $R^L$, and wherein $R^2$ is substituted with $R^7$; and $R^1$ is hydrogen. In another embodiment of the present invention, $R^2$ is ethyl, wherein ethyl is substituted with one or two substituents independently selected from $R^L$, and wherein $R^2$ is substituted with $R^7$; and $R^1$ is hydrogen. In another embodiment of the present invention, $R^2$ is ethyl, wherein ethyl is substituted with one substituent independently selected from $R^L$, and wherein $R^2$ is substituted with $R^7$; and $R^1$ is hydrogen. In another embodiment of the present invention, $R^2$ is ethyl, wherein ethyl is substituted with two substituents independently selected from $R^L$, and wherein $R^2$ is substituted with $R^7$; and $R^1$ is hydrogen.

In another embodiment, $R^1$ is selected from: a bond, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^1$ is substituted with $R^7$.

In another embodiment of the present invention, $R^1$ is selected from: a bond, hydrogen, halogen, —$OR^k$, and —CN. In another embodiment of the present invention, $R^1$ is selected from: hydrogen, halogen, —$OR^k$, and —CN. In another embodiment of the present invention, $R^1$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents independently selected from $R^L$, and wherein $R^1$ is substituted with $R^7$. In a class of this embodiment, each alkyl, cycloalkyl and cycloheteroalkyl is unsubstituted or substituted with one or two substituents independently selected from $R^L$. In another embodiment of the present invention, $R^1$ is selected from: —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents independently selected from $R^L$, and wherein $R^1$ is substituted with $R^7$, and $R^2$ is hydrogen. In a class of this embodiment, each alkyl, cycloalkyl and cycloheteroalkyl is unsubstituted or substituted with one or two substituents independently selected from $R^L$.

In another embodiment of the present invention, $R^1$ is selected from: hydrogen, and —$C_{1-6}$alkyl, wherein alkyl is unsubstituted or substituted with one to three substituents independently selected from $R^L$, and wherein $R^1$ is substituted with $R^7$. In a class of this embodiment, alkyl is unsubstituted or substituted with one or two substituents independently selected from $R^L$. In another embodiment of the present invention, $R^1$ is —$C_{1-6}$alkyl, wherein alkyl is unsubstituted or substituted with one to three substituents independently selected from $R^L$, and wherein $R^1$ is substituted with $R^7$. In a class of this embodiment, alkyl is unsubstituted or substituted with one or two substituents independently selected from $R^L$. In another embodiment of the present invention, $R^1$ is —$C_{1-6}$alkyl, wherein alkyl is unsubstituted or substituted with one to three substituents independently selected from $R^L$, and wherein $R^1$ is substituted with $R^7$, and $R^2$ is hydrogen. In a class of this embodiment, alkyl is unsubstituted or substituted with one or two substituents independently selected from $R^L$.

In another embodiment of the present invention, $R^1$ is selected from: hydrogen, and ethyl, wherein ethyl is unsubstituted or substituted with one to three substituents independently selected from $R^L$, and wherein $R^1$ is substituted with $R^7$. In a class of this embodiment, ethyl is unsubstituted or substituted with one or two substituents independently selected from $R^L$. In another embodiment of the present invention, $R^1$ is ethyl, wherein ethyl is unsubstituted or substituted with one to three substituents independently selected from $R^L$, and wherein $R^1$ is substituted with $R^7$. In a class of this embodiment, ethyl is unsubstituted or substituted with one or two substituents independently selected from $R^L$. In another embodiment of the present invention, $R^1$ is ethyl, wherein ethyl is unsubstituted or substituted with one to three substituents independently selected from $R^L$, and wherein $R^1$ is substituted with $R^7$, and $R^2$ is hydrogen. In a class of this embodiment, ethyl is unsubstituted or substituted with one or two substituents independently selected from $R^L$. In another embodiment of the present invention, $R^1$ is hydrogen.

In another embodiment, $R^2$ is selected from: a bond, halogen, —$OR^k$, —CN, —$C_{1-6}$alkyl, —$C_{3-6}$cycloalkyl, $C_{3-6}$cycloalkyl-$C_{1-3}$alkyl-, —$C_{2-6}$cycloheteroalkyl, and $C_{2-6}$cycloheteroalkyl-$C_{1-3}$alkyl-, wherein each alkyl, cycloalkyl and cycloheteroalkyl is unsubstituted or substituted with one to three substituents selected from $R^L$, and wherein $R^2$ is substituted with $R^7$. In another embodiment of the present invention, $R^2$ is selected from: a bond, hydrogen, halogen, —OR$^k$, and —CN. In another embodiment of the present invention, R$^2$ is selected from: hydrogen, halogen, —OR$^k$, and —CN.

In another embodiment of the present invention, R$^2$ is selected from: —C$_{1-6}$alkyl, —C$_{3-6}$cycloalkyl, C$_{3-6}$cycloalkyl-C$_{1-3}$alkyl-, —C$_{2-6}$cycloheteroalkyl, and C$_{2-6}$cycloheteroalkyl-C$_{1-3}$alkyl-, wherein each alkyl, cycloalkyl and cycloheteroalkyl is unsubstituted or substituted with one to three substituents independently selected from R$^L$, and wherein R$^2$ is substituted with R$^7$. In a class of this embodiment, each alkyl, cycloalkyl and cycloheteroalkyl is unsubstituted or substituted with one or two substituents independently selected from R$^L$. In another embodiment of the present invention, R$^2$ is selected from: —C$_{1-6}$alkyl, —C$_{3-6}$cycloalkyl, C$_{3-6}$cycloalkyl-C$_{1-3}$alkyl-, —C$_{2-6}$cycloheteroalkyl, and C$_{2-6}$cycloheteroalkyl-C$_{1-3}$alkyl-, wherein each alkyl, cycloalkyl and cycloheteroalkyl is unsubstituted or substituted with one to three substituents independently selected from R$^L$, and wherein R$^2$ is substituted with R$^7$, and R$^1$ is hydrogen. In a class of this embodiment, each alkyl, cycloalkyl and cycloheteroalkyl is unsubstituted or substituted with one or two substituents independently selected from R$^L$. In another embodiment of the present invention, R$^2$ is selected from: hydrogen, and —C$_{1-6}$alkyl, wherein alkyl is unsubstituted or substituted with one to three substituents independently selected from R$^L$, and wherein R$^2$ is substituted with R$^7$. In a class of this embodiment, alkyl is unsubstituted or substituted with one or two substituents independently selected from R$^L$.

In another embodiment of the present invention, R$^2$ is —C$_{1-6}$alkyl, wherein each alkyl is unsubstituted or substituted with one to three substituents independently selected from R$^L$, and wherein R$^2$ is substituted with R$^7$. In a class of this embodiment, alkyl is unsubstituted or substituted with one or two substituents independently selected from R$^L$. In another embodiment of the present invention, R$^2$ is —C$_{1-6}$alkyl, wherein alkyl is unsubstituted or substituted with one to three substituents independently selected from R$^L$, and wherein R$^2$ is substituted with R$^7$, and R$^1$ is hydrogen. In a class of this embodiment, alkyl is unsubstituted or substituted with one or two substituents independently selected from R$^L$.

In another embodiment of the present invention, R$^2$ is selected from: hydrogen, and ethyl, wherein ethyl is unsubstituted or substituted with one to three substituents independently selected from R$^L$, and wherein R$^2$ is substituted with R$^7$. In a class of this embodiment, ethyl is unsubstituted or substituted with one or two substituents independently selected from R$^L$.

In another embodiment of the present invention, R$^2$ is ethyl, wherein ethyl is unsubstituted or substituted with one to three substituents independently selected from R$^L$, and wherein R$^2$ is substituted with R$^7$. In a class of this embodiment, ethyl is unsubstituted or substituted with one or two substituents independently selected from R$^L$. In another embodiment of the present invention, R$^2$ is ethyl, wherein ethyl is unsubstituted or substituted with one to three substituents independently selected from R$^L$, and wherein R$^2$ is substituted with R$^7$, and R$^1$ is hydrogen. In a class of this embodiment, ethyl is unsubstituted or substituted with one or two substituents independently selected from R$^L$. In another embodiment of the present invention, R$^2$ is hydrogen.

In one class of the embodiments of the present invention, at least one of R$^1$ and R$^2$ is selected from: —C$_{1-6}$alkyl, —C$_{3-6}$cycloalkyl, —C$_{3-6}$cycloalkyl-C$_{1-3}$alkyl-, —C$_{2-6}$cycloheteroalkyl, and —C$_{2-6}$cycloheteroalkyl-C$_{1-3}$alkyl-, wherein each alkyl, cycloalkyl and cycloheteroalkyl is unsubstituted or substituted with one to three substituents independently selected from R$^L$, and wherein one alkyl, cycloalkyl or cycloheteroalkyl is substituted with R$^7$. In another class of the embodiments of the present invention, one of R$^1$ and R$^2$ is selected from: —C$_{1-6}$alkyl, —C$_{3-6}$cycloalkyl, C$_{3-6}$cycloalkyl-C$_{1-3}$alkyl-, —C$_{2-6}$cycloheteroalkyl, and C$_{2-6}$cycloheteroalkyl-C$_{1-3}$alkyl-, wherein each alkyl, cycloalkyl and cycloheteroalkyl is unsubstituted or substituted with one to three substituents independently selected from R$^L$, and wherein one alkyl, cycloalkyl or cycloheteroalkyl is substituted with R$^7$. In another class of the embodiments of the present invention, at least one of R$^1$ and R$^2$ is —C$_{1-6}$alkyl, wherein alkyl is unsubstituted or substituted with one to three substituents independently selected from R$^L$, and wherein one alkyl is substituted with R$^7$. In another class of the embodiments of the present invention, one of R$^1$ and R$^2$ is —C$_{1-6}$alkyl, wherein alkyl is unsubstituted or substituted with one to three substituents independently selected from R$^L$, and wherein alkyl is substituted with R$^7$. In another class of the embodiments of the present invention, one of R$^1$ and R$^2$ is —C$_{1-6}$alkyl, wherein alkyl is substituted with one or two substituents independently selected from R$^L$, and wherein alkyl is substituted with R$^7$. In another class of the embodiments of the present invention, at least one of R$^1$ and R$^2$ is ethyl, wherein ethyl is unsubstituted or substituted with one to three substituents independently selected from R$^L$, and wherein one alkyl is substituted with R$^7$. In another class of the embodiments of the present invention, one of R$^1$ and R$^2$ is ethyl, wherein ethyl is unsubstituted or substituted with one to three substituents independently selected from R$^L$, and wherein ethyl is substituted with R$^7$. In another class of the embodiments of the present invention, one of R$^1$ and R$^2$ is ethyl, wherein ethyl is substituted with one or two substituents independently selected from R$^L$, and wherein ethyl is substituted with R$^7$.

In another embodiment of the present invention, R$^3$ is absent or selected from the group consisting of: hydrogen, halogen, and —C$_{1-6}$alkyl, wherein alkyl is unsubstituted or substituted with one to three substituents independently selected from R$^i$. In another embodiment of the present invention, R$^3$ is selected from the group consisting of: hydrogen, halogen, and —C$_{1-6}$alkyl, wherein alkyl is unsubstituted or substituted with one to three substituents independently selected from R$^i$. In another embodiment of the present invention, R$^3$ is absent or selected from the group consisting of: hydrogen, and halogen. In another embodiment of the present invention, R$^3$ is selected from the group consisting of: hydrogen, and halogen. In another embodiment of the present invention, R$^3$ is absent or hydrogen. In another embodiment of the present invention, R$^3$ is absent. In another embodiment of the present invention, R$^3$ is hydrogen.

In another embodiment of the present invention, R$^{4a}$ is selected from the group consisting of: hydrogen, halogen, OR$^e$, C$_{0-5}$alkylNR$^c$R$^d$, C$_{1-6}$alkyl, and C$_{1-6}$alkyl-O—, wherein each alkyl is unsubstituted or substituted with one to three substituents selected from R$^j$, provided that when R$^{4a}$ is selected from the group consisting of: —OR$^e$, and C$_{1-6}$alkyl-O—, then X is selected from the group consisting of: —CR$^g$R$^g$, C=O, —C(R$^g$)OC$_{1-6}$alkyl, and —CF$_2$. In another embodiment of the present invention, R$^{4a}$ is selected from the group consisting of: hydrogen, halogen, C$_{0-5}$alkylNR$^c$R$^d$, and C$_{1-6}$alkyl, wherein alkyl is unsubstituted or substituted with one to three substituents selected from R$^j$. In another embodiment of the present invention, R$^{4a}$ is selected from the group consisting of: hydrogen, halogen, and —$C_{1-6}$alkyl, wherein alkyl is unsubstituted or substituted with one to three substituents selected from $R^j$. In another embodiment of the present invention, $R^{4a}$ is selected from the group consisting of: hydrogen, and —$C_{1-6}$alkyl, wherein alkyl is unsubstituted or substituted with one to three substituents selected from $R^j$. In another embodiment of the present invention, $R^{4a}$ is —$C_{1-6}$alkyl, wherein alkyl is unsubstituted or substituted with one to three substituents selected from $R^j$. In another embodiment of the present invention, $R^{4a}$ is hydrogen.

In another embodiment of the present invention, $R^{4b}$ is selected from the group consisting of: hydrogen, halogen, and —$C_{1-6}$alkyl, wherein alkyl is unsubstituted or substituted with one to three substituents independently selected from $R^j$. In another embodiment of the present invention, $R^{4b}$ is selected from the group consisting of: hydrogen, and —$C_{1-6}$alkyl, wherein alkyl is unsubstituted or substituted with one to three substituents independently selected from $R^j$. In another embodiment of the present invention, $R^{4b}$ is —$C_{1-6}$alkyl, wherein alkyl is unsubstituted or substituted with one to three substituents independently selected from $R^j$. In another embodiment of the present invention, $R^{4b}$ is hydrogen.

In another embodiment of the present invention, $R^5$ is absent or selected from the group consisting of: hydrogen, and —$C_{1-6}$alkyl, wherein alkyl is unsubstituted or substituted with one to three substituents independently selected from $R^j$. In another embodiment of the present invention, $R^5$ is absent or —$C_{1-6}$alkyl, wherein alkyl is unsubstituted or substituted with one to three substituents independently selected from $R^j$. In another embodiment of the present invention, $R^5$ is —$C_{1-6}$alkyl, wherein alkyl is unsubstituted or substituted with one to three substituents independently selected from $R^j$. In another embodiment of the present invention, $R^5$ is absent or hydrogen. In another embodiment of the present invention, $R^5$ is absent. In another embodiment of the present invention, $R^5$ is hydrogen.

In another embodiment of the present invention, $R^{6a}$ is selected from the group consisting of: hydrogen, halogen, $OR^e$, —$C_{1-6}$alkyl, and —$C_{1-6}$alkyl-O—, wherein each alkyl is unsubstituted or substituted with one to three substituents independently selected from $R^j$. In another embodiment of the present invention, $R^{6a}$ is selected from the group consisting of: hydrogen, halogen, and —$C_{1-6}$alkyl, wherein alkyl is unsubstituted or substituted with one to three substituents independently selected from $R^j$. In another embodiment of the present invention, $R^{6a}$ is selected from the group consisting of: hydrogen, and —$C_{1-6}$alkyl, wherein alkyl is unsubstituted or substituted with one to three substituents independently selected from $R^j$. In another embodiment of the present invention, $R^{6a}$ is —$C_{1-6}$alkyl, wherein alkyl is unsubstituted or substituted with one to three substituents independently selected from $R^j$. In another embodiment of the present invention, $R^{6a}$ is hydrogen.

In another embodiment of the present invention, $R^{6b}$ is absent or selected from the group consisting of: hydrogen, and —$C_{1-6}$alkyl. In another embodiment of the present invention, $R^{6b}$ is absent or —$C_{1-6}$alkyl. In another embodiment of the present invention, $R^{6b}$ is —$C_{1-6}$alkyl. In another embodiment of the present invention, $R^{6b}$ is absent or hydrogen. In another embodiment of the present invention, $R^{6b}$ is absent. In another embodiment of the present invention, $R^{6b}$ is hydrogen.

In another embodiment of the present invention, $R^7$ is selected from the group consisting of: —$CO_2R^8$, and —$C_{1-6}$alkyl-$CO_2R^8$. In another embodiment of the present invention, $R^7$ is —$CO_2R^8$. In a class of this embodiment, $R^7$ is —$CO_2H$.

In another embodiment of the present invention, $R^8$ is selected from the group consisting of: hydrogen, —$C_{1-6}$alkyl and —$C_{3-6}$cycloalkyl, wherein each alkyl and cycloalkyl is unsubstituted or substituted with one to three substituents selected from $R^j$. In a class of this embodiment, $R^8$ is selected from the group consisting of: hydrogen and —$C_{1-6}$alkyl, wherein alkyl is unsubstituted or substituted with one to three substituents selected from $R^j$. In another class of this embodiment, $R^8$ is —$C_{1-6}$alkyl, wherein alkyl is unsubstituted or substituted with one to three substituents selected from $R^j$. In another class of this embodiment, $R^8$ is hydrogen.

In another embodiment of the present invention, each $R^a$ is independently selected from the group consisting of: —$C_{1-6}$alkyl, halogen, —$OR^e$, —$NR^cS(O)_nR^e$, —$S(O)_nR^e$, —$S(O)_nNR^cR^d$, —$C_{0-5}$alkyl-$NR^cR^d$, —$C(O)R^e$, —$OC(O)R^e$, —$CO_2R^e$, —$CN$, —$C(O)NR^cR^d$, —$NR^cC(O)R^e$, —$NR^cC(O)OR^e$, —$NR^cC(O)NR^cR^d$, —$CF_3$, —$OCF_3$, —$OCHF_2$, —$C_{0-5}$alkyl-aryl, —$C_{0-5}$alkyl-heteroaryl, —$C_{0-5}$alkyl-$C_{3-6}$cycloalkyl, —$C_{0-5}$alkyl-$C_{3-6}$cycloalkenyl, and —$C_{0-5}$alkyl-$C_{2-5}$cycloheteroalkyl, wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alkyl, —$CN$, —$OCHF_2$, —$OCF_3$, —$CF_3$, and —$C_{0-6}$alkyl-$NR^cR^d$. In another embodiment of the present invention, each $R^a$ is independently selected from the group consisting of: —$C_{1-6}$alkyl, halogen, —$CF_3$, —$OCF_3$, —$OCHF_2$, —$C_{0-6}$alkyl-aryl, —$C_{0-6}$alkyl-heteroaryl, —$C_{0-6}$alkyl-$C_{3-10}$cycloalkyl, —$C_{0-6}$alkyl-$C_{3-10}$cycloalkenyl, and —$C_{0-6}$alkyl-$C_{2-10}$cycloheteroalkyl, wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$alkyl, —$S(O)_2$—$C_{1-4}$alkyl, —$CN$, —$OCHF_2$, —$OCF_3$, —$CF_3$, and —$C_{0-6}$alkyl-$NR^cR^d$. In another embodiment of the present invention, each $R^a$ is independently selected from the group consisting of: —$C_{1-6}$alkyl, halogen, —$CF_3$, —$OCF_3$, and —$OCHF_2$, wherein alkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —$CN$, —$OCHF_2$, —$OCF_3$, —$CF_3$, and —$C_{0-6}$alkyl-$NR^cR^d$.

In another embodiment of the present invention, each $R^a$ is independently selected from the group consisting of: —$C_{1-6}$alkyl, and halogen, wherein alkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —$CN$, —$OCHF_2$, —$OCF_3$, —$CF_3$, and —$C_{0-6}$alkyl-$NR^cR^d$. In another embodiment of the present invention, $R^a$ is —$C_{1-6}$alkyl, wherein alkyl is unsubstituted or substituted with one to five substituents independently selected from: —$C_{1-6}$alkyl, halogen, OH, —O—$C_{1-6}$alkyl, —$S(O)_2$—$C_{1-4}$alkyl, —$CN$, —$OCHF_2$, —$OCF_3$, —$CF_3$, and —$C_{0-6}$alkyl-$NR^cR^d$. In another embodiment of the present invention, $R^a$ is —$C_{1-6}$alkyl. In another embodiment of the present invention, $R^a$ is halogen. In a class of this embodiment, $R^a$ is selected from: Br, Cl and F. In another class of this embodiment, $R^a$ is selected from: Cl and F. In another class of this embodiment, $R^a$ is F.

In another embodiment of the present invention, each $R^b$ is independently selected from the group consisting of: —$C_{1-10}$alkyl, —$C_{2-10}$alkenyl, —$CF_3$, halogen, —$CN$, —OH, —OC$_{1-10}$alkyl, and —O(CH$_2$)$_p$C$_{3-6}$cycloalkyl, wherein each CH$_2$, alkyl, alkenyl, and cycloalkyl is unsubstituted or substituted with one to five substituents independently selected from: —C$_{1-6}$alkyl, halogen, OH, —O—C$_{1-6}$alkyl and —CF$_3$. In another embodiment of the present invention, each R$^b$ is independently selected from the group consisting of: —C$_{1-10}$alkyl, —CF$_3$, halogen, —OC$_{1-10}$alkyl, and —O(CH$_2$)$_p$C$_{3-6}$cycloalkyl, wherein each CH$_2$, alkyl, and cycloalkyl is unsubstituted or substituted with one to five substituents independently selected from: —C$_{1-6}$alkyl, halogen, OH, —O—C$_{1-6}$alkyl and —CF$_3$. In another embodiment of the present invention, each R$^b$ is independently selected from the group consisting of: —C$_{1-10}$alkyl, —CF$_3$, halogen, —OC$_{1-10}$alkyl, and —O(CH$_2$)$_p$C$_{3-6}$cycloalkyl. In a class of this embodiment of the present invention, each R$^b$ is independently selected from the group consisting of: —C$_{1-10}$alkyl, —CF$_3$, halogen, —OC$_{1-10}$alkyl, and —OC$_{3-6}$cycloalkyl. In another class of this embodiment, R$^b$ is independently selected from the group consisting of: —CH$_3$, —CF$_3$, F, —OCH$_3$, and —O-cyclopropyl. In another class of this embodiment, R$^b$ is independently selected from the group consisting of: F, —OCH$_3$, and —CF$_3$. In another embodiment of the present invention, each R$^b$ is independently selected from the group consisting of: halogen, and —OC$_{1-10}$alkyl, wherein alkyl is unsubstituted or substituted with one to five substituents independently selected from: —C$_{1-6}$alkyl, halogen, OH, —O—C$_{1-6}$alkyl and —CF$_3$. In another embodiment of the present invention, each R$^b$ is independently selected from the group consisting of: halogen, and —OC$_{1-10}$alkyl. In a class of this embodiment, R$^b$ is independently selected from the group consisting of: F, and —OCH$_3$.

In another embodiment of the present invention, R$^c$ and R$^d$ are each independently selected from the group consisting of: hydrogen, C$_{1-10}$alkyl, C$_{2-10}$alkenyl, C$_{3-6}$cycloalkyl, C$_{3-6}$ cycloalkyl-C$_{1-10}$alkyl-, C$_{2-5}$cycloheteroalkyl, C$_{2-5}$cycloheteroalkyl-C$_{1-10}$alkyl-, aryl, heteroaryl, aryl-C$_{1-10}$alkyl-, and heteroaryl-C$_{1-10}$alkyl-, wherein each alkyl, alkenyl, cycloalkyl, cycloheteroalkyl, aryl and heteroaryl is unsubstituted or substituted with one to three substituents independently selected from R$^f$. In another embodiment of the present invention, R$^c$ and R$^d$ are each independently selected from the group consisting of: hydrogen, C$_{1-10}$alkyl, and C$_{2-10}$alkenyl, wherein each alkyl and alkenyl is unsubstituted or substituted with one to three substituents independently selected from R$^f$, or R$^c$ and R$^d$ together with the atom(s) to which they are attached form a C$_{2-10}$cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$. In another embodiment of the present invention, R$^c$ and R$^d$ are each independently selected from the group consisting of: hydrogen, C$_{1-10}$alkyl, and C$_{2-10}$alkenyl, wherein each alkyl and alkenyl is unsubstituted or substituted with one to three substituents independently selected from R$^f$. In another embodiment of the present invention, R$^c$ and R$^d$ are each independently selected from the group consisting of: hydrogen, and C$_{1-10}$alkyl, wherein each alkyl is unsubstituted or substituted with one to three substituents independently selected from R$^f$, or R$^c$ and R$^d$ together with the atom(s) to which they are attached form a C$_{2-10}$ cycloheteroalkyl ring containing 0-2 additional heteroatoms independently selected from oxygen, sulfur and N—R$^g$, wherein each R$^e$ and R$^d$ is unsubstituted or substituted with one to three substituents independently selected from R$^f$. In another embodiment of the present invention, R$^c$ and R$^d$ are each independently selected from the group consisting of: hydrogen, and C$_{1-10}$alkyl, wherein each alkyl is unsubstituted or substituted with one to three substituents independently selected from R$^f$.

In another embodiment of the present invention, R$^c$ is selected from the group consisting of: hydrogen, C$_{1-10}$alkyl, C$_{2-10}$alkenyl, C$_{3-6}$cycloalkyl, C$_{3-6}$ cycloalkyl-C$_{1-10}$alkyl-, C$_{2-5}$cycloheteroalkyl, C$_{2-5}$ cycloheteroalkyl-C$_{1-10}$alkyl-, aryl, heteroaryl, aryl-C$_{1-10}$alkyl-, and heteroaryl-C$_{1-10}$alkyl-, wherein each alkyl, alkenyl, cycloalkyl, cycloheteroalkyl, aryl and heteroaryl is unsubstituted or substituted with one to three substituents independently selected from R$^f$. In another embodiment of the present invention, R$^c$ is selected from the group consisting of: hydrogen, C$_{1-10}$alkyl, and C$_{2-10}$alkenyl, wherein each alkyl and alkenyl is unsubstituted or substituted with one to three substituents independently selected from R$^f$, or R$^c$ and R$^d$ together with the atom(s) to which they are attached form a C$_{2-10}$ cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$. In another embodiment of the present invention, R$^c$ is selected from the group consisting of: hydrogen, C$_{1-10}$alkyl, and C$_{2-10}$alkenyl, wherein each alkyl and alkenyl is unsubstituted or substituted with one to three substituents independently selected from R$^f$.

In another embodiment of the present invention, R$^c$ is selected from the group consisting of: hydrogen, and C$_{1-10}$alkyl, wherein alkyl is unsubstituted or substituted with one to three substituents independently selected from R$^f$, or R$^c$ and R$^d$ together with the atom(s) to which they are attached form a C$_{2-10}$ cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$. In another embodiment of the present invention, R$^c$ is selected from the group consisting of: hydrogen, and C$_{1-10}$alkyl, wherein alkyl is unsubstituted or substituted with one to three substituents independently selected from R$^f$. In another embodiment of the present invention, R$^c$ is —C$_{1-10}$alkyl, wherein each alkyl is unsubstituted or substituted with one to three substituents independently selected from R$^f$. In another embodiment of the present invention, R$^c$ is —C$_{1-10}$alkyl. In another embodiment of the present invention, R$^c$ is hydrogen.

In another embodiment of the present invention, R$^d$ is selected from the group consisting of: hydrogen, C$_{1-10}$alkyl, C$_{2-10}$alkenyl, C$_{3-6}$cycloalkyl, C$_{3-6}$ cycloalkyl-C$_{1-10}$alkyl-, C$_{2-5}$cycloheteroalkyl, C$_{2-5}$ cycloheteroalkyl-C$_{1-10}$alkyl-, aryl, heteroaryl, aryl-C$_{1-10}$alkyl-, and heteroaryl-C$_{1-10}$alkyl-, wherein each alkyl, alkenyl, cycloalkyl, cycloheteroalkyl, aryl and heteroaryl is unsubstituted or substituted with one to three substituents independently selected from R$^f$. In another embodiment of the present invention, R$^d$ is selected from the group consisting of: hydrogen, C$_{1-10}$alkyl, and C$_{2-10}$alkenyl, wherein each alkyl and alkenyl is unsubstituted or substituted with one to three substituents independently selected from R$^f$, or R$^c$ and R$^d$ together with the atom(s) to which they are attached form a C$_{2-10}$ cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$. In another embodiment of the present invention, R$^d$ is selected from the group consisting of: hydrogen, C$_{1-10}$alkyl, and C$_{2-10}$alkenyl, wherein each alkyl and alkenyl is unsubstituted or substituted with one to three substituents independently selected from $R^f$. In another embodiment of the present invention, $R^d$ is selected from the group consisting of: hydrogen, and $C_{1-10}$alkyl, wherein alkyl is unsubstituted or substituted with one to three substituents independently selected from $R^f$, or $R^c$ and $R^d$ together with the atom(s) to which they are attached form a $C_{2-10}$ cycloheteroalkyl ring containing 0-2 additional heteroatoms independently selected from oxygen, sulfur and N—$R^g$, wherein each $R^c$ and $R^d$ is unsubstituted or substituted with one to three substituents independently selected from $R^f$. In another embodiment of the present invention, $R^d$ is selected from the group consisting of: hydrogen, and $C_{1-10}$alkyl, wherein alkyl is unsubstituted or substituted with one to three substituents independently selected from $R^f$. In another embodiment of the present invention, $R^d$ is —$C_{1-10}$alkyl, wherein alkyl is unsubstituted or substituted with one to three substituents independently selected from $R^f$. In another embodiment of the present invention, $R^d$ is —$C_{1-10}$alkyl. In another embodiment of the present invention, $R^d$ is hydrogen.

In another embodiment of the present invention, each $R^e$ is independently selected from the group consisting of: hydrogen, —$C_{1-10}$alkyl, and —$C_{2-10}$ alkenyl, wherein each alkyl, and alkenyl is unsubstituted or substituted with one to three substituents independently selected from $R^h$. In another embodiment of the present invention, each $R^e$ is independently selected from the group consisting of: hydrogen, and —$C_{1-10}$alkyl, wherein alkyl is unsubstituted or substituted with one to three substituents independently selected from $R^h$. In another embodiment of the present invention, each $R^e$ is —$C_{1-10}$alkyl, wherein alkyl is unsubstituted or substituted with one to three substituents independently selected from $R^h$. In another embodiment of the present invention, each $R^e$ is —$C_{1-10}$alkyl. In another embodiment of the present invention, each $R^e$ is hydrogen.

In another embodiment of the present invention, each $R^f$ is selected from the group consisting of: halogen, $C_{1-10}$alkyl, —OH, —O—$C_{1-4}$alkyl, —CN, and —$CF_3$, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^f$ is selected from the group consisting of: halogen, and $C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^f$ is halogen. In another embodiment of the present invention, each $R^f$ is —$C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^f$ is —$C_{1-10}$alkyl.

In another embodiment of the present invention, each $R^g$ is selected from the group consisting of: hydrogen, and —$C_{1-10}$ alkyl, wherein alkyl is unsubstituted or substituted with one to five halogens. In another embodiment of the present invention, each $R^g$ is —$C_{1-10}$alkyl, wherein alkyl is unsubstituted or substituted with one to five halogens. In another embodiment of the present invention, each $R^g$ is hydrogen.

In another embodiment of the present invention, each $R^h$ is selected from the group consisting of: halogen, $C_{1-10}$alkyl, —OH, —O—$C_{1-4}$alkyl, —$S(O)_m$—$C_{1-4}$alkyl, —CN, —$CF_3$, —$OCHF_2$, and —$OCF_3$, wherein each alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is selected from the group consisting of: halogen, $C_{1-10}$alkyl, —OH, —O—$C_{1-4}$alkyl, —CN, and —$CF_3$, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is selected from the group consisting of: halogen, and $C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is halogen. In another embodiment of the present invention, each $R^h$ is —$C_{1-10}$alkyl, wherein alkyl is unsubstituted or substituted with one to three substituents independently selected from: —OH, halogen, $C_{1-6}$alkyl, cyano and $S(O)_2C_{1-6}$alkyl. In another embodiment of the present invention, each $R^h$ is —$C_{1-10}$alkyl.

In another embodiment of the present invention, each $R^1$ is independently selected from the group consisting of: —$C_{1-6}$alkyl, —$OR^e$, halogen, —$NR^cR^d$, —CN, —$CF_3$, —$OCF_3$, and —$OCHF_2$. In another embodiment of the present invention, each $R^1$ is independently selected from the group consisting of: —$C_{1-6}$alkyl, halogen, —CN, and —$CF_3$. In another embodiment of the present invention, each $R^i$ is independently selected from the group consisting of: —$C_{1-6}$alkyl, and halogen. In another embodiment of the present invention, $R^1$ is halogen. In another embodiment of the present invention, $R^1$ is —$C_{1-6}$alkyl.

In another embodiment of the present invention, each $R^j$ is independently selected from the group consisting of: —$C_{1-6}$alkyl, —$OR^e$, halogen, —$NR^cR^d$, —CN, —$CF_3$, —$OCF_3$, and —$OCHF_2$. In another embodiment of the present invention, each $R^j$ is independently selected from the group consisting of: —$C_{1-6}$alkyl, halogen, —CN, and —$CF_3$. In another embodiment of the present invention, each $R^j$ is independently selected from the group consisting of: —$C_{1-6}$alkyl, and halogen. In another embodiment of the present invention, $R^j$ is halogen. In another embodiment of the present invention, $R^j$ is —$C_{1-6}$alkyl.

In another embodiment of the present invention, $R^k$ is selected from the group consisting of: hydrogen, and —$C_{1-6}$ alkyl, wherein alkyl is unsubstituted or substituted with one to three substituents independently selected from: —OH, —$OC_{1-6}$alkyl, halogen, cyano, and —$S(O)_2C_{1-6}$alkyl. In another embodiment of the present invention, $R^k$ is —$C_{1-6}$ alkyl, wherein alkyl is unsubstituted or substituted with one to three substituents independently selected from: —OH, —$OC_{1-6}$alkyl, halogen, cyano, and —$S(O)_2C_{1-6}$alkyl. In another embodiment of the present invention, $R^k$ is —$C_{1-6}$ alkyl. In another embodiment of the present invention, $R^k$ is hydrogen.

In another embodiment of the present invention, each $R^L$ is independently selected from the group consisting of: —$CO_2C_{1-6}$alkyl, —$C_{1-10}$alkyl, —$C_{2-10}$ alkenyl, —$C_{2-10}$ alkynyl, —$C_{3-6}$cycloalkyl, and —$C_{2-6}$cycloheteroalkyl, wherein each alkyl, alkenyl, alkynyl, cycloalkyl and cycloheteroalkyl is unsubstituted or substituted with one to four substituents independently selected from $C_{1-6}$alkyl, halogen, and —$OC_{1-6}$alkyl. In another embodiment of the present invention, each $R^L$ is independently selected from the group consisting of: —$CO_2C_{1-6}$alkyl, —$C_{1-10}$alkyl, —$C_{2-10}$ alkenyl, —$C_{2-10}$alkynyl, and —$C_{3-6}$cycloalkyl, wherein each alkyl, alkenyl, alkynyl, and cycloalkyl is unsubstituted or substituted with one to four substituents independently selected from $C_{1-6}$alkyl, halogen, and —$OC_{1-6}$alkyl. In another embodiment of the present invention, each $R^L$ is independently selected from the group consisting of:

—CO$_2$C$_{1-6}$alkyl, —C$_{1-10}$alkyl, and —C$_{3-6}$cycloalkyl, wherein each alkyl and cycloalkyl is unsubstituted or substituted with one to four substituents independently selected from C$_{1-6}$alkyl, halogen, and —OC$_{1-6}$alkyl. In another embodiment of the present invention, each R$^L$ is independently selected from the group consisting of: —C$_{1-10}$alkyl, and —C$_{3-6}$cycloalkyl, wherein each alkyl and cycloalkyl is unsubstituted or substituted with one to four substituents independently selected from C$_{1-6}$alkyl, halogen, and —OC$_{1-6}$ alkyl. In another embodiment of the present invention, each R$^L$ is independently selected from the group consisting of: —C$_{1-10}$alkyl, and —C$_{3-6}$cycloalkyl. In another embodiment of the present invention, each R$^L$ is independently selected from the group consisting of: —CH$_3$ and -cyclopropyl, wherein each —CH$_3$ and -cyclopropyl is unsubstituted or substituted with one to four substituents independently selected from C$_{1-6}$alkyl, halogen, and —OC$_{1-6}$ alkyl. In another embodiment of the present invention, each R$^L$ is independently selected from the group consisting of: —CH$_3$ and -cyclopropyl.

In another embodiment of the present invention, each R$^m$ is independently selected from the group consisting of: —C$_{1-10}$alkyl, and —C$_{2-10}$ alkenyl. In another embodiment of the present invention, each R$^m$ is —C$_{1-10}$alkyl. In another embodiment of the present invention, each R$^m$ is —C$_{2-10}$ alkenyl.

In another embodiment of the present invention, n is 0, 1 or 2. In a class of this embodiment, n is 0 or 1. In another class of this embodiment, n is 1 or 2. In another class of this embodiment, n is 0. In another class of this embodiment, n is 1. In another class of this embodiment, n is 2.

In another embodiment of the present invention, m is 0, 1 or 2. In a class of this embodiment, m is 0 or 1. In another class of this embodiment, m is 1 or 2. In another class of this embodiment, m is 0. In another class of this embodiment, m is 1. In another class of this embodiment, m is 2.

In another embodiment of the present invention, each p is independently selected from: 0, 1, 2, 3, 4, 5 or 6. In another embodiment of the present invention, p is 0, 1, 2, 3 or 4. In a class of this embodiment, p is 0, 1, 2 or 3. In a class of this embodiment, p is 0, 1 or 2. In another embodiment of the present invention, p is 1, 2, 3 or 4. In a class of this embodiment, p is 1, 2 or 3. In a class of this embodiment, p is 1 or 2. In another class of this embodiment, p is 0 or 1. In another class of this embodiment, p is 0 or 2. In another class of this embodiment, p is 0. In another class of this embodiment, p is 1. In another class of this embodiment, p is 2. In another class of this embodiment, p is 3. In another class of this embodiment, p is 4. In another class of this embodiment, p is 5. In another class of this embodiment, p is 6.

In another embodiment of the present invention, each r is independently selected from: 0, 1, 2 or 3. In a class of this embodiment, r is 0, 1 or 2. In another class of this embodiment, r is 1, 2 or 3. In a class of this embodiment, r is 1 or 2. In another class of this embodiment, r is 0 or 1. In another class of this embodiment, r is 0 or 2. In another class of this embodiment, r is 0 or 1. In another class of this embodiment, r is 1 or 3. In another class of this embodiment, r is 2 or 3. In another class of this embodiment, r is 0 or 2. In another class of this embodiment, r is 0. In another class of this embodiment, r is 1. In another class of this embodiment, r is 2. In another class of this embodiment, r is 3.

In another embodiment of the present invention, the invention relates to compounds of structural formula Ia:

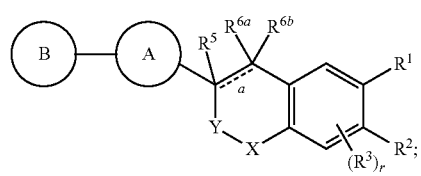

or a pharmaceutically acceptable salt thereof.

In another embodiment of the present invention, the invention relates to compounds of structural formula Ib:

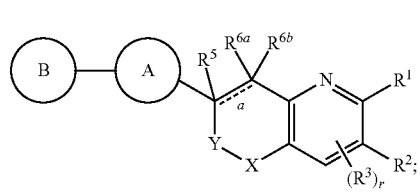

or a pharmaceutically acceptable salt thereof.

In another embodiment of the present invention, the invention relates to compounds of structural formula Ic:

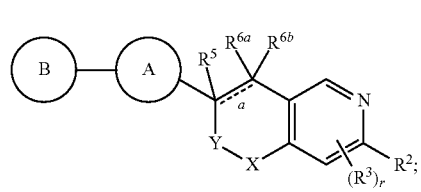

or a pharmaceutically acceptable salt thereof.

In another embodiment of the present invention, the invention relates to compounds of structural formula Id:

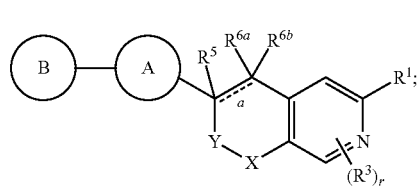

or a pharmaceutically acceptable salt thereof.

In another embodiment of the present invention, the invention relates to compounds of structural formula Ie:

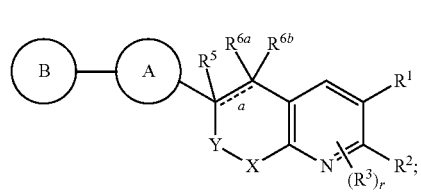

or a pharmaceutically acceptable salt thereof.

In another embodiment of the present invention, the invention relates to compounds of structural formula If:

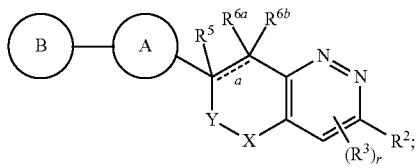

If or a pharmaceutically acceptable salt thereof.

In another embodiment of the present invention, the invention relates to compounds of structural formula Ig:

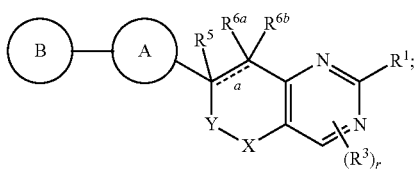

Ig or a pharmaceutically acceptable salt thereof.

In another embodiment of the present invention, the invention relates to compounds of structural formula Ih:

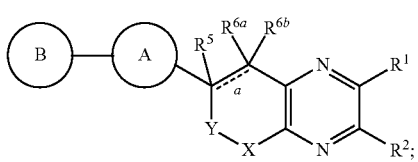

Ih or a pharmaceutically acceptable salt thereof.

In another embodiment of the present invention, the invention relates to compounds of structural formula Ii:

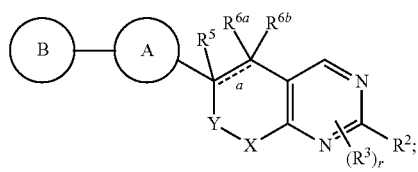

Ii or a pharmaceutically acceptable salt thereof.

In another embodiment of the present invention, the invention relates to compounds of structural formula Ij:

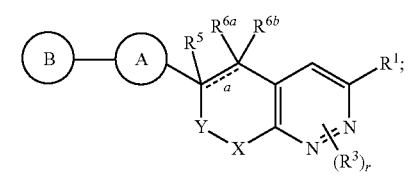

Ij or a pharmaceutically acceptable salt thereof.

In another embodiment of the present invention, the invention relates to compounds of structural formula Ik:

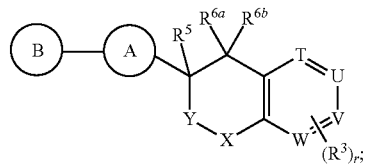

Ik or a pharmaceutically acceptable salt thereof.

In another embodiment of the present invention, the invention relates to compounds of structural formula Il:

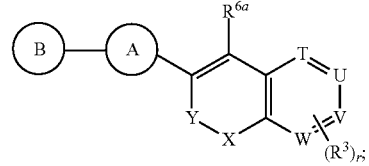

Il or a pharmaceutically acceptable salt thereof.

In another embodiment of the present invention, the invention relates to compounds of structural formula Im:

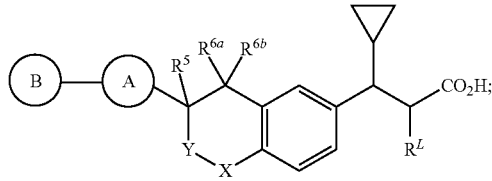

Im or a pharmaceutically acceptable salt thereof.

The compound of structural formula I includes the compounds of structural formulas Ia, Ib, Ic, Id, Ie, If, Ig, Ih, Ii, Ij, Ik, Il and Im, and pharmaceutically acceptable salts, hydrates and solvates thereof.

Another embodiment of the present invention relates to compounds of structural formula 1:

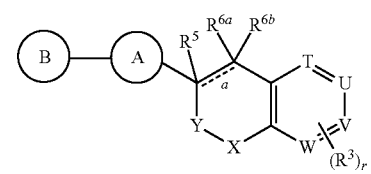

I wherein
"a" is a single bond or a double bond, provided that if "a" is a double bond, then $R^5$ and $R^{6b}$ are absent;
T is CH;
U is $CR^1$;
V is $CR^2$;
W is CH;
X is selected from the group consisting of:
 (1) oxygen,
 (2) sulfur,
 (3) $S(O)_2$,
 (4) —$CR^gR^g$, and
 (5) C=O;

Y is selected from the group consisting of:
(1) oxygen, and
(2) —CR$^{4a}$R$^{4b}$,
provided that if X is oxygen or sulfur, then Y is not oxygen, and further provided that if X is S(O)$_2$, then Y is not oxygen;
A is selected from the group consisting of:
(1) aryl, and
(2) C$_{3-5}$ cycloheteroalkyl,
wherein each aryl and cycloheteroalkyl is unsubstituted or substituted with one to five substituents independently selected from R$^a$;
B is selected from the group consisting of:
(1) aryl,
(2) aryl-C$_{1-10}$ alkyl-, and
(3) heteroaryl,
wherein each alkyl, aryl and heteroaryl is unsubstituted or substituted with one to five substituents independently selected from R$^b$;
R$^1$ and R$^2$ are each independently selected from:
(1) hydrogen, and
(2) —C$_{1-6}$alkyl,
wherein one of R$^1$ and R$^2$ is —C$_{1-6}$alkyl substituted with R$^7$, and wherein alkyl is unsubstituted or substituted with one to three substituents independently selected from R$^L$;
R$^3$ is absent or hydrogen;
R$^{4a}$ is hydrogen;
R$^{4b}$ is hydrogen;
R$^5$ is absent or hydrogen;
R$^{6a}$ is hydrogen; and
R$^{6b}$ is absent or hydrogen;
R$^7$ is —CO$_2$R$^8$;
R$^8$ is hydrogen;
R$^a$ is halogen;
each R$^b$ is independently selected from the group consisting of: —C$_{1-10}$alkyl, —CF$_3$, halogen, —OC$_{1-10}$alkyl, and —OC$_{3-6}$cycloalkyl;
R$^g$ is hydrogen; and
each R$^L$ is independently selected from the group consisting of: —C$_{1-10}$alkyl, and —C$_{3-6}$cycloalkyl;
or a pharmaceutically acceptable salt thereof.

Another embodiment of the present invention relates to compounds of structural Formula I:

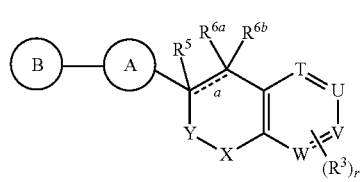

I wherein
"a" is a single bond or a double bond, provided that if "a" is a double bond, then R$^5$ and R$^{6b}$ are absent;
T is CH;
U is CR$^1$;
V is CH;
W is CH;
X is selected from the group consisting of:
(1) oxygen,
(2) sulfur, and
(3) —CR$^g$R$^g$;

Y is selected from the group consisting of:
(1) oxygen, and
(2) —CH$_2$,
provided that if X is oxygen or sulfur, then Y is not oxygen;
A is aryl, wherein aryl is unsubstituted or substituted with one to five substituents independently selected from R$^a$;
B is selected from the group consisting of:
(1) aryl, and
(2) heteroaryl,
wherein each aryl and heteroaryl is unsubstituted or substituted with one to five substituents independently selected from R$^b$;
R$^1$ is ethyl, wherein ethyl is unsubstituted or substituted with one to three substituents independently selected from R$^L$, and wherein R$^1$ is substituted with R$^7$;
R$^3$ is absent or hydrogen;
R$^{4a}$ is hydrogen;
R$^{4b}$ is hydrogen;
R$^5$ is absent or hydrogen;
R$^{6a}$ is hydrogen; and
R$^{6b}$ is absent or hydrogen;
R$^7$ is —CO$_2$R$^8$;
R$^8$ is hydrogen;
R$^a$ is halogen;
each R$^b$ is independently selected from the group consisting of: halogen, and —OC$_{1-10}$alkyl; R$^g$ is hydrogen; and
each R$^L$ is independently selected from the group consisting of: —C$_{1-10}$alkyl, and —C$_{3-6}$cycloalkyl; or a pharmaceutically acceptable salt thereof.

Illustrative, but non-limiting, examples of the compounds of the present invention that are useful as agonists of G-protein-coupled receptor 40 (GPR40) are the following compounds:

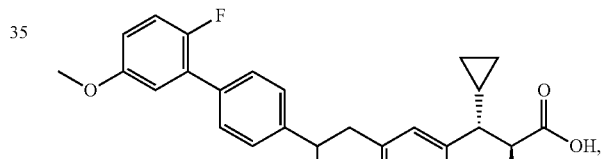

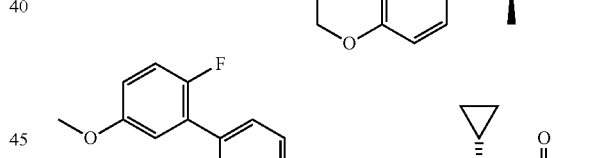

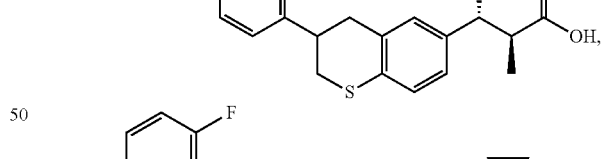

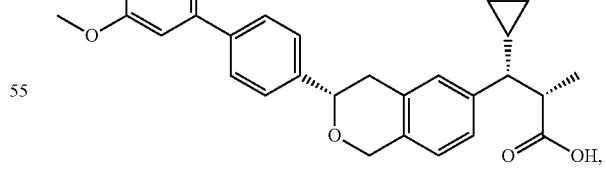

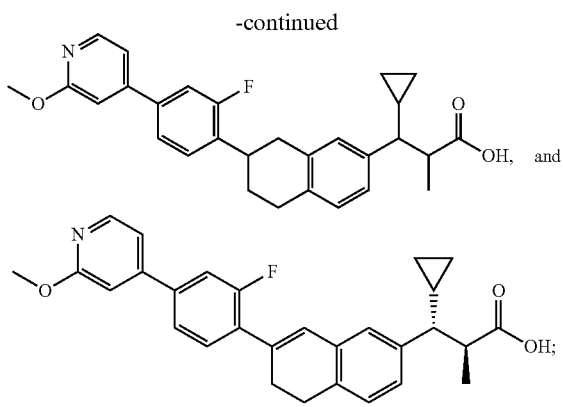

and pharmaceutically acceptable salts thereof.

Although the specific stereochemistries described above are preferred, other stereoisomers, including diastereoisomers, enantiomers, epimers, and mixtures of these may also have utility in treating GPR40 mediated diseases.

Synthetic methods for making the compounds are disclosed in the Examples shown below. Where synthetic details are not provided in the examples, the compounds are readily made by a person of ordinary skill in the art of medicinal chemistry or synthetic organic chemistry by applying the synthetic information provided herein. Where a stereochemical center is not defined, the structure represents a mixture of stereoisomers at that center. For such compounds, the individual stereoisomers, including enantiomers, diastereoisomers, and mixtures of these are also compounds of the invention.

Definitions

"Ac" is acetyl, which is $CH_3C(\!=\!O)\!-\!$.

"Alkyl" means saturated carbon chains which may be linear or branched or combinations thereof, unless the carbon chain is defined otherwise. Other groups having the prefix "alk", such as alkoxy and alkanoyl, also may be linear or branched, or combinations thereof, unless the carbon chain is defined otherwise. The term $-C_2$alkyl is ethyl. Examples of alkyl groups include methyl, ethyl, propyl, isopropyl, butyl, sec- and tert-butyl, pentyl, hexyl, heptyl, octyl, nonyl, and the like. In one embodiment of the present invention, alkyl is methyl. In another embodiment of the present invention, alkyl is ethyl.

"Alkenyl" means carbon chains which contain at least one carbon-carbon double bond, and which may be linear or branched, or combinations thereof, unless otherwise defined. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched, or combinations thereof, unless otherwise defined. Examples of alkynyl include ethynyl, propargyl, 3-methyl-1-pentynyl, 2-heptynyl and the like.

"Cycloalkyl" means a saturated monocyclic, bicyclic or bridged carbocyclic ring, having a specified number of carbon atoms. The term may also be used to describe a carbocyclic ring fused to an aryl group. Examples of cycloalkyl include cyclopropyl, cyclopentyl, cyclohexyl, cycloheptyl, and the like. In one embodiment of the present invention, cycloalkyl is selected from: cyclopropyl.

"Cycloalkenyl" means a nonaromatic monocyclic or bicyclic carbocyclic ring containing at least one double bond. Examples of cycloalkenyl include cyclopropenyl, cyclobutenyl, cyclopentenyl, cyclohexenyl, cycloheptenyl, cyclooxtenyl and the like.

"Cycloheteroalkyl" means a saturated monocyclic, bicyclic or bridged carbocyclic ring or ring system containing at least one ring heteroatom selected from N, NH, S (including SO and $SO_2$) and O. The cycloheteroalkyl ring may be substituted on the ring carbons and/or the ring nitrogen(s). Examples of cycloheteroalkyl include tetrahydrofuran, pyrrolidine, tetrahydrothiophene, azetidine, piperazine, piperidine, morpholine, oxetane and tetrahydropyran. In one embodiment of the present invention, cycloheteroalkyl is piperidine.

"Cycloheteroalkenyl" means a nonaromatic monocyclic, bicyclic or bridged carbocyclic ring or ring system containing at least one double bond and containing at least one heteroatom selected from N, NH, S (including SO and $SO_2$) and O.

"Aryl" means a monocyclic, bicyclic or tricyclic carbocyclic aromatic ring or ring system containing 5-14 carbon atoms, wherein at least one of the rings is aromatic. Examples of aryl include phenyl and naphthyl. In one embodiment of the present invention, aryl is phenyl.

"Heteroaryl" means monocyclic, bicyclic or tricyclic ring or ring system containing 5-14 carbon atoms and containing at least one ring heteroatom selected from N, NH, S (including SO and $SO_2$) and O, wherein at least one of the heteroatom containing rings is aromatic. Examples of heteroaryl include pyrrolyl, isoxazolyl, isothiazolyl, pyrazolyl, pyridyl, oxazolyl, oxadiazolyl, thiadiazolyl, thiazolyl, imidazolyl, triazolyl, tetrazolyl, furanyl, triazinyl, thienyl, pyrimidyl, pyridazinyl, pyrazinyl, benzisoxazolyl, benzoxazolyl, benzothiazolyl, benzimidazolyl, benzofuranyl, benzpyrazole (or indazole), benzothiophenyl (including S-oxide and dioxide), furo(2,3-b)pyridyl, quinolyl, indolyl, isoquinolyl, quinazolinyl, dibenzofuranyl, and the like. In one embodiment of the present invention, heteroaryl is pyridine.

"Halogen" includes fluorine, chlorine, bromine and iodine. In one embodiment of the present invention, halogen is bromine, chlorine or fluorine. In another embodiment of the present invention, halogen is chlorine or fluorine. In another embodiment of the present invention, halogen is bromine. In another embodiment of the present invention, halogen is chlorine. In another embodiment of the present invention, halogen is fluorine.

"Me" represents methyl.

"Oxo" is $=\!O$.

When any variable (e.g., $R^1$, $R^a$, etc.) occurs more than one time in any constituent or in formula I, its definition on each occurrence is independent of its definition at every other occurrence. Also, combinations of substituents and/or variables are permissible only if such combinations result in stable compounds. A squiggly line across a bond in a substituent variable represents the point of attachment.

Under standard nomenclature used throughout this disclosure, the terminal portion of the designated side chain is described first, followed by the adjacent functionality toward the point of attachment. For example, a $C_{1-5}$ alkyl-carbonylamino $C_{1-6}$ alkyl substituent is equivalent to:

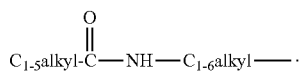

For example, —NR$^c$C(O)R$^e$ is equivalent to —N(R$^c$)C(O)R$^e$.

Unless expressly depicted or described otherwise, substituents depicted in a structural formula with a "floating" bond, such as but not limited to R$^3$, is permitted on any available carbon atom in the ring to which the substituent is attached. In one embodiment of the present invention, R$^3$ may be substituted on any CH in the ring to which R$^3$ is attached.

In choosing compounds of the present invention, one of ordinary skill in the art will recognize that the various substituents, i.e. R$^1$, R$^2$, etc., are to be chosen in conformity with well-known principles of chemical structure connectivity and stability.

The term "substituted" shall be deemed to include multiple degrees of substitution by a named substituent. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

The phrase "pharmaceutically acceptable" is employed herein to refer to those compounds, materials, compositions, salts and/or dosage forms which are, using sound medical judgment, and following all applicable government regulations, safe and suitable for administration to a human being or an animal.

The term "% enantiomeric excess" (abbreviated "ee") shall mean the % major enantiomer less the % minor enantiomer. Thus, a 70% enantiomeric excess corresponds to formation of 85% of one enantiomer and 15% of the other. The term "enantiomeric excess" is synonymous with the term "optical purity."

Compounds of Formula I may contain one or more asymmetric centers and can thus occur as racemates and racemic mixtures, single enantiomers, diastereomeric mixtures and individual diastereomers. The present invention is meant to comprehend all such isomeric forms of the compounds of Formula I.

Some of the compounds described herein contain olefinic double bonds, and unless specified otherwise, are meant to include both E and Z geometric isomers.

Tautomers are defined as compounds that undergo rapid proton shifts from one atom of the compound to another atom of the compound. Some of the compounds described herein may exist as tautomers with different points of attachment of hydrogen. Such an example may be a ketone and its enol form known as keto-enol tautomers. The individual tautomers as well as mixture thereof are encompassed with compounds of Formula I.

In the compounds of general formula I, the atoms may exhibit their natural isotopic abundances, or one or more of the atoms may be artificially enriched in a particular isotope having the same atomic number, but an atomic mass or mass number different from the atomic mass or mass number predominately found in nature. The present invention is meant to include all suitable isotopic variations of the compounds of structural formula I. For example, different isotopic forms of hydrogen (H) include protium ($^1$H), deuterium ($^2$H), and tritium ($^3$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Tritium is radioactive and may therefore provide for a radiolabeled compound, useful as a tracer in metabolic or kinetic studies. Isotopically-enriched compounds within structural formula I, can be prepared without undue experimentation by conventional techniques well known to those skilled in the art or by processes analogous to those described in the Schemes and Examples herein using appropriate isotopically-enriched reagents and/or intermediates.

The independent syntheses of optical isomers and diastereoisomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well-known in the art, such as the coupling of a racemic mixture of compounds to an enantiomerically pure compound to form a diastereoisomeric mixture, followed by separation of the individual diastereoisomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

Furthermore, some of the crystalline forms for compounds of the present invention may exist as polymorphs and as such are intended to be included in the present invention. In addition, some of the compounds of the instant invention may form solvates with water or common organic solvents. Such solvates are encompassed within the scope of this invention.

It is generally preferable to administer compounds of the present invention as enantiomerically pure formulations. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

Salts:

It will be understood that, as used herein, references to the compounds of the present invention are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of the present invention are included in the present invention as well.

Utilities

The compounds of the present invention are potent agonists of the GPR40 receptor. The compounds, and pharmaceutically acceptable salts thereof, may be efficacious in the treatment of diseases that are modulated by GPR40 ligands, which are generally agonists. Many of these diseases are summarized below.

One or more of these diseases may be treated by the administration of a therapeutically effective amount of a compound of the present invention, or a pharmaceutically acceptable salt thereof, to a patient in need of treatment. Also, the compounds of the present invention may be used for the manufacture of a medicament which may be useful for treating one or more of these diseases: (1) non-insulin dependent diabetes mellitus (Type 2 diabetes); (2) hyperglycemia; (3) insulin resistance; (4) Metabolic Syndrome; (5) obesity; (6) hypercholesterolemia; (7) hypertriglyceridemia (elevated levels of triglyceride-rich-lipoproteins); (8) mixed or diabetic dyslipidemia; (9) low HDL cholesterol; (10) high LDL cholesterol; (11) hyperapo-B liproteinemia; and (12) atherosclerosis.

Preferred uses of the compounds may be for the treatment of one or more of the following diseases by administering a therapeutically effective amount to a patient in need of treatment. The compounds may be used for manufacturing a medicament for the treatment of one or more of these diseases: (1) Type 2 diabetes, and specifically hyperglycemia associated with Type 2 diabetes; (2) Metabolic Syndrome; (3) obesity; and (4) hypercholesterolemia.

The compounds may be effective in lowering glucose and lipids in diabetic patients and in non-diabetic patients who have impaired glucose tolerance and/or are in a pre-diabetic condition. The compounds may ameliorate hyperinsulinemia, which often occurs in diabetic or pre-diabetic patients, by modulating the swings in the level of serum glucose that often occurs in these patients. The compounds may also be effective in treating or reducing insulin resistance. The compounds may be effective in treating or preventing gestational diabetes.

The compounds may also be effective in treating or preventing lipid disorders. The compounds may be effective in treating or preventing diabetes related disorders. The compounds may also be effective in treating or preventing obesity related disorders.

The compounds of this invention may also have utility in improving or restoring β-cell function, so that they may be useful in treating Type 1 diabetes or in delaying or preventing a patient with Type 2 diabetes from needing insulin therapy.

The invention also includes pharmaceutically acceptable salts of the compounds, and pharmaceutical compositions comprising the compounds and a pharmaceutically acceptable carrier. The compounds may be useful in treating insulin resistance, Type 2 diabetes, hypperglycemia, and dyslipidemia that is associated with Type 2 diabetes and insulin resistance. The compounds may also be useful for the treatment of obesity A compound of the present invention, or a pharmaceutically acceptable salt thereof, may be used in the manufacture of a medicament for the treatment of Type 2 diabetes in a human or other mammalian patient.

A method of treating Type 2 diabetes comprises the administration of a therapeutically effective amount of a compound of the present invention, or a pharmaceutically acceptable salt thereof, or a pharmaceutical composition comprising the compound, to a human or other mammalian subject or patient in need of treatment. Other medical uses of the compounds of the present invention are described herein.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention may be useful for treating both Type 1 and Type 2 diabetes. The term "diabetes associated with obesity" refers to diabetes caused by obesity or resulting from obesity.

Diabetes is characterized by a fasting plasma glucose level of greater than or equal to 126 mg/dl. A diabetic subject has a fasting plasma glucose level of greater than or equal to 126 mg/dl. A pre diabetic subject is someone suffering from prediabetes. Prediabetes is characterized by an impaired fasting plasma glucose (FPG) level of greater than or equal to 110 mg/dl and less than 126 mg/dl; or impaired glucose tolerance; or insulin resistance. A prediabetic subject is a subject with impaired fasting glucose (a fasting plasma glucose (FPG) level of greater than or equal to 110 mg/dl and less than 126 mg/dl); or impaired glucose tolerance (a 2 hour plasma glucose level of >140 mg/dl and <200 mg/dl); or insulin resistance, resulting in an increased risk of developing diabetes.

Treatment of diabetes mellitus refers to the administration of a compound or combination of the present invention to treat a diabetic subject. One outcome of treatment may be decreasing the glucose level in a subject with elevated glucose levels. Another outcome of treatment may be decreasing insulin levels in a subject with elevated insulin levels. Another outcome of treatment may be decreasing plasma triglycerides in a subject with elevated plasma triglycerides. Another outcome of treatment is decreasing LDL cholesterol in a subject with high LDL cholesterol levels. Another outcome of treatment may be increasing HDL cholesterol in a subject with low HDL cholesterol levels. Another outcome of treatment is increasing insulin sensivity. Another outcome of treatment may be enhancing glucose tolerance in a subject with glucose intolerance. Yet another outcome of treatment may be decreasing insulin resistance in a subject with increased insulin resistance or elevated levels of insulin. Prevention of diabetes mellitus, in particular diabetes associated with obesity, refers to the administration of a compound or combination of the present invention to prevent the onset of diabetes in a subject in need thereof. A subject in need of preventing diabetes is a prediabetic subject that is overweight or obese.

The term "diabetes related disorders" should be understood to mean disorders that are associated with, caused by, or result from diabetes. Examples of diabetes related disorders include retinal damage, kidney disease, and nerve damage.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of a GPR40 agonist in combination with a therapeutically effective amount of an anti-hypertensive agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

The term "atherosclerosis related disorders" should be understood to mean disorders associated with, caused by, or resulting from atherosclerosis.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated (>140 mmHg/>90 mmHg), and isolated systolic hypertension, in which only the systolic pressure is elevated to greater than or equal to 140 mm Hg, while the diastolic pressure is less than 90 mm Hg. Normal blood pressure may be defined as less than 120 mmHg systolic and less than 80 mmHg diastolic. A hypertensive subject is a subject with hypertension. A pre-hypertensive subject is a subject with a blood pressure that is between 120 mmHg over 80 mmHg and 139 mmHg over 89 mmHg. One outcome of treatment is decreasing blood pressure in a subject with high blood pressure. Treatment of hypertension refers to the administration of the compounds and combinations of the present invention to treat hypertension in a hypertensive subject. Treatment of hypertension-related disorder refers to the administration of a compound or combination of the present invention to treat the hypertension-related disorder. Prevention of hypertension, or a hypertension related disorder, refers to the administration of the combinations of the present invention to a pre-hypertensive subject to prevent the onset of hypertension or a hypertension related disorder. The hypertension-related disorders herein are associated with, caused by, or result from hypertension. Examples of hypertension-related disorders include, but are not limited to: heart disease, heart failure, heart attack, kidney failure, and stroke.

Dyslipidemias and lipid disorders are disorders of lipid metabolism including various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides. Treatment of dyslipidemia refers to the administration of the combinations of the present invention to a dyslipidemic subject. Prevention of dyslipidemia refers to the administration of the combinations of the present invention to a pre-dyslipidemic subject. A pre-dyslipidemic subject is a subject with higher than normal lipid levels, that is not yet dyslipidemic.

The terms "dyslipidemia related disorders" and "lipid disorder related disorders" should be understood to mean disorders associated with, caused by, or resulting from dyslipidemia or lipid disorders. Examples of dylipidemia related disorder and lipid disorder related disorders include, but are not limited to: hyperlipidemia, hypertriglyceridemia, hypercholesterolemia, low high density lipoprotein (HDL) levels, high plasma low density lipoprotein (LDL) levels, atherosclerosis and its sequelae, coronary artery or carotid artery disease, heart attack, and stroke.

The term "obesity" as used herein is a condition in which there is an excess of body fat. The operational definition of obesity is based on the Body Mass Index (BMI), which is calculated as body weight per height in meters squared (kg/m$^2$). "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. An overweight subject is a subject at risk of obesity. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes mellitus, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, and other obesity-related conditions.

Treatment of obesity and obesity-related disorders refers to the administration of the compounds of the present invention to reduce or maintain the body weight of an obese subject. One outcome of treatment may be reducing the body weight of an obese subject relative to that subject's body weight immediately before the administration of the compounds of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds of the present invention to reduce or maintain the body weight of a subject at risk of obesity. One outcome of prevention may be reducing the body weight of a subject at risk of obesity relative to that subject's body weight immediately before the administration of the compounds of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type II diabetes, polycystic ovarian disease, cardiovascular diseases, osteoarthritis, dermatological disorders, hypertension, insulin resistance, hypercholesterolemia, hypertriglyceridemia, and cholelithiasis.

The obesity-related disorders herein are associated with, caused by, or result from obesity. Examples of obesity-related disorders include overeating and bulimia, hypertension, diabetes, elevated plasma insulin concentrations and insulin resistance, dyslipidemias, hyperlipidemia, endometrial, breast, prostate and colon cancer, osteoarthritis, obstructive sleep apnea, cholelithiasis, gallstones, heart disease, abnormal heart rhythms and arrythmias, myocardial infarction, congestive heart failure, coronary heart disease, sudden death, stroke, polycystic ovarian disease, craniopharyngioma, the Prader-Willi Syndrome, Frohlich's syndrome, GH-deficient subjects, normal variant short stature, Turner's syndrome, and other pathological conditions showing reduced metabolic activity or a decrease in resting energy expenditure as a percentage of total fat-free mass, e.g, children with acute lymphoblastic leukemia. Further examples of obesity-related disorders are metabolic syndrome, also known as syndrome X, insulin resistance syndrome, sexual and reproductive dysfunction, such as infertility, hypogonadism in males and hirsutism in females, gastrointestinal motility disorders, such as obesity-related gastro-esophageal reflux, respiratory disorders, such as obesity-hypoventilation syndrome (Pickwickian syndrome), cardiovascular disorders, inflammation, such as systemic inflammation of the vasculature, arteriosclerosis, hypercholesterolemia, hyperuricaemia, lower back pain, gallbladder disease, gout, and kidney cancer. The compounds of the present invention are also useful for reducing the risk of secondary outcomes of obesity, such as reducing the risk of left ventricular hypertrophy.

The term "metabolic syndrome", also known as syndrome X, is defined in the Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. E. S. Ford et al., JAMA, vol. 287 (3), Jan. 16, 2002, pp 356-359. Briefly, a person is defined as having metabolic syndrome if the person has three or more of the following disorders: abdominal obesity, hypertriglyceridemia, low HDL cholesterol, high blood pressure, and high fasting plasma glucose. The criteria for these are defined in ATP-III. Treatment of metabolic syndrome refers to the administration of the combinations of the present invention to a subject with metabolic syndrome. Prevention of metabolic syndrome refers to the administration of the combinations of the present invention to a subject with two of the disorders that define metabolic syndrome. A subject with two of the disorders that define metabolic syndrome is a subject that has developed two of the disorders that define metabolic syndrome, but has not yet developed three or more of the disorders that define metabolic syndrome.

The terms "administration of" and or "administering a" compound should be understood to mean providing a compound of the invention or a prodrug of a compound of the invention to a human or other mammal in need of treatment.

The term "patient" should be understood to mean a human or other mammal in need of treatment.

The administration of the compound of structural formula I in order to practice the present methods of therapy is carried out by administering a therapeutically effective amount of the compound of structural formula I to the mammal (human or other mammal) in need of such treatment or prophylaxis. The need for a prophylactic administration according to the methods of the present invention is determined via the use of well known risk factors. The therapeutically effective amount of an individual compound is determined, in the final analysis, by the physician or veterinarian in charge of the case, but depends on factors such as the exact disease to be treated, the severity of the disease and other diseases or conditions from which the patient suffers, the chosen route of administration other drugs and treatments which the patient may concomitantly require, and other factors in the physician's judgment.

The usefulness of the present compounds in these diseases or disorders may be demonstrated in animal disease models that have been reported in the literature.

Administration and Dose Ranges

Any suitable route of administration may be employed for providing a mammal, especially a human, with a therapeutically effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of the present invention are administered orally.

In the treatment or prevention of conditions which require agonism of GPR40 receptor activity, an appropriate dosage level will generally be about 0.01 to 500 mg per kg patient body weight per day which may be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may preferably be provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention may be indicated, generally satisfactory results could be obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the patient undergoing therapy.

The compounds of this invention may be used in pharmaceutical compositions comprising (a) the compound(s) or a pharmaceutically acceptable salt thereof, and (b) a pharmaceutically acceptable carrier. The compounds of this invention may be used in pharmaceutical compositions that include one or more other active pharmaceutical ingredients. The compounds of this invention may also be used in pharmaceutical compositions in which the compound of the present invention or a pharmaceutically acceptable salt thereof is the only active ingredient.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

Combination Therapy

The compounds of the present invention may be useful in methods for the prevention or treatment of the aforementioned diseases, disorders and conditions in combination with other therapeutic agents.

The compounds of the present invention may be useful in combination with one or more other drugs in the treatment, prevention, suppression or amelioration of diseases or conditions for which compounds of formula I or the other drugs may have utility, where the combination of the drugs together are safer, more effective or more therapeutically effective than either drug alone. Such other drug(s) may be administered, by a route and in an amount commonly used therefore, contemporaneously or sequentially with a compound of formula I. When a compound of formula I is used contemporaneously with one or more other drugs, a pharmaceutical composition in unit dosage form containing such other drugs and the compound of formula I is preferred. However, the combination therapy may also include therapies in which the compound of formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of formula I.

Examples of other active ingredients that may be administered separately or in the same pharmaceutical composition in combination with a compound of the formulas described herein include, but are not limited to: (1) dipeptidyl peptidase-IV (DPP-4) inhibitors (e.g., sitagliptin, omarigliptin, trelagliptin, tenegliptin, bisegliptin, anagliptin, vildagliptin, saxagliptin, alogliptin, melogliptin, linagliptin, gosogliptin, evogliptin, and gemigliptin), (2) insulin sensitizers, including (i) PPARγ agonists, such as the glitazones (e.g. pioglitazone, AMG 131, MBX2044, mitoglitazone, lobeglitazone, IDR-105, rosiglitazone, and balaglitazone), and other PPAR ligands, including (1) PPARα/γ dual agonists (e.g., ZYH2, ZYH1, GFT505, chiglitazar, muraglitazar, aleglitazar, sodelglitazar, and naveglitazar); (2) PPARα agonists such as fenofibric acid derivatives (e.g., gemfibrozil, clofibrate, ciprofibrate, fenofibrate, bezafibrate), (3) selective PPARγ modulators (SPPARγM's), (e.g., such as those disclosed in WO 02/060388, WO 02/08188, WO 2004/019869, WO 2004/020409, WO 2004/020408, and WO 2004/066963); and (4) PPARγ partial agonists; (ii) biguanides, such as metformin and its pharmaceutically acceptable salts, in particular, metformin hydrochloride, and extended-release formulations thereof, such as Glumetza™, Fortamet™, and GlucophageXR™; and (iii) protein tyrosine phosphatase-1B (PTP-1B) inhibitors (e.g., ISIS-113715 and TTP814); (3) insulin or insulin analogs (e.g., insulin detemir, insulin glulisine, insulin degludec, insulin glargine, insulin lispro and inhalable formulations of each); (4) leptin and leptin derivatives and agonists; (5) amylin and amylin analogs (e.g., pramlintide); (6) sulfonylurea and non-sulfonylurea insulin secretagogues (e.g., tolbutamide, glyburide, glipizide, glimepiride, mitiglinide, meglitinides, nateglinide and repaglinide); (7) α-glucosidase inhibitors (e.g., acarbose, voglibose and miglitol); (8) glucagon receptor antagonists (e.g., MK-3577, MK-0893, LY-2409021 and KT6-971); (9) incretin mimetics, such as GLP-1, GLP-1 analogs, derivatives, and mimetics; and GLP-1 receptor agonists (e.g., dulaglutide, semaglutide, albiglutide, exenatide, liraglutide, lixisenatide, taspoglutide, CJC-1131, and BIM-51077, including intranasal, transdermal, and once-weekly formulations thereof); (10) LDL cholesterol lowering agents such as (i) HMG-CoA reductase inhibitors (e.g., simvastatin, lovastatin, pravastatin, crivastatin, fluvastatin, atorvastatin, pitavastatin and rosuvastatin), (ii) bile acid sequestering agents (e.g., colestilan, colestimide, colesevalam hydrochloride, colestipol, cholestyramine, and dialkylaminoalkyl derivatives of a cross-linked dextran), (iii) inhibitors of cholesterol absorption, (e.g., ezetimibe), and (iv) acyl CoA: cholesterol acyltransferase inhibitors, (e.g., avasimibe); (11) HDL-raising drugs, (e.g., niacin and nicotinic acid receptor agonists, and extended-release versions thereof; (12) antiobesity compounds; (13) agents intended for use in inflammatory conditions, such as aspirin, non-steroidal anti-inflammatory drugs or NSAIDs, glucocorticoids, and selective cyclooxygenase-2 or COX-2 inhibitors; (14) antihypertensive agents, such as ACE inhibitors (e.g., lisinopril, enalapril, ramipril, captopril, quinapril, and tandolapril), A-II receptor blockers (e.g., losartan, candesartan, irbesartan, olmesartan, medoxomil, valsartan, telmisartan, and eprosartan), renin inhibitors (e.g., aliskiren), beta blockers, and calcium channel blockers; (15) glucokinase activators (GKAs) (e.g., AZD6370); (16) inhibitors of 11β-hydroxysteroid dehydrogenase type 1, (e.g., such as those disclosed in U.S. Pat. No. 6,730,690, and LY-2523199); (17) CETP inhibitors (e.g., anacetrapib, evacetrapib, torcetrapib, and AT-03); (18) inhibitors of fructose 1,6-bisphosphatase, (e.g., MB-07803, and such as those disclosed in U.S. Pat. Nos. 6,054,587; 6,110,903; 6,284,748; 6,399,782; and 6,489,476); (19) inhibitors of acetyl CoA carboxylase-1 or 2 (ACC1 or ACC2); (20) AMP-activated Protein Kinase (AMPK) activators (e.g., MB-11055); (21) other agonists of the G-protein-coupled receptors: (i) GPR-109, (ii) GPR-119 (e.g., MBX2982 and PSN821), (iii) GPR-40 (e.g., fasiglifam, JTT-851, TAK-875, and P-11187, and (iv) GPR-120 (e.g., KDT-501); (22) SSTR3 antagonists (e.g., pasireotide, and such as those disclosed in WO 2009/011836); (23) neuromedin U receptor agonists (e.g., such as those disclosed in WO 2009/042053, including, but not limited to, neuromedin S (NMS)); (24) SCD inhibitors; (25) GPR-105 antagonists (e.g., such as those disclosed in WO 2009/000087); (26) SGLT inhibitors (e.g., LIK-066, ASP1941, SGLT-3, ertugliflozin, empagliflozin, dapagliflozin, canagliflozin, BI-10773, PF-04971729, remogloflozin, luseogliflozin, tofogliflozin, ipragliflozin, and LX-4211); (27) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (28) inhibitors of fatty acid synthase; (29) inhibitors of acyl coenzyme A:monoacylglycerol acyltransferase 1 and 2 (MGAT-1 and MGAT-2); (30) agonists of the TGR5 receptor (also known as GPBAR1, BG37, GPCR19, GPR131, and M-BAR) (eg., sodium taurocholate); (31) ileal bile acid transporter inhibitors (eg., elobixibat); (32) PACAP, PACAP mimetics, and PACAP receptor 3 agonists; (33) PPAR agonists; (34) protein tyrosine phosphatase-1B (PTP-1B) inhibitors; (35) IL-1b antibodies and inhibitors, (e.g., gevokizumab, canakinumab, danazol, AC-201, and BLX-1002); and (36) bromocriptine mesylate and rapid-release formulations thereof.

Of particular interest are dipeptidyl peptidase-IV (DPP-4) inhibitors that may be useful in combination with compounds of the present invention. Such inhibitors include, without limitation, sitagliptin (disclosed in U.S. Pat. No. 6,699,871), omarigliptin, trelagliptin, tenegliptin, biseglipitn, anagliptin, LC15-0444, vildagliptin, saxagliptin, alogliptin, melogliptin, linagliptin, gosogliptin, evogliptin, gemigliptin, and pharmaceutically acceptable salts thereof, and fixed-dose combinations of these compounds with metformin hydrochloride, pioglitazone, rosiglitazone, simvastatin, atorvastatin, or a sulfonylurea.

Other GPR-40 agonists that may be useful in combination with compounds of the formulas described herein include, but are not limited to: (1) 5-[4-[[(1R)-4-[6-(3-hydroxy-3-methylbutoxy)-2-methylpyridine-3-yl]-2,3-dihydro-1H-indene-1-yl]oxy]phenyl]isothiazole-3-ol 1-oxide; (2) 5-(4-((3-(2,6-dimethyl-4-(3-(methylsulfonyl)propoxy)phenyl) phenyl)-methoxy)-phenyl)isothiazole-3-ol 1-oxide; and (3) 5-(4-((3-(2-methyl-6-(3-hydroxypropoxy)-pyridine-3-yl)-2-methylphenyl)methoxy)-phenyl)isothiazole-3-ol 1-oxide; and (4) 5-[4-[[3-[4-(3-aminopropoxy)-2,6-dimethylphenyl] phenyl]-methoxy]phenyl]isothiazole-3-ol 1-oxide, and pharmaceutically acceptable salts thereof.

Antiobesity compounds that may be combined with compounds of formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide $Y_1$ or $Y_5$ antagonists (such as MK-0557); $β_3$ adrenergic receptor agonists; CB-1 receptor inverse agonists and antagonists; ghrelin antagonists; bombesin receptor agonists (such as bombesin receptor subtype-3 agonists); and 5-hydroxytryptamine-2c (5-HT2c) agonists, such as lorcaserin. For a review of anti-obesity compounds that may be useful in combination with a compound of the present invention, see S. Chaki et al., "Recent advances in feeding suppressing agents: potential therapeutic strategy for the treatment of obesity," Expert Opin. Ther. Patents, 11: 1677-1692 (2001); D. Spanswick and K. Lee, "Emerging antiobesity drugs," Expert Opin. Emerging Drugs, 8: 217-237 (2003); J. A. Fernandez-Lopez, et al., "Pharmacological Approaches for the Treatment of Obesity," Drugs, 62: 915-944 (2002); and K. M. Gadde, et al., "Combination pharmaceutical therapies for obesity," Exp. Opin. Pharmacother., 10: 921-925 (2009).

Glucagon receptor antagonists that may be useful in combination with the compounds of formula I include, but are not limited to: (1) N-[4-((1S)-1-{3-(3,5-dichlorophenyl)-5-[6-(trifluoromethoxy)-2-naphthyl]-1H-pyrazol-1-yl}ethyl)benzoyl]-P-alanine; (2) N-[4-((1R)-1-{3-(3,5-dichlorophenyl)-5-[6-(trifluoromethoxy)-2-naphthyl]-1H-pyrazol-1-yl}ethyl)benzoyl]-P-alanine; (3) N-(4-{1-[3-(2,5-dichlorophenyl)-5-(6-methoxy-2-naphthyl)-1H-pyrazol-1-yl]ethyl}benzoyl)-3-alanine; (4) N-(4-{(1S)-1-[3-(3,5-dichlorophenyl)-5-(6-methoxy-2-naphthyl)-1H-pyrazol-1-yl]ethyl}benzoyl)-P-alanine; (5) N-(4-{(1S)-1-[(R)-(4-chlorophenyl)(7-fluoro-5-methyl-1H-indol-3-yl)methyl]butyl}benzoyl)-P-alanine; and (6) N-(4-{(1S)-1-[(4-chlorophenyl)(6-chloro-8-methylquinolin-4-yl)methyl]butyl}benzoyl)-3-alanine; and pharmaceutically acceptable salts thereof.

Another embodiment of the present invention relates to a pharmaceutical composition comprising one or more of the following agents: (a) a compound of structural formula I; (b) one or more compounds selected from the group consisting of: (1) dipeptidyl peptidase-IV (DPP-4) inhibitors (e.g., sitagliptin, omarigliptin, trelagliptin, teneligliptin, bisegliptin, anagliptin, vildagliptin, saxagliptin, alogliptin, melogliptin, linagliptin, gosogliptin, evogliptin, and gemigliptin); (2) insulin sensitizers, including (i) PPARγ agonists, such as the glitazones (e.g. AMG 131, MBX2044, mitoglitazone, lobeglitazone, IDR-105, pioglitazone, rosiglitazone, and balaglitazone) and other PPAR ligands, including (1) PPARα/γ dual agonists, such as ZYH1, YYH2, chiglitazar, GFT505, muraglitazar, aleglitazar, sodelglitazar, and naveglitazar, (2) PPARα agonists, such as fenofibric acid derivatives (e.g., gemfibrozil, clofibrate, ciprofibrate, fenofibrate and bezafibrate), (3) selective PPARγ modulators (SPPARγM's), (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors, such as ISI-113715, and TTP814; (3) sulfonylurea and non-sulfonylurea insulin secretagogues, (e.g., tolbutamide, glyburide, glipizide, glimepiride, mitiglinide, and meglitinides, such as nateglinide and repaglinide); (4) α-glucosidase inhibitors (e.g., acarbose, voglibose and miglitol); (5) glucagon receptor antagonists; (6) LDL cholesterol lowering agents such as (i) HMG-CoA reductase inhibitors (e.g., lovastatin, simvastatin, pravastatin, cerivastatin, fluvastatin, atorvastatin, pitavastatin, and rosuvastatin), (ii) bile acid sequestering agents (e.g., colestilan, cholestyramine, colestimide, colesevelam hydrochloride, colestipol, and dialkylaminoalkyl derivatives of a cross-linked dextran), (iii) inhibitors of cholesterol absorption, (e.g., ezetimibe), and (iv) acyl CoA:cholesterol acyltransferase inhibitors (e.g., avasimibe); (7) HDL-raising drugs, such as niacin or a salt thereof and extended-release versions thereof; and nicotinic acid receptor agonists; (8) antiobesity compounds; (9) agents intended for use in inflammatory conditions, such as aspirin, non-steroidal anti-inflammatory drugs (NSAIDs), glucocorticoids, and selective cyclooxygenase-2 (COX-2) inhibitors; (10) antihypertensive agents, such as ACE inhibitors (e.g., enalapril, lisinopril, ramipril, captopril, quinapril, and tandolapril), A-II receptor blockers (e.g., losartan, candesartan, irbesartan, olmesartan medoxomil, valsartan, telmisartan, and eprosartan), renin inhibitors (e.g., aliskiren), beta blockers (e.g., calcium channel blockers); (11) glucokinase activators (GKAs) (e.g., AZD6370, GKM-001, TMG-123, HMS-5552, DS-7309, PF-04937319, TTP-399, ZYGK-1); (12) inhibitors of 11β-hydroxysteroid dehydrogenase type 1 (e.g., such as those disclosed in U.S. Pat. No. 6,730,690; WO 03/104207; and WO 04/058741); (13) inhibitors of cholesteryl ester transfer protein (CETP), (e.g., torcetrapib, evacetrapib, anacetrapib, and AT-03); (14) inhibitors of fructose 1,6-bisphosphatase (e.g., MB-07803, and such as those disclosed in U.S. Pat. Nos. 6,054,587; 6,110,903; 6,284,748; 6,399,782; and 6,489,476); (15) inhibitors of acetyl CoA carboxylase-1 or 2 (ACC1 or ACC2); (16) AMP-activated Protein Kinase (AMPK) activators (e.g., MB-11055); (17) agonists of the G-protein-coupled receptors: (i) GPR-109, (ii) GPR-119 (e.g., MBX2982, and PSN821), (iii) GPR-40 (e.g., fasiglifam, JTT-851, P-11187, 5-[4-[[(1R)-4-[6-(3-hydroxy-3-methylbutoxy)-2-methylpyridin-3-yl]-2,3-dihydro-1H-indene-1-yl]oxy]phenyl]isothiazole-3-ol 1-oxide, 5-(4-((3-(2,6-dimethyl-4-(3-(methylsulfonyl)propoxy)phenyl)phenyl)-methoxy)phenyl)-isothiazole-3-ol 1-oxide, 5-(4-((3-(2-methyl-6-(3-hydroxypropoxy)pyridine-3-yl)-2-methyl-phenyl)methoxy)phenyl)-isothiazole-3-ol 1-oxide, and 5-[4-[[3-[4-(3-aminopropoxy)-2,6-dimethylphenyl]phenyl]-methoxy]phenyl]isothiazole-3-ol 1-oxide), and (iv) GPR-120 (e.g., KDT-501); (18) SSTR3 antagonists (e.g., pasireotide, and such as those disclosed in WO 2009/011836); (19) neuromedin U receptor agonists (e.g., such as those disclosed in WO2009/042053, including, but not limited to, neuromedin S (NMS)); (20) inhibitors of stearoyl-coenzyme A delta-9 desaturase (SCD); (21) GPR-105 antagonists (e.g., such as those disclosed in WO 2009/000087); (22) inhibitors of glucose uptake, such as sodium-glucose transporter (SGLT) inhibitors and its various isoforms, such as SGLT-1; SGLT-2 (e.g., LIK-066, ertuglifozin, ASP1941, luseogliflozin, BI10773, tofogliflozin, LX4211, canagliflozin, dapagliflozin and remogliflozin; and SGLT-3); (23) inhibitors of (i) acyl coenzyme A:diacylglycerol acyltransferase 1, DGAT-1 (e.g., pradigastat, and P-7435) and acyl coenzyme A:diacylglycerol acyltransferase 2, DGAT-2; (24) inhibitors of fatty acid synthase; (25) inhibitors of acyl coenzyme A:monoacylglycerol acyltransferase 1 and 2 (MGAT-1 and MGAT-2); (26) agonists of the TGR5 receptor (also known as GPBAR1, BG37, GPCR19, GPR131, and M-BAR) (eg., sodium taurocholate); (28) bromocriptine mesylate and rapid-release formulations thereof, and (29) IL-lb antibodies and inhibitors (e.g., gevokizumab, canakinumab, danazol, AC-201, and BLX-1002); and (c) a pharmaceutically acceptable carrier.

Specific compounds that may be useful in combination with a compound of the present invention include: simvastatin, mevastatin, ezetimibe, atorvastatin, rosuvastatin, sitagliptin, omarigliptin, metformin, sibutramine, orlistat, topiramate, naltrexone, bupriopion, phentermine, losartan, losartan with hydrochlorothiazide, olmesartan, canagliflozin, dapagliflozin, ipragliflozin and ertugliflozin.

The above combinations include combinations of a compound of the present invention not only with one other active compound, but also with two or more other active compounds. Non-limiting examples include combinations of compounds with two or more active compounds selected from biguanides, sulfonylureas, HMG-CoA reductase inhibitors, PPARγ agonists, DPP-4 inhibitors, anti-obesity compounds, and anti-hypertensive agents.

The present invention may also provide a method for the treatment or prevention of a G-protein coupled receptor 40 (GPR40) mediated disease, which method comprises administration to a patient in need of such treatment or at risk of developing a GPR40 mediated disease of an amount of a GPR40 agonist and an amount of one or more active ingredients, such that together they give effective relief.

In a further aspect of the present invention, there is provided a pharmaceutical composition comprising a GPR40 agonist and one or more active ingredients, together with at least one pharmaceutically acceptable carrier or excipient.

Thus, according to a further aspect of the present invention there is provided the use of a GPR40 agonist and one or more active ingredients for the manufacture of a medicament for the treatment or prevention of a GPR40 mediated disease. In a further or alternative aspect of the present invention, there is therefore provided a product comprising a GPR40 agonist and one or more active ingredients as a combined preparation for simultaneous, separate or sequential use in the treatment or prevention of a GPR40 mediated disease. Such a combined preparation may be, for example, in the form of a twin pack.

For the treatment or prevention of diabetes, obesity, hypertension, Metabolic Syndrome, dyslipidemia, cancer, atherosclerosis, and related disorders thereof, a compound of the present invention may be used in conjunction with another pharmaceutical agent effective to treat that disorder.

The present invention may also provide a method for the treatment or prevention of diabetes, obesity, hypertension, Metabolic Syndrome, dyslipidemia, cancer, atherosclerosis, and related disorders thereof, which method comprises administration to a patient in need of such treatment an effective amount of a compound of the present invention and an amount of another pharmaceutical agent effective to threat that disorder, such that together they give effective relief.

The present invention may also provide a method for the treatment or prevention of diabetes, obesity, hypertension, Metabolic Syndrome, dyslipidemia, cancer, atherosclerosis, and related disorders thereof, which method comprises administration to a patient in need of such treatment an amount of a compound of the present invention and an amount of another pharmaceutical agent useful in treating that particular condition, such that together they give effective relief.

The term "therapeutically effective amount" or "a therapeutically effective dose" means the amount the compound of structural formula I that will elicit the biological or medical response of a tissue, system, animal, mammal or human that is being sought by the researcher, veterinarian, medical doctor or other clinician, which includes alleviation of the symptoms of the disorder being treated. The novel methods of treatment of this invention are for disorders known to those skilled in the art. The term "mammal" includes, but is not limited to, humans, and companion animals such as dogs and cats.

The weight ratio of the compound of the Formula I to the second active ingredient may be varied and will depend upon the effective dose of each ingredient. Generally, a therapeutically effective dose of each will be used. Thus, for example, when a compound of the Formula I is combined with a DPIV inhibitor the weight ratio of the compound of the Formula I to the DPIV inhibitor will generally range from about 1000:1 to about 1:1000, preferably about 200:1 to about 1:200. Combinations of a compound of the Formula I and other active ingredients will generally also be within the aforementioned range, but in each case, an effective dose of each active ingredient should be used.

Methods of Synthesis of the Compounds of the Present Invention:

The following reaction schemes and Examples illustrate methods which may be employed for the synthesis of the compounds of structural formula I described in this invention. Those skilled in the art will readily understand that known variations of protecting groups, as well as of the conditions and processes of the following preparative procedures, can be used to prepare these compounds. It is also understood that whenever a chemical reagent such as a boronic acid or a boronate is not commercially available, such a chemical reagent can be readily prepared following one of numerous methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI). All temperatures are degrees Celsius unless otherwise noted.

List of Abbreviations

Ac is acetyl; AcCN is acetonitrile; $Ac_2O$ is acetic anhydride; Alk is alkyl; anh. is anhydrous; aq or aq. is aqueous; Ar is aryl; atm is atmosphere; Boc is tert-butoxycarbonyl; Bn-O is phenyl-$CH_2$—O or benzyloxy; n-BuLi is n-butyl lithium; t-BuOK is potassium tert-butoxide; ° C. is degrees celsius; Cataxium precatalyst or Cataxium Pd precat or precatalyst or cataCXium A Pd G3 (Aldrich) is Mesylate [(di(1-adamantyl)-n-butylphosphine)-2-(2'-amino-1,1'-biphenyl)]palladium(II), [(di(1-adamantyl)-butylphosphine)-2-(2'-amino-1,1'-biphenyl)]palladium(II) methanesulfonate; Cbz is benzyloxycarbonyl; $CH_2Cl_2$ is dichloromethane; conc or conc. is concentrated; CDI is carbonyl-diimidazole; CPME is cyclopropyl methyl ether; CV is column volumes; DCM is dichloromethane; DEA is diethyl amine; DIPEA is N,N-diisopropylethylamine; DIPA is diisopropyl amine; DMAP is 4-dimethylaminopyridine; DMF is N,N-dimethylformamide; DMS is dimethyl sulfide; DMSO is dimethylsulfoxide; EA or EtOAc is ethyl acetate; Et is ethyl; $Et_3N$ is triethyl amine; $Et_2O$ is diethyl ether; EtMgBr is ethyl magnesium bromide; $Et_2O$ is diethyl ether; EtOH is ethanol; g is gram(s); h or hr or hrs is hour(s); hex is hexanes; HPLC is high pressure liquid chromatography; HOAc or AcOH is acetic acid; kg is kilogram(s); IPA is isopropanol; Josiphos is CAS: 223121-01-5; KOAc is potassium acetate; KOtBu is potassium tert-butoxide; KHMDS is potassium hexamethyl disilazide; L is liter; LAH is lithium aluminum hydride; M is molar; LC-MS, LCMS or LC/MS is liquid chromatography-mass spectroscopy; LDA is lithium diisopropyl amide; Me is methyl; MeO is methoxy; m-CPBA, MCPBA, or mCPBA is meta chloroperbenzoic acid; ml or mL is milliliter; min or mins is minute(s); mol is mole(s); mmol is mmole(s); mg is milligram(s); MeOH is methyl alcohol or methanol; MPa is megapascals; MPLC is medium pressure liquid chromatography; MS is mass spectroscopy; MsCl or Ms-Cl is methane sulfonyl chloride; MeCN is acetonitrile; MeI is methyl iodide; MTBE is methyl tert-butyl ether; N is normal; NaHMDS is sodium hexamethyl disilazide; NH$_4$OAc is ammonium acetate; NBS is N-bromo succinamide; NEt$_3$ is triethyl amine; NIS is N-iodo succinamide; NMO is 4-methyl morpholine N-oxide; NMP is 1-methyl-2-pyrrolidinone; NMR is nuclear magnetic resonance spectroscopy; o.n. or ON is overnight; PE is petroleum ether; PG is protecting group; i-PrOH is isopropanol; Pd(OAc)$_2$ is palladium acetate; Pd(PPh$_3$)$_4$ is tetrakis or tetrakis(triphenylphosphine)palladium(0); PPh$_3$ is triphenyl phosphine; Pd(PPh$_3$)$_2$Cl$_2$ is bis(triphenyl-phosphine)palladium dichloride; PdCl$_2$(dppf) CH$_2$Cl$_2$ is [1,1'-Bis(diphenyl-phosphino) ferrocene]-dichloropalladium(II), complex with dichloromethane; precat is precatalyst; prep is preparative; prep. TLC or prep-TLC, or prep TCL is preparative thin layer chromatography; psi is pounds per square inch; rt or r.t. or RT is room temperature; Ru-catalyst is CAS: 12289-94-0; Ru-Josiphos is generated using (Me-allyl)$_2$Ru(COD) (Aldrich) and Josiphos SL-J502-2 (Aldrich); RuCl[(S,S)-TSDPEN]-(Mesitylene) is [N-[(1R,2R)-2-(Amino-KN)-1,2-diphenylethyl]-4-methylbenzene-sulfonamidato-κN]chloro [(1,2,3,4,5,6-η)-1,3,5-trimethylbenzene]-ruthenium; RuCl[(R,R)-TSDPEN](Mesitylene) is [N-[(1R,2R)-2-(Amino-KN)-1,2-diphenylethyl]-4-methylbenzene-sulfonamidato-KN]chloro [(1,2,3,4,5,6-η)-1,3,5-trimethylbenzene]-ruthenium; R$_f$ is retention factor; sat or sat. is saturated; SEM is trimethylsilyl ethoxy methyl, SEMCl is trimethylsilyl ethoxy methyl chloride; SFC is supercritical fluid chromatography; S-Phos is 2-dicyclohexylphosphino-2',6'-dimethoxy-biphenyl; S-Phos(Pd) is chloro(2-dicyclohexylphosphino-2',6'-dimethoxy-1,1'-biphenyl)[2-(2-aminoethyl-phenyl)]-palladium (II) (CASNo. 1028206-58-7); S-Phos precatalyst or S-Phos Pd G2 precatalyst—Aldrich or S-Phos second generation precatalyst, S-PhosBiaryl precatalyst 2nd gen or 2$^{nd}$ generation palladium SPhos precatalyst is Chloro (2-dicyclohexyl-phosphino-2',6'-dimethoxy-1,1'-biphenyl) [2-(2'-amino-1,1'-biphenyl)]palladium-(II), SPhos-Pd-G2) (CAS-No. 1375325-64-6); TBAF is tetrabutylammonium fluoride; TBSCl is tert-butyl dimethylsilyl chloride; TEA is triethyl amine; Tf is trifluoromethane sulfonyl; 2-Me THF is 2-methyltetrahydrofuran; THF is tetrahydrofuran; TFA is trifluoroacetic acid; TLC is thin-layer chromatography; p-Tos, Tos and Ts is p-toluene sulfonyl; TosCl and TsCl is p-toluene sulfonyl chloride; pTSA, pTsOH and TsOH is p-toluenesulfonic acid, and Ts$_2$O is tosic anhydride or p-toluene sulfonic anhydride; and XPhos second generation precatalyst or 2$^{nd}$ generation palladium xphos precatalyst is Chloro(2-dicyclohexylphosphino-2',4',6'-triisopropyl-1,1'-biphenyl)[2-(2'-amino-1,1'-biphenyl)]palladium(II), THF adduct (CAS No. 1310584-14-5).

Several methods for preparing the compounds of this invention are illustrated in the following Schemes and Examples. Starting materials are either commercially available or made by known procedures in the literature or as illustrated. The present invention further provides processes for the preparation of compounds of structural formula I as defined above. In some cases the order of carrying out the foregoing reaction schemes may be varied to facilitate the reaction or to avoid unwanted reaction products. The following Schemes and Examples are provided to illustrate the invention and are not to be construed as limiting the invention in any manner. The scope of the invention is defined by the appended claims.

Scheme A

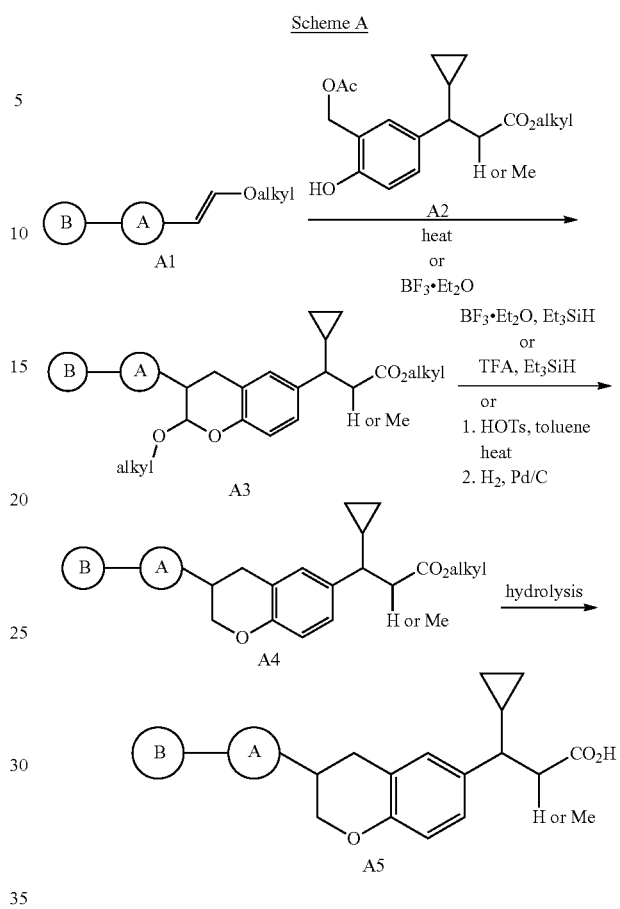

Scheme A describes a general method for the synthesis of chromans such as compound A5. Enol ether A1 undergoes a Diels-Alder reaction with a ortho-quinone methide, which was formed from a compound such as compound A2 via ether thermal conditions or Lewis Acid mediated conditions, such as treatment with BF$_3$.Et$_2$O and the like, in a solvent, such as CH$_2$Cl$_2$ and the like, to afford the cycloadduct A3. Compound A4 is prepared via treatment of A3 with a Lewis acid such as BF$_3$.Et$_2$O, followed by triethylsilane or a protic acid such as TFA, and followed by triethylsilane. Alternatively, a 2-step sequence can be performed wherein A3 is treated with a protic acid such as TsOH in refluxing toluene, followed by hydrogenation of the resulting chromene to afford A4. The ester present in A4 then undergoes hydrolysis with an aqueous base, such as lithium hydroxide and the like, in a solvent mixture, such as THF:MeOH and the like, to afford the desired final compounds A5.

Scheme B

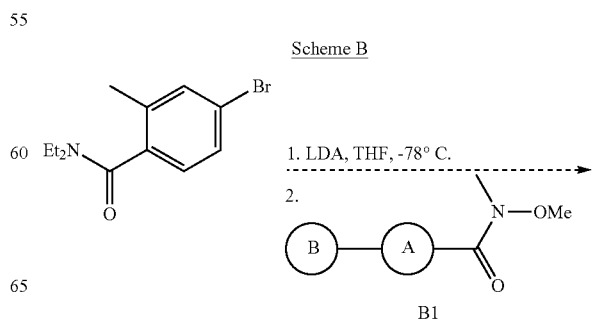

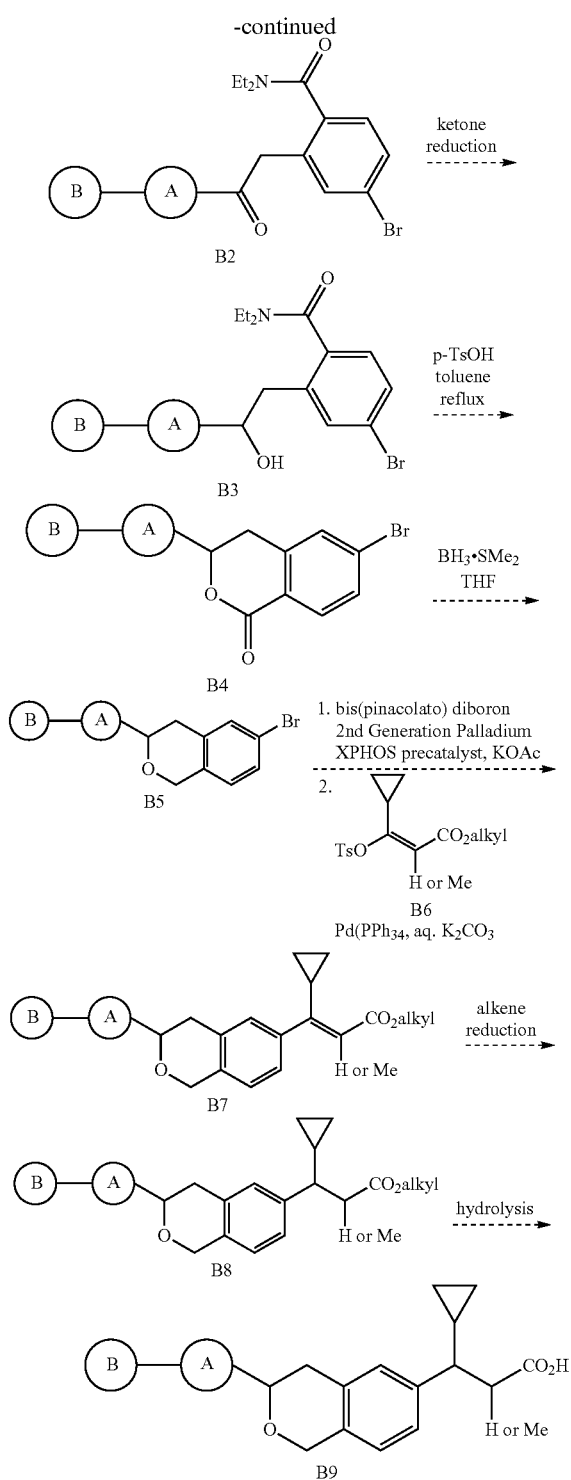

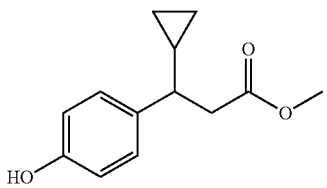

Scheme B describes a general method for the synthesis of isochromans such as compound B9. Lithiation of 4-bromo-N,N-diethyl-2-methylbenzamide, followed by addition of a Weinreb amide such as B1 affords ketones B2. Racemic reduction of B2 with sodium borohydride affords compounds B3. Alternatively asymmetric reduction of B2 via established Noyori-type conditions can be accomplished. Acid-mediated cyclization of B3 results in the lactone B4. Reduction of the lactone B4 can be accomplished with BH$_3$·Me$_2$S to provide isochroman B5. Palladium-mediated conversion of B5 to the pinacol boronate, followed by palladium-mediated cross-coupling with tosylates B6 provides the cinnamates B7. As an alternative to B6, the vinyl triflate can be used. Reduction of the alkene present in B7 with methods such as hydrogen and rhodium on alumina or hydrogen and palladium on carbon affords compounds B8. Alternatively, B7 can undergo ruthenium-catalyzed asymmetric hydrogenation. Hydrolysis of B8 via a method similar to that described in Scheme A affords final compounds B9.

Intermediate 1 methyl 3-cyclopropyl-3-(4-hydroxyphenyl)propanoate

Step 1: 5-(4-hydroxybenzylidene)-2,2-dimethyl-1,3-dioxane-4,6-dione

4-Hydroxybenzaldehyde (50 g, 410 mmol), and Meldrum's Acid (65 g, 451 mmol) were suspended in water (1500 mL) and heated to 75° C. After approximately 2 hours, the reaction mixture was cooled to ambient temperature, filtered and rinsed with H$_2$O. The resulting solids were dried in vacuo to afford the desired product. $^1$H NMR DMSO 400 MHz: δ: 1.72 (s, 6H) 6.85-6.95 (m, 2H) 8.14-8.22 (m, 2H) 8.23-8.28 (m, 1H).

Step 2: 5-(cyclopropyl(4-hydroxyphenyl)methyl)-2,2-dimethyl-1,3-dioxane-4,6-dione The product from Step 1 (50 g, 201 mmol), was dissolved in THF (1100 mL) and cooled to 0° C. A 0.5M THF solution of cyclopropynylmagnesium bromide (1500 mL, 700 mmol) was added and the resulting reaction mixture was warmed to ambient temperature over 15 hours. The reaction mixture was then diluted with EtOAc, and 1N HCl (1000 mL)/ice-water was added. The resulting pH 1 bi-phasic mixture was separated and the combined organic layers were treated with pyridine to increase the pH to pH=7; and concentrated under reduced pressure to afford the desired product, which was used in the next step without further purification.

Step 3: 3-cyclopropyl-3-(4-hydroxyphenyl)propanoic acid

The product from Step 2(16 g, crude), was dissolved in pyridine (1100 mL)/water (220 mL) and heated at 100° C. over 10 h. Then the reaction mixture was concentrated and the resulting residue was partitioned between aqueous 1N NaOH and EtOAc. The aqueous layer was separated, re-extracted with EtOAc and acidified with aqueous 5N HCl to pH=0. The aqueous layer was then extracted with EtOAc. The EtOAc layer was dried (Na$_2$SO$_4$), filtered and concentrated to afford the crude product, which was used for next step without further purification. 1HNMR CDCl3 400 MHz δ: 0.00-0.13 (m, 1H), 0.14-0.23 (m, 1H), 0.24-0.34 (m, 1H), 0.40-0.53 (m, 1H), 0.88-1.01 (m, 1H), 2.14-2.25 (m, 1H), 2.53-2.67 (m, 2H), 6.66-6.68 (d, J=8 Hz, 2H), 7.02-7.04 (d, J=8 Hz, 2H), 9.16 (s, 1H), 12.05 (s, 1H).

Step 4

The product from Step 3 (16 g, 0.0775 mol) was dissolved in MeOH (200 mL) and treated with sulfuric acid (0.5 mL). The reaction mixture was heated to 70° C. using a metal reaction block and stirred over ~15 h. Then the reaction mixture was cooled to room temperature and NaHCO$_3$ solid was added to adjust the ph to pH=7. The reaction mixture was concentrated, and the resulting residue was purified by silica gel flash column chromatography to afford Intermediate 1. $^1$HNMR CDCl3 400 MHz δ: 0.03-0.11 (m, 1H), 0.12-0.20 (m, 1H), 0.25-0.36 (m, 1H), 0.38-0.61 (m, 1H), 0.92-1.02 (m, 1H), 2.13-2.27 (m, 1H), 2.60-2.75 (m, 2H), 3.50 (s, 3H), 6.67-6.69 (d, J=8 Hz, 2H), 7.03-7.05 (d, J=8 Hz, 2H), 9.18 (s, 1H).

Intermediates 2 and 3

(S)-methyl 3-cyclopropyl-3-(4-hydroxyphenyl)propanoate (Peak 1) and (R)-methyl 3-cyclopropyl-3-(4-hydroxyphenyl)propanoate (Peak 2)

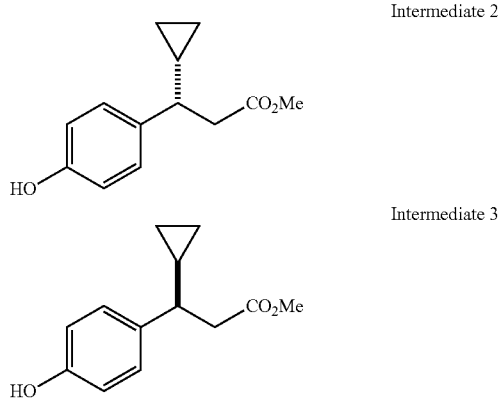

Intermediate 2

Intermediate 3

Intermediate 1 was subjected to chiral SFC chromatography (Conditions: Instrument: Thar preparative SFC 200; Column: Chiral Cel. OJ-H, 300×50 mm I.D. 10 um; Mobile phase: A for CO$_2$ and B for IPA (0.1% NH$_3$H$_2$O); Gradient: B 15%; Flow rate: 200 mL/min; Back pressure: 100 bar; Column temperature: 40° C.; Wavelength: 220 nm) to afford Intermediates 2 (Peak 1) and 3 (Peak 2).

Intermediate 4 methyl 3-cyclopropyl-3-(4-hydroxyphenyl)-2-methylpropanoate

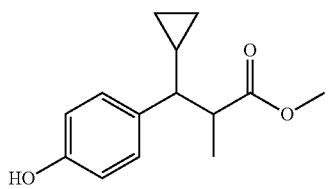 [SMILES: COC(=O)C(C)C(c1ccc(O)cc1)C1CC1]

Step 1: 5-(cyclopropyl(4-hydroxyphenyl)methyl)-2,2,5-trimethyl-1,3-dioxane-4,6-dione Iodomethane (0.986 ml, 15.77 mmol) was added to a stirred, room temperature mixture of 5-(cyclopropyl(4-hydroxyphenyl)methyl)-2,2-dimethyl-1,3-dioxane-4,6-dione (prepared in Step 2 of Intermediate 1, 4360 mg, 15.02 mmol) and K$_2$CO$_3$ (6890 mg, 49.9 mmol) in DMF (65 ml). The reaction mixture was stirred at room temperature for 3 h, then partitioned between ethyl acetate and 1N aqueous hydrochloric acid. The layers were separated and the organic layer was washed with brine, dried over anhydrous Na$_2$SO$_4$, filtered and evaporated to afford a crude residue. The resulting residue was purified via column chromatography on silica gel (ISCO RediSep 80 g silica gel column, gradient elution with 0% to 100% EtOAc in hexanes) to give 5-(cyclopropyl(4-hydroxyphenyl)methyl)-2,2,5-trimethyl-1,3-dioxane-4,6-dione.

Step 2: 3-cyclopropyl-3-(4-hydroxyphenyl)-2-methylpropanoic acid 5-(cyclopropyl(4-hydroxyphenyl)methyl)-2,2,5-trimethyl-1,3-dioxane-4,6-dione (2 g, 6.57 mmol) was suspended in 2M NaOH (aqueous, 50 ml, 100 mmol). The reaction mixture was heated at 100° C. for 1 h, then cooled to room temperature, and partitioned between ethyl acetate (200 mL) and 2N aqueous hydrochloric acid (100 mL). The layers were separated and the organic layer was washed with brine, dried over anhydrous sodium sulfate, filtered and evaporated to afford 2-(cyclopropyl(4-hydroxyphenyl)methyl)-2-methylmalonic acid, which was used without further purification in the next step. A solution of 2-(cyclopropyl(4-hydroxy-phenyl)methyl)-2-methylmalonic acid (1.77 g, 6.70 mmol) in DMSO (10 ml) was heated at 130° C. for 2 h. The reaction was then cooled and partitioned between ethyl acetate and 1N aqueous hydrochloric acid. The layers were separated and the aqueous layer was extracted with EtOAc. The organic layers were combined, washed with brine, dried over anhydrous Na$_2$SO$_4$, filtered and evaporated to afford 3-cyclopropyl-3-(4-hydroxyphenyl)-2-methylpropanoic acid, which was used in the next step without further purification.

Step 3: methyl 3-cyclopropyl-3-(4-hydroxyphenyl)-2-methylpropanoate

Sulfuric acid (0.2 mL, 3.75 mmol) was added to a stirred, room temperature mixture of 3-cyclopropyl-3-(4-hydroxyphenyl)-2-methylpropanoic acid (1.45 g, 6.58 mmol) in methanol (20 ml) and the mixture was stirred at reflux overnight. The reaction mixture was then cooled to room temperature and partitioned between ethyl acetate and brine. The organic layer was separated, washed with brine, dried over anhydrous Na$_2$SO$_4$, filtered and evaporated to afford a crude residue. The resulting residue was purified via column chromatography on silica gel (ISCO RediSep 40 g silica gel column, gradient elution with 0% to 100% EtOAc in hexanes) to give methyl 3-cyclopropyl-3-(4-hydroxyphenyl)-2-methylpropanoate (Intermediate 4).

Intermediate 5

(2S,3R)-methyl 3-cyclopropyl-3-(4-hydroxyphenyl)-2-methylpropanoate

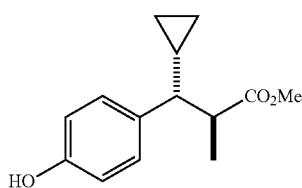 [SMILES: COC(=O)[C@@H](C)[C@H](c1ccc(O)cc1)C1CC1]

Step 1: (S)-methyl 3-(4-((tert-butyldimethylsilyl)oxy)phenyl)-3-cyclopropylpropanoate To a solution of (S)-methyl 3-cyclopropyl-3-(4-hydroxyphenyl)propanoate (47.09 g, 214 mmol) in DMF (178 ml) was added TBSCl (33.8 g, 224 mmol) and imidazole (29.1 g, 428 mmol). The resulting reaction mixture was stirred for 18 h at room temperature, and then partitioned between hexanes and water. The layers were separated, and the aqueous layer was extracted with hexanes. The organic layers were combined, washed twice with brine, dried over anhydrous $MgSO_4$ and concentrated to afford (S)-methyl 3-(4-((tert-butyldimethylsilyl)oxy)phenyl)-3-cyclopropylpropanoate.

Step 2: (3R)-methyl 3-(4-((tert-butyldimethylsilyl)oxy)phenyl)-3-cyclopropyl-2-methylpropanoate To a cooled THF (5 mL) solution of (S)-methyl 3-(4-((tert-butyldimethylsilyl)oxy)-phenyl)-3-cyclopropylpropanoate (1.99 g, 5.95 mmol) was added LDA (2M in THF, 4.46 ml, 8.92 mmol). After 30 min at −78, MeI (0.930 ml, 14.87 mmol) was added dropwise. The reaction was then warmed to room temperature and stirred for 20 min. The reaction was then poured into saturated aqueous sodium sulfate and extracted twice with EtOAc. The combined organic layers were dried (anhydrous $MgSO_4$), filtered and concentrated. The resulting residue was purified via column chromatography on silica gel (ISCO RediSep 80 g silica gel column, gradient elution with 0% to 50% EtOAc in hexanes) to give (3R)-methyl 3-(4-((tert-butyldimethylsilyl)oxy)phenyl)-3-cyclopropyl-2-methylpropanoate.

Step 3: (2S,3R)-methyl 3-cyclopropyl-3-(4-hydroxyphenyl)-2-methylpropanoate

To a stirred solution of (3R)-methyl 3-(4-((tert-butyldimethylsilyl)oxy)phenyl)-3-cyclopropyl-2-methylpropanoate (1.84 g, 5.28 mmol) in THF (3.11 ml) at 0° C. was added a solution of KOt-Bu (1M in THF, 5.28 ml, 5.28 mmol). After stirring at 0° C. for 20 min, the reaction was quenched with 1N HCl at 0° C., and immediately diluted with water and extracted with EtOAc. The organic layer was dried over anhydrous sodium sulfate, filtered and concentrated. The resulting crude oil was diluted with THF (40 mL), treated with TBAF (6.33 ml, 6.33 mmol) and stirred at rt for 15 minutes. The reaction was then diluted with brine and extracted with EtOAc. The organic layer was dried over anhydrous sodium sulfate, filtered and concentrated to give an oil. The oil was purified via column chromatography on silica gel (ISCO RediSep 40 g silica gel column, gradient elution with 0% to 100% EtOAc in hexanes) to give the desired product, which was suspended in heptane and heated to 100° C. EtOAc was added until the suspension became clear, and the solution was cooled to room temperature, forming a crystalline solid precipitate, which was collected by filtration, washed with heptane and dried to afford (2S,3R)-methyl 3-cyclopropyl-3-(4-hydroxyphenyl)-2-methylpropanoate (Intermediate 5): $[a]^D{}_{25}$=+89.10 (c=1, $CH_2Cl_2$).

Intermediate 6

(2R,3S)-methyl 3-cyclopropyl-3-(4-hydroxyphenyl)-2-methylpropanoate

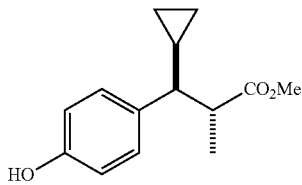 [SMILES: COC(=O)[C@H](C)[C@@H](c1ccc(O)cc1)C1CC1]

Starting from (R)-methyl 3-cyclopropyl-3-(4-hydroxyphenyl)propanoate and utilizing a method similar to that outlined in the synthesis of Intermediate 4, (2R,3S)-methyl 3-cyclopropyl-3-(4-hydroxyphenyl)-2-methylpropanoate (Intermediate 6) was prepared: $[a]^D{}_{25}$=−62.2° (c=1.0, $CH_2Cl_2$).

Intermediate 7 methyl 3-(3-(acetoxymethyl)-4-hydroxyphenyl)-3-cyclopropylpropanoate

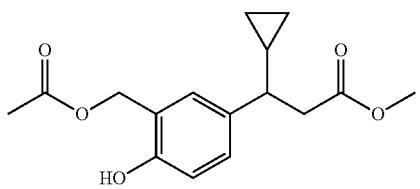 [SMILES: COC(=O)CC(c1ccc(O)c(COC(C)=O)c1)C1CC1]

Step 1: methyl 3-cyclopropyl-3-(3-formyl-4-hydroxyphenyl)propanoate

Magnesium chloride (1.096 g, 11.51 mmol) was added to a stirred, room temperature mixture of methyl 3-cyclopropyl-3-(4-hydroxyphenyl)propanoate (Intermediate 1) (1.69 g, 7.67 mmol), paraformaldehyde (1.152 g, 38.4 mmol) and $Et_3N$ (4.01 ml, 28.8 mmol) in acetonitrile (51.2 ml). The reaction mixture was stirred at reflux for 90 minutes, then cooled to room temperature. The reaction was partitioned between EtOAc in hexanes and ice-cold 0.5 M hydrochloric acid. The organic layer was separated, washed with brine, dried over anhydrous $Na_2SO_4$, filtered and evaporated to afford a crude residue, which was purified via column chromatography on silica gel (ISCO RediSep 40 g silica gel column, gradient elution with 0% to 100% EtOAc in hexanes) to give methyl 3-cyclopropyl-3-(3-formyl-4-hydroxyphenyl)propanoate.

Step 2: methyl 3-cyclopropyl-3-(4-hydroxy-3-(hydroxymethyl)phenyl)propanoate

A solution of methyl 3-cyclopropyl-3-(3-formyl-4-hydroxyphenyl)propanoate (1.43 g, 5.76 mmol) in ethanol (28.8 ml) was cooled to 0° C. and treated with sodium borohydride (0.218 g, 5.76 mmol). The reaction mixture was stirred at 0° C. for 10 min, and then quenched with saturated aqueous NH$_4$Cl (200 mL) at 0° C. The aqueous layer (pH 8) was adjusted to pH 3 with 1N HCl, and saturated aq. NaCl (30 mL) was added. The aqueous layer was extracted with EtOAc (200 mL), and the combined organic layers were dried (Na$_2$SO$_4$), filtered and concentrated in vacuo. The resulting crude residue was purified via MPLC (ISCO 40 g) with gradient elution 0-100% EtOAc in hexanes. The desired fractions were combined, concentrated and dried in vacuo to afford methyl 3-cyclopropyl-3-(4-hydroxy-3-(hydroxymethyl)phenyl)propanoate.

Step 3: methyl 3-(3-(acetoxymethyl)-4-hydroxyphenyl)-3-cyclopropylpropanoate

Pyridine (97 µl, 1.199 mmol) was added dropwise to a stirred, 0° C. mixture of methyl 3-cyclopropyl-3-(4-hydroxy-3-(hydroxymethyl)phenyl)propanoate (300 mg, 1.199 mmol) in CH$_2$Cl$_2$ (2397 µl). Then acetyl chloride (85 µl, 1.199 mmol) was added dropwise, and the reaction was stirred at 0° C. for 2 h. Then the reaction was partitioned between dichloromethane and aqueous ammonium chloride (sat.). The organic layer was separated, washed with brine, dried over anhydrous MgSO$_4$, filtered and evaporated to afford Intermediate 7 as a crude residue, which was used in the next step without further purification.

Using the appropriate starting material and a method similar to that outlined in the synthesis of Intermediate 7, the following intermediates were prepared:

Intermediate 11

2-fluoro-5-methoxy-4'-(2-methoxyvinyl)-1,1'-biphenyl

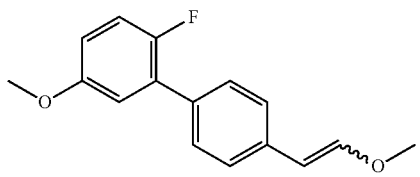

Step 1: 2'-fluoro-5'-methoxy-[1,1'-biphenyl]-4-carbaldehyde

2-Fluoro-5-methoxyphenylboronic acid (12.35 g, 72.6 mmol), 4-bromobenzaldehyde (11.2 g, 60.5 mmol) and 1,1'-bis(di-tert-butylphosphino)ferrocene palladium dichloride (793 mg, 1.217 mmol) were dissolved in DMF (70 ml) and 50% K$_3$PO$_4$ (aq., 77 ml, 182 mmol) was added. The mixture was degassed, purged with N$_2$ for 5 min, and heated at 90° C. for 30 min. The reaction was then heated overnight at 60° C. Then the mixture was quenched with water and extracted with EtOAc (2×). The combined EtOAc layers were washed with water and brine, dried over anhydrous MgSO$_4$ and filtered through a pad of Celite™ on top of silica gel, and washed with EtOAc. The combined filtrates were evaporated to give a crude material, which was purified by silica gel chromatography (gradient elution 0% to 30% EtOAc in hexanes) to afford 2'-fluoro-5'-methoxy-[1,1'-biphenyl]-4-carbaldehyde.

| Intermediate Number | Starting Material | Structure |
|---|---|---|
| 8 | | 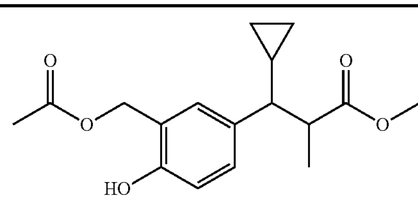 |
| 9 | | 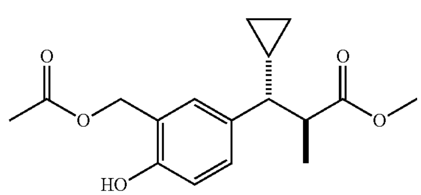 [SMILES: COC(=O)[C@@H](C)[C@H](c1ccc(O)c(COC(C)=O)c1)C1CC1] |
| 10 | | 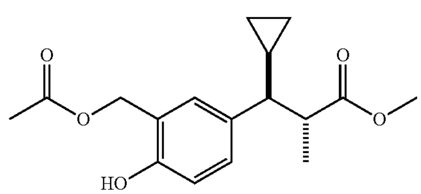 [SMILES: COC(=O)[C@H](C)[C@@H](c1ccc(O)c(COC(C)=O)c1)C1CC1] |

Step 2: 2-fluoro-5-methoxy-4'-(2-methoxyvinyl)-1, 1'-biphenyl

Potassium tert-butoxide (1M in THF, 8.69 ml, 8.69 mmol) was added dropwise over 15 minutes to a stirred, 0° C. mixture of 2'-fluoro-5'-methoxy-[1,1'-biphenyl]-4-carbaldehyde (1000 mg, 4.34 mmol) and (methoxymethyl)triphenylphosphonium chloride (2978 mg, 8.69 mmol) in THF (15 ml). The mixture was stirred at 0° C. for 30 min, then hexanes (75 mL) was added with stirring and the reaction mixture was allowed to age without stirring overnight. Then the reaction mixture was filtered through a pad of silica gel and the filter pad was washed with 3:1 hexanes:EtOAc. The combined filtrates were concentrated to afford a crude residue. The resulting residue was purified via column chromatography on silica gel (ISCO RediSep 80 g silica gel column, gradient elution with 0% to 50% EtOAc in hexanes) to give 2-fluoro-5-methoxy-4'-(2-methoxyvinyl)-1,1'-biphenyl (Intermediate 11) as a mixture of cis/trans isomers.

Using the appropriate aldehyde starting material, and a method similar to that outlined in the preparation of Intermediate 11, the following intermediates were prepared:

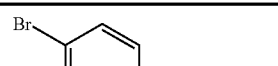

Intermediate 14 (Method A)

methyl 3-cyclopropyl-3-(3-(2'-fluoro-5'-methoxy-[1, 1'-biphenyl]-4-yl)-2-methoxychroman-6-yl)propanoate Boron trifluoride diethyl etherate (0.178 ml, 1.403 mmol) was added dropwise to a stirred, 0° C. mixture of 2-fluoro-5-methoxy-4'-(2-methoxyvinyl)-1,1'-biphenyl (Intermediate 11, 145 mg, 0.561 mmol) and methyl 3-cyclopropyl-3-(4-hydroxy-3-(hydroxymethyl)phenyl)propanoate (Intermediate 7, 141 mg, 0.561 mmol) in DCM (3 ml). The resulting mixture was stirred at 0° C. for 1 hour, then triethylsilane (0.377 ml, 2.358 mmol) was added dropwise and the reaction was stirred at 0° C. for 20 minutes. Then the reaction was partitioned between dichloromethane and saturated aqueous ammonium chloride. The organic layer was separated, washed with brine, dried over anhydrous sodium sulfate, filtered and concentrated. The resulting residue was purified via column chromatography on silica gel (ISCO RediSep 24 g silica gel column, gradient elution with 0% to 50% EtOAc in hexanes) to give methyl 3-cyclopropyl-3-(3-(2'-fluoro-5'-methoxy-[1,1'-biphenyl]-4-yl)-2-methoxychroman-6-yl)propanoate (Intermediate 14).

Intermediate 14 (Method B)

methyl 3-cyclopropyl-3-(3-(2'-fluoro-5'-methoxy-[1, 1'-biphenyl]-4-yl)-2-methoxychroman-6-yl)propanoate A neat mixture of methyl 3-(3-(acetoxymethyl)-4-hydroxyphenyl)-3-cyclopropyl-propanoate (Intermediate 7, 350 mg, 1.197 mmol) and 2-fluoro-5-methoxy-4'-(2-methoxyvinyl)-1,1'-biphenyl (Intermediate 11, 618 mg, 2.395 mmol) was heated at 120° C. in a 20 mL scintillation vial with a pressure release cap for 1 h. The reaction was then cooled to room temperature and allowed to sit overnight. The reaction mixture was dissolved in a minimal amount of methylene chloride and was purified via column chromatography on silica gel (ISCO RediSep 40 g silica gel column, gradient elution with 0% to 60% EtOAc in hexanes) to give methyl 3-cyclopropyl-3-(3-(2'-fluoro-5'-methoxy-[1, 1'-biphenyl]-4-yl)-2-methoxychroman-6-yl)propanoate (Intermediate 14).

Utilizing the appropriate starting materials, and a procedure similar to that outlined in the preparation of Intermediate 14, Method B, the following intermediates were prepared:

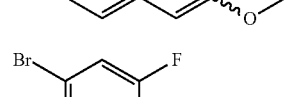

-continued
| | | |
|---|---|---|
| 17 | 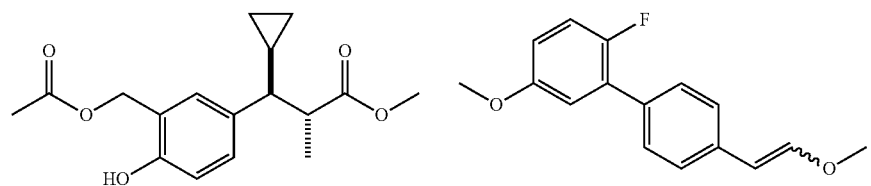 | |
| 18 | 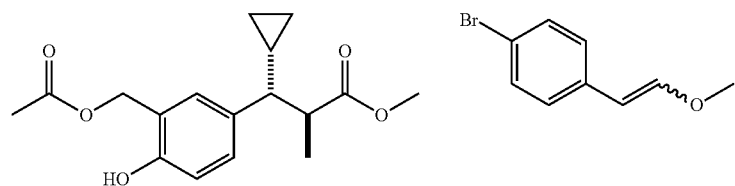 | |
| 19 | 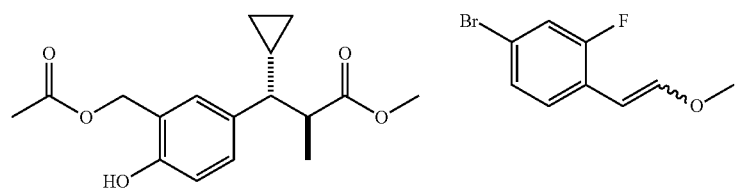 | |
| Intermediate Number | Structure |
|---|---|
| 15 | 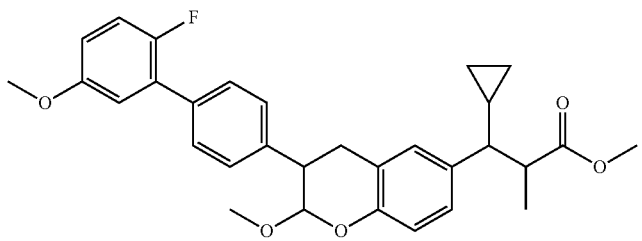 |
| 16 | 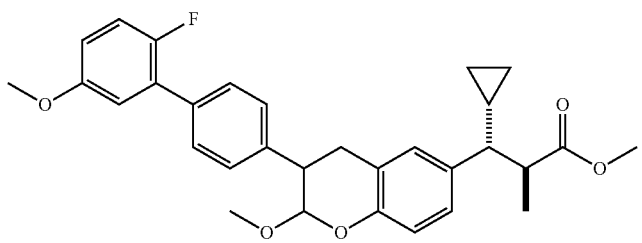 |
| 17 | 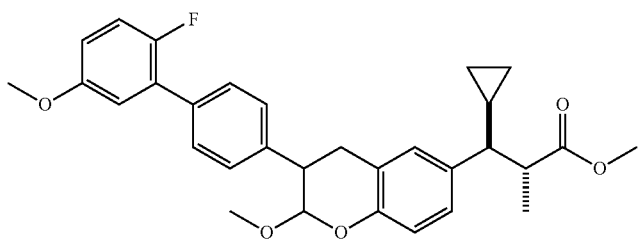 |
| 18 | 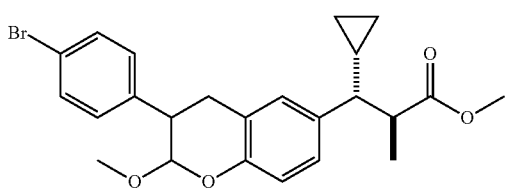 [SMILES: COC(=O)[C@@H](C)[C@H](c1ccc2c(c1)CC(c1ccc(Br)cc1)C(OC)O2)C1CC1] |

19

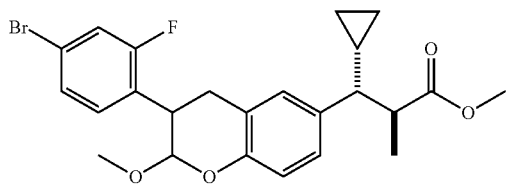 [SMILES: COC(=O)[C@@H](C)[C@H](c1ccc2c(c1)CC(c1ccc(Br)cc1F)C(OC)O2)C1CC1]

Intermediate 20 (Method A)

methyl 3-cyclopropyl-3-(3-(2'-fluoro-5'-methoxy-[1,1'-biphenyl]-4-yl)chroman-6-yl)propanoate Boron trifluoride diethyletherate (10.98 µl, 0.087 mmol) was added to a stirred, 0° C. mixture of methyl 3-cyclopropyl-3-(3-(2'-fluoro-5'-methoxy-[1,1'-biphenyl]-4-yl)-2-methoxychroman-6-yl)propanoate (Intermediate 14, 17 mg, 0.035 mmol) and triethylsilane (50 µl, 0.313 mmol) in DCM (693 µl). The mixture was stirred at 0° C. for 10 min., then allowed to warm to room temperature. After 3.25 h, an additional 2 drops (approximately 20 µl) of BF$_3$.Et$_2$O were added and the reaction was stirred for 2 h. The reaction was then partitioned between dichloromethane and saturated aqueous ammonium chloride. The organic layer was separated, dried over anhydrous Na$_2$SO$_4$, filtered and evaporated to afford a crude residue. The resulting residue was purified via column chromatography on silica gel (ISCO RediSep 12 g silica gel column, gradient elution with 0% to 60% EtOAc in hexanes) to give a partially pure material. The product-containing fractions were subjected to silica gel prep TLC (20 cm×20 cm plate, 1 mm thickness, 6:1 hexanes:EtOAc) to afford methyl 3-cyclopropyl-3-(3-(2'-fluoro-5'-methoxy-[1,1'-biphenyl]-4-yl)chroman-6-yl)propanoate (Intermediate 20).

Intermediate 20 (Method B)

methyl 3-cyclopropyl-3-(3-(2'-fluoro-5'-methoxy-[1,1'-biphenyl]-4-yl)chroman-6-yl)propanoate

Step 1: methyl 3-cyclopropyl-3-(3-(2'-fluoro-5'-methoxy-[1,1'-biphenyl]-4-yl)-4H-chromen-6-yl)propanoate A mixture of methyl 3-cyclopropyl-3-(3-(2'-fluoro-5'-methoxy-[1,1'-biphenyl]-4-yl)-2-methoxychroman-6-yl)propanoate (Intermediate 20, 335 mg, 0.683 mmol), p-toluenesulfonic acid monohydrate (44 mg, 0.231 mmol) and 3 angstrom molecular sieves (1 g) in toluene (5 ml) in a 40 dram vial with pressure release cap was heated in a 120° C. oil bath. After 3 h, 6 mL toluene and TsOH.H$_2$O (62 mg) were added and heating was continued for 2 h. The reaction was then cooled to room temperature, filtered through Celite™ and the pad was washed with toluene. Then, TsOH.H$_2$O (108 mg) was added to the filtrate, and the mixture was heated at reflux overnight. The mixture was then cooled to room temperature and concentrated. The resulting residue was purified via column chromatography on silica gel (ISCO RediSep 24 g silica gel column, gradient elution with 0% to 50% EtOAc in hexanes) to give methyl 3-cyclopropyl-3-(3-(2'-fluoro-5'-methoxy-[1,1'-biphenyl]-4-yl)-4H-chromen-6-yl)propanoate.

Step 2: methyl 3-cyclopropyl-3-(3-(2'-fluoro-5'-methoxy-[1,1'-biphenyl]-4-yl)chroman-6-yl)propanoate Methyl 3-cyclopropyl-3-(3-(2'-fluoro-5'-methoxy-[1,1'-biphenyl]-4-yl)-4H-chromen-6-yl)propanoate (30 mg, 0.065 mmol) was dissolved in ethyl acetate (3 ml) and the solution was purged with nitrogen. Palladium on carbon (10% on carbon, 6.96 mg, 0.065 mmol) was added and the mixture was purged with hydrogen. A hydrogen balloon was affixed to the top of the flask and the reaction was stirred for 3 h at room temp. The reaction was then purged with nitrogen and the mixture was filtered through Celite™. The filtrate was concentrated to afford a crude residue. The resulting residue was purified via column chromatography on silica gel (ISCO RediSep 12 g silica gel column, gradient elution with 0% to 30% EtOAc in hexanes) to give methyl 3-cyclopropyl-3-(3-(2'-fluoro-5'-methoxy-[1,1'-biphenyl]-4-yl)chroman-6-yl)propanoate.

Intermediate 21 methyl 3-cyclopropyl-3-(3-(2'-fluoro-5'-methoxy-[1,1'-biphenyl]-4-yl)chroman-6-yl)-2-methylpropanoate Trifluoroacetic acid (1 ml, 12.98 mmol), followed by triethylsilane (0.5 ml, 3.13 mmol) was added to a stirred, room temperature mixture of methyl 3-cyclopropyl-3-(3-(2'-fluoro-5'-methoxy-[1,1'-biphenyl]-4-yl)-2-methoxychroman-6-yl)-2-methylpropanoate (Table 3, 15 mg, 0.030 mmol) in CH$_2$Cl$_2$ (1 ml). The mixture was stirred at room temperature for 1 h, then carefully poured into a mixture of dichloromethane (30 mL) and saturated aqueous sodium bicarbonate (30 mL) and stirred for 2 h. The layers were separated and the aqueous layer was extracted with CH$_2$Cl$_2$. The organic layers were combined, washed with brine, dried over anhydrous MgSO$_4$, filtered and evaporated to afford a crude residue. The resulting residue was purified via column chromatography on silica gel (ISCO RediSep 4 g silica column, gradient elution with 0% to 60% EtOAc in hexanes) to give methyl 3-cyclopropyl-3-(3-(2'-fluoro-5'-methoxy-[1,1'-biphenyl]-4-yl)chroman-6-yl)-2-methylpropanoate (Intermediate 21) as a mixture of isomers.

Utilizing the requisite starting material and a method similar to that outlined in the synthesis of Intermediate 21, the following Intermediates were prepared:

| Intermediate Number | Starting Material | Structure |
|---|---|---|
| 22 | | 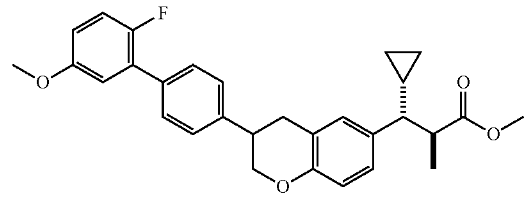 |
| 23 | | 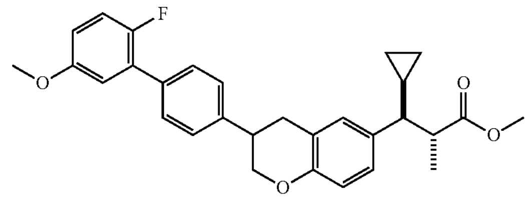 |
| 24 | | 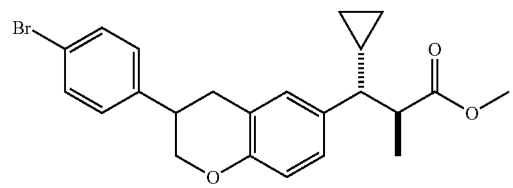 [SMILES: COC(=O)[C@@H](C)[C@H](c1ccc2c(c1)CC(c1ccc(Br)cc1)CO2)C1CC1] |
| 25 | | 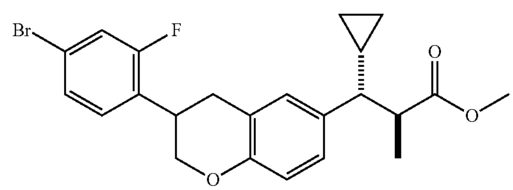 [SMILES: COC(=O)[C@@H](C)[C@H](c1ccc2c(c1)CC(c1ccc(Br)cc1F)CO2)C1CC1] |

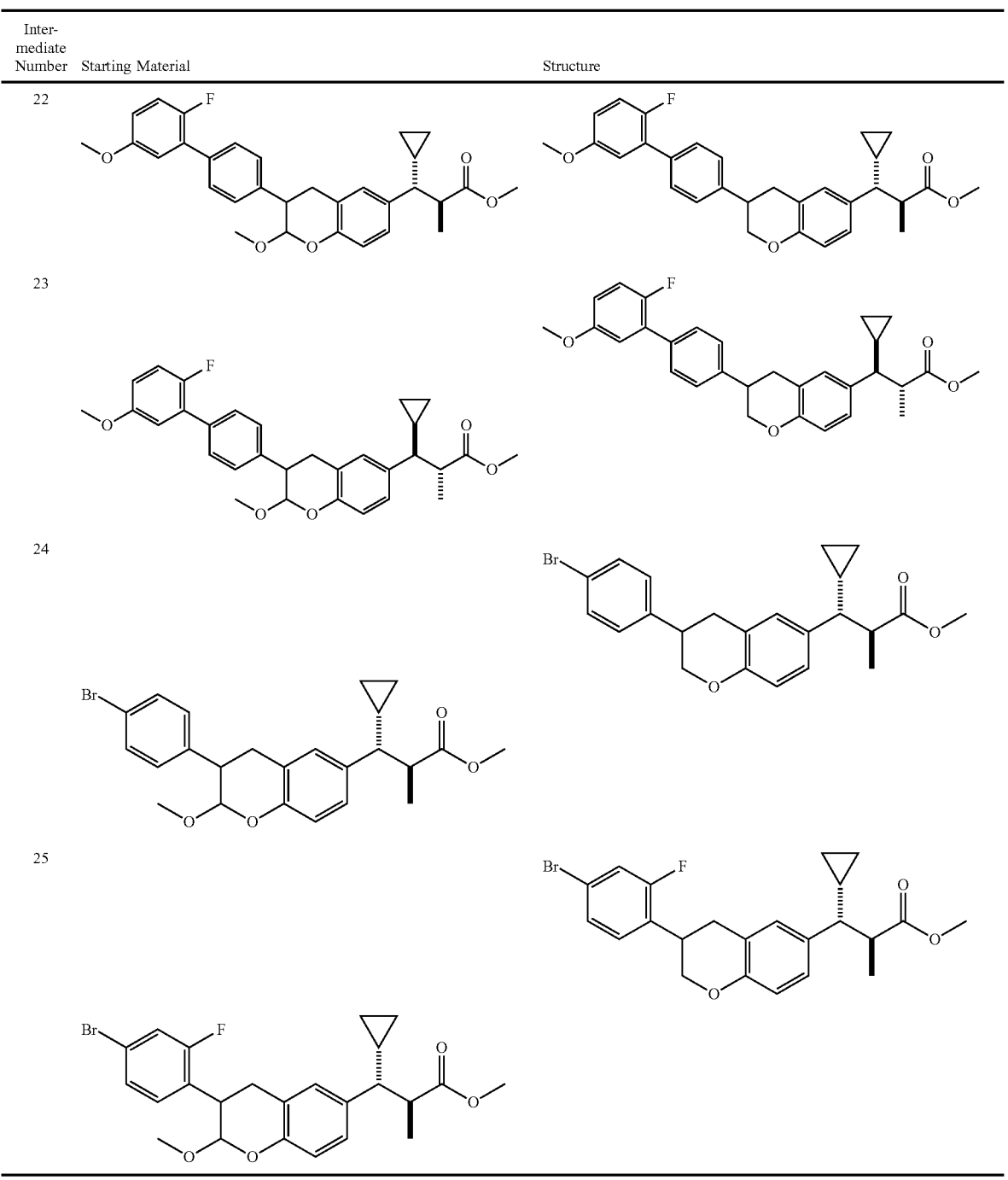

Intermediate 26

(2S,3R)-methyl 3-cyclopropyl-3-(3-(4-(5-fluoro-2-methoxypyridin-4-yl)phenyl)chroman-6-yl)-2-methylpropanoate A mixture of 2nd Generation Palladium SPHOS precatalyst (8.39 mg, 0.012 mmol), Intermediate 24 (100 mg, 0.233 mmol) and (5-fluoro-2-methoxypyridin-4-yl)boronic acid (59.7 mg, 0.349 mmol) in THF (2 ml) was purged with nitrogen. Then 2M aqueous $K_3PO_4$ (0.349 ml, 0.699 mmol) was added, and the mixture was purged with nitrogen, capped and heated at 80° C. for 18 h. Then anhydrous sodium sulfate was added to the mixture, followed by $CH_2Cl_2$ (2 mL). The reaction mixture was decanted and loaded onto a ISCO RediSep 24 g silica gel column. The remaining sodium sulfate residue was triturated with 1 mL $CH_2Cl_2$ and the liquid was added to the ISCO column. The column was dried with a nitrogen stream and then subjected to gradient elution with 0% to 100% EtOAc in hexanes to give (2S,3R)-methyl 3-cyclopropyl-3-(3-(4-(5-fluoro-2-methoxypyridin-4-yl)phenyl)chroman-6-yl)-2-methylpropanoate.

Using the appropriate aryl boronic acid, aryl halide and a method similar to that outlined in the synthesis of Intermediate 26, the following intermediates were prepared:

| Intermediate Number | Bromide Starting Material | Structure |
|---|---|---|
| 27 | 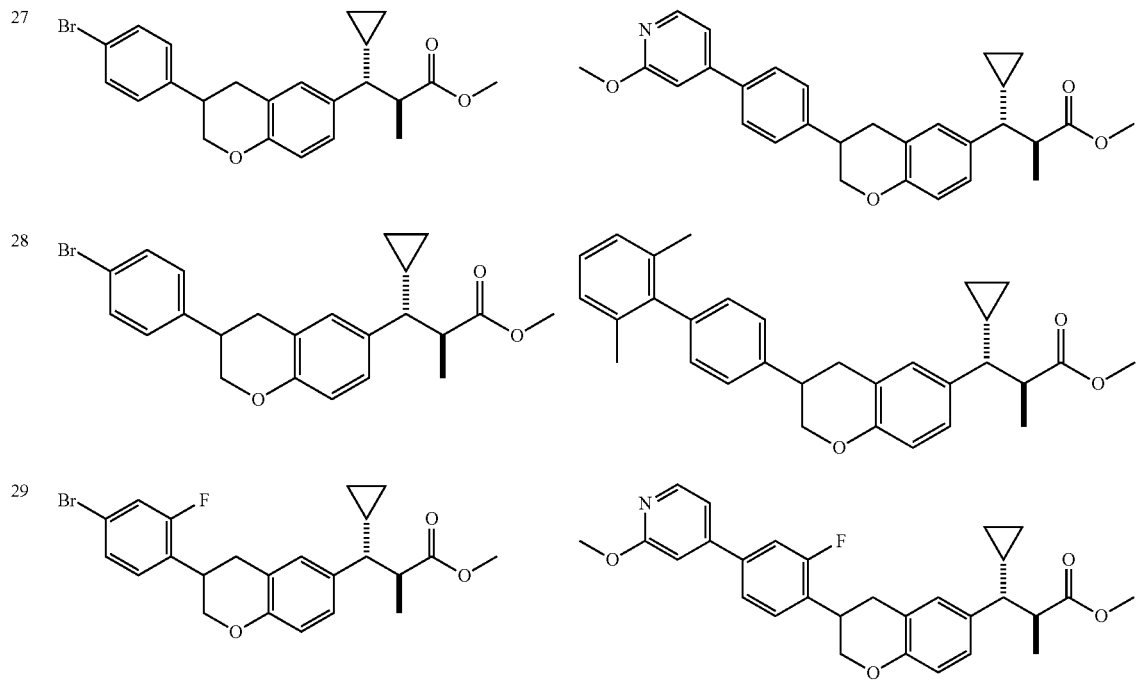 | 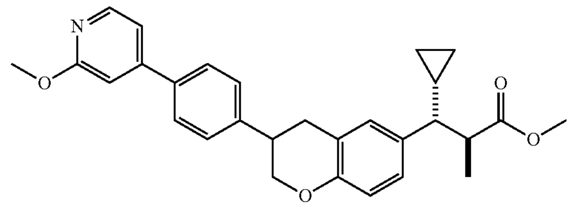 |
| 28 | | 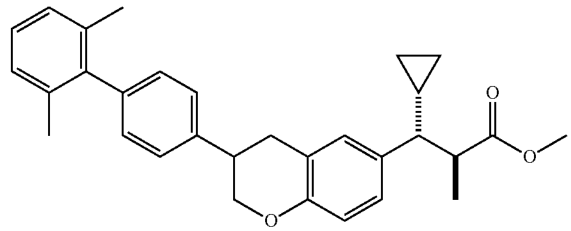 [SMILES: COC(=O)[C@@H](C)[C@H](c1ccc2c(c1)CC(c1ccc(-c3c(C)cccc3C)cc1)CO2)C1CC1] |
| 29 | | 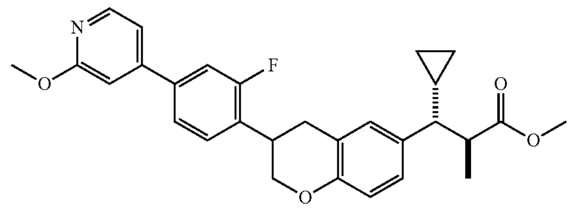 |

Intermediate 30

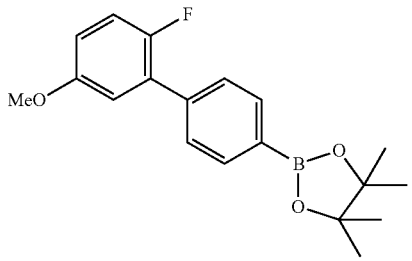 [SMILES: COc1ccc(F)c(-c2ccc(B3OC(C)(C)C(C)(C)O3)cc2)c1]

Step A

To a solution of 2-(2-fluoro-5-methoxyphenyl)-4,4,5,5-tetramethyl-1,3,2-dioxaborolane (5.0 g, 19.83 mmol) in 1,4-dioxane (50 ml) and water (10 ml) were added 1-bromo-4-iodobenzene (5.61 g, 19.83 mmol), K$_2$CO$_3$ (8.22 g, 59.5 mmol) and PdCl$_2$(dppf) (1.451 g, 1.983 mmol) at room temperature under a nitrogen atmosphere. The mixture was then warmed to 100° C. and stirred for 4 hours. The mixture was then cooled to room temperature, diluted with water (10 mL) and extracted with EtOAc (5.0 mL×3). The organic layers were separated, dried over anhydrous MgSO$_4$ and filtered. The filtrate was concentrated in vacuo to give a residue, which was purified by flash column chromatography on silica gel (PE:EtOAc=30:1 to 20:1) to give 4'-bromo-2-fluoro-5-methoxy-1,1'-biphenyl.

Step B

To a solution of 4'-bromo-2-fluoro-5-methoxy-1,1'-biphenyl (2.00 g, 7.11 mmol) in DMF (20 ml) were added 4,4,4',4',5,5,5',5'-octamethyl-2,2'-bi(1,3,2-dioxaborolane) (2.168 g, 8.54 mmol), potassium acetate (2.095 g, 21.34 mmol) and PdCl$_2$(dppf) (0.521 g, 0.711 mmol) under a nitrogen atmosphere. Then the reaction mixture was stirred at 90° C. for 5 h. After cooling to room temperature, the reaction mixture was diluted with water (10 mL), then extracted with EtOAc (5 mL×3). The organic layers were combined, washed with brine (5.0 mL), dried over anhydrous MgSO$_4$ and filtered. The filtrate was concentrated to give a residue, which was purified by flash column chromatography on silica gel (PE:EtOAc=20:1 to 10:1) to give the compound 2-(2'-fluoro-5'-methoxy-[1,1'-biphenyl]-4-yl)-4,4,5,5-tetramethyl-1,3,2-dioxaborolane.

Intermediate 31

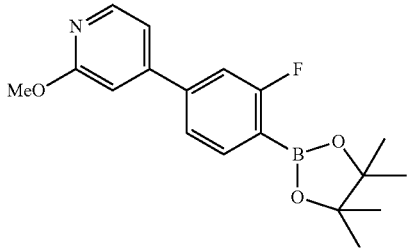 [SMILES: COc1cc(-c2ccc(B3OC(C)(C)C(C)(C)O3)c(F)c2)ccn1]

Step A

To a mixture of (2-methoxypyridin-4-yl)boronic acid (2.0 g, 13.08 mmol) in THF (30 ml) and water (6.0 mL) was added 4-bromo-2-fluorophenol (3.00 g, 15.69 mmol), K₂CO₃ (5.42 g, 39.2 mmol) and PdCl₂(dppf) (0.957 g, 1.308 mmol) under a nitrogen atmosphere. The reaction mixture was stirred at 100° C. for 4 h, and then cooled to room temperature. Water (40 mL) was added to the mixture, and the mixture was extracted with EtOAc (30 mL×3). The combined organic layers were washed with water (50 mL) and brine (50 mL), dried over anhydrous MgSO₄ and filtered. The filtrate was concentrated under reduced pressure. The resulting residue was purified by silica gel chromatography eluting with PE/EtOAc (50:1-10:1, v/v) to give compound 2-fluoro-4-(2-methoxypyridin-4-yl)phenol.

Step B

To a solution of 2-fluoro-4-(2-methoxypyridin-4-yl)phenol (2.2 g, 10.04 mmol) in DCM (30 ml) was added TEA (4.20 ml, 30.1 mmol) under nitrogen at 25° C. The mixture was cooled to 0° C. and trifluoromethanesulfonic anhydride (4.25 g, 15.05 mmol) was added dropwise. Then the reaction was stirred at 0° C. for 1 h, and at 25° C. for 1 h. The reaction was then quenched with water (40 mL) at 0° C. The aqueous layer was separated and extracted with DCM (25 mL×3). The combined organic layers were washed with water (40 mL) and brine (40 mL), dried over anhydrous MgSO₄ and filtered. The filtrate was concentrated under reduced pressure. The resulting residue was purified by silica gel chromatography eluting with PE/EtOAc (50:1~30:1, v/v)) to give 2-fluoro-4-(2-methoxypyridin-4-yl)phenyl trifluoromethanesulfonate.

Step C

To a solution of 2-fluoro-4-(2-methoxypyridin-4-yl)phenyl trifluoromethane-sulfonate (3.1 g, 8.83 mmol) in 1,4-dioxane (50 ml) was added potassium acetate (2.165 g, 22.06 mmol) and PdCl₂(dppf) (0.646 g, 0.883 mmol) under nitrogen. The reaction mixture was stirred at 100° C. for 2 h, and then cooled to room temperature. Then water (50 mL) was added to the mixture. The resulting mixture was extracted with EtOAc (50 mL×3). The combined organic layers were washed with water (100 mL) and brine (100 mL), dried over anhydrous MgSO₄ and filtered. The filtrate was concentrated under reduced pressure. The resulting residue was purified by silica gel chromatography eluted with PE/EtOAc (1:0-30:1, v/v)) to give compound 4-(3-fluoro-4-(4,4,5,5-tetramethyl-1,3,2-dioxaborolan-2-yl)phenyl)-2-methoxypyridine.

Intermediate 32

4-Bromo-2-fluoro-N-methoxy-N-methylbenzamide

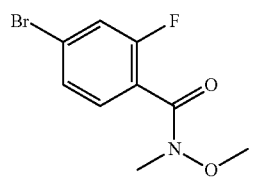

To a solution of 4-bromo-2-fluorobenzoic acid (26.8 g, 122 mmol) in DCM (260 mL) was added CDI (23.8 g, 147 mmol) portionwise over 10 min under a nitrogen atmosphere. The reaction mixture was stirred for 1 h at 25° C. To this mixture was added N,O-dimethyl-hydroxylamine hydrochloride (14.3 g, 147 mmol) and Et₃N (37.1 g, 367 mmol). The mixture was stirred for 16 h at 25° C., then quenched by adding H₂O (100 mL). The organic layer was extracted with DCM (50 mL×2). The combined organic layers were washed with aqueous HCl (2 M), then saturated aqueous NaHCO₃ (100 mL) and finally saturated brine. The organic layer was then dried over anhydrous Na₂SO₄ and filtered. The filtrate was concentrated by rotary evaporator. The resulting residue was purified by flash column chromatography (silica gel, DCM) to give the title compound. ¹H NMR (400 MHz, CDCl₃): δ=7.37-7.30 (m, 3H), 3.54 (br. s, 3H), 3.35 (br. s., 3H)

Intermediate 33

2-Fluoro-N-methoxy-4-(2-methoxypyridin-4-yl)-N-methylbenzamide

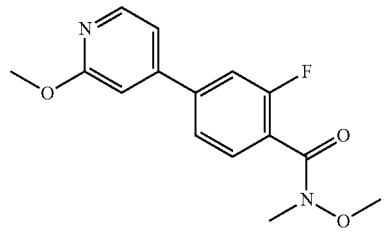

To a flask was added 4-bromo-2-fluoro-N-methoxy-N-methylbenzamide (1.00 g, 3.82 mmol, intermediate 32), (2-methoxypyridin-4-yl)boronic acid (0.700 g, 4.58 mmol), [1,1'-bis(diphenyl-phosphino)ferrocene]dichloropalladium (II) (0.140 g, 0.191 mmol) and K₂CO₃ (1.32 g, 9.54 mmol). The flask was evacuated and refilled with nitrogen three times, then THF (10 mL) and H₂O (2 mL) were added. The reaction mixture was heated to 100° C. for 12 h, then cooled to rt, and diluted with EtOAc (20 mL). The aqueous layer was separated, and extracted with EtOAc (10 mL×2). The combined organic layers were washed with brine (10 mL), dried over anhydrous Na₂SO₄ and filtered. The filtrate was concentrated by rotary evaporator. The resulting residue was purified by flash column chromatography (silica gel, PE:EtOAc=5:1, v/v) to give the title compound. ¹H NMR (400 MHz, CDCl₃): δ=8.25 (d, J=5.6 Hz, 1H), 7.55 (t, J=7.4 Hz, 1H), 7.45 (d, J=7.8 Hz, 1H), 7.36 (d, J=10.8 Hz, 1H), 7.08 (d, J=5.5 Hz, 1H), 6.94 (s, 1H), 4.00 (s, 3H), 3.59 (br. s., 3H), 3.39 (br. s., 3H).

Intermediate 34

4-Bromo-N,N-diethyl-2-(2-(2-fluoro-4-(2-methoxypyridin-4-yl)phenyl)-2-oxoethyl)benzamide

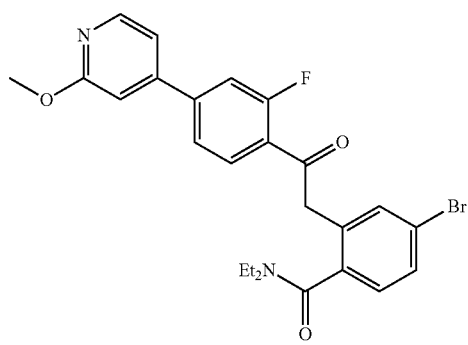

4-Bromo-N, N-diethyl-2-methylbenzamide (12.3 g, 45.5 mmol) was dissolved in anhydrous THF (120 mL) under a nitrogen atmosphere. The reaction mixture was cooled to −70° C. in a dry ice-acetone bath. LDA (27.3 mL, 54.6 mmol) was added dropwise over 15 min, and the reaction was stirred at −70° C. for 1.5 h. Then a solution of 2-fluoro-N-methoxy-4-(2-methoxypyridin-4-yl)-N-methylbenzamide (11.0 g, 37.9 mmol, intermediate 33) in anhydrous THF (120 mL) was added dropwise over 15 min while maintaining the temperature below −60° C. After stirring at −70° C. for 0.5 h, the reaction was quenched by the addition of water (100 mL). The reaction mixture was extracted with EtOAc (100 mL×3). The combined organic layers were washed with saturated brine (100 mL), dried over anhydrous $Na_2SO_4$ and filtered. The filtrate was concentrated by rotary evaporator. The resulting residue was purified by flash column chromatography (silica gel, PE:EtOAc=20:1-2:1, v/v) to give the title compound. $^1H$ NMR (400 MHz, $CDCl_3$): δ=8.27 (d, J=5.2 Hz, 1H), 7.95 (t, J=7.8 Hz, 1H), 7.51-7.44 (m, 3H), 7.41 (d, J=12.4 Hz, 1H), 7.15 (d, J=7.8 Hz, 1H), 7.09 (d, J=5.2 Hz, 1H), 6.96 (s, 1H), 4.44 (br. s, 1H), 4.01 (s, 3H), 3.55-3.35 (m, 2H), 3.29-3.18 (m, 2H), 1.12 (t, J=7.0 Hz, 3H), 1.06 (t, J=7.0 Hz, 3H).

Intermediate 35

4-Bromo-N,N-diethyl-2-(2-(2-fluoro-4-(2-methoxypyridin-4-yl)phenyl)-2-hydroxyethyl)benzamide

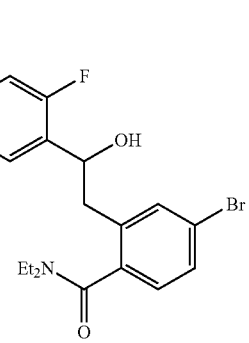

4-Bromo-N,N-diethyl-2-(2-(2-fluoro-4-(2-methoxypyridin-4-yl)-phenyl)-2-oxoethyl)benzamide (14.2 g, 28.4 mmol, intermediate 34) was dissolved in anhydrous MeOH (150 mL) under a nitrogen atmosphere. The solution was cooled to 0° C. prior to addition of $NaBH_4$ (1.29 g, 34.1 mmol) over 5 min. Upon complete addition, the reaction was stirred at rt for 30 min. Then the reaction mixture was concentrated by rotary evaporation. The resulting residue was dissolved in 30 mL of EtOAc, washed with saturated brine (15 mL×3) three times, dried over anhydrous $Na_2SO_4$ and filtered. The filtrate was concentrated by rotary evaporation to give the title compound. LC/MS: m/e 501.2 $(M+H)^+$.

Intermediate 36

6-Bromo-3-(2-fluoro-4-(2-methoxypyridin-4-yl)phenyl)isochroman-1-one

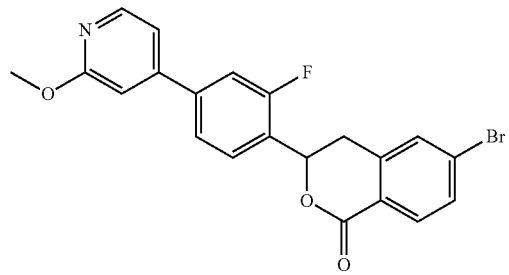 [SMILES: COc1cc(-c2ccc(C3Cc4cc(Br)ccc4C(=O)O3)c(F)c2)ccn1]

To a solution of Intermediate 35 (14.2 g, 28.3 mmol) in toluene (200 mL) was added p-toluenesulfonic acid monohydrate (8.0 g, 43 mmol). The suspension was stirred for 12 h at 110° C. To the resulting suspension were added 50 mL of DCM, and $Et_3N$ to neutralize the solution to pH 7. The resulting solution was washed with saturated brine (50 mL×2). The organic layer was separated, dried over anhydrous $Na_2SO_4$ and filtered. The filtrate was then concentrated under reduced pressure. The resulting material was purified by flash column chromatography (silica gel, DCM) to give the title compound. $^1H$ NMR (400 MHz, $CDCl_3$): δ=8.25 (d, J=5.5 Hz, 1H), 8.04 (d, J=8.2 Hz, 1H), 7.74 (t, J=8.2 Hz, 1H), 7.61 (d, J=8.2 Hz, 1H), 7.54-7.46 (m, 2H), 7.37 (d, J=11.0 Hz, 1H), 7.09 (d, J=4.7 Hz, 1H), 6.94 (s, 1H), 5.89 (dd, J=3.1, 11.7 Hz, 1H), 4.00 (s, 3H), 3.37-3.18 (m, 2H)

Intermediate 37

2-(5-Bromo-2-(hydroxymethyl)phenyl)-1-(2-fluoro-4-(2-methoxypyridin-4-yl)phenyl)ethanol

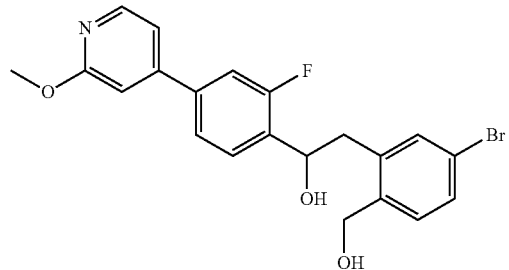 [SMILES: COc1cc(-c2ccc(C(O)Cc3cc(Br)ccc3CO)c(F)c2)ccn1]

A suspension of intermediate 36 (9.50 g, 22.2 mmol) in anhydrous THF (400 mL) was cooled to 0° C. under a nitrogen atmosphere. $LiAlH_4$ (1.010 g, 26.6 mmol) was added portionwise over 20 min. The resulting solution was stirred for 30 min at 0° C., then for 30 min at 10° C. The reaction was cooled to 0° C. and quenched slowly by the addition of 1 mL of $H_2O$, followed by the addition of 1 mL of 15% (wt %) NaOH aqueous solution, and 3 mL of $H_2O$. After stirring for 15 min, 10 g of anhydrous $MgSO_4$ was added and the resulting mixture was filtered. The filtrate was washed with 50 mL of saturated $NH_4Cl$ solution and 50 mL of brine. The organic layer was separated, dried over $Na_2SO_4$ and filtered. The filtrate was concentrated by rotary evaporator to give the title compound. ¹H NMR (400 MHz, CDCl₃): δ=8.23 (d, J=5.2 Hz, 1H), 7.62 (t, J=7.8 Hz, 1H), 7.45 (d, J=8.2 Hz, 1H), 7.42-7.38 (m, 2H), 7.34 (d, J=11.2 Hz, 1H), 7.24 (d, J=8.6 Hz, 1H), 7.09 (d, J=5.2 Hz, 1H), 6.97-6.93 (m, 1H), 5.28 (dd, J=2.8, 9.0 Hz, 1H), 4.79 (d, J=11.6 Hz, 1H), 4.58 (d, J=11.6 Hz, 1H), 4.00 (s, 3H), 3.27 (br.s, 1H), 3.16-3.03 (m, 2H).

Intermediate 38

4-(4-(6-Bromoisochroman-3-yl)-3-fluorophenyl)-2-methoxypyridine

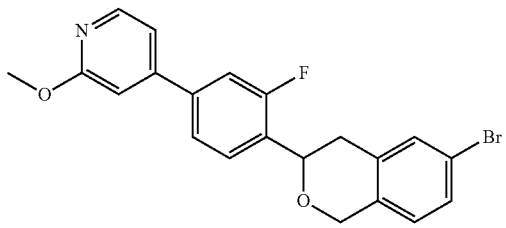 [SMILES: COc1cc(-c2ccc(C3Cc4cc(Br)ccc4CO3)c(F)c2)ccn1]

A solution of intermediate 37 (800 mg, 1.85 mmol) in phosphoric acid (20 mL, 102 mmol) was heated to 100° C. for 3 h. Then the solution was cooled to rt and poured into ice water. Saturated aqueous NaHCO₃ solution was added to neutralize the mixture to pH 7. Then EtOAc (15 mL×3) was added to extract the organic material. The combined organic layers were separated, washed with brine (15 mL×2), dried over anhydrous Na₂SO₄ and filtered. The filtrate was concentrated by rotary evaporator. The resulting residue was purified by flash column chromatography (silica gel, DCM) to give the title compound. 1H NMR (400 MHz, CDCl₃): δ=8.24 (d, J=5.6 Hz, 1H), 7.66 (t, J=7.4 Hz, 1H), 7.47 (d, J=8.2 Hz, 1H), 7.38-7.29 (m, 3H), 7.10 (d, J=4.8 Hz, 1H), 6.99-6.92 (m, 2H), 5.04 (dd, J=4.0, 10.2 Hz, 1H), 4.98-4.92 (m, 2H), 4.00 (s, 3H), 3.07-2.95 (m, 2H)

Intermediate 39

4-(3-Fluoro-4-(6-(4,4,5,5-tetramethyl-1,3,2-dioxaborolan-2-yl)isochroman-3-yl)phenyl)-2-methoxypyridine

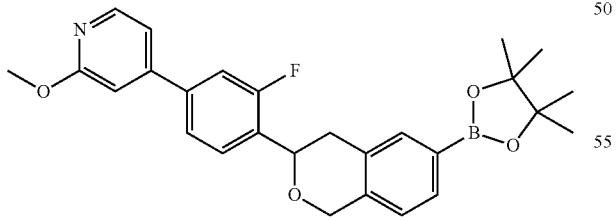

To a flask was added intermediate 38 (500 mg, 1.21 mmol), bis(pinacolato)diboron (368 mg, 1.45 mmol), potassium acetate (237 mg, 2.41 mmol) and [1,1'-bis(diphenylphosphino)-ferrocene]dichloropalladium(II) (26.5 mg, 0.04 mmol). The flask was evacuated and refilled with nitrogen three times. Then 1,4-Dioxane (10 mL) was added, and the reaction mixture was heated to 100° C. for 3 h. The mixture was cooled, diluted with EtOAc (15 mL), washed with saturated brine (10 mL), dried over anhydrous Na₂SO₄, and filtered. The filtrate was evaporated under reduced pressure. The resulting residue was purified by flash column chromatography (silica gel, PE:EtOAc=50:1, v/v) to give the title compound. ¹H NMR (400 MHz, CDCl₃): δ=8.23 (d, J=5.6 Hz, 1H), 7.67-7.64 (m, 2H), 7.62 (s, 1H), 7.47 (dd, J=1.5, 8.0 Hz, 1H), 7.33 (dd, J=1.2, 11.0 Hz, 1H), 7.12-7.07 (m, 2H), 6.95 (s, 1H), 5.10-5.07 (m, 1H), 5.06-5.03 (m, 2H), 3.99 (s, 3H), 3.07-3.04 (m, 2H), 1.37 (s, 12H)

Intermediate 40

(E)-methyl-3-cyclopropyl-3-(3-(2-fluoro-4-(2-methoxypyridin-4-yl)phenyl)isochroman-6-yl)-2-methylacrylate

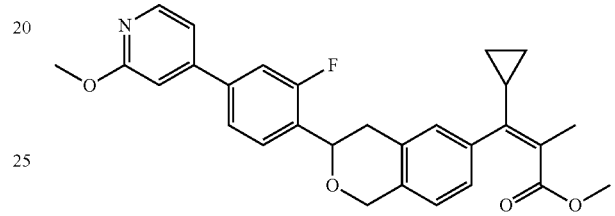

To a flask was added intermediate 39 (610 mg, 1.32 mmol), (Z)-methyl 3-cyclopropyl-2-methyl-3-(tosyloxy)acrylate (492 mg, 1.58 mmol), [1,1'-bis(diphenylphosphino)ferrocene]dichloro-palladium(II) (48.4 mg, 0.066 mmol) and K₂CO₃ (365 mg, 2.64 mmol). The flask was evacuated and refilled with nitrogen three times. Then THF (6.0 mL) and H₂O (0.6 mL) were added, and the reaction mixture was heated to 70° C. for 3 h. The reaction was cooled to room temperature. The organic layer was separated and extracted with EtOAc (30 mL). The combined organic layers were washed with brine (10 mL), dried over anhydrous Na₂SO₄ and filtered. The filtrate was concentrated by rotary evaporator. The resulting residue was purified by flash column chromatography (silica gel, PE:EtOAc=50:1, v/v) to give the title compound. ¹H NMR (400 MHz, CDCl₃): δ=8.24 (d, J=5.6 Hz, 1H), 7.67 (t, J=8.2 Hz, 1H), 7.46 (d, J=7.4 Hz, 1H), 7.33 (d, J=11.0 Hz, 1H), 7.10 (d, J=4.4 Hz, 1H), 6.98 (d, J=7.8 Hz, 1H), 6.95 (s, 1H), 6.84 (d, J=7.8 Hz, 1H), 6.75 (s, 1H), 5.08 (dd, J=6.0, 8.8 Hz, 1H), 5.01 (s, 2H), 3.99 (s, 3H), 3.43 (s, 3H), 3.01-3.00 (m, 2H), 2.16 (s, 3H), 1.89-1.83 (m, 1H), 0.76 (d, J=6.8 Hz, 2H), 0.33 (d, J=3.2 Hz, 2H).

Intermediate 41

4-Bromo-N,N-diethyl-2-methylbenzamide

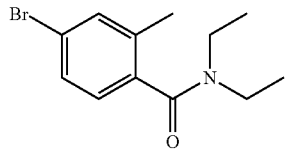

To a solution of 4-bromo-2-methylbenzoic acid (50.0 g, 233 mmol) in DCM (50 mL) was added oxalyl chloride (35.4 g, 279 mmol). The mixture was stirred for 2 h at 25° C., then concentrated and additional DCM (50 mL), diethylamine (20.4 g, 279 mmol) and triethylamine (70.6 g, 698 mmol) were added sequentially. The mixture was stirred for another 16 h at 25° C., then diluted with water (10 mL) and extracted with DCM (40 mL×3). The combined organic layers were washed with brine (20 mL), dried over $Na_2SO_4$, filtered and concentrated to afford the crude product, which was purified by flash column chromatography (PE:EtOAc=20:1 to 5:1, v/v) to give the title compound. MS (ESI) m/z: 270.2 $[M+H]^+$ Intermediate 42

4-Bromo-N-methoxy-N-methylbenzamide

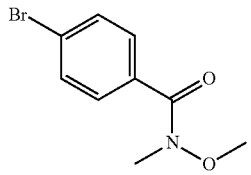

To a solution of 4-bromobenzoic acid (30.0 g, 149 mmol) in DCM (400 mL) was added CDI (29.0 g, 179 mmol). The mixture was stirred for 2 h at 25° C., then N,O-dimethylhydroxylamine hydrochloride (17.5 g, 179 mmol) and $Et_3N$ (45.3 g, 448 mmol) were added. The mixture was stirred for 16 h at 25° C., then diluted with water (100 mL) and extracted with DCM (100 mL×3). The combined organic layers were washed with brine (100 mL), dried over $Na_2SO_4$, filtered and concentrated to afford the title compound. MS (ESI) m/z: 244.1 $[M+H]^+$ $^1H$ NMR (400 MHz, $CDCl_3$): δ=7.60-7.54 (m, 4H), 3.54 (s, 3H), 3.36 (s, 3H).

Intermediate 43

4-(5-Fluoro-2-methoxypyridin-4-yl)-N-methoxy-N-methylbenzamide

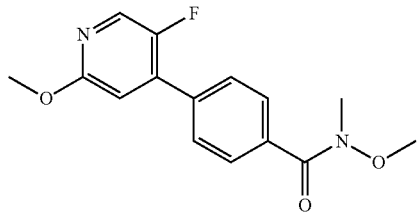

To a solution of Intermediate 42 (6.0 g, 24.6 mmol) in THF (60 mL) and $H_2O$ (12 mL) was added (5-fluoro-2-methoxypyridin-4-yl) boronic acid (5.04 g, 29.5 mmol), $K_2CO_3$ (10.3 g, 73.7 mmol) and $Pd(dppf)Cl_2$ (0.180 g, 0.246 mmol). The mixture was stirred for 2 h at 90° C., then diluted with water (10 mL), and extracted with EtOAc (40 mL×3). The combined organic layers were washed with brine (30 mL), dried over $Na_2SO_4$, filtered and concentrated to afford the crude product, which was purified by flash column chromatography (PE:EtOAc=30:1 to 3:1, v/v) to give the title compound. MS (ESI) m/z: 291.2$[M+H]^+$ $^1H$ NMR (400 MHz, $CDCl_3$): δ=8.10 (s, 1H), 7.81 (d, J=8.0 Hz, 2H), 7.64 (d, J=7.2 Hz, 2H), 6.84 (s, 1H), 3.96 (s, 3H), 3.60 (s, 3H), 3.40 (s, 3H).

Intermediate 44

4-Bromo-N,N-diethyl-2-(2-(4-(5-fluoro-2-methoxypyridin-4-yl)phenyl)-2-oxoethyl)benzamide

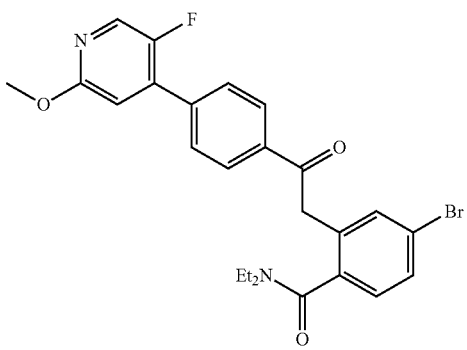

To a solution of Intermediate 41 (5.81 g, 21.5 mmol) in THF (60 mL) was added LDA (13.4 mL, 26.9 mmol) dropwise at −78° C. under a $N_2$ atmosphere. The mixture was stirred for 30 min at −78° C., then Intermediate 43 (5.2 g, 18 mmol) was added. The mixture was stirred for 1 h at −78° C., then diluted with $H_2O$ (30 mL), and extracted with EtOAc (30 mL×3). The combined organic layers were washed with brine (30 mL), dried over $Na_2SO_4$, filtered and concentrated to afford crude product, which was purified by flash column chromatography on silica gel (eluted from PE:EtOAc=50:1 to 10:1, v/v) to give the title compound. MS (ESI) m/z: 494.1 $[M+H]^+$ Intermediate 45

4-Bromo-N,N-diethyl-2-(2-(4-(5-fluoro-2-methoxypyridin-4-yl)phenyl)-2-hydroxyethyl)benzamide

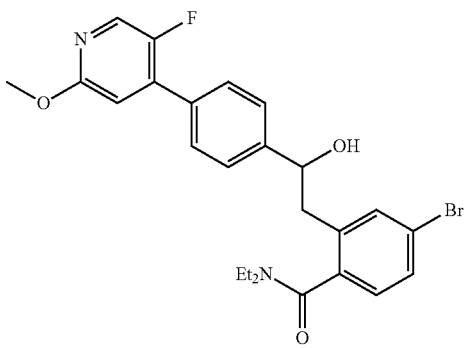

To a solution of Intermediate 44 (12.6 g, 25.2 mmol) in MeOH (150 mL) was added $NaBH_4$ (1.15 g, 30.3 mmol) portionwise at 0° C. The mixture was stirred for 2 h at 0° C. Then the solvent was removed in vacuo, and the residue was extracted with EtOAc (100 mL×3). The combined organic layers were washed with brine (100 mL), dried over $Na_2SO_4$, filtered and concentrated to afford the title compound. MS (ESI) m/z: 501.3$[M+H]^+$

Intermediate 46

(R,S)-6-Bromo-3-(4-(5-fluoro-2-methoxypyridin-4-yl)phenyl) isochroman-1-one

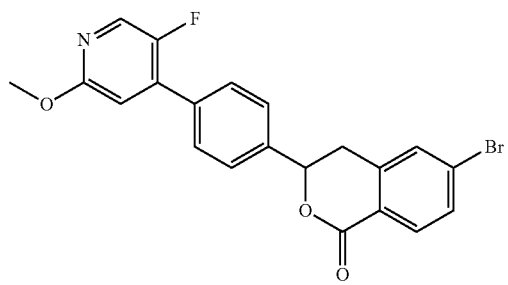 [SMILES: COc1cc(-c2ccc(C3Cc4cc(Br)ccc4C(=O)O3)cc2)c(F)cn1]

To a solution of Intermediate 45 (12.3 g, 24.5 mmol) in toluene (150 mL) was added TsOH (5.60 g, 29.4 mmol). The mixture was stirred for 2 h at 120° C., then diluted with EtOAc (300 mL), washed with saturated Na$_2$CO$_3$ (100 mL×2), and then brine (100 mL). The combined organic layers were dried over Na$_2$SO$_4$, filtered and concentrated to afford crude (R,S)-6-bromo-3-(4-(5-fluoro-2-methoxypyridin-4-yl)phenyl) isochroman-1-one. MS (ESI) m/z: 428.25 [M+H]$^+$.

Intermediate 47

2-(5-Bromo-2-(hydroxymethyl)phenyl)-1-(4-(5-fluoro-2-methoxypyridin-4-yl)-phenyl)ethanol

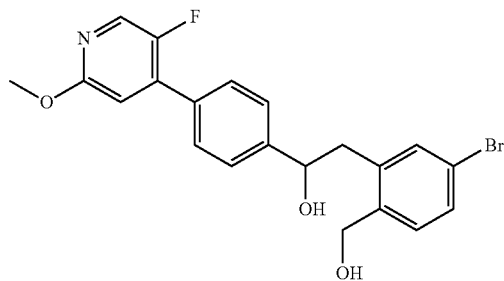 [SMILES: COc1cc(-c2ccc(C(O)Cc3cc(Br)ccc3CO)cc2)c(F)cn1]

To a solution of Intermediate 46 (11.0 g, 25.7 mmol) in THF (150 mL) was added LiAlH$_4$ (1.46 g, 38.5 mmol) at 0° C. The mixture was stirred for 30 min at 0° C., then diluted with EtOAc (300 mL) and saturated Na$_2$CO$_3$ (50.0 mL) at 0° C. The mixture was stirred for 30 min, filtered and concentrated to afford the crude product, which was purified by column chromatography (SiO$_2$, PE:EtOAc=20:1 to 5:1, v/v) to give the title compound. MS (ESI) m/z: 432.28[M+H]$^+$

Intermediate 48

1-(4-(5-fluoro-2-methoxypyridin-4-yl)phenyl)-2-(2-(hydroxymethyl)-5-(4,4,5,5-tetramethyl-1,3,2-dioxaborolan-2-yl)phenyl)ethanol

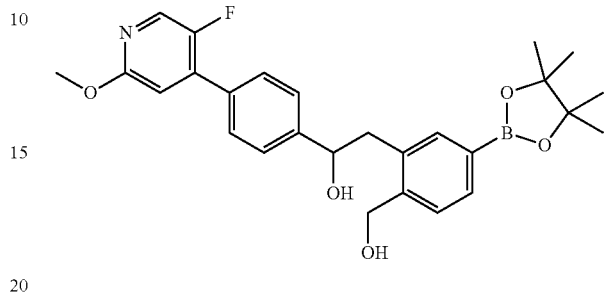

To a solution of Intermediate 47 (7.25 g, 16.8 mmol) in dioxane (100 mL) was added 4,4,4',4',5,5,5',5'-octamethyl-2,2'-bi(1,3,2-dioxaborolane) (5.11 g, 20.1 mmol), potassium acetate (4.94 g, 50.3 mmol) and Pd(dppf)Cl$_2$ (1.23 g, 1.68 mmol). The mixture was stirred for 2 h at 110° C. under a N$_2$ atmosphere, then filtered and concentrated to afford crude product, which was purified by column chromatography (SiO$_2$, PE:EtOAc=20:1 to 5:1, v/v) to give the title compound. MS (ESI) m/z: 503.3 [M+Na]$^+$ $^1$H NMR (400 MHz, CDCl$_3$): δ=8.07 (s, 1H), 7.76-7.71 (m, 2H), 7.62-7.58 (m, 2H), 7.39 (d, J=7.2 Hz, 1H), 6.84 (d, J=5.6 Hz, 1H), 5.03-5.01 (m, 1H), 4.88 (d, J=12.0 Hz, 1H), 4.56 (d, J=12 Hz, 1H), 3.96 (s, 3H), 3.19-3.13 (m, 2H), 1.37 (s, 12H)

Intermediate 49

(E)-Methyl 3-cyclopropyl-3-(3-(2-(4-(5-fluoro-2-methoxypyridin-4-yl) phenyl)-2-hydroxy-ethyl)-4-(hydroxymethyl)phenyl)-2-methylacrylate

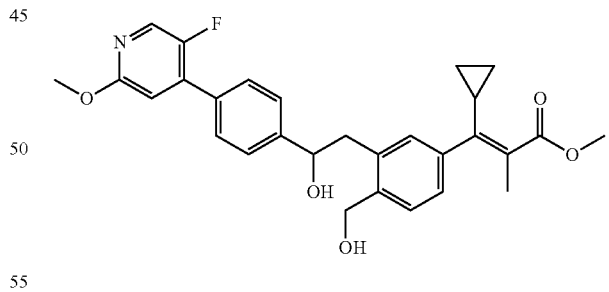

To a solution of Intermediate 48 (7.28 g, 15.2 mmol) in THF (100 mL) and water (20 mL) were added K$_2$CO$_3$ (6.30 g, 45.6 mmol), (Z)-methyl 3-cyclopropyl-2-methyl-3-(tosyloxy)acrylate (5.18 g, 16.7 mmol) and Pd(PPh$_3$)$_4$(1.76 g, 1.52 mmol). The mixture was stirred for 16 h at 50° C., then diluted with water (30 mL) and extracted with EtOAc (30 mL×2). The combined organic layers were washed with brine (30 mL), dried over Na$_2$SO$_4$, filtered and concentrated to afford crude product, which was purified by column chromatography (SiO$_2$, PE:EtOAc=5:1 to 2:1, v/v) to give the title compound. MS (ESI) m/z: 474.2 [M-OH]$^+$

Intermediate 50

(RS)-(E)-methyl 3-cyclopropyl-3-(3-(4-(5-fluoro-2-methoxypyridin-4-yl) phenyl)-isochroman-6-yl)-2-methylacrylate

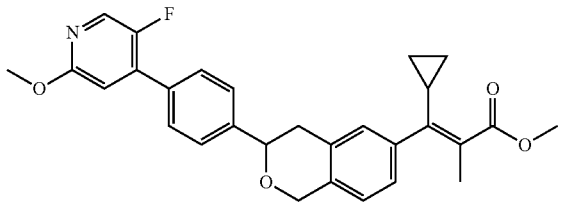

To a solution of (E)-methyl 3-cyclopropyl-3-(3-(2-(4-(5-fluoro-2-methoxypyridin-4-yl)phenyl)-2-hydroxyethyl)-4-(hydroxymethyl)-phenyl)-2-methylacrylate (800 mg, 1.6 mmol, intermediate 49) in CHCl$_3$ (8.0 mL) were added silica gel (196 mg, 3.26 mmol) and p-TsOH (619 mg, 3.26 mmol). The mixture was stirred for 2 h at 60° C. under a N$_2$ atmosphere, then diluted with DCM (10 mL) and washed with saturated NaHCO$_3$ (6.0 mL). The combined organic layers were washed with brine (3.0 mL), dried over Na$_2$SO$_4$, filtered and concentrated to afford crude product, which was purified by prep-TLC (SiO$_2$, PE:EtOAc=5:1, v/v) to give the title compound. MS (ESI) m/z: 474.2 [M+H]$^+$ $^1$H NMR (400 MHz, CDCl$_3$): δ=8.07 (s, 1H), 7.62 (d, J=7.2 Hz, 2H), 7.56 (d, J=8.4 Hz, 2H), 6.98 (d, J=7.6 Hz, 1H), 6.84 (d, J=4.8 Hz, 2H), 6.67 (s, 1H), 5.01 (s, 2H), 4.82-4.78 (m, 1H), 3.96 (s, 1H), 3.44 (s, 3H), 3.44-2.95 (m, 2H), 2.16 (s, 3H), 1.89-1.83 (m, 1H), 0.77-0.75 (m, 2H), 0.34-0.32 (m, 2H)

Intermediate 51 tert-Butyl 4-(2-(3-bromophenyl)-1-hydroxyethyl) piperidine-1-carboxylate

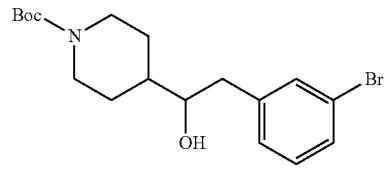 [SMILES: CC(C)(C)OC(=O)N1CCC(C(O)Cc2cccc(Br)c2)CC1]

To a solution of tert-butyl 4-formylpiperidine-1-carboxylate (10.0 g, 46.9 mmol) in Et$_2$O (150 mL) was added (3-bromobenzyl)magnesium bromide (52 ml, 52 mmol, 1 M in Et$_2$O) at 0° C. under a nitrogen atmosphere. The reaction mixture was stirred at 20° C. for 18 h, then cooled to room temperature. Then the mixture was added to saturated aqueous NH$_4$Cl (50 mL) at 0° C. The organic layers were separated and the aqueous phase was extracted with EtOAc (50 mL×3). The combined organic layers were washed with brine (100 mL), dried over anhydrous Na$_2$SO$_4$ and filtered. The filtrate was concentrated under reduced pressure to give a residue, which was purified by column chromatography (SiO$_2$, PE/EtOAc=10:1, v/v) to give the title compound. MS (ESI) m/z: 371.1 [M-Boc+MeCN+H]$^+$ $^1$H NMR (400 MHz, CDCl$_3$): δ=7.37-7.35 (m, 2H), 7.20-7.12 (m, 2H), 4.38 (s, 1H), 4.17 (d, 12.8 Hz), 3.61-3.60 (m, 1H), 2.86-2.82 (m, 1H), 2.69-2.67 (m, 2H), 2.69-2.56 (m, 1H), 1.87-1.83 (m, 1H), 1.69-1.65 (m, 1H), 1.59-1.50 (m, 1H), 1.46 (s, 9H), 1.33-1.30 (m, 2H).

Intermediate 52 tert-Butyl 4-(2-(3-bromophenyl)-1-((2-methoxyethoxy)methoxy)ethyl) piperidine-1-carboxylate

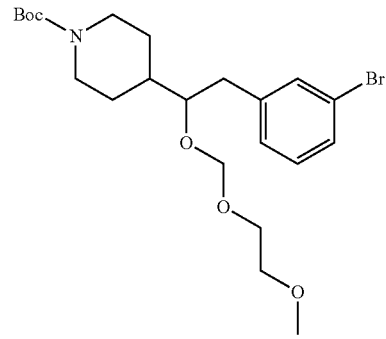 [SMILES: COCCOCOC(Cc1cccc(Br)c1)C1CCN(C(=O)OC(C)(C)C)CC1]

To a solution of Intermediate 51 (1.60 g, 4.16 mmol) and 1-(chloromethoxy)-2-methoxyethane (1.56 g, 12.49 mmol) in DCM (15 mL) was added DIPEA (1.61 g, 12.49 mmol) under a nitrogen atmosphere. The reaction mixture was stirred at 20° C. for 18 h. The mixture was then diluted with DCM (60 mL), washed with brine (20 mL×3), dried over anhydrous MgSO$_4$ and filtered. The filtrate was concentrated under reduced pressure to give a crude residue, which was purified by column chromatography (SiO$_2$, PE/EtOAc=10:1 to 5:1, v/v) to give the title compound. MS (ESI) m/z: 474.2 [M+H]$^+$

Intermediate 53

4-(6-Bromoisochroman-3-yl)piperidine

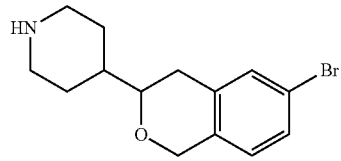 [SMILES: Brc1ccc2c(c1)CC(C1CCNCC1)OC2]

To a solution of Intermediate 52 (1.90 g, 4.02 mmol) in MeCN (20 mL) was added trimethylsilyl trifluoromethanesulfonate (3.6 mL, 20.1 mmol) dropwise at 0° C. The reaction mixture was stirred at 20° C. for 2.5 h, then quenched with saturated NaHCO$_3$ (15 mL). The resulting mixture was extracted with EtOAc (40 mL×3). The combined organic layers were washed with brine (30 mL), dried over anhydrous Na$_2$SO$_4$ and filtered. The filtrate was concentrated under reduced pressure to give the title compound, which was used in the next step. MS (ESI) m/z: 298.0 [M+H]$^+$

Intermediate 54 tert-Butyl 4-(6-bromoisochroman-3-yl)piperidine-1-carboxylate

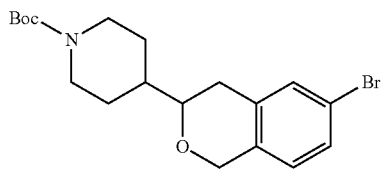 [SMILES: CC(C)(C)OC(=O)N1CCC(C2Cc3cc(Br)ccc3CO2)CC1]

To a solution of Intermediate 53 (730 mg, 1.53 mmol, 62% purity), triethylamine (464 mg, 4.58 mmol) and N,N-dimethylpyridin-4-amine (9.33 mg, 0.0764 mmol) in DCM (10 mL) was added di-tert-butyl dicarbonate (1.00 g, 4.58 mmol) dropwise at 0° C. under a nitrogen atmosphere. The reaction mixture was stirred at 25° C. for 3 h. Then the solvent was removed under reduced pressure to give the crude product, which was purified by column chromatography (SiO$_2$, PE/EtOAc=20:1 to 10:1, v/v) to give the title compound. MS (ESI) m/z: 383.1 [M-Boc+MeCN+H]$^+$ $^1$H NMR (400 MHz, CDCl$_3$): δ=7.31-7.27 (m, 2H), 6.88 (d, J=1.0 Hz, 1H), 4.80 (d, J=1.0 Hz, 1H), 4.69 (d, J=1.0 Hz, 1H), 4.30-4.09 (m, 2H), 3.42-3.31 (m, 1H), 2.81-2.62 (m, 4H), 2.04-1.94 (m, 1H), 1.75-1.61 (m, 2H), 1.48 (s, 9H), 1.35-1.19 (m, 2H).

Intermediate 55 tert-Butyl 4-(6-(4,4,5,5-tetramethyl-1,3,2-dioxaborolan-2-yl)isochroman-3-yl)-piperidine-1-carboxylate

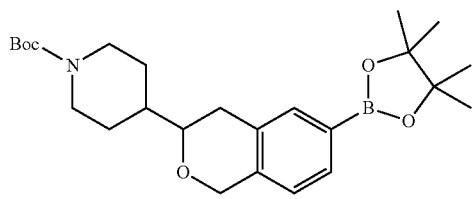 [SMILES: CC(C)(C)OC(=O)N1CCC(C2Cc3cc(B4OC(C)(C)C(C)(C)O4)ccc3CO2)CC1]

To a solution of Intermediate 54 (550 mg, 1.39 mmol) in dioxane (10 mL) was added 4,4,4',4',5,5,5',5'-octamethyl-2,2'-bi(1,3,2-dioxaborolane) (705 mg, 2.78 mmol), PdCl$_2$(dppf) (102 mg, 0.14 mmol) and KOAc (409 mg, 4.1 mmol). The reaction mixture was stirred at 80° C. for 2 h under a nitrogen atmosphere, then cooled to room temperature. The mixture was diluted with EtOAc (60 mL), then washed with brine (15 mL×3), dried over anhydrous Na$_2$SO$_4$ and filtered. The filtrate was concentrated under reduced pressure to give the crude product, which was purified by prep-TLC (SiO$_2$, PE/EtOAc=5:1, v/v) to give the title compound. MS (ESI) m/z: 344.3 [M-Boc+H]$^+$ $^1$H NMR (400 MHz, CDCl$_3$): δ=7.64-7.53 (m, 2H), 7.01 (d, J=7.6 Hz, 1H), 4.85 (d, J=1.0 Hz, 1H), 4.77 (d, J=1.0 Hz, 1H), 4.29-4.14 (m, 2H), 3.43-3.33 (m, 1H), 2.80-2.66 (m, J=6.8 Hz, 4H), 2.04-1.96 (m, 1H), 1.72-1.63 (m, 2H), 1.47 (s, 9H), 1.35 (s, 12H), 1.29-1.27 (m, 2H).

Intermediate 56

(RS,Z)-tert-butyl 4-(6-(1-cyclopropyl-3-methoxy-2-methyl-3-oxoprop-1-en-1-yl)-isochroman-3-yl)piperidine-1-carboxylate

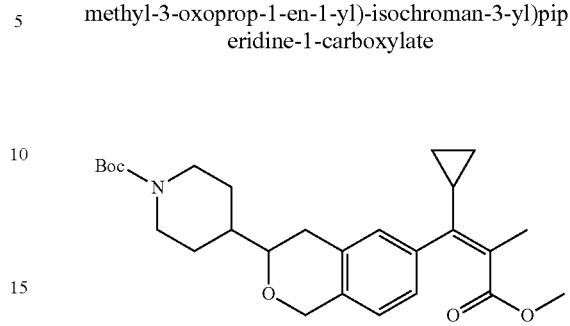

To a solution of Intermediate 55 (250 mg, 0.564 mmol) and (Z)-methyl 3-cyclopropyl-2-methyl-3-(tosyloxy)acrylate (193 mg, 0.620 mmol) in THF (5 mL) and H$_2$O (1 mL) was added Pd(PPh$_3$)$_4$ (65.2 mg, 0.0564 mmol) and K$_2$CO$_3$ (234 mg, 1.69 mmol). The mixture was stirred at 50° C. under a nitrogen atmosphere for 3 h. Then the mixture was diluted with water (15 mL) and extracted with EtOAc (30 mL×3). The combined organic layers were washed with brine (20 mL), dried over anhydrous Na$_2$SO$_4$ and filtered. The filtrate was concentrated under reduced pressure to give the crude product, which was purified by prep-HPLC (TFA) to give the title compound. MS (ESI) m/z: 456.3 [M+H]$^+$ $^1$H NMR (400 MHz, CDCl$_3$): δ=6.89 (d, J=1.0 Hz, 1H), 6.78 (d, J=1.0 Hz, 1H), 6.71 (s, 1H), 4.83 (d, J=1.0 Hz, 1H), 4.75 (d, J=1.0 Hz, 1H), 4.17 (d, J=1.0 Hz, 2H), 3.41 (s, 4H), 2.80-2.66 (m, 4H), 2.15 (s, 3H), 2.06-1.96 (m, 1H), 1.89-1.80 (m, 1H), 1.75-1.62 (m, 1H), 1.47 (s, 9H), 1.36-1.22 (m, 2H), 0.80-0.71 (m, 2H), 0.34-0.25 (m, 2H).

Intermediate 57

(2S,3S)-Methyl 3-cyclopropyl-2-methyl-3-(3-piperidin-4-yl)isochroman-6-yl)propanoate

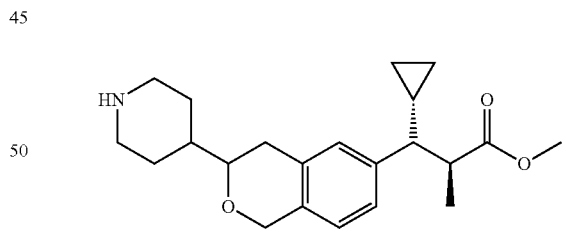

A solution of intermediate 56 (200 mg, 0.439 mmol), Ru-catalyst (23.8 mg, 0.0746 mmol), Josiphos (42.9 mg, 0.0790 mmol), HBF$_4$.Et$_2$O (48.3 mg, 0.149 mmol, 50% in Et$_2$O) in MeOH (5.0 mL) and DCM (0.5 mL) was stirred at 80° C. under 4.0 MPa for 40 h. Then the mixture was diluted with H$_2$O (10 mL). The aqueous phase was separated and extracted with EtOAc (15 mL×3). The combined organic layers were washed with brine (10 mL), dried over anhydrous MgSO$_4$ and filtered. The filtrate was concentrated under reduced pressure to give the crude product, which was purified by prep-HPLC TFA) to give the title compound. MS (ESI) m/z: 358.3 [M+H]$^+$

Example 1

3-cyclopropyl-3-(3-(2'-fluoro-5'-methoxy-[1,1'-biphenyl]-4-yl) chroman-6-yl)propanoic acid

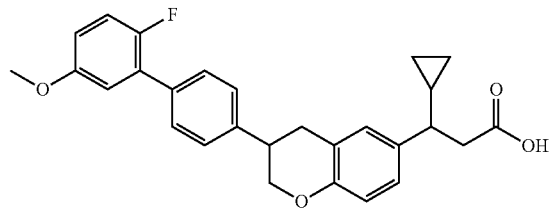 [SMILES: COc1ccc(F)c(-c2ccc(C3COc4ccc(C(CC(=O)O)C5CC5)cc4C3)cc2)c1]

Methyl 3-cyclopropyl-3-(3-(2'-fluoro-5'-methoxy-[1,1'-biphenyl]-4-yl)chroman-6-yl)propanoate (10 mg, 0.022 mmol, Intermediate 20) and lithium hydroxide monohydrate (82 mg, 1.954 mmol) were combined in THF (4 ml), MeOH (2 ml) and water (2 ml). The mixture was heated overnight at 50° C. Then the reaction was partitioned between ethyl acetate and 1N aqueous hydrochloric acid. The organic layer was separated, washed with brine, dried over anhydrous Na$_2$SO$_4$, filtered and evaporated to afford a crude residue. The crude residue was dissolved in DMSO and purified via reverse-phase chromatography (Column: Phenomenex Synergi Polar-RP 80A, 10 micron, 250 mm×21.2 mm; Gradient elution: 0% to 100% MeCN in water over 20 minutes at 30 mL/min; Detection: 210 nm UV). The corresponding product fractions were combined and lyophilized to afford a partially pure product, which was subjected to reverse phase HPLC on a 19×100 mm, Waters Sunfire C18 column, 5μ particle size, linear gradient, standard 48% ACN/H$_2$O to 78% ACN/H$_2$O buffering with 0.16% TFA @ flow rate 25 mL/min over 10.4 min to afford 3-cyclopropyl-3-(3-(2'-fluoro-5'-methoxy-[1,1'-biphenyl]-4-yl)chroman-6-yl)propanoic acid (Example 1). LC/MS: m/e 447 (M+H)$^+$ $^1$H NMR δ (ppm)(CHCl$_3$-d): 0.19 (1H, dt, J=9.53, 4.92 Hz), 0.31 (1H, dt, J=9.49, 4.85 Hz), 0.48-0.45 (1H, m), 0.61-0.58 (1H, m), 1.08-0.99 (1H, m), 2.33 (1H, q, J=8.30 Hz), 2.64 (1H, s), 2.85-2.75 (2H, m), 3.08-3.01 (1H, m), 3.12-3.10 (1H, m), 3.38-3.27 (1H, s), 3.84 (3H, s), 4.07 (1H, t, J=10.61 Hz), 4.41-4.38 (1H, m), 6.86-6.83 (2H, m), 6.96 (1H, dd, J=6.29, 3.17 Hz), 6.99 (1H, s), 7.04 (1H, d, J=8.61 Hz), 7.11-7.07 (1H, m), 7.35 (2H, d, J=8.08 Hz), 7.56 (2H, dd, J=8.02, 1.69 Hz).

Utilizing the appropriate starting material and conditions similar to that outlined in the synthesis of Example 1, the following compound was prepared:

Examples 3-5

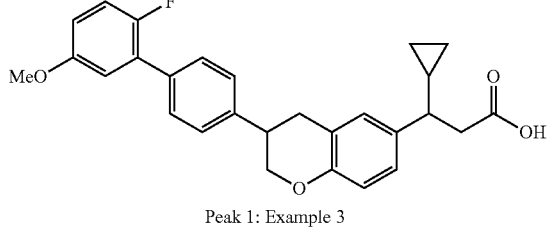

Peak 1: Example 3

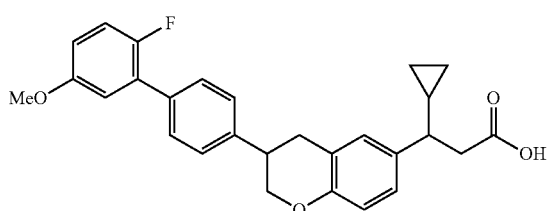

Peak 4: Example 5

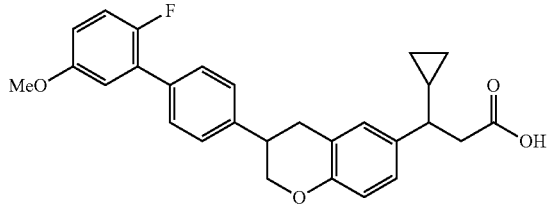

Peak 3: Example 4

Example 1 (10 mg) was subjected to chiral SFC chromatography (Chiralpak AS column, 30 mm×250 mm, 30% MeOH/CO$_2$, 70 mL/min, 120 bar, 35° C., 220 nm detection) to afford four peaks: Peak 1: Example 3; LC/MS: m/e 447 (M+H)$^+$; Peak 3: Example 4; LC/MS: m/e 447 (M+H)$^+$; and Peak 4: Example 5; LC/MS: m/e 447 (M+H)$^+$.

| Example Number | Structure | LC/MS: m/e (M + H)$^+$ |
| --- | --- | --- |
| EXAMPLE 2 | 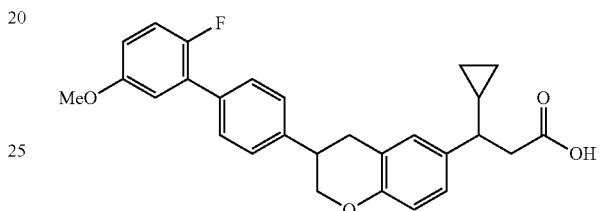 | 461 |

Examples 6 and 7

(2S,3R)-3-cyclopropyl-3-(3-(2'-fluoro-5'-methoxy-[1,1'-biphenyl]-4-yl)chroman-6-yl)-2-methylpropanoic acid (Peak 1, Example 6) and (2S,3R)-3-cyclopropyl-3-(3-(2'-fluoro-5'-methoxy-[1,1'-biphenyl]-4-yl)chroman-6-yl)-2-methylpropanoic acid (Peak 2, Example 7)

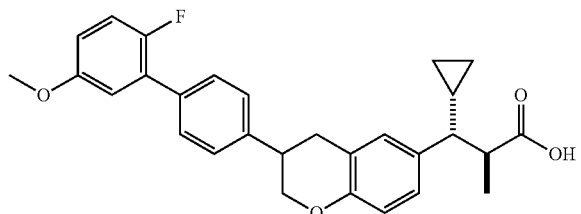

Peak 1: Example 6

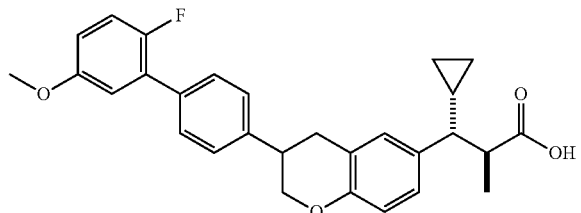

Peak 2: Example 7

Intermediate 22 was subjected to conditions similar to that described in the preparation of Example 1 to afford (2S,3R)-3-cyclopropyl-3-(3-(2'-fluoro-5'-methoxy-[1,1'-biphenyl]-4-yl)chroman-6-yl)-2-methylpropanoic acid, which was dissolved in MeOH:MeCN (1:1) and subjected to chiral SFC chromatography (Chiralpak AS-H column, 21 mm×250 mm, 1.5 mL injection volume, 210 nm detection, 35% MeOH in CO$_2$, 65 ml/min, 120 bar, 40° C.) to afford two peaks: Peak 1 (Faster eluting, Example 6): LC/MS: m/e 461 (M+H)$^+$ and Peak 2, (Slower eluting, Example 7): LC/MS: m/e 461 (M+H)$^+$.

Examples 8 and 9

(2R,3S)-3-Cyclopropyl-3-(3-(2'-fluoro-5'-methoxy-[1,1'-biphenyl]-4-yl)chroman-6-yl)-2-methylpropanoic acid (Peak 1, Example 8) and (2R,3S)-3-Cyclopropyl-3-(3-(2'-fluoro-5'-methoxy-[1,1'-biphenyl]-4-yl)chroman-6-yl)-2-methylpropanoic acid (Peak 2, Example 9)

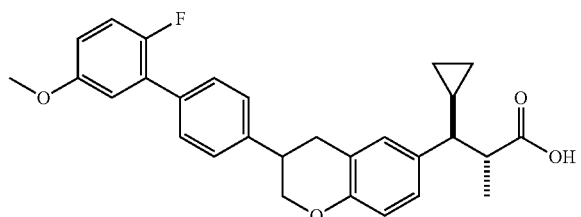

Peak 1: Example 8

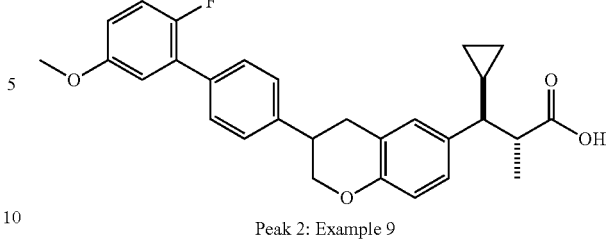

Peak 2: Example 9

Intermediate 23 was subjected to conditions similar to that described in the preparation of Example 1 to afford (2R,3S)-3-Cyclopropyl-3-(3-(2'-fluoro-5'-methoxy-[1,1'-biphenyl]-4-yl)chroman-6-yl)-2-methylpropanoic acid, which was dissolved in MeOH:MeCN (1:1) and subjected to chiral SFC chromatography (Chiralpak OJ-H column, 21 mm×250 mm, 1.0 mL injection volume, 210 nm detection, 50% MeOH in CO$_2$, 65 ml/min, 120 bar, 40° C.) to afford two peaks, Peak 1 (Faster eluting, Example 8): LC/MS: m/e 461 (M+H)$^+$ and Peak 2 (Slower eluting, Example 9): LC/MS: m/e 461 (M+H)$^+$.

Examples 10 and 11

(2S,3R)-3-cyclopropyl-3-(3-(4-(5-fluoro-2-methoxypyridin-4-yl)phenyl)chroman-6-yl)-2-methylpropanoic acid (Peak 1, Example 10) and (2S,3R)-3-cyclopropyl-3-(3-(4-(5-fluoro-2-methoxypyridin-4-yl)phenyl)chroman-6-yl)-2-methylpropanoic acid (Peak 2, Example 11)

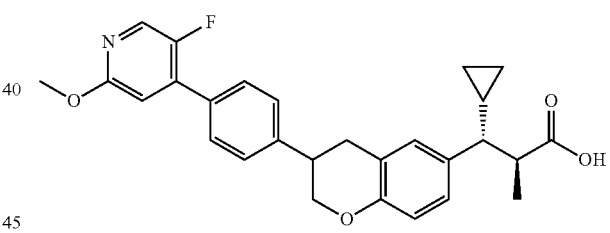

Peak 1, Example 10

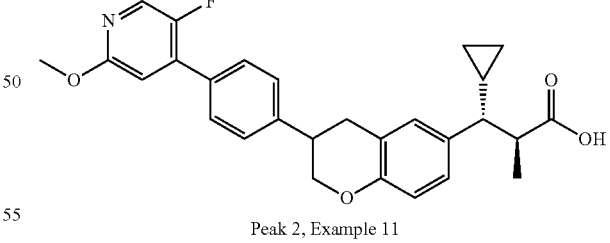

Peak 2, Example 11

Step 1: (2S,3R)-3-cyclopropyl-3-(3-(4-(5-fluoro-2-methoxypyridin-4-yl)phenyl)chroman-6-yl)-2-methylpropanoic acid To a stirred, room temperature mixture of Intermediate 26 (83 mg, 0.175 mmol) in MeOH (1 ml) and THF (2 ml) was added 2M aq. LiOH (1 ml, 2.000 mmol) and the mixture was stirred at 60° C. for 18 h. The reaction was then cooled to room temperature and partitioned between ethyl acetate, water and 1 ml 2M HCl. The layers were separated and the aqueous layer was extracted with EtOAc. The organic layers were combined, dried over anhydrous sodium sulfate, filtered and evaporated to afford a crude residue. The resulting residue was purified via column chromatography on silica gel (ISCO RediSep 24 g silica gel column, gradient elution with 0% to 100% EtOAc in hexanes) to give the desired product.

Step 2: (2S,3R)-3-cyclopropyl-3-(3-(4-(5-fluoro-2-methoxypyridin-4-yl)phenyl)chroman-6-yl)-2-methylpropanoic acid (Peak 1, Example 10) and (2S,3R)-3-cyclopropyl-3-(3-(4-(5-fluoro-2-methoxypyridin-4-yl)phenyl)chroman-6-yl)-2-methylpropanoic acid (Peak 2, Example 11)

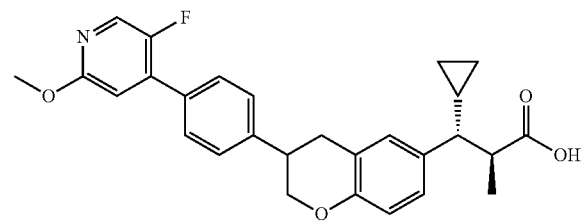

Peak 1, Example 10

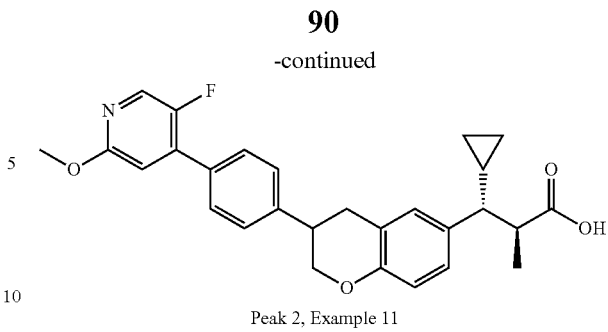

Peak 2, Example 11

(2S,3R)-3-Cyclopropyl-3-(3-(4-(5-fluoro-2-methoxypyridin-4-yl)phenyl)chroman-6-yl)-2-methylpropanoic acid was dissolved in MeOH:MeCN (1:1) and subjected to chiral SFC chromatography (Chiralpak OJ-H column, 21 mm×250 mm, 1.0 mL injection volume, 210 nm detection, 45% EtOH in $CO_2$, 50 ml/min, 120 bar, 40° C.) to afford two peaks: Peak 1 (Faster eluting, Example 10): LC/MS: m/e 462 $(M+H)^+$ and Peak 2 (Slower eluting, Example 11): LC/MS: m/e 462 $(M+H)^+$.

Using the appropriate starting material and a method similar to that outlined in Step 1 of the preparation of Examples 10 and 11, the following Examples were prepared:

| Example Number | Structure | $^1$H NMR or LC/MS: m/e $(M + H)^+$ | Starting Material |
|---|---|---|---|
| 12 | 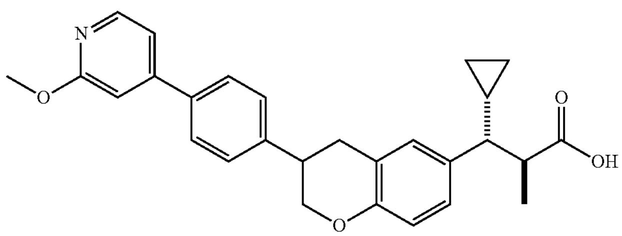 [SMILES: COc1cc(-c2ccc(C3COc4ccc([C@H](C5CC5)[C@H](C)C(=O)O)cc4C3)cc2)ccn1] | 444 | Intermediate 27 |
| 13 | 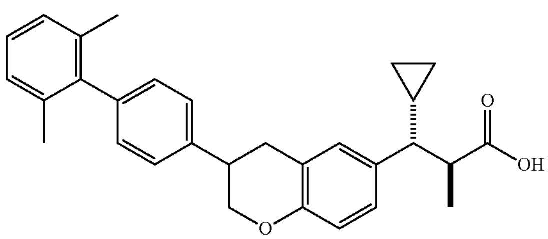 [SMILES: Cc1cccc(C)c1-c1ccc(C2COc3ccc([C@H](C4CC4)[C@H](C)C(=O)O)cc3C2)cc1] | $^1$H NMR δ (ppm)(CHCl$_3$-d): 0.10-0.06 (1 H, m), 0.44-0.38 (2 H, m), 0.69-0.65 (1 H, m), 1.04 (3 H, d, J = 6.86 Hz), 1.18-1.11 (1 H, m), 1.98 (1 H, t, J = 9.87 Hz), 2.07 (6 H, s), 2.87-2.81 (1 H, m), 3.11-3.04 (1 H, m), 3.20-3.12 (1 H, m), 3.37-3.31 (1 H, m), 4.11 (1 H, td, J = 10.69, 1.98 Hz), 4.45 (1 H, d, J = 10.54 Hz), 6.87 (1 H, d, J = 8.35 Hz), 6.94 (1 H, s), 6.99 (1 H, d, J = 8.55 Hz), 7.20-7.14 (3 H, m), 7.33 (2 H, d, J = 7.81 Hz). | Intermediate 28 |
| 14 | 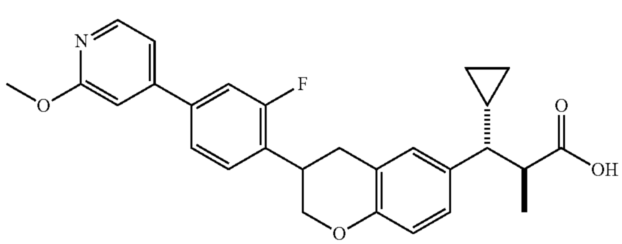 [SMILES: COc1cc(-c2ccc(C3COc4ccc([C@H](C5CC5)[C@H](C)C(=O)O)cc4C3)c(F)c2)ccn1] | 462 | Intermediate 29 |

Examples 15 and 16

(2S,3R)-3-cyclopropyl-3-(3-(4-(2-methoxypyridin-4-yl)phenyl)chroman-6-yl)-2-methylpropanoic acid (Peak 1, Example 15) and (2S,3R)-3-cyclopropyl-3-(3-(4-(2-methoxypyridin-4-yl)phenyl)chroman-6-yl)-2-methylpropanoic acid (Peak 2, Example 15)

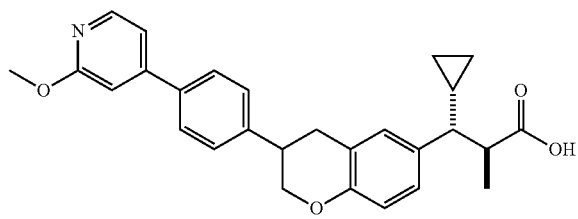

Peak 1, Example 15

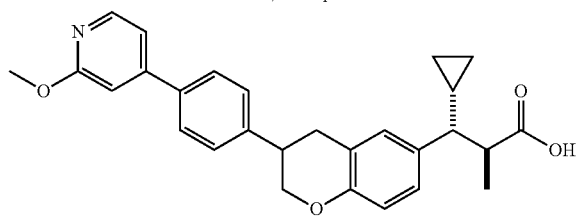

Peak 2, Example 16

Example 12 was dissolved in MeOH and subjected to chiral SFC chromatography (Chiralpak OJ-H column, 21 mm×250 mm, 0.5 mL injection volume, 210 nm detection, 45% EtOH in $CO_2$, 50 ml/min, 120 bar, 40° C.) to afford two peaks: Peak 1 (Faster eluting, Example 15): LC/MS: m/e 444 $(M+H)^+$, and Peak 2 (Slower eluting, Example 16): LC/MS: m/e 444 $(M+H)^+$.

Examples 17 and 18

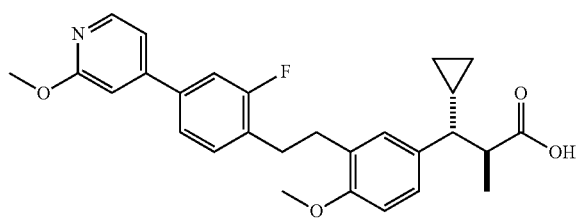

Peak 1, Example 17

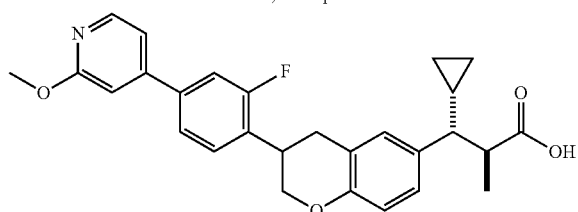

Peak 2, Example 18

(2S,3R)-3-cyclopropyl-3-(3-(2-fluoro-4-(2-methoxypyridin-4-yl)phenyl)chroman-6-yl)-2-methylpropanoic acid (Peak 1, Example 17) and (2S,3R)-3-cyclopropyl-3-(3-(2-fluoro-4-(2-methoxypyridin-4-yl)phenyl)chroman-6-yl)-2-methylpropanoic acid (Peak 2, Example 18)

Example 14 was dissolved in MeOH and subjected to chiral SFC chromatography (Chiralpak OJ-H column, 21 mm×250 mm, 1.0 mL injection volume, 210 nm detection, 55% MeOH in $CO_2$, 50 ml/min, 120 bar, 40° C.) to afford two peaks: Peak 1 (Faster eluting, Example 17): LC/MS: m/e 462 $(M+H)^+$, and Peak 2 (Slower eluting, Example 18): LC/MS: m/e 462 $(M+H)^+$.

Example 19

(2S,3R)-3-(3-(3'-cyclopropoxy-[1,1'-biphenyl]-4-yl)chroman-6-yl)-3-cyclopropyl-2-methylpropanoic acid

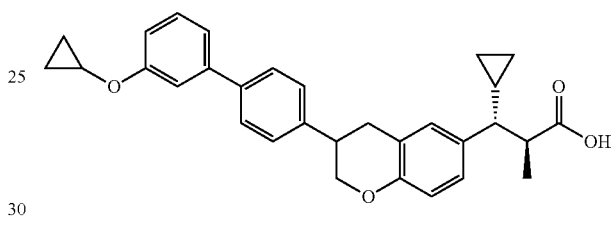

Step 1: (2S,3R)-3-(3-(4-bromophenyl)chroman-6-yl)-3-cyclopropyl-2-methylpropanoic acid Intermediate 24 was hydrolyzed using a procedure similar to that described in Step 1 of the synthesis of Examples 10 and 11 to afford (2S,3R)-3-(3-(4-bromophenyl)chroman-6-yl)-3-cyclopropyl-2-methylpropanoic acid.

Step 2: (2S,3R)-3-(3-(3'-cyclopropoxy-[1,1'-biphenyl]-4-yl)chroman-6-yl)-3-cyclopropyl-2-methylpropanoic acid Utilizing a procedure similar to the synthesis of Intermediate 26, (2S,3R)-3-(3-(4-bromophenyl)chroman-6-yl)-3-cyclopropyl-2-methylpropanoic acid was cross coupled with (3-cyclopropoxyphenyl)boronic acid to afford (2S,3R)-3-(3-(3'-cyclopropoxy-[1,1'-biphenyl]-4-yl)chroman-6-yl)-3-cyclopropyl-2-methylpropanoic acid (Example 19). LC/MS: m/e 469 $(M+H)^+$

Example 20

3-cyclopropyl-3-(3-(2'-fluoro-5'-methoxy-[1,1'-biphenyl]-4-yl)isochroman-6-yl)propanoic acid

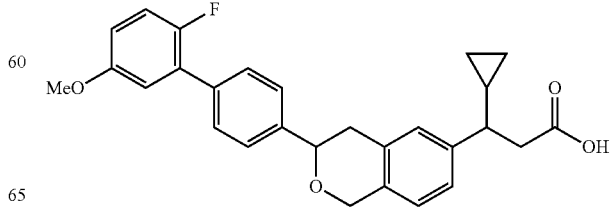

Step 1: 4-bromo-N-methoxy-N-methylbenzamide

To a solution of 4-bromobenzoyl chloride (5 g, 22.78 mmol) and Et$_3$N (7.94 ml, 57.0 mmol) in DCM (152 ml) was added N,O-dimethylhydroxylamine hydrochloride (2.222 g, 22.78 mmol). The reaction stirred at room temperature for 3 hours, then quenched with 0.5N HCl (200 mL) and extracted with 500 mL of DCM. The organic layer was dried over sodium sulfate, filtered and concentrated. The resulting residue was dissolved in 30 mL of DCM and filtered. The filtrate was concentrated to give the desired product. $^1$H NMR (500 MHz; CDCl$_3$): 7.57 (d, J=8.17 Hz, 2H), 7.52 (d, J=8.46 Hz, 2H), 3.51 (s, 3H), 3.34 (s, 3H).

Step 2: 2'-fluoro-N,5'-dimethoxy-N-methyl-[1,1'-biphenyl]-4-carboxamide

A reaction vessel was charged with (2-fluoro-5-methoxyphenyl)boronic acid (1.00 g, 5.89 mmol), 4-bromo-N-methoxy-N-methylbenzamide (1.15 g, 4.71 mmol), S-Phos-Biaryl Precatalyst-2nd Gen. (0.068 g, 0.094 mmol) and 2-Me THF (15.70 ml). The solution was degassed and then a degassed 1M solution of potassium phosphate (14.13 ml, 14.13 mmol) was added. The reaction was heated to 80° C. for 3 hours, then cooled. The reaction layers were separated. The aqueous layer extracted with 100 mL of Et$_2$O. The combined organic layers were washed with brine, dried over sodium sulfate, filtered and concentrated. The resulting residue was purified via MPLC using an ISCO 80 g column (10-60% EtOAc: hexanes) to give 2'-fluoro-N,5'-dimethoxy-N-methyl-[1,1'-biphenyl]-4-carboxamide LC/MS: m/e 290 (M+H)$^+$.

Step 3: 4-bromo-N,N-diethyl-2-(2-(2'-fluoro-5'-methoxy-[1,1'-biphenyl]-4-yl)-2-oxoethyl)benzamide A solution of 4-bromo-N,N-diethyl-2-methylbenzamide (525 mg, 1.943 mmol) in THF (6478 µl) was cooled to −78° C. and then LDA (1457 µl, 2.91 mmol) was added via syringe under nitrogen. After 1 hour at −78° C., a solution of 2'-fluoro-N,5'-dimethoxy-N-methyl-[1,1'-biphenyl]-4-carboxamide (703 mg, 2.429 mmol) in THF (6478 µl) was added slowly via syringe, and the reaction allowed to warm to room temperature. After stirring at room temperature for 1 hour, the reaction was quenched with 1N HCl and extracted with EtOAc. The organic layer was washed with brine, dried over sodium sulfate, filtered and concentrated. The resulting residue was purified via MPLC using an ISCO 80 g column (10-60% EtOAc: hexanes) giving rise to 4-bromo-N,N-diethyl-2-(2-(2'-fluoro-5'-methoxy-[1,1'-biphenyl]-4-yl)-2-oxoethyl)benzamide. LC/MS: m/e 498 (M+H)$^+$.

Step 4: 4-bromo-N,N-diethyl-2-(2-(2'-fluoro-5'-methoxy-[1,1'-biphenyl]-4-yl)-2-hydroxyethyl)benzamide A solution of 4-bromo-N,N-diethyl-2-(2-(2'-fluoro-5'-methoxy-[1,1'-biphenyl]-4-yl)-2-oxoethyl)benzamide (730 mg, 1.465 mmol) in EtOH (3662 µl)/THF (3662 µl) was treated with NaBH$_4$ (83 mg, 2.197 mmol) at room temp and then warmed to 40° C. for 1 hour. The reaction was then cooled and partitioned between EtOAc and saturated ammonium chloride solution. The organic layer was separated, washed with brine, dried over sodium sulfate, filtered and concentrated to afford 4-bromo-N,N-diethyl-2-(2-(2'-fluoro-5'-methoxy-[1,1'-biphenyl]-4-yl)-2-hydroxyethyl)benzamide, which was used without further purification. LC/MS: m/e 500 (M+H)$^+$.

Step 5: 6-bromo-3-(2'-fluoro-5'-methoxy-[1,1'-biphenyl]-4-yl)isochroman-1-one A sealed tube containing 4-bromo-N,N-diethyl-2-(2-(2'-fluoro-5'-methoxy-[1,1'-biphenyl]-4-yl)-2-hydroxyethyl)benzamide (600 mg, 1.199 mmol) and p-toluenesulfonic acid monohydrate (228 mg, 1.199 mmol) in toluene (4796 µl) was heated to 100° C. for 1 hour, and then stirred at 80° C. overnight. The reaction mixture was cooled, then transferred to a flask using chloroform and methanol, and then concentrated. The resulting residue was triturated with DCM/MeOH, and the title compound was collected. The mother liquor was concentrated and purified via MPLC using an ISCO 24 g column (10-25% EtOAc: hexanes) giving rise to additional 6-bromo-3-(2'-fluoro-5'-methoxy-[1,1'-biphenyl]-4-yl)isochroman-1-one. 1H NMR (500 MHz; CDCl$_3$): 8.00 (d, J=8.32 Hz, 1H), 7.58 (m, 3H), 7.52 (m, 2H), 7.47 (s, 1H), 7.07 (t, J=9.29 Hz, 1H), 6.93 (m, 1H), 6.83 (m, 1H), 5.58 (dd, J=3.39 Hz, 12.16 Hz, 1H), 3.81 (s, 3H), 3.35 (m, 1H), 3.14 (m, 1H).

Step 6: 6-bromo-3-(2'-fluoro-5'-methoxy-[1,1'-biphenyl]-4-yl)isochroman

A solution of 6-bromo-3-(2'-fluoro-5'-methoxy-[1,1'-biphenyl]-4-yl)isochroman-1-one (200 mg, 0.468 mmol) in THF (3121 µl) was cooled to 0° C. and borane-methyl sulfide complex (2M in THF; 468 µl, 0.936 mmol) was added dropwise via syringe. The reaction mixture was warmed to r.t. over 16 h. Then sat. aq NH$_4$Cl solution (10 mL) was added and the mixture was extracted with CH$_2$Cl$_2$ (3×15 mL). The combined organic layers were washed with brine (10 mL), dried (MgSO$_4$), filtered, and concentrated in vacuo. The resulting residue was purified by flash chromatography using an ISCO 24 g column (10-100% EtOAc: hexanes) afforded the title compound. LC/MS: m/e 413 (M+H)$^+$.

Step 7: (Z)-methyl 3-cyclopropyl-3-(3-(2'-fluoro-5'-methoxy-[1,1'-biphenyl]-4-yl)isochroman-6-yl)acrylate 6-bromo-3-(2'-fluoro-5'-methoxy-[1,1'-biphenyl]-4-yl) isochroman (165 mg, 0.399 mmol), bis(pinacolato)-diboron (203 mg, 0.798 mmol), 2nd Generation XPHOS Precatalyst (15.71 mg, 0.020 mmol) and KOAc (118 mg, 1.198 mmol) were placed in a sealed tube, which was evacuated and backfilled with nitrogen 2 times. Then cyclopropyl methyl ether (CPME, 1996 µl) was added and the reaction heated to 110° C. for 2 hours. Then the reaction was cooled, diluted with EtOAc, filtered and concentrated to give a residue. The residue was purified via MPLC using an ISCO 12 g column (10-65% EtOAc: hexanes) to give 2-(3-(2'-fluoro-5'-methoxy-[1,1'-biphenyl]-4-yl)isochroman-6-yl)-4,4,5,5-tetramethyl-1,3,2-dioxaborolane, which was placed in a sealable tube with (Z)-methyl 3-cyclopropyl-3-(((trifluoromethyl)sulfonyl)oxy)acrylate (133 mg, 0.486 mmol) and tetrakis(triphenylphosphine) palladium (18.70 mg, 0.016 mmol) under nitrogen. Then 1,4-dioxane (1618 µl) was added, followed by the addition of a solution of 2M K$_2$CO$_3$ (486 µl, 0.971 mmol) via syringe. The reaction heated to 110° C. for 3 hours. Then the mixture was cooled, diluted with ethyl acetate (75 mL), washed with brine, dried over Na₂SO₄, filtered and the filtrate was evaporated under reduced pressure. The resulting residue was purified via MPLC using an ISCO 12 g column (10-65% EtOAc: hexanes) to give the title compound as a mixture of E and Z isomers, which was used directly in the next step. LC/MS: m/e 459 (M+H)⁺

Step 8: methyl 3-cyclopropyl-3-(3-(2'-fluoro-5'-methoxy-[1,1'-biphenyl]-4-yl)isochroman-6-yl)propanoate A solution of (Z)-methyl 3-cyclopropyl-3-(3-(2'-fluoro-5'-methoxy-[1,1'-biphenyl]-4-yl)isochroman-6-yl)acrylate (80 mg, 0.174 mmol) and rhodium on alumina (71.8 mg, 0.035 mmol) in ethyl acetate (1745 µl)/MeOH (1745 µl) was stirred overnight under H₂ atmosphere. The reaction was then filtered, concentrated and the resulting residue was purified via MPLC using an ISCO 12 g column (10-100% EtOAc: hexanes) to give methyl 3-cyclopropyl-3-(3-(2'-fluoro-5'-methoxy-[1,1'-biphenyl]-4-yl)isochroman-6-yl)propanoate. H NMR (500 MHz; CDCl₃): 7.53 (m, 2H), 7.46 (m, 2H), 7.28 (d, J=9.27 Hz, 1H), 7.11 (m, 1H), 7.06 (t, J=9.39 Hz, 1H), 7.01 (m, 1H), 6.92 (m, 1H), 6.82 (m, 1H), 4.98 (m, 1H), 7.76 (d, J=11.6 Hz, 1H), 4.55 (dd, J=3.32 & 12.17 Hz, 1H), 3.81 (s, 3H), 3.57 (s, 3H), 3.12 (m, 2H), 2.68 (m, 2H), 2.30 (m, 1H), 0.95 (m, 1H), 0.54 (m, 1H), 0.38 (m, 1H), 0.23 (m, 1H), 0.09 (m, 1H).

Step 9: 3-cyclopropyl-3-(3-(2'-fluoro-5'-methoxy-[1,1'-biphenyl]-4-yl)isochroman-6-yl)propanoic acid A solution of methyl 3-cyclopropyl-3-(3-(2'-fluoro-5'-methoxy-[1,1'-biphenyl]-4-yl)isochroman-6-yl)propanoate (25 mg, 0.054 mmol) and 1M LiOH (271 µl, 0.271 mmol) in THF (271 µl)/MeOH (271 µl) and stirred at 22° C. overnight. The reaction was then partitioned between ethyl acetate and 0.5N hydrochloric acid. The organic layer was separated, dried over Na₂SO₄, filtered and concentrated. The resulting residue was purified via MPLC using an ISCO 12 g column (30-100% EtOAc: hexanes) to afford the title compound as a mixture of 4 diastereomers. LC/MS: m/e 447 (M+H)). ¹H NMR (500 MHz; CDCl₃): 7.51 (d, J=7.3 Hz, 2H), 7.40 (d, J=8.13 Hz, 2H), 7.22 (d, J=7.78 Hz, 1H), 7.05 (m, 2H), 6.98 (m, 1H), 6.92 (m, 1H), 6.81 (m, 1H), 4.88 (m, 1H), 4.71 (m, 1H), 4.49 (m, 1H), 3.80 (s, 3H), 3.05 (m, 2H), 2.75 (m, 2H), 2.26 (m, 1H), 0.95 (m, 1H), 0.54 (m, 1H), 0.38 (m, 1H), 0.23 (m, 1H), 0.10 (m, 1H).

Example 21

(2S,3R)-3-cyclopropyl-3-((S)-3-(2'-fluoro-5'-methoxy-[1,1'-biphenyl]-4-yl)isochroman-6-yl)-2-methylpropanoic acid

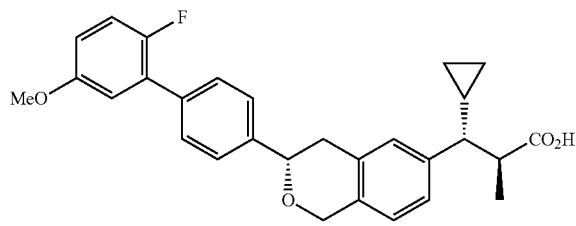 [SMILES: COc1ccc(F)c(-c2ccc([C@@H]3Cc4cc([C@H](C5CC5)[C@H](C)C(=O)O)ccc4CO3)cc2)c1]

Step 1: (S)-6-bromo-3-(2'-fluoro-5'-methoxy-[1,1'-biphenyl]-4-yl)isochroman-1-one A solution of formic acid (246 µl, 6.42 mmol) in ethyl acetate (3210 µl) was cooled to 0° C., then TEA (358 µl, 2.57 mmol) was added. This solution was then added to a reaction vessel containing 4-bromo-N,N-diethyl-2-(2-(2'-fluoro-5'-methoxy-[1,1'-biphenyl]-4-yl)-2-oxoethyl)benzamide (320 mg, 0.642 mmol, Example 10) and RuCl[(S,S)-TSDPEN] (mesitylene) (8.00 mg, 0.013 mmol). The reaction was stirred at room temperature overnight, then concentrated to give a crude residue. The residue was redissolved in toluene (4 mL) and p-TsOH (24.43 mg, 0.128 mmol) was added. The reaction heated to 110° C. for 6 hours, then concentrated to give a crude residue. The residue was purified via MPLC using an ISCO 24 g column (15-75% EtOAc: hexanes) to afford the title compound. ¹H NMR (500 MHz; CDCl₃): 8.00 (d, J=8.32 Hz, 1H), 7.58 (m, 3H), 7.52 (m, 2H), 7.47 (s, 1H), 7.07 (t, J=9.29 Hz, 1H), 6.93 (m, 1H), 6.83 (m, 1H), 5.58 (dd, J=3.39 Hz, 12.16 Hz, 1H), 3.81 (s, 3H), 3.35 (m, 1H), 3.14 (m, 1H).

Step 2: (S)-6-bromo-3-(2'-fluoro-5'-methoxy-[1,1'-biphenyl]-4-yl)isochroman

To a solution of (S)-6-bromo-3-(2'-fluoro-5'-methoxy-[1,1'-biphenyl]-4-yl)isochroman-1-one (90 mg, 0.211 mmol) in CPME (1404 µl), was added borane-methyl sulfide complex (2M in THF, 211 µl, 0.421 mmol) dropwise via syringe. The reaction mixture was warmed to 40° C. for 2 hours, then stirred at r.t. for 16 h. The reaction was then quenched with methanol (2 mL), heated to 40° C. for 30 minutes and then concentrated to give the lactol intermediate. The lactol intermediate was redissolved in DCM (0.5 mL) and treated with TFA (162 µl, 2.106 mmol), followed by triethylsilane (101 µl, 0.632 mmol). The reaction was stirred for 3 days, and then concentrated. The resulting residue was purified via MPLC using an ISCO 24 g column (10-20% EtOAc: hexanes) to afford the title compound. ¹H NMR (500 MHz; CDCl₃): 7.55 (d, J=6.87 Hz, 2H), 7.48 (d, J=8.22 Hz, 2H), 7.31 (m, 2H), 7.06 (t, J=9.21 Hz, 1H), 6.93 (m, 2H), 6.81 (m, 2H), 4.94 (m, 2H), 4.72 (dd, J=3.43 & 10.78 Hz, 1H), 3.81 (s, 3H), 3.07 (m, 1H), 2.96 (m, 1H).

Step 3: (S,Z)-methyl 3-cyclopropyl-3-(3-(2'-fluoro-5'-methoxy-[1,1'-biphenyl]-4-yl)isochroman-6-yl)-2-methylacrylate In a reaction vessel (S)-6-bromo-3-(2'-fluoro-5'-methoxy-[1,1'-biphenyl]-4-yl)isochroman (24 mg, 0.058 mmol) and bis(pinacolato)diboron (22.12 mg, 0.087 mmol) were combined, followed by potassium acetate (10.29 mg, 0.174 mmol) and PdCl₂(dppf).CH₂Cl₂ (4.74 mg, 5.81 µmol). This mixture was then evacuated and backfilled with N₂ (3 times). Dry, degassed 1,4-dioxane (290 µl) was added to this flask and the reaction mixture was heated at 100° C. for 12 hours. The reaction was then cooled to room temperature and (Z)-methyl 3-cyclopropyl-2-methyl-3-(tosyloxy)acrylate (27.0 mg, 0.087 mmol), bis(triphenyl-phosphine)palladium (II) dichloride (4 mg, 5.81 µmol) and 2M aq.sodium carbonate (58.1 µl, 0.116 mmol) were added. The reaction vessel was evacuated, sparged with nitrogen, and then the reaction was heated at 80° C. overnight. The reaction was then concentrated to give a residue, which was purified via MPLC using an ISCO 12 g column (5-30% EtOAc: hexanes) to afford the title compound. LC/MS: m/e 473(M+H)⁺.

Step 4: (2S,3R)-methyl 3-cyclopropyl-3-((S)-3-(2'-fluoro-5'-methoxy-[1,1'-biphenyl]-4-yl)isochroman-6-yl)-2-methylpropanoate (S,Z)-methyl 3-cyclopropyl-3-(3-(2'-fluoro-5'-methoxy-[1,1'-biphenyl]-4-yl)isochroman-6-yl)-2-methylacrylate (12 mg, 0.025 mmol) was charged into a reaction manifold with MeOH (0.67 mL). Then, 70 microliters of a catalyst solution prepared by dissolving bis(2-methylallyl)(1,5-cyclooctadiene)Ruthenium(II) (192 mg) and Josiphos (342 mg) in DCM (2 mL), agitated for 15 min at rt, was added. Then the tetrafluoroboric acid-diethyl ether complex (194 mg) was added slowly and the reaction mixture was stirred for 20 min at rt. The reaction manifold was then purged with nitrogen, followed by hydrogen gas and then pressurized to 500 psi with hydrogen. The reaction was then heated to 80° C. and shaken for 20 h. Then the reaction was cooled, filtered and concentrated to give the crude product, which was purified via MPLC using an ISCO 12 g column (5-30% EtOAc: hexanes) to afford the title compound. LC/MS: m/e 475(M+H)$^+$.

Step 5: (2S,3R)-3-cyclopropyl-3-((S)-3-(2'-fluoro-5'-methoxy-[1,1'-biphenyl]-4-yl)isochroman-6-yl)-2-methylpropanoic acid (Example 21)

A solution of (2S,3R)-methyl 3-cyclopropyl-3-((S)-3-(2'-fluoro-5'-methoxy-[1,1'-biphenyl]-4-yl)isochroman-6-yl)-2-methylpropanoate (7 mg, 0.015 mmol) and 1M aqueous LiOH (49.2 µl, 0.074 mmol) in THF (73.8 µl)/MeOH (73.8 µl) was stirred at 55° C. overnight. The reaction was then cooled and partitioned between ethyl acetate and 0.5N hydrochloric acid. The organic layer was separated, dried over anhydrous Na$_2$SO$_4$, filtered and concentrated. The resulting residue was purified via MPLC using ISCO 4 g column (5-75% EtOAc: hexanes) to give the title compound. LC/MS: m/e 461 (M+H)$^+$. $^1$H NMR (500 MHz; CDCl$_3$): 7.55 (d, J=8.23 Hz, 2H), 7.50 (d, J=7.66 Hz, 2H), 7.05 (t, J=9.28 Hz, 1H), 7.00 (m, 2H), 6.93 (m, 2H), 6.81 (m, 1H), 4.98 (m, 2H), 4.76 (m, 1H), 3.81 (s, 3H), 3.09 (m, 1H), 2.99 (m, 1H), 2.84 (m, 1H), 1.96 (d, J=9.85 Hz, 1H), 1.11 (m, 1H), 0.99 (d, J=6.87 Hz, 3H), 0.61 (m, 1H), 0.36 (m, 2H), 0.02 (m, 1H).

Example 22

(2S,3R)-3-cyclopropyl-3-((R)-3-(2'-fluoro-5'-methoxy-1,1'-biphenyl-4-yl)isochroman-6-yl)-2-methylpropanoic acid

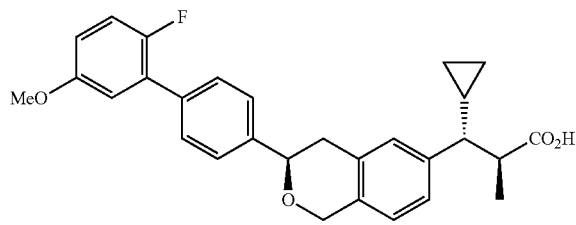 [SMILES: COc1ccc(F)c(-c2ccc([C@H]3Cc4cc([C@H](C5CC5)[C@H](C)C(=O)O)ccc4CO3)cc2)c1]

Example 22 was prepared in an analogous manner to Example 21 except for using RuCl[(R,R)-TSDPEN](mesitylene) as the chiral reduction catalyst in the reaction sequence (Step 1). LC/MS: m/e 461 (M+H)$^+$. $^1$H NMR (500 MHz; CDCl$_3$): 7.55 (d, J=8.3 Hz, 2H), 7.49 (d, J=7.6 Hz, 2H), 7.05 (t, J=9.28 Hz, 1H), 7.00 (m, 2H), 6.93 (m, 2H), 6.81 (m, 1H), 4.99 (m, 2H), 4.76 (m, 1H), 3.81 (s, 3H), 3.09 (m, 1H), 2.99 (m, 1H), 2.84 (m, 1H), 1.96 (d, J=9.85 Hz, 1H), 1.11 (m, 1H), 0.99 (d, J=6.87 Hz, 3H), 0.61 (m, 1H), 0.36 (m, 2H), 0.02 (m, 1H).

Example 23

(2S,3R)-3-cyclopropyl-3-((S)-3-(2'-fluoro-5'-methoxy-[1,1'-biphenyl]-4-yl)-1-oxoisochroman-6-yl)-2-methylpropanoic acid

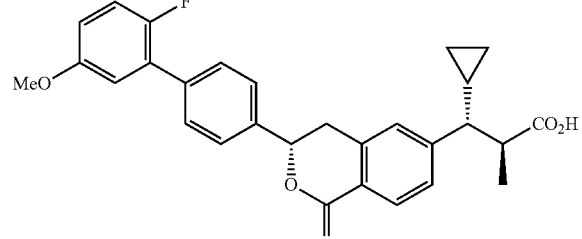

Example 23 was prepared in an analogous manner to Example 21 with the exception that the lactone reduction in Step 2 was omitted from the synthetic sequence. LC/MS: m/e 475(M+H)$^+$. $^1$H NMR (500 MHz; CDCl$_3$): 7.98 (d, J=8.23 Hz, 1H), 7.49 (d, J=7.9 Hz, 2H), 7.38 (d, J=7.0 Hz, 2H), 7.14 (d, J=8.37 Hz, 1H), 7.03 (t, J=9.35 Hz, 1H), 6.90 (m, 2H), 6.80 (m, 1H), 5.07 (m, 1H), 3.79 (s, 3H), 3.46 (m, 1H), 3.37 (m, 1H), 2.77 (m, 1H), 2.00 (m, 1H), 1.05 (m, 1H), 0.93 (d, J=6.86 Hz, 3H), 0.60 (m, 1H), 0.32 (m, 2H), −0.06 (m, 1H).

Example 24

(2S,3R)-3-cyclopropyl-3-((S)-3-(2'-fluoro-5'-methoxy-[1,1'-biphenyl]-4-yl)-1-oxoisochroman-6-yl)-2-methylpropanoic acid

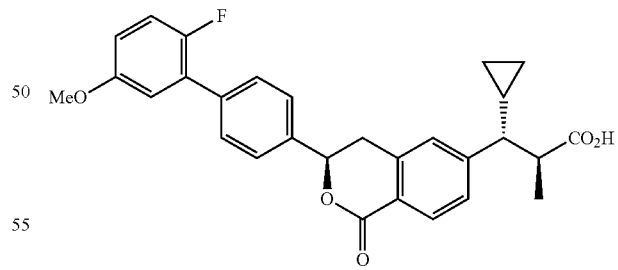

Example 24 was prepared in an analogous manner to Example 23 except RuCl[(R,R)-TSDPEN](Mesitylene) was used as the reduction catalyst in Step 1. LC/MS: m/e 475(M+H)$^+$. $^1$H NMR (500 MHz; CDCl$_3$): 7.97 (d, J=7.93 Hz, 1H), 7.49 (d, J=7.83 Hz, 2H), 7.41 (d, J=7.88 Hz, 2H), 7.13 (d, J=7.85 Hz, 1H), 7.04 (t, J=10 Hz, 1H), 6.91 (m, 2H), 6.80 (m, 1H), 5.05 (m, 1H), 3.80 (s, 3H), 3.44 (m, 1H), 3.36 (m, 1H), 2.78 (m, 1H), 2.01 (m, 1H), 1.05 (m, 1H), 0.92 (d, J=6.69 Hz, 3H), 0.60 (m, 1H), 0.32 (m, 2H), −0.06 (m, 1H).

Example 25

Sodium (2S,3R)-3-(3-(1-(2,5-bis(trifluoromethyl)benzyl)piperidin-4-yl)chroman-6-yl)-3-cyclopropyl-2-methylpropanoate

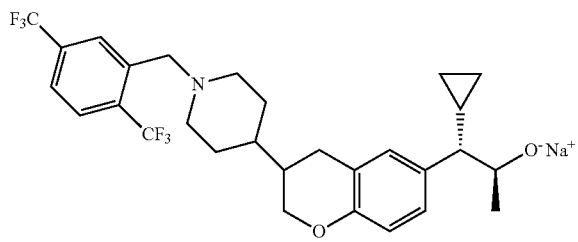

Step 1: 1-(2,5-Bis(trifluoromethyl)benzyl)-4-(6-bromo-2H-chromen-3-yl)piperidine

Step 1A

A stirred solution of 4-bromo-2-(hydroxymethyl)phenol (3.05 g, 15.0 mmol) in acetonitrile (50 mL) was treated with triphenylphosphine hydrobromide (5.16 g, 15.0 mmol). The resulting suspension was heated to 100° C. for 12 h. The acetonitrile was removed by rotary evaporation to give 4-bromo-2-((bromotriphenylphosphoranyl)-methyl)phenol, which was used in the next step.

Step 1B

A stirred solution of 4-bromo-2-((bromotriphenylphosphoranyl)methyl)phenol (0.78 g, 1.5 mmol) in THF (20 mL) was treated with KOtBu (1.5 mL, 1.5 mmol) at rt. After 20 minutes, tert-butyl 4-(2-bromoacetyl)piperidine-1-carboxylate (0.450 g, 1.5 mmol) was added in one portion. The resulting solution was heated to 80° C. for 30 minutes, then treated with an additional equivalent of KOtBu (1.470 ml, 1.470 mmol). The dark solution was heated to 80° C. for 3 h, then cooled, diluted with brine and extracted with EtOAc (3×100 mL). The organic layer was separated, dried, filtered and concentrated to give an oil. The oil was purified using 0-60% EtOAc:hexanes on a 120 g ISCO cartridge to yield tert-butyl 4-(6-bromo-2H-chromen-3-yl)piperidine-1-carboxylate. LC/MS: m/e 394.15 (M+H)+.

Step 1C

A stirred solution of tert-butyl 4-(6-bromo-2H-chromen-3-yl)piperidine-1-carboxylate (361 mg, 0.92 mmol) in DCM (15 mL) was treated with TFA (0.071 mL, 0.92 mmol). After 1 h, the solution was concentrated to dryness and used in next step.

Step 1D

To 2,5-bis(trifluoromethyl)benzyl bromide (295 mg, 0.960 mmol) in DMF (5 mL) at rt was added 4-(6-bromo-2H-chromen-3-yl)piperidine (269 mg, 0.92 mmol, product of Step 1C) and K2CO3 (379 mg, 2.74 mmol). The resulting mixture was stirred at rt for 12 h, then diluted with H2O, and extracted with EtOAc (3×50 mL). The combined organic layers were dried over MgSO4, filtered, and concentrated. The resulting residue was purified by flash chromatography (ISCO 120 g, 0-30% EtOac/hexanes) to give 1-(2,5-bis(trifluoromethyl)-benzyl)-4-(6-bromo-2H-chromen-3-yl)piperidine. LC/MS: m/e 521.32 (M+H)+.

Step 2: 1-(2,5-Bis(trifluoromethyl)benzyl)-4-(6-(4,4,5,5-tetramethyl-1,3,2-dioxaborolan-2-yl)-2H-chromen-3-yl)piperidine A solution of 1-(2,5-bis(trifluoromethyl)benzyl)-4-(6-bromo-2H-chromen-3-yl)piperidine (305 mg, 0.586 mmol), bis(pinacolato)diboron (298 mg, 1.172 mmol), 2nd Generation XPHOS Precatalyst (23.06 mg, 0.029 mmol) and KOAc (173 mg, 1.759 mmol) in CPME (2.9 mL) was degassed and heated at 110° C. for 4 h. The reaction mixture was then cooled, diluted with H2O and extracted with EtOAc. The combined organic layers were washed with brine, dried over anhydrous MgSO4, filtered and concentrated. The resulting residue was purified by silica gel column chromatography using 0-15% EtOAc/hexanes as eluent to give the title compound. LC/MS: m/e 568.44 (M+H)+.

Step 3: (Z)-Methyl 3-(3-(1-(2,5-bis(trifluoromethyl)benzyl)piperidin-4-yl)-2H-chromen-6-yl)-3-cyclopropyl-2-methylacrylate 1-(2,5-Bis(trifluoromethyl)benzyl)-4-(6-(4,4,5,5-tetramethyl-1,3,2-dioxaborolan-2-yl)-2H-chromen-3-yl)piperidine (252 mg, 0.4 mmol), (Z)-methyl 3-cyclopropyl-2-methyl-3-(tosyloxy)acrylate (207 mg, 0.7 mmol) and Pd(Ph3P)4 (26 mg, 0.02 mmol) were added to a sealed tube with 1,4-dioxane (3 mL) and sparged with nitrogen. Then K2CO3 (444 µL, 0.9 mmol, 2 M aq) was added. The reaction mixture was heated at 100° C. for 4 h. Then the reaction mixture was cooled, diluted with H2O and extracted with EtOAc. The combined organic layers were washed with brine, dried over anhydrous MgSO4, filtered, and concentrated. The resulting residue was purified via silica gel column chromatography using 0-10% EtOAc/hexanes as eluent to yield the title compound. LC/MS: m/e 580.47 (M+H)+.

Step 4: (2S,3R)-Methyl 3-(3-(1-(2,5-bis(trifluoromethyl)benzyl)piperidin-4-yl)chroman-6-yl)-3-cyclopropyl-2-methylpropanoate The title compound was prepared from (Z)-methyl 3-(3-(1-(2,5-bis(trifluoromethyl)benzyl)piperidin-4-yl)-2H-chromen-6-yl)-3-cyclopropyl-2-methylacrylate according to the procedure described in Step 4 of Example 21. LC/MS: m/e 584.58 (M+H)+.

Step 5: Sodium (2S,3R)-3-(3-(1-(2,5-bis(trifluoromethyl)benzyl)piperidin-4-yl)chroman-6-yl)-3-cyclopropyl-2-methylpropanoate To a solution of (2S,3R)-methyl 3-(3-(1-(2,5-bis(trifluoromethyl)benzyl)piperidin-4-yl)chroman-6-yl)-3-cyclopropyl-2-methyl-propanoate (29 mg, 0.050 mmol) in THF (0.75 mL)/MeOH (0.75 mL)/water (0.5 mL) at rt was added lithium hydroxide hydrate (8.31 mg, 0.2 mmol). The reaction mixture was stirred at 55° C. for 48 h. Then the reaction mixture was cooled and diluted with H2O, acidified with 1N HCl to pH 4-5, and extracted with EtOAc. The combined organic layers were washed with brine, dried over MgSO4, filtered, and concentrated. The resulting residue was purified by column chromatography using 0-100% EtOAc/hexanes as eluent to give (2S,3R)-3-(3-(1-(2,5-bis(trifluoromethyl)benzyl)piperidin-4-yl)chroman-6-yl)-3-cyclopropyl-2- methylpropanic acid. The carboxylic acid (22 mg) was dissolved in MeCN (1 mL), treated with 1M NaOH (47 μl), and lyophilized to dryness to give the title compound. $^1$H NMR (500 MHz, CD$_3$OD): δ 0.35-0.31 (m, 1H); 0.52 (dd, J=9.3, 5.0 Hz, 1H); 0.67-0.64 (m, 1H); 0.93 (d, J=6.9 Hz, 3H); 1.19-1.15 (m, 1H); 1.45 (dd, J=17.4, 8.3 Hz, 2H); 1.60-1.55 (m, 2H); 2.01-1.88 (m, 3H); 2.23 (t, J=11.6 Hz, 2H); 2.73-2.68 (m, 2H); 3.04-2.96 (m, 3H); 3.84 (s, 2H); 3.93 (t, J=10.0 Hz, 1H); 4.41 (d, J=10.7 Hz, 1H); 6.75 (d, J=8.3 Hz, 1H); 6.99-6.97 (m, 2H); 7.86 (d, J=8.3 Hz, 1H); 8.01 (d, J=8.2 Hz, 1H); 8.33 (s, 1H). LC/MS: m/e 570.43 (M+H).

Example 26

3-cyclopropyl-3-(7-(2'-fluoro-5'-methoxy-[1,1'-biphenyl]-4-yl)-5,6,7,8-tetrahydronaphthalen-2-yl)-2-methylpropanoic acid

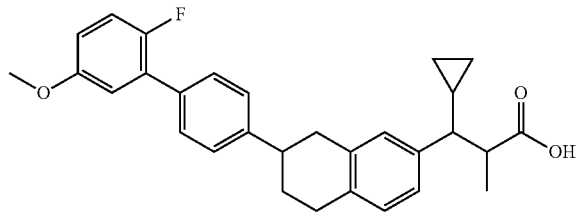 [SMILES: COc1ccc(F)c(-c2ccc(C3CCc4ccc(C(C5CC5)C(C)C(=O)O)cc4C3)cc2)c1]

Step 1: 7-bromo-3,4-dihydronaphthalen-2(1H)-one

To a suspension of aluminum trichloride (18.2 g, 137 mmol) in DCM (25 ml) was added 3, 4-dihydronaphthalen-2(1H)-one (10.0 g, 68.4 mmol) in DCM (100 ml) at 0° C. under a nitrogen atmosphere. The reaction mixture was stirred for 10 minutes, then bromine (12.0 g, 75.1 mmol) was added. The reaction mixture was warmed to room temperature (20° C.) and stirred for 16 h. Then the reaction mixture was poured into 250 mL of ice-water and extracted with DCM (100 mL×3). The organic layers were combined, dried over anhydrous MgSO$_4$ and filtered. The filtrate was concentrated in vacuo to give a residue, which was purified by flash column chromatography on silica gel (PE:EtOAc=30:1 to 10:1) to give the title compound. $^1$H NMR (400 MHz, CDCl$_3$): δ 7.33 (d, J=7.6 Hz, 1H), 7.26 (s, 1H), 7.10 (d, J=7.6 Hz, 1H), 3.53 (s, 2H), 3.00 (t, J=6.6 Hz, 2H), 2.52 (t, J=5.8 Hz, 2H).

Step 2: 7-(4, 4, 5, 5-tetramethyl-1, 3, 2-dioxaborolan-2-yl)-3, 4-dihydronaphthalen-2(1H)-one To a solution of 7-bromo-3,4-dihydronaphthalen-2(1H)-one (5.52 g, 24.5 mmol) in DMF (60 ml) were added 4,4,4',4',5,5,5',5'-octamethyl-2,2'-bi(1,3,2-dioxaborolane) (7.47 g, 29.4 mmol), potassium acetate (7.22 g, 73.6 mmol) and Pd(dppf)Cl$_2$ (1.79 g, 2.45 mmol) under a nitrogen atmosphere. The reaction was stirred at 90° C. for 2 h. Then the reaction mixture was cooled to room temperature, diluted with water (100 mL), and extracted with EtOAc (50 mL×3). The organic layers were combined, washed with brine (50 mL), dried over anhydrous MgSO$_4$ and filtered. The filtrate was concentrated to give a residue, which was purified by flash column chromatography on silica gel (PE:EtOAc=20:1 to 10:1) to give the title compound. $^1$H NMR (400 MHz, CDCl$_3$): δ 7.65 (d, J=7.2 Hz, 1H), 7.56 (s, 1H), 7.23 (d, J=7.2 Hz, 1H), 3.57 (s, 2H), 3.05 (t, J=6.4 Hz, 2H), 2.52 (t, J=6.6 Hz, 2H), 1.32 (s, 12H).

Step 3: (E)-methyl 3-cyclopropyl-2-methyl-3-(7-oxo-5,6,7,8-tetrahydronaphthalen-2-yl) acrylate To a solution of 7-(4,4,5,5-tetramethyl-1,3,2-dioxaborolan-2-yl)-3,4-dihydronaphthalen-2(1H)-one (3.00 g, 11.0 mmol) in THF (30 ml) and water (6.0 ml) were added (E)-methyl 3-cyclopropyl-2-methyl-3-(((trifluoromethyl)sulfonyl)oxy)acrylate (3.42 g, 11.0 mmol), Pd(PPh$_3$)$_2$Cl$_2$ (0.773 g, 1.10 mmol) and K$_2$CO$_3$ (4.57 g, 33.1 mmol) under a nitrogen atmosphere. The reaction mixture was stirred at 25° C. for 6 h. Then water (15 mL) was added, and the mixture was extracted with EtOAc (30 mL×3). The combined organic layers were washed with water (30 mL) and brine (30 mL), dried over anhydrous MgSO$_4$ and filtered. The filtrate was concentrated in vacuo to give a residue, which was purified by flash column chromatography on silica gel (PE:EtOAc=30:1 to 10:1) to give the title compound. $^1$H NMR (400 MHz, CDCl$_3$) δ 7.14 (d, J=7.6 Hz, 1H), 6.83 (d, J=7.0 Hz, 1H), 6.74 (s, 1H), 3.56 (s, 2H), 3.41 (s, 3H), 3.04 (t, J=6.6 Hz, 1H), 2.56 (t, J=6.6 Hz, 1H), 2.16 (s, 1H), 1.89-1.82 (m, 1H), 0.78-0.73 (m, 2H), 0.34-0.28 (m, 2H).

Step 4: methyl 3-cyclopropyl-2-methyl-3-(7-oxo-5,6,7,8-tetrahydronaphthalen-2-yl)propanoate To a solution of (E)-methyl 3-cyclopropyl-2-methyl-3-(7-oxo-5,6,7,8-tetrahydro-naphthalen-2-yl) acrylate (1.05 g, 3.69 mmol) in MeOH (10 ml) was added Pd(OH)$_2$/C (1.30 g, 20%). The mixture was stirred for 2 h under a hydrogen balloon at room temperature. Then the reaction mixture was filtered and the filtrate was concentrated in vacuo to give a residue, which was purified by preparative TLC (PE:EtOAc=3:1, v/v) to give the title compound. $^1$H NMR (400 MHz, CDCl3) δ 7.18-7.12 (m, 1H), 7.06-6.95 (m, 1H), 6.90 (s, 1H), 3.73 (s, 2H), 3.58 (s, 3H), 3.06-3.03 (m, 2H), 2.88-2.77 (m, 1H), 2.58-2.55 (m, 2H), 1.28-1.24 (m, 1H), 1.08-1.01 (m, 1H), 0.95-0.92 (m, 3H), 0.60-0.53 (m, 1H), 0.36-0.23 (m, 2H), 0.01-0.04 (m, 1H).

Step 5: methyl 3-cyclopropyl-2-methyl-3-(7-(((trifluoromethyl) sulfonyl) oxy)-5,6-dihydronaphthalen-2-yl) propanoate To a solution of (E)-methyl 3-cyclopropyl-2-methyl-3-(7-oxo-5,6,7,8-tetrahydro-naphthalen-2-yl)acrylate (300 mg, 1.06 mmol) in THF (4.0 ml) was added KHMDS (2.11 mL, 2.11 mmol, 1M) dropwise at −78° C. under a nitrogen atmosphere. After the mixture was stirred for 0.5 h, 1,1,1-trifluoro-N-phenyl-N-((trifluoromethyl)sulfonyl)-methanesulfonamide (565 mg, 1.58 mmol) in THF (1.0 ml) was added dropwise. The reaction was warmed to room temperature (20° C.) and stirred for 16 h. Then the reaction was quenched with water (10 mL), and extracted with EtOAc (10 mL×3). The combined organic layers were washed with brine (10 mL), dried over anhydrous MgSO$_4$ and filtered. The filtrate was concentrated to give a residue, which was purified by preparative TLC (PE:EtOAc=2:1, v/v) to give the title compound.
$^1$H NMR (400 MHz, CDCl3) δ 7.42-7.38 (m, 2H), 7.33-7.29 (m, 2H), 3.74 (s, 3H), 3.06-3.01 (m, 1H), 2.87-2.76 (m, 1H), 2.72-2.68 (m, 2H), 1.68 (s, 2H), 1.27 (d, J=7.0 Hz, 3H), 1.06-1.04 (m, 1H), 0.61-0.54 (m, 1H), 0.37-0.23 (m, 2H), 0.00-0.07 (m, 1H).

Step 6: methyl 3-cyclopropyl-3-(7-(2'-fluoro-5'-methoxy-[1, 1'-biphenyl]-4-yl)-5,6-dihydronaphthalen-2-yl)-2-methylpropanoate To a solution of (2S,3R)-methyl 3-cyclopropyl-2-methyl-3-(7-(((trifluoromethyl)-sulfonyl)oxy)-5,6-dihydronaphthalen-2-yl)propanoate (100 mg, 0.239 mmol) in THF (1.0 ml) and water (0.2 ml) were added 2-(2'-fluoro-5'-methoxy-[1, 1'-biphenyl]-4-yl)-4,4,5,5-tetramethyl-1,3,2-dioxaborolane (118 mg, 0.358 mmol), $K_2CO_3$ (99.1 mg, 0.717 mmol) and Pd(dppf)Cl$_2$ (17.0 mg, 0.024 mmol) at room temperature under a nitrogen atmosphere. The reaction mixture was heated to 100° C. and stirred for 2 h. Then the reaction was cooled to room temperature, diluted with water (5.0 mL) and extracted with EtOAc (10 mL×3). The organic layers were combined, dried over anhydrous MgSO$_4$ and filtered. The filtrate was concentrated in vacuo to give a residue, which was purified by preparative TLC (PE:EtOAc=5:1, v/v) to give the title compound.

Step 7: methyl 3-cyclopropyl-3-(7-(2'-fluoro-5'-methoxy-[1, 1'-biphenyl]-4-yl)-5,6,7,8-tetrahydronaphthalen-2-yl)-2-methylpropanoate To a solution of methyl 3-cyclopropyl-3-(7-(2'-fluoro-5'-methoxy-[1, 1'-biphenyl]-4-yl)-5,6-dihydronaphthalen-2-yl)-2-methylpropanoate (10 mg, 0.021 mmol) in MeOH (2.0 ml) was added PdOH$_2$/C (14.9 mg, 20%). The reaction mixture was stirred for 2 h under a hydrogen balloon at room temperature. Then the reaction mixture was filtered and the filtrate was concentrated in vacuo to give a residue, which was purified by preparative TLC (PE:EtOAc=5:1, v/v) to give the title compound.

Step 8: 3-cyclopropyl-3-(7-(2'-fluoro-5'-methoxy-[1, 1'-biphenyl]-4-yl)-5,6,7,8-tetrahydronaphthalen-2-yl)-2-methylpropanoic acid (Example 20)

To a solution of methyl 3-cyclopropyl-3-(7-(2'-fluoro-5'-methoxy-[1, 1'-biphenyl]-4-yl)-5,6,7,8-tetrahydronaphthalen-2-yl)-2-methylpropanoate (5.0 mg, 10.6 µmol) in a co-solvent of MeOH (1.5 ml), THF (1.5 ml) and water (1.5 ml) was added lithium hydroxide (2.53 mg, 0.106 mmol). The mixture was stirred at 50° C. for 16 h. The resulting mixture was acidified with HCl (2M) to pH=2, and extracted with EtOAc (5.0 mL×3). The combined organic layers were washed with brine (5.0 mL), dried over anhydrous MgSO$_4$ and filtered. The filtrate was concentrated to give a residue, which was purified by preparative HPLC (preparative HPLC on a GILSON 281 instrument fitted with a Phenomenex Synergi C18 100*21.2 mm*4 um using water and acetonitrile as the eluents. Mobile phase A: water (containing 0.1% TFA, v/v), mobile phase B: acetonitrile; Gradient 66-81% B, 0-10 min; 100% B, 10.5-12.5 min; 5% B, 13-15 min) and lyophilized to give the title compound. MS (ESI) m/z: 459.1 [M+H]$^+$; 1H NMR (400 MHz, CDCl$_3$) δ: 7.54 (d, J=7.6, 2H), 7.38 (d, J=7.6, 2H), 7.10-7.06 (m, 2H), 6.97-6.95 (m, 2H), 6.89-6.82 (m, 2H), 3.83 (s, 3H), 3.03-2.83 (m, 4H), 2.19-2.17 (m, 2H), 2.06-1.93 (m, 2H), 1.68-1.60 (m, 2H), 1.26 (s, 3H), 1.02-1.00 (m, 1H), 0.89-0.85 (m, 2H), 0.39-0.38 (m, 2H).

Example 27

(2S,3R)-3-cyclopropyl-3-(3-(2'-fluoro-5'-methoxy-[1,1'-biphenyl]-4-yl)thiochroman-6-yl)-2-methylpropanoic acid

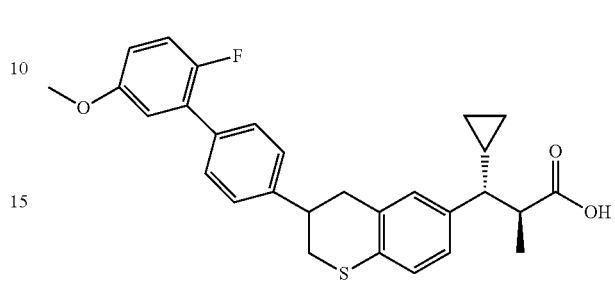

Step 1: 2-Bromo-1-(2'-fluoro-5'-methoxy-[1,1'-biphenyl]-4-yl)ethanone

Step 1A

A solution of (2-fluoro-5-methoxyphenyl)boronic acid (3.95 g, 23.24 mmol), 1-(4-bromophenyl)ethanone (3.7 g, 18.59 mmol), S-PhosBiaryl Precatalyst-2nd Gen. (0.268 g, 0.372 mmol) and 2-Me THF (62.0 mL) was degassed. Then degassed potassium phosphate (55.8 ml, 55.8 mmol, 1 M aqueous) solution was added and the reaction was heated to 80° C. for 12 hours. Then the reaction was allowed to cool to rt. The reaction layers were separated and the aqueous layer extracted with 100 mL of Et$_2$O. The combined organic layers were washed with brine, dried over sodium sulfate, filtered and concentrated. The resulting crude oil was purified using MPLC (220 g ISCO, 0-30% EtOAc:hexanes) to give 1-(2'-fluoro-5'-methoxy-[1,1'-biphenyl]-4-yl)ethanone.

Step 1B

Br$_2$ (1.3 mL, 8.1 mmol) in DCM (10 mL) was added dropwise to a stirred solution of 1-(2'-fluoro-5'-methoxy-[1,1'-biphenyl]-4-yl)ethanone (1.9 g, 8.1 mmol) in DCM (40 mL) at room temperature for 1 hour. Then the reaction mixture was washed with aqueous sodium hydrogen carbonate, dried (MgSO$_4$), filtered and evaporated under reduced pressure to give a residue, which was used in the next step.

Step 2: 2-(3-(2'-Fluoro-5'-methoxy-[1,1'-biphenyl]-4-yl)-2H-thiochromen-6-yl)-4,4,5,5-tetramethyl-1,3,2-dioxaborolane

Step 2A

A stirred solution of 5-chloro-2-mercaptobenzoic acid (1.86 g, 9.9 mmol) in THF (40 mL) was treated with LAH (0.71 g, 18.7 mmol) at −78° C. After 1 h, the solution was quenched with water (0.71 mL), followed by 15% NaOH (0.71 mL), and then water (2.1 mL). The mixture was allowed to warm to rt and stirred vigorously. The salt which was formed was filtered through a pad of Celite™ using Et$_2$O as an eluent. The filtrate was then rewashed with MeOH and DCM to remove additional amounts of material.

The filtrate was concentrated down to provide crude 5-chloro-2-mercaptophenylmethanol. LC/MS: m/e 174.1 (M+H)+.

Step 2B

A stirred solution of 5-chloro-2-mercaptophenylmethanol (1.72 g, 9.9 mmol) in acetonitrile (50 mL) was treated with triphenylphosphine hydrobromide (3.38 g, 9.9 mmol). The resulting suspension was heated to 80° C. for 12 h. Then the acetonitrile was removed by rotary evaporation to give 2-((bromotriphenylphosphoranyl)methyl)-4-chlorobenzenethiol, which was used in the next step.

Step 2C

A stirred solution of 4-bromo-2-((bromotriphenylphosphoranyl)methyl)-4-chlorobenzenethiol (0.96 g, 1.9 mmol) in THF (20 mL) was treated with KOtBu (1.47 mL, 1.47 mmol, 1M in THF) at rt. After 20 minutes, 2-bromo-1-(2'-fluoro-5'-methoxy-[1,1'-biphenyl]-4-yl)ethanone (0.475 g, 1.47 mmol) was added in one portion. The reaction mixture was heated to 80° C. for 30 min. Then the reaction was treated with an additional equivalent of KOtBu (1.47 ml, 1.47 mmol, 1M in THF) and heated to 80° C. for 12 h. The reaction mixture was then diluted with 1N HCl and EtOAc. The organic layer was separated, dried, filtered and concentrated to give an oil. The oil was purified using an ISCO (0-25% EtOAc:hexanes) to give 6-chloro-3-(2'-fluoro-5'-methoxy-[1,1'-biphenyl]-4-yl)-2H-thiochromene. LC/MS: m/e 383.0 (M+H)+.

Step 2D

The solution of 6-chloro-3-(2'-fluoro-5'-methoxy-[1,1'-biphenyl]-4-yl)-2H-thiochromene (212 mg, 0.5 mmol), bispinacolatodiboron (281 mg, 1.1 mmol), 2nd Generation XPHOS Precatalyst (44 mg, 0.05 mmol) and KOAc (109 mg, 1.1 mmol) in CPME (28 mL) was degassed and heated at 110° C. for 12 h. The reaction mixture was then cooled, diluted with H2O, and extracted with EtOAc. The combined organic layers were washed with brine, dried over MgSO4, filtered and concentrated. The resulting residue was purified by column chromatography using 0-35% EtOAc/hexanes as eluent to give the title compound. LC/MS: m/e 475.4 (M+H)+.

Step 3: (Z)-Methyl 3-cyclopropyl-3-(3-(2'-fluoro-5'-methoxy-[1,1'-biphenyl]-4-yl)-2H-thiochromen-6-yl)-2-methylacrylate 2-(3-(2'-fluoro-5'-methoxy-[1,1'-biphenyl]-4-yl)-2H-thiochromen-6-yl)-4,4,5,5-tetramethyl-1,3,2-dioxaborolane (199 mg, 0.419 mmol), (Z)-methyl 3-cyclopropyl-2-methyl-3-(tosyloxy)acrylate (195 mg, 0.629 mmol) and Pd(Ph3P)4 (24.24 mg, 0.021 mmol) were charged into a sealed tube with dioxane (2.1 mL) and sparged with nitrogen. Then aqueous K2CO3 (419 µL, 0.84 mmol, 0.5 M) solution was added and the reaction was heated to 100° C. for 4 h. Then the reaction mixture was cooled, diluted with H2O, and extracted with EtOAc. The combined organic layers were washed with brine, dried over MgSO4, filtered, and concentrated. The resulting residue was purified by column chromatography using 0-20% EtOAc/hexanes as eluent to give title compound. LC/MS: m/e 487.35 (M+H)+.

Step 4: (2S,3R)-Methyl 3-cyclopropyl-3-(3-(2'-fluoro-5'-methoxy-[1,1'-biphenyl]-4-yl)thiochroman-6-yl)-2-methylpropanoate The title compound was prepared from (Z)-Methyl 3-cyclopropyl-3-(3-(2'-fluoro-5'-methoxy-[1,1'-biphenyl]-4-yl)-2H-thiochromen-6-yl)-2-methylacrylate according to the procedure described in Step 4 of Example 21._LC/MS: m/e 491.48 (M+H)+.

Step 5: (2S,3R)-3-Cyclopropyl-3-(3-(2'-fluoro-5'-methoxy-[1,1'-biphenyl]-4-yl)thiochroman-6-yl)-2-methylpropanoic acid To (2S,3R)-methyl 3-cyclopropyl-3-(3-(2'-fluoro-5'-methoxy-[1,1'-biphenyl]-4-yl)thiochroman-6-yl)-2-methylpropanoate (21.5 mg, 0.04 mmol) in THF (0.75 mL)/MeOH (0.75 mL)/water (0.5 mL) at rt was added lithium hydroxide hydrate (7.4 mg, 0.17 mmol). The reaction mixture was stirred at 55° C. for 12 h. Then the reaction mixture was cooled, diluted with H2O, acidified with 1N HCl to pH 4-5, and extracted with EtOAc. The organic layer was separated, dried over MgSO4, filtered, and concentrated. The resulting residue was purified by column chromatography using 0-100% EtOAc/hexanes as eluent to give the title compound. 1H NMR (500 MHz, acetone): δ 0.14 (s, 1H); 0.33 (t, J=10.4 Hz, 2H); 0.57 (s, 1H); 0.95 (t, J=6.9 Hz, 3H); 1.18 (m, 1H); 1.30 (m, 1H); 2.00 (m, 1H); 2.80 (m, 3H); 3.10 (d, J=14.2 Hz, 2H); 3.88 (s, 3H); 6.95 (d, J=8.9 Hz, 1H); 7.09-7.03 (m, 4H); 7.17 (t, J=9.7 Hz, 1H); 7.50 (d, J=7.8 Hz, 1H); 7.60-7.58 (m, 3H). LC/MS: m/e 477.42 (M+H)+.

Example 28

(2S,3R)-3-Cyclopropyl-3-(3-(2'-fluoro-5'-methoxy-[1,1'-biphenyl]-4-yl)-1,1-dioxidothiochroman-6-yl)-2-methylpropanoic acid

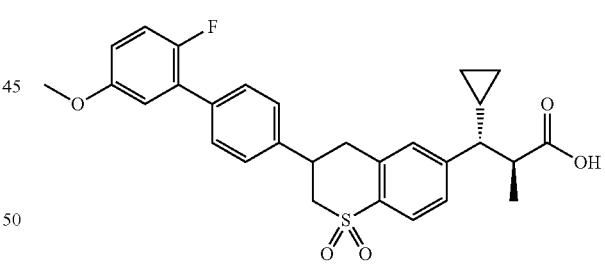

A solution of (2S,3R)-3-cyclopropyl-3-(3-(2'-fluoro-5'-methoxy-[1,1'-biphenyl]-4-yl)thiochroman-6-yl)-2-methylpropanoic acid (16 mg, 0.034 mmol) in MeOH (84 µL) was treated with a solution of oxone (83 mg, 0.13 mmol) in water (84 µL) at room temperature for 2.5 h. Then the reaction mixture was partitioned between H2O and EtOAc. The organic layer was separated, dried over sodium sulfate, filtered and concentrated. The resulting residue was purified by HPLC to give the title compound. 1H NMR (500 MHz, acetone): δ 0.12 (s, 1H); 0.39-0.29 (m, 2H); 0.61-0.58 (m, 1H); 0.94 (d, J=6.9 Hz, 3H); 1.21-1.17 (m, 1H); 1.23-1.37 (m, 1H); 2.12 (t, J=9.8 Hz, 1H); 2.70-2.90 (m, 1H); 3.33 (s, 2H); 3.54 (d, J=9.4 Hz, 1H); 3.90-3.85 (m, 4H); 6.95 (dt, J=9.0, 3.5 Hz, 1H); 7.06 (dd, J=6.3, 3.2 Hz, 1H); 7.17 (t, J=9.6 Hz, 1H); 7.33 (s, 1H); 7.43 (d, J=8.2 Hz, 1H); 7.64-7.59 (m, 4H); 7.82 (d, J=8.2 Hz, 1H). LC/MS: m/e 509.52 (M+H)+.

Example 29

(2S,3S)-3-cyclopropyl-3-(7-(2-fluoro-4-(2-methoxypyridin-4-yl)phenyl)-5,6-dihydronaphthalen-2-yl)-2-methylpropanoic acid

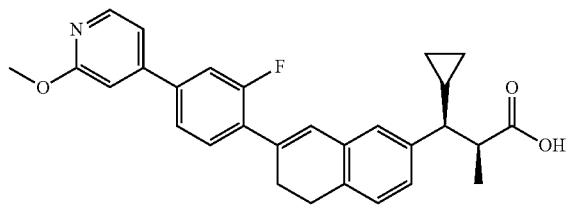 [SMILES: COc1cc(-c2ccc(C3=Cc4cc([C@@H](C5CC5)[C@H](C)C(=O)O)ccc4CC3)c(F)c2)ccn1]

Step 1: methyl 3-cyclopropyl-3-(7-(2-fluoro-4-(2-methoxypyridin-4-yl) phenyl)-5,6-dihydronaphthalen-2-yl)-2-methylpropanoate To a solution of methyl 3-cyclopropyl-2-methyl-3-(7-(((trifluoromethyl)sulfonyl)oxy)-5,6-dihydronaphthalen-2-yl)propanoate (1.40 g, 3.35 mmol) in 1,4-dioxane (30 ml) and water (6.0 ml) were added 4-(3-fluoro-4-(4,4,5,5-tetramethyl-1,3,2-dioxaborolan-2-yl)phenyl)-2-methoxypyridine (1.32 g, 4.02 mmol), $K_2CO_3$ (1.39 g, 10.0 mmol) and Pd(dppf)Cl$_2$ (0.245 g, 0.335 mmol) under a nitrogen atmosphere. The reaction mixture was stirred at 100° C. for 2 h. Then the reaction mixture was cooled to room temperature, and diluted with water (100 mL). The aqueous phase was extracted with EtOAc (50 mL×3). The combined organic layers were washed with water (50 mL) and brine (20 mL), dried over anhydrous MgSO$_4$ and filtered. The filtrate was concentrated in vacuo to give a residue, which was purified by flash column chromatography on silica gel (PE: EtOAc=30:1 to 10:1) to give the title compound. $^1$H NMR (400 MHz, CDCl3) δ 1.27 (d, J=7.0 Hz, 1H), 7.53-7.48 (m, 1H), 7.43-7.39 (m, 1H), 7.37-7.31 (m, 1H), 7.12-7.08 (m, 2H), 6.99-6.94 (m, 3H), 6.85 (s, 1H), 4.00 (m, 3H), 3.74 (s, 2H), 2.94 (d, J=7.6 Hz, 2H), 2.76 (d, J=7.6 Hz, 2H), 1.68 (s, 2H), 1.12-1.05 (m, 1H), 0.98 (d, J=7.2 Hz, 3H), 0.60-0.54 (m, 1H), 0.38-0.31 (m, 1H), 0.29-0.23 (m, 1H), 0.05-0.00 (m, 1H).

Step 2: (2S,3S)-methyl 3-cyclopropyl-3-(7-(2-fluoro-4-(2-methoxypyridin-4-yl)phenyl)-5,6-dihydronaphthalen-2-yl)-2-methylpropanoate (Peak 1); (2S,3R)-methyl-3-cyclopropyl-3-(7-(2-fluoro-4-(2-methoxypyridin-4-yl)phenyl)-5,6-dihydronaphthalen-2-yl)-2-methylpropanoate (Peak; (2R,3S)-methyl 3-cyclopropyl-3-(7-(2-fluoro-4-(2-methoxypyridin-4-yl)phenyl)-5,6-dihydronaphthalen-2-yl)-2-methylpropanoate (Peak 3); and (2R,3R)-methyl 3-cyclopropyl-3-(7-(2-fluoro-4-(2-methoxypyridin-4-yl)phenyl)-5,6-dihydronaphthalen-2-yl)-2-methylpropanoate (Peak 4)

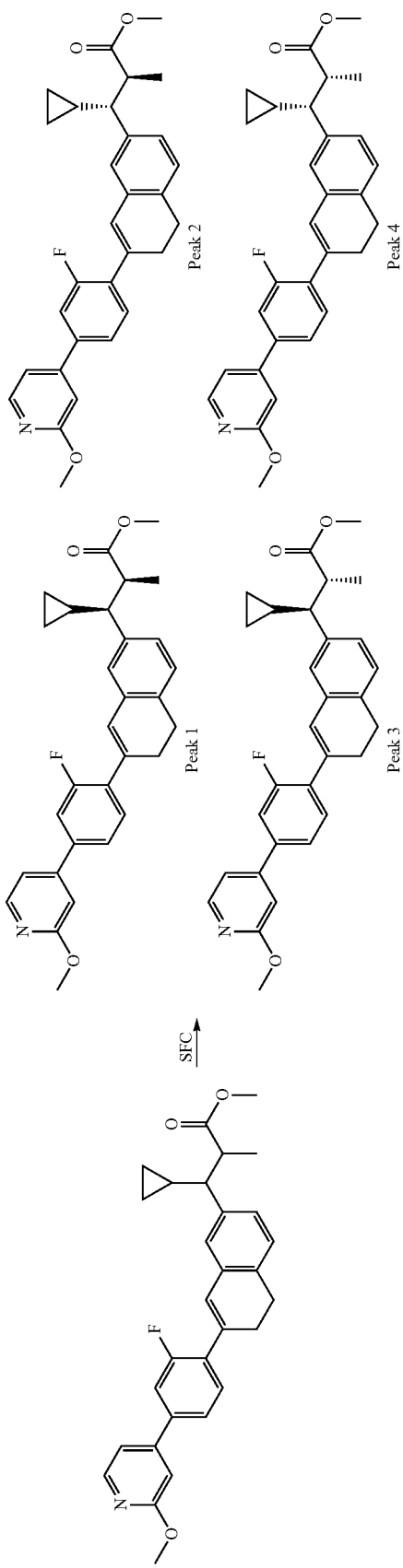

Methyl 3-cyclopropyl-3-(7-(2-fluoro-4-(2-methoxypyridin-4-yl)phenyl)-5,6-dihydro-naphthalen-2-yl)-2-methylpropanoate (80 mg, 0.170 mmol) was subjected to chiral SFC chromatography (SFC Instrument and conditions: Instrument: Berger MultiGram™ SFC, Mettler Toledo Co, Ltd; Column: OJ (250*30 mm 5 um); Mobile phase: 25% EtOH+NH$_3$H$_2$O 60 ml/min; Column Temp: 38° C.; Nozzle Pressure: 100 Bar; Nozzle Temp: 60° C.; Evaporator Temp: 20° C.; Trimmer Temp: 25° C. and Wavelength: 220 nm.) to separate the four diastereomers into four peaks, which eluted from fastest to slowest as follows: (2S,3S)-methyl 3-cyclopropyl-3-(7-(2-fluoro-4-(2-methoxypyridin-4-yl)phenyl)-5,6-dihydronaphthalen-2-yl)-2-methylpropanoate (Peak 1); (2S,3R)-methyl 3-cyclopropyl-3-(7-(2-fluoro-4-(2-methoxypyridin-4-yl)phenyl)-5,6-dihydronaphthalen-2-yl)-2-methylpropanoate (Peak 2); (2R,3S)-methyl 3-cyclopropyl-3-(7-(2-fluoro-4-(2-methoxypyridin-4-yl)phenyl)-5,6-dihydronaphthalen-2-yl)-2-methylpropanoate (Peak 3); and (2R,3R)-methyl 3-cyclopropyl-3-(7-(2-fluoro-4-(2-methoxypyridin-4-yl)phenyl)-5,6-dihydronaphthalen-2-yl)-2-methylpropanoate (Peak 4).

Step 3: (2S,3S)-3-cyclopropyl-3-(7-(2-fluoro-4-(2-methoxypyridin-4-yl) phenyl)-5,6-dihydronaphthalen-2-yl)-2-methylpropanoic acid To a solution of (2S,3S)-methyl 3-cyclopropyl-3-(7-(2-fluoro-4-(2-methoxy-pyridin-4-yl) phenyl)-5,6-dihydronaphthalen-2-yl)-2-methylpropanoate (Peak 1 from SFC separation of Step 2, 7.0 mg, 0.0148 mmol) in a co-solvent of MeOH (1.5 ml), THF (1.5 ml) and water (1.5 ml) was added LiOH (4.0 mg, 0.148 mmol). The mixture was stirred at 50° C. for 16 h. Then the reaction mixture was acidified with HCl (2 M) to pH=2, and extracted with EtOAc (5.0 mL×3). The combined organic layers were washed with brine (5 mL), dried over anhydrous MgSO$_4$ and filtered. The filtrate was concentrated to give a residue, which was purified by preparative HPLC (neutral, on a GILSON 281 instrument fitted with a Phenomenex Gemini C18 250*21.2 mm*5 um using water and acetonitrile as the eluents. Mobile phase A: water (containing 0.1% TFA, v/v), mobile phase B: acetonitrile. Gradient: 28-58% B, 0-10 min; 100% B, 10.5-12.5 min; 5% B, 13-15 min) to give the title compound. MS (ESI) m/z: 458.1 [M+H]$^+$ $^1$H NMR (400 MHz, CDCl$_3$): δ 8.23 (d, J=5.6 Hz, 1H), 7.50 (d, J=8.0 Hz, 1H), 7.42 (d, J=8.4 Hz, 1H), 7.36 (d, J=12.4 Hz, 1H), 7.12-7.10 (m, 2H), 7.07-7.05 (m, 1H), 7.01 (s, 1H), 6.96 (s, 1H), 6.84 (s, 1H), 4.00 (s, 3H), 2.95-2.91 (m, 3H), 2.75 (t, J=7.6 Hz, 2H), 2.20 (t, J=9.0 Hz, 1H), 1.33 (d, J=6.8 Hz, 3H), 1.09-1.07 (m, 1H), 0.71-0.70 (m, 1H), 0.43-0.38 (m, 2H), 0.04-0.01 (m, 1H).

Example 30

(2R,3S)-3-cyclopropyl-3-(7-(2-fluoro-4-(2-methoxypyridin-4-yl)phenyl)-5,6-dihydronaphthalen-2-yl)-2-methylpropanoic acid

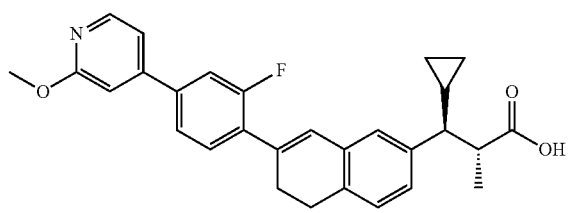 [SMILES: COc1cc(-c2ccc(C3=Cc4cc([C@@H](C5CC5)[C@@H](C)C(=O)O)ccc4CC3)c(F)c2)ccn1]

The title compound was prepared starting with (2R,3S)-methyl 3-cyclopropyl-3-(7-(2-fluoro-4-(2-methoxypyridin-4-yl)phenyl)-5,6-dihydronaphthalen-2-yl)-2-methylpropanoate (Peak 3 from the SFC separation in Step 2 of Example 29) and utilizing a procedure similar to that in Step 3 of Example 29. MS (ESI) m/z: 458.1 [M+H]$^+$ $^1$H NMR (400 MHz, CDCl$_3$): δ 8.40 (d, J=5.6 Hz, 1H), 7.57 (t, J=8.0 Hz, 1H), 7.48 (d, J=7.6 Hz, 1H), 7.42 (d, J=12.4 Hz, 1H), 7.29 (s, 1H), 7.17 (d, J=7.6 Hz, 1H), 7.09 (s, 1H), 7.04 (d, J=7.6 Hz, 1H), 6.99 (s, 1H), 6.90 (s, 1H), 4.11 (s, 3H), 2.98 (t, J=7.6 Hz, 2H), 2.91-2.87 (m, 1H), 2.79 (t, J=7.8 Hz, 2H), 2.01 (t, J=9.8 Hz, 1H), 1.19-1.17 (m, 1H), 1.06 (d, J=6.4 Hz, 3H), 0.68-0.67 (m, 1H), 0.43-0.41 (m, 2H), 0.10-0.07 (m, 1H).

Example 31

(2S,3R)-3-cyclopropyl-3-(7-(2-fluoro-4-(2-methoxypyridin-4-yl)phenyl)-5,6-dihydronaphthalen-2-yl)-2-methylpropanoic acid

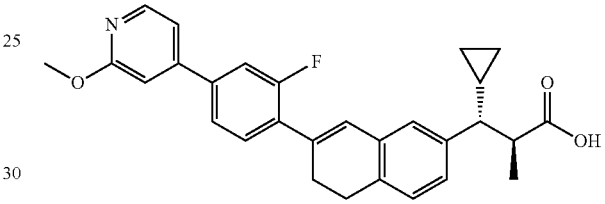

The title compound was prepared starting from (2S,3R)-methyl 3-cyclopropyl-3-(7-(2-fluoro-4-(2-methoxypyridin-4-yl)phenyl)-5,6-dihydronaphthalen-2-yl)-2-methylpropanoate (Peak 2 from the SFC separation in Step 2 of Example 29) and utilizing a procedure similar to that in Step 3 of Example 29. MS (ESI) m/z: 458.1 [M+H]$^+$ $^1$H NMR (400 MHz, CDCl$_3$): δ 8.25 (d, J=4.8 Hz, 1H), 7.51 (t, J=7.6 Hz, 1H), 7.43-7.41 (m, 1H), 7.37 (d, J=12.4 Hz, 1H), 7.13-7.12 (m, 2H), 7.01-6.99 (m, 1H), 6.96 (s, 2H), 6.85 (s, 1H), 4.00 (s, 3H), 2.96-2.93 (m, 2H), 2.88-2.87 (m, 1H), 2.78-2.77 (m, 2H), 2.00 (t, J=9.6 Hz, 1H), 1.17-1.16 (m, 1H), 1.04 (d, J=6.0 Hz, 3H), 0.66-0.65 (m, 1H), 0.40-0.39 (m, 2H), 0.06-0.05 (m, 1H).

Example 32

(2R,3R)-3-cyclopropyl-3-(7-(2-fluoro-4-(2-methoxypyridin-4-yl)phenyl)-5,6-dihydronaphthalen-2-yl)-2-methylpropanoic acid

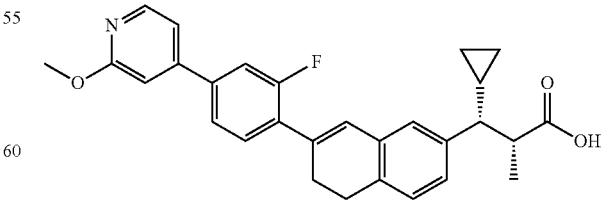

The title compound was prepared starting from (2R,3R)-methyl 3-cyclopropyl-3-(7-(2-fluoro-4-(2-methoxypyridin-4-yl)phenyl)-5,6-dihydronaphthalen-2-yl)-2-methyl-propanoate (Peak 4 from the SFC separation in Step 2 of Example 29) and utilizing a procedure similar to that in Step 3 of Example 29. MS (ESI) m/z: 458.2 [M+H]+ 1H NMR (400 MHz, CDCl3): δ 8.23 (d, J=4.8 Hz, 1H), 7.49 (t, J=8.0 Hz, 1H), 7.41 (d, J=8.4 Hz, 1H), 7.36 (d, J=12.4 Hz, 1H), 7.11-7.09 (m, 2H), 7.07-7.05 (m, 1H), 7.00 (s, 1H), 6.96 (m, 1H), 6.84 (s, 1H), 3.99 (s, 3H), 2.95-2.91 (m, 3H), 2.75 (t, J=7.8 Hz, 2H), 2.21 (t, J=8.8 Hz, 1H), 1.31 (d, J=7.2 Hz, 3H), 1.11-1.10 (m, 1H), 0.70-0.69 (m, 1H), 0.47-0.37 (m, 2H), 0.02-0.01 (m, 1H).

Example 33

3-cyclopropyl-3-(7-(2-fluoro-4-(2-methoxypyridin-4-yl) phenyl)-5,6,7,8-tetrahydronaphthalen-2-yl)-2-methylpropanoic acid

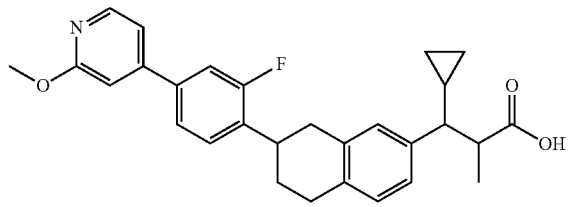 [SMILES: COc1cc(-c2ccc(C3CCc4ccc(C(C5CC5)C(C)C(=O)O)cc4C3)c(F)c2)ccn1]

Step 1: methyl 3-cyclopropyl-3-(7-(2-fluoro-4-(2-methoxypyridin-4-yl) phenyl)-5,6,7,8-tetrahydronaphthalen-2-yl)-2-methylpropanoate To a solution of methyl 3-cyclopropyl-3-(7-(2-fluoro-4-(2-methoxypyridin-4-yl)phenyl)-5,6-dihydronaphthalen-2-yl)-2-methylpropanoate (800 mg, 1.70 mmol) in MeOH (10 ml) was added Pd(OH)2/C (1.19 g). The reaction mixture was stirred for 3 h under a hydrogen atmosphere under 15 psi at 18° C. Then the reaction mixture was filtered. The filtrate was concentrated in vacuo to give a residue, which was purified by preparative TLC (PE:EtOAc=10:1, v/v) to give the title compound. 1H NMR (400 MHz, CDCl3): δ 8.23 (d, J=5.2 Hz, 1H), 7.43-7.31 (m, 3H), 7.13-7.08 (m, 2H), 6.98-6.94 (m, 2H), 6.87-6.85 (m, 1H), 4.00 (s, 3H), 3.74 (s, 3H), 3.43-3.39 (m, 1H), 3.08-3.04 (m, 1H), 2.98-2.95 (m, 3H), 2.87-2.75 (m, 1H), 2.17-1.90 (m, 2H), 1.88 (d, J=10.4 Hz, 1H), 1.08-1.07 (m, 1H), 0.97 (d, J=6.4 Hz, 3H), 0.75-0.56 (m, 1H), 0.50-0.24 (m, 2H), 0.02-0.01 (m, 1H).

Step 2: Chiral separation of methyl 3-cyclopropyl-3-(7-(2-fluoro-4-(2-methoxypyridin-4-yl) phenyl)-5,6,7,8-tetrahydronaphthalen-2-yl)-2-methylpropanoate (Peaks 1 through 5)

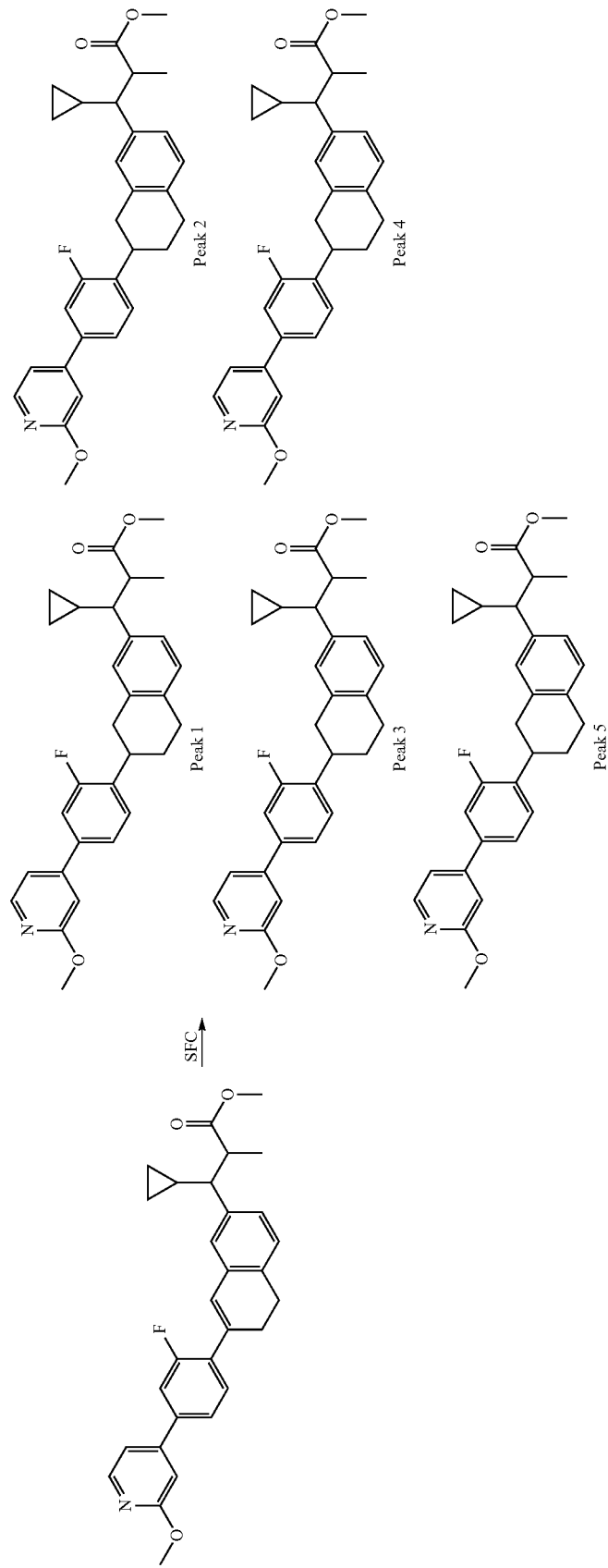

Methyl 3-cyclopropyl-3-(7-(2-fluoro-4-(2-methoxypyridin-4-yl)phenyl)-5,6,7,8-tetrahydronaphthalen-2-yl)-2-methylpropanoate (450 mg, 0.950 mmol) was subjected to chiral SFC chromatography (SFC Instrument and Conditions: Instrument: Berger MultiGram™ SFC, Mettler Toledo Co, Ltd; Column: OJ (250 mm*30 mm, 5 uM); Mobile phase: 30% MeOH NH₃H₂O 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm) to separate the diastereomers. The largest peaks 1 through 5 were collected.

Step 3

To a solution of methyl 3-cyclopropyl-3-(7-(2-fluoro-4-(2-methoxypyridin-4-yl) phenyl)-5, 6, 7, 8-tetrahydronaphthalen-2-yl)-2-methylpropanoate (Step 2, Peak 2, 65 mg, 0.137 mmol) in a co-solvent of MeOH (1.5 ml), THF (1.5 ml) and water (1.5 ml) was added LiOH (33 mg, 1.37 mmol). The mixture was stirred at 50° C. for 16 h. Then the reaction mixture was acidified with HCl (2M) to pH=2, and extracted with EtOAc (5.0 mL×3). The combined organic layers were washed with brine (5.0 mL), dried over anhydrous MgSO₄ and filtered. The filtrate was concentrated under reduce pressure to give a residue, which was purified by preparative HPLC (preparative HPLC on a GILSON 281 instrument fitted with a Phenomenex Gemini C18 250*21.2 mm*5 um using water and acetonitrile as the eluents. Mobile phase A: water (containing 0.1% TFA, v/v), mobile phase B: acetonitrile. Gradient: 28-58% B, 0-10 min; 100% B, 10.5-12.5 min; 5% B, 13-15 min) to give Example 33. MS (ESI) m/z: 460.2 [M+H]+ ¹H NMR (400 MHz, CDCl₃): δ 8.24 (d, J=5.2 Hz, 1H), 7.41-7.31 (m, 3H), 7.11 (d, J=5.6 Hz, 2H), 6.98-6.95 (m, 2H), 6.90 (m, 1H), 4.00 (s, 3H), 3.41-3.40 (m, 1H), 3.08-2.83 (m, 5H), 2.14-2.13 (m, 1H), 2.03-1.93 (m, 2H), 1.15-1.14 (m, 1H), 1.02 (d, J=6.0 Hz, 3H), 0.65-0.63 (m, 1H), 0.40-0.38 (m, 2H), 0.07-0.06 (m, 1H).

Example 34

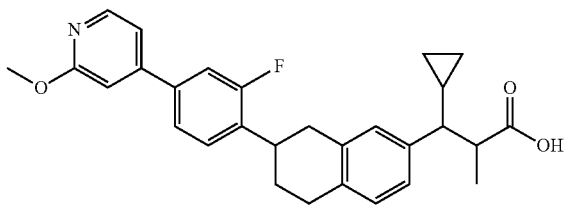 [SMILES: COc1cc(-c2ccc(C3CCc4ccc(C(C5CC5)C(C)C(=O)O)cc4C3)c(F)c2)ccn1]

Example 34 was prepared starting from methyl 3-cyclopropyl-3-(7-(2-fluoro-4-(2-methoxypyridin-4-yl) phenyl)-5,6,7,8-tetrahydronaphthalen-2-yl)-2-methylpropanoate (Example 33, Step 2, Peak 3) using a procedure similar to that outlined in Example 33, Step 3. MS (ESI) m/z: 460.2 [M+H]+ ¹H NMR (400 MHz, CDCl₃): δ 8.24 (d, J=5.2 Hz, 1H), 7.41-7.31 (m, 3H), 7.10 (d, J=6.4 Hz, 2H), 6.98-6.95 (m, 2H), 6.90 (m, 1H), 4.00 (s, 3H), 3.40-3.39 (m, 1H), 3.08-2.81 (m, 5H), 2.15-2.13 (m, 1H), 2.08-1.93 (m, 2H), 1.15-1.14 (m, 1H), 1.02 (d, J=6.4 Hz, 3H), 0.65-0.63 (m, 1H), 0.40-0.37 (m, 2H), 0.08-0.05 (m, 1H).

Example 35

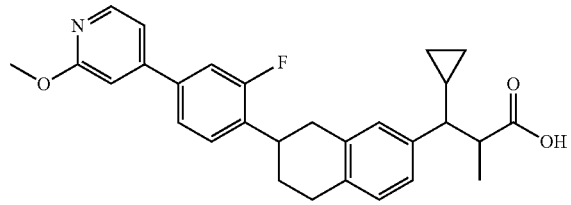 [SMILES: COc1cc(-c2ccc(C3CCc4ccc(C(C5CC5)C(C)C(=O)O)cc4C3)c(F)c2)ccn1]

Example 35 was prepared starting from methyl 3-cyclopropyl-3-(7-(2-fluoro-4-(2-methoxypyridin-4-yl) phenyl)-5,6,7,8-tetrahydronaphthalen-2-yl)-2-methylpropanoate (Example 33, Step 2, Peak 1) using a procedure similar to that in Example 33, Step 2. MS (ESI) m/z: 460.2 [M+H]+ ¹H NMR (400 MHz, CDCl₃): δ 8.40 (d, J=5.6 Hz, 1H), 7.44-7.34 (m, 3H), 7.29 (d, J=6.0 Hz, 1H), 7.09-7.03 (m, 3H), 6.95 (s, 1H), 4.11 (s, 3H), 3.40-3.38 (m, 1H), 3.07-3.02 (m, 1H), 2.97-2.89 (m, 4H), 2.22-2.12 (m, 2H), 2.07-1.99 (m, 1H), 1.30 (d, J=7.2 Hz, 3H), 1.09-1.03 (m, 1H), 0.71-0.64 (m, 1H), 0.47-0.40 (m, 1H), 0.37-0.34 (m, 1H), 0.03-0.01 (m, 1H).

Example 36

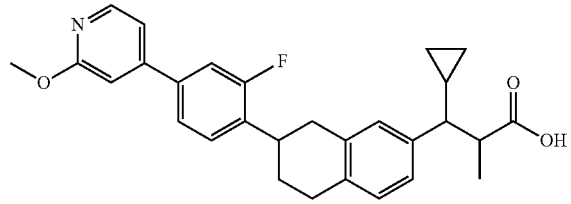 [SMILES: COc1cc(-c2ccc(C3CCc4ccc(C(C5CC5)C(C)C(=O)O)cc4C3)c(F)c2)ccn1]

Step 1

Methyl 3-cyclopropyl-3-(7-(2-fluoro-4-(2-methoxypyridin-4-yl) phenyl)-5,6,7,8-tetrahydronaphthalen-2-yl)-2-methylpropanoate (Example 33, Step 2, Peak 4, 105 mg, 0.222 mmol) was subjected to chiral SFC chromatography (SFC Instrument and conditions: Instrument: Berger Multi-Gram™ SFC, Mettler Toledo Co, Ltd; Column: Chiralpak AS (250 mm*30 mm, 5 uM); Mobile phase: 40% IPA NH₃H₂O 40 ML/MIN 3; Column Temp: 38° C.; Nozzle Pressure: 100 Bar; Nozzle Temp: 60° C.; Evaporator Temp: 20° C.; Trimmer Temp: 25° C.; Wavelength: 220 nm) to give two major peaks (Step A, Peak 1 and Step A, Peak 2).

Step 2

Methyl 3-cyclopropyl-3-(7-(2-fluoro-4-(2-methoxypyridin-4-yl) phenyl)-5,6,7,8-tetrahydronaphthalen-2-yl)-2-methylpropanoate (Step 1, Peak 1) was subjected to conditions similar to that outlined in Example 33, Step 3 to afford Example 36. MS (ESI) m/z: 460.2 [M+H]+ ¹H NMR (400 MHz, CDCl₃): δ 8.24 (d, J=5.2 Hz, 1H), 7.41-7.36 (m, 2H), 7.34 (d, J=11.6 Hz, 1H), 7.11 (d, J=6.4 Hz, 2H), 6.98-6.95 (m, 2H), 6.90 (m, 1H), 4.00 (s, 3H), 3.40-3.39 (m, 1H), 3.08-2.83 (m, 5H), 2.15-2.13 (m, 1H), 2.08-1.94 (m, 2H), 1.15-1.14 (m, 1H), 1.03 (d, J=6.8 Hz, 3H), 0.65-0.63 (m, 1H), 0.40-0.37 (m, 2H), 0.08-0.06 (m, 1H).

Example 37

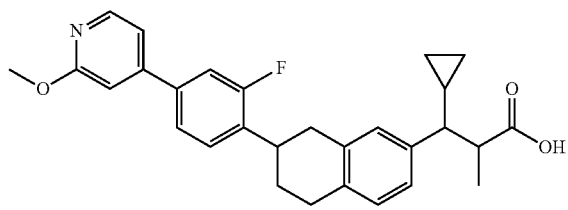 [SMILES: COc1cc(-c2ccc(C3CCc4ccc(C(C5CC5)C(C)C(=O)O)cc4C3)c(F)c2)ccn1]

Methyl 3-cyclopropyl-3-(7-(2-fluoro-4-(2-methoxypyridin-4-yl) phenyl)-5,6,7,8-tetrahydronaphthalen-2-yl)-2-methylpropanoate (Step 1, Peak 2 in the synthesis of Example 36) was subjected to conditions similar to that outlined in Example 33, Step 3 to afford Example 37. MS (ESI) m/z: 460.2 [M+H]+ 1H NMR (400 MHz, CDCl3): δ 8.24 (d, J=5.2 Hz, 1H), 7.41-7.36 (m, 3H), 7.34 (d, J=11.6 Hz, 2H), 6.98-6.95 (m, 2H), 6.90 (m, 1H), 4.00 (s, 3H), 3.40-3.39 (m, 1H), 3.08-2.81 (m, 5H), 2.15-2.13 (m, 1H), 2.08-1.93 (m, 2H), 1.15-1.14 (m, 1H), 1.02 (d, J=6.4 Hz, 3H), 0.65-0.63 (m, 1H), 0.40-0.37 (m, 2H), 0.07-0.05 (m, 1H).

Examples 38A and 38B (2S,3R)-3-cyclopropyl-3-((S)-3-(2-fluoro-4-(2-methoxypyridin-4-yl)phenyl)isochroman-6-yl)-2-methylpropanoic acid and (2S,3R)-3-cyclopropyl-3-((R)-3-(2-fluoro-4-(2-methoxy-pyridin-4-yl)phenyl) isochroman-6-yl)-2-methylpropanoic acid

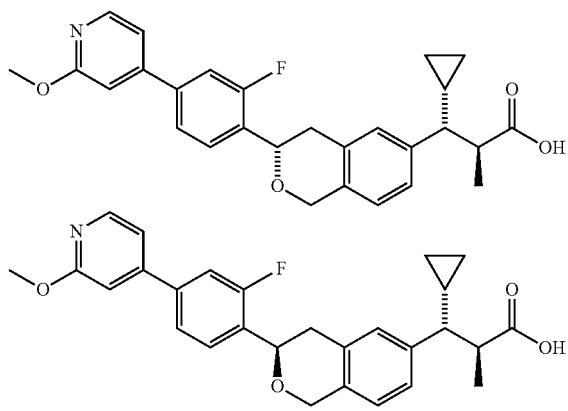

Step 1

Intermediate 40 (100 mg, 0.2 mmol) was added to a reaction manifold with MeOH (2 mL). Then 70 microliters of a catalyst solution (prepared by dissolving bis(2-methylallyl)(1,5-cyclooctadiene)Ruthenium(II) (192 mg) and Josiphos (342 mg) in DCM (2 mL) and agitating for 15 min at rt) was added. Then tetrafluoroboric acid-diethyl ether (194 mg) was added slowly and the reaction mixture was stirred for 20 min at rt. The reaction manifold was then purged with nitrogen, followed by hydrogen gas and then pressurized to 500 psi with hydrogen. The reaction was then heated to 80° C. and shaken for 20 h. Then the reaction was cooled, filtered and concentrated to give the crude product, which was purified via MPLC using an ISCO 40 g column (0-40% EtOAc: hexanes) to afford methyl (2S,3R)-3-cyclopropyl-3-(3 (S)-(2-fluoro-4-(2-methoxypyridin-4-yl)-phenyl)isochroman-6-yl)-2-methyl-propanoate and (2S,3R)-3-cyclopropyl-3-(3-(R)-(2-fluoro-4-(2-methoxy-pyridin-4-yl) phenyl)isochroman-6-yl)-2-methylpropanoate. LC/MS: m/e 475.2 (M+H)+.

Step 2

A solution of (2S,3R)-3-cyclopropyl-3-(3 (S)-(2-fluoro-4-(2-methoxypyridin-4-yl) phenyl)isochroman-6-yl)-2-methylpropanoate and (2S,3R)-3-cyclopropyl-3-(3-(R)-(2-fluoro-4-(2-methoxypyridin-4-yl)phenyl)isochroman-6-yl)-2-methylpropanoate (64 mg, 0.15 mmol) and LiOH (5.6 mg, 0.1 mmol) in THF (75 μl)/MeOH (75 μl)/H2O (75 μL) was stirred at 52° C. for 48 h. The reaction was then cooled and partitioned between ethyl acetate and 0.5N hydrochloric acid. The organic layer was separated, dried over anhydrous Na2SO4, filtered and concentrated. The resulting residue was purified via MPLC using ISCO 4 g column (5-100% EtOAc: hexanes) to give the title compounds. LC/MS: m/e 462.66 (M+H)+. 1H NMR (500 MHz, CD3OD): δ 8.27-8.30 (m, 1H), 7.79-7.82 (m, 1H), 7.67-7.70 (m, 1H), 7.57-7.60 (m, 1H), 7.35-7.36 (m, 1H), 7.06-7.19 (m, 4H), 5.05-5.17 (m, 1H), 5.08 (s, 2H), 4.03-4.07 (m, 3H), 3.04-3.09 (m, 2H), 2.73-2.75 (m, 1H), 2.04-2.09 (m, 1H), 1.19 (br s, 1H), 0.90-0.95 (m, 3H), 0.63-0.66 (m, 1H), 0.51-0.55 (m, 1H), 0.32 (br s, 1H), 0.01 (br s, 1H).

Step 3

(2S,3R)-3-cyclopropyl-3-(3 (S)-(2-fluoro-4-(2-methoxy-pyridin-4-yl)phenyl) isochroman-6-yl)-2-methylpropanoate and (2S,3R)-3-cyclopropyl-3-(3-(R)-(2-fluoro-4-(2-methoxypyridin-4-yl)phenyl)isochroman-6-yl)-2-methylpropanoate (54 mg, 0.12 mmol) were subjected to chiral SFC chromatography (SFC Instrument and conditions: Instrument: Berger MultiGram™ SFC, Mettler Toledo Co, Ltd; Column: Whelko-1 (21×250 mm) Mobile phase: 25% MeOH; Column Temp: 38° C.; Nozzle Pressure: 100 Bar; Nozzle Temp: 60° C.; Evaporator Temp: 20° C.; Trimmer Temp: 25° C. and wavelength: 220 nm.) to separate the two diastereomers to provide the title compounds.

Examples 39A and 39B (2S,3R)-3-cyclopropyl-3-((R)-3-(4-(5-fluoro-2-methoxypyridin-4-yl)phenyl)isochroman-6-yl)-2-methylpropanoic acid, and (2S,3R)-3-cyclopropyl-3-((S)-3-(4-(5-fluoro-2-methoxy-pyridin-4-yl) phenyl)isochroman-6-yl)-2-methylpropanoic acid

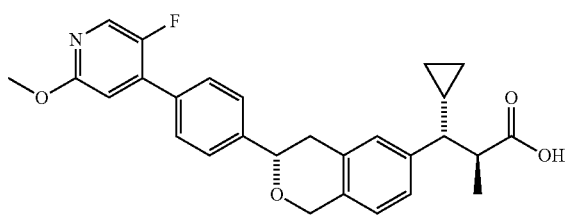

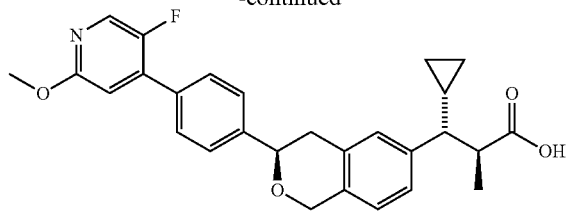

Step 1

Intermediate 50 (100 mg, 0.2 mmol) was added to a reaction manifold with MeOH (2 mL). Then 70 microliters of a catalyst solution (prepared by dissolving bis(2-methyl-allyl)(1,5-cyclooctadiene)Ruthenium(II) (192 mg) and Josiphos (342 mg) in DCM (2 mL) and agitating for 15 min at rt) was added. Then tetrafluoroboric acid-diethyl ether (194 mg) was added slowly and the reaction mixture was stirred for 20 min at rt. The reaction manifold was purged with nitrogen, followed by hydrogen gas and then pressurized to 500 psi with hydrogen. The reaction was heated to 80° C. and shaken for 20 h. Then the reaction was cooled, filtered and concentrated to give the crude product, which was purified via MPLC using an ISCO 40 g column (0-40% EtOAc:hexanes) to give methyl (2S,3R)-3-cyclopropyl-3-((R)-3-(4-(5-fluoro-2-methoxypyridin-4-yl)phenyl)isochroman-6-yl)-2-methylpropanoate, and methyl (2S,3R)-3-cyclopropyl-3-((S)-3-(4-(5-fluoro-2-methoxy-pyridin-4-yl)-phenyl)-isochroman-6-yl)-2-methylpropanoate. LC/MS: m/e 475.2 (M+H)+.

Step 2

A solution of methyl (2S,3R)-3-cyclopropyl-3-((R)-3-(4-(5-fluoro-2-methoxy-pyridin-4-yl)phenyl)isochroman-6-yl)-2-methylpropanoate, methyl (2S,3R)-3-cyclo-propyl-3-((S)-3-(4-(5-fluoro-2-methoxypyridin-4-yl)phenyl) isochroman-6-yl)-2-methylpropanoate (59 mg, 0.15 mmol) and LiOH (5.2 mg, 0.1 mmol) in THF (75 μl)/MeOH (75 μl)/H₂O (75 μL) was stirred at 52° C. for 24 h. The reaction was then cooled and partitioned between ethyl acetate and 0.5N hydrochloric acid. The organic layer was separated, dried over anhydrous Na₂SO₄, filtered and concentrated. The resulting residue was purified via MPLC using ISCO 4 g column (0-100% EtOAc: hexanes) to give the title compounds. LC/MS: m/e 462.66 (M+H)+. ¹H NMR (500 MHz, CD₃OD): δ 8.15-8.17 (m, 1H), 7.69-7.75 (m, 4H), 7.08-7.14 (m, 3H), 7.01 (d, J=5.3 Hz, 1H), 5.03-5.08 (m, 2H), 4.91-4.95 (m, 1H), 3.99-4.02 (s, 3H), 3.04-3.16 (m, 2H), 2.71-2.74 (m, 1H), 2.04-2.08 (m, 1H), 1.18 (s, 1H), 0.90-0.93 (m, 3H), 0.62-0.66 (m, 1H), 0.49-0.54 (m, 1H), 0.30-0.32 (m, 1H), 0.18 (t, J=0.7 Hz, 1H).

Step 3

(2S,3R)-3-cyclopropyl-3-(3 (S)-(2-fluoro-4-(2-methoxy-pyridin-4-yl)phenyl)-isochroman-6-yl)-2-methylpropanoate and (2S,3R)-3-cyclopropyl-3-(3-(R)-(2-fluoro-4-(2-methoxypyridin-4-yl)phenyl)isochroman-6-yl)-2-methylpropanoate (54 mg, 0.12 mmol) were subjected to chiral SFC chromatography (SFC Instrument and conditions: Instrument: Berger MultiGram™ SFC, Mettler Toledo Co, Ltd; Column: OJ-H (21×250 mm) Mobile phase: 25% IPA; Column Temp: 38° C.; Nozzle Pressure: 100 Bar; Nozzle Temp: 60° C.; Evaporator Temp: 20° C.; Trimmer Temp: 25° C. and wavelength: 220 nm.) to separate the two diastereomers to give the title compounds.

Example 40

(2S,3R)-3-cyclopropyl-2-methyl-3-(3-(1-(3-(trifluoromethyl)pyridin-2-yl) piperidin-4-yl)isochroman-6-yl)propanoic acid

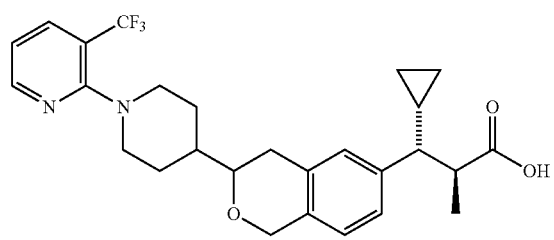 [SMILES: C[C@H](C(=O)O)[C@H](c1ccc2c(c1)CC(C1CCN(c3ncccc3C(F)(F)F)CC1)OC2)C1CC1]

Step 1: (2S,3R)-Methyl 3-cyclopropyl-2-methyl-3-(3-(1-(3-(trifluoromethyl)pyridin-2-yl)piperidin-4-yl) isochroman-6-yl)propanoate To a solution of intermediate 57 (30.0 mg, 0.08 mmol) and TEA (85 mg, 0.8 mmol) in DMF (2.0 mL) was added 2-bromo-3-(trifluoromethyl)-pyridine (22.8 mg, 0.101 mmol). The mixture was heated to 90° C. for 5 h, then cooled to room temperature (25° C.).

Water (5.0 mL) was added to the reaction mixture and the mixture was extracted with EtOAc (10 mL×3). The combined organic layers were washed with water (10 mL), brine (10 mL), dried over anhydrous MgSO₄ and filtered. The filtrate was concentrated under reduced pressure to give the crude product, which was purified by prep-TLC (SiO₂, PE/EtOAc=4:1, v/v) to give the title compound. MS (ESI) m/z: 503.3 [M+H]+

Step 2

To a solution of (2S,3R)-methyl 3-cyclopropyl-2-methyl-3-(3-(1-(3-(trifluoromethyl)pyridin-2-yl)piperidin-4-yl)isochroman-6-yl)propanoate (15.0 mg, 0.03 mmol) in THF (1.0 mL), MeOH (1.0 mL) and H₂O (1.0 mL) was added LiOH (35.7 mg, 1.49 mmol) under a nitrogen atmosphere. The reaction mixture was stirred at 50° C. for 16 h. The reaction mixture was concentrated in vacuo to remove the solvent. Then water (5.0 mL) was added to the resulting residue, and citric acid was added to the solution to give a pH-5-6. The solution was then extracted with EtOAc (5.0 mL×3). The combined organic layers were washed with brine (5.0 mL), dried over anhydrous MgSO₄ and filtered. The filtrate was concentrated under reduced pressure to give rise to the crude product, which was purified by prep-TLC (SiO₂, PE/EtOAc=2/1, v/v) to give the title compound. MS (ESI) m/z: 489.3 [M+H]+ ¹H NMR (400 MHz, CD₃OD): δ=8.42 (d, J=1.0 Hz, 1H), 7.98 (d, J=1.0 Hz, 1H), 7.15-7.08 (m, 1H), 7.02-6.92 (m, 3H), 4.79 (q, J=1.0 Hz, 1H), 3.66-3.55 (m, 2H), 3.52-3.43 (m, 1H), 2.99-2.87 (m, 2H), 2.82-2.71 (m, 3H), 2.16-2.07 (m, 1H), 1.93 (t, J=1.0 Hz, 1H), 1.88-1.81 (m, 1H), 1.73-1.64 (m, 1H), 1.62-1.49 (m, 2H), 1.16-1.05 (m, 1H), 0.91 (d, J=7.1 Hz, 3H), 0.65-0.55 (m, 1H), 0.39-0.24 (m, 2H), 0.02-0.07 (m, 1H).

Example of a Pharmaceutical Composition

As a specific embodiment of an oral pharmaceutical composition, a 100 mg potency tablet is composed of 100 mg of any one of Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

Biological Assays

Generation of GPR40-Expressing Cells:

Human and mouse GPR40 stable cell-lines were generated in CHO cells stably expressing NFAT BLA (Beta-lactamase). A human GPR40 stable cell-line was generated in HEK cells stably expressing the aequorin expressing reporter. The expression plasmids were transfected using lipofectamine (Life Technologies) following manufacturer's instructions. Stable cell-lines were generated following drug selection.

Inositol Phosphate Turnover (IP1) Assay 1:

The assay is performed in 384-well format. HEK cells stably expressing human GPR40 are plated at 15,000 cells per well in growth medium (DMEM/10% fetal calf serum). Cell plates are then incubated 16 hours at 37 degrees in a 5% $CO_2$ incubator.

Measurement of Inositol Phosphate Turnover (IP1) is performed using the CisBio IP-One kit (Part number 62IPA-PEB). After the 16 hour incubation, the cells are washed with HEPES buffer and 10 ul of stimulation buffer (prepared as described in the kit) is added to each well. In a separate plate, compounds are diluted in DMSO (400-fold over the final concentration in the assay well) and 25 nl is transferred via pocket tip to the appropriate well in the assay cell plate. The plates are then incubated for 60 minutes at 37 degrees. 10 ul of detection buffer (also prepared as described in the IP-One kit) is added to each well and the plates are incubated for 60 minutes in the dark. The plates are then read in a Perkin Elmer EnVision or equivalent reader able to measure FRET. Fluorescent ratio of emission at 665 and 620 nm is then converted to IP1 concentration by back calculating from an IP1 standard curve prepared at the time of the assay. Inositol Phosphate Turnover (IP1) Assay 1 $EC_{50}$ values for specific compounds are listed in Table I.

Inositol Phosphate Turnover (IP1) Assay 2:

The assay is performed in 384-well format. HEK cells stably expressing human GPR40 are plated at 15,000 cells per well in growth medium (DMEM/10% fetal calf serum). Cell plates are then incubated 16 hours at 37 degrees in a 5% $CO_2$ incubator.

Measurement of Inositol Phosphate Turnover (IP1) is performed using the CisBio IP-One kit (Part number 62IPA-PEB). After the 16 hour incubation, the cells are washed with HEPES buffer and 10 ul of stimulation buffer (prepared as described in the kit) is added to each well. In a separate plate, compounds are diluted in DMSO (400-fold over the final concentration in the assay well) and 25 nl is acoustically transferred to the appropriate well in the assay cell plate. The plates were then incubated for 60 minutes at 37 degrees. 10 ul of detection buffer (also prepared as described in the IP-One kit) is added to each well and the plates are incubated for 60 minutes in the dark. The plates are then read in a Perkin Elmer EnVision or equivalent reader able to measure FRET. Fluorescent ratio of emission at 665 and 620 nm is then converted to IP1 concentration by back calculating from an IP1 standard curve prepared at the time of the assay. Inositol Phosphate Turnover (IP1) Assay 2 $EC_{50}$ values for specific compounds are listed in Table II.

The compounds of the present invention, including the compounds in Examples 1-40, have $EC_{50}$ values less than 6500 nanomolar (nM) in either the Inositol Phosphate Turnover (IP1) Assay 1 described above or in the Inositol Phosphate Turnover (IP1) Assay 2 described above.

TABLE I

| Example Number | Human IP1 $EC_{50}$ (nM) (IP1) Assay 1 |
|---|---|
| 1 | 155 |
| 2 | 9 |
| 3 | 330 |
| 4 | 75 |
| 5 | 106 |
| 6 | 5.6 |
| 7 | 3.0 |
| 8 | 169 |
| 9 | 60 |
| 10 | 13 |
| 11 | 6.3 |
| 12 | 12 |
| 13 | 592 |
| 14 | 32 |
| 15 | 26 |
| 16 | 12 |
| 19 | 250 |
| 20 | 5378 |
| 23 | 424 |
| 24 | 166 |
| 25 | 729 |
| 26 | 24 |
| 27 | 6.9 |
| 28 | 69 |

TABLE II

| Example Number | Human IP1 $EC_{50}$ (nM) (IP1) Assay 2 |
|---|---|
| 17 | 15 |
| 21 | 0.21 |
| 22 | 0.50 |
| 18 | 8.1 |
| 29 | 3961 |
| 30 | 3.8 |
| 31 | 0.5 |
| 32 | 28 |
| 33 | 1.4 |
| 34 | 13 |
| 35 | 257 |
| 36 | 4.8 |
| 37 | 0.42 |
| 38A | 4.2 |
| 38B | 24.5 |
| 39A | 0.76 |
| 39B | 5.2 |
| 40 | 54 |

In Vivo Studies:

Male C57BL/6N mice (7-12 weeks of age) are housed 10 per cage and given access to normal diet rodent chow and water ad libitum. Mice are randomly assigned to treatment groups and fasted 4 to 6 h. Baseline blood glucose concentrations are determined by glucometer from tail nick blood. Animals are then treated orally with vehicle (0.25% methylcellulose) or test compound. Blood glucose concentration is measured at a set time point after treatment (t=0 min) and mice are then intraperitoneally-challenged with dextrose (2 g/kg). One group of vehicle-treated mice is challenged with saline as a negative control. Blood glucose levels are determined from tail bleeds taken at 20, 40, 60 min after dextrose challenge. The blood glucose excursion profile from t=0 to t=60 min is used to integrate an area under the curve (AUC) for each treatment. Percent inhibition values for each treatment are generated from the AUC data normalized to the saline-challenged controls.

While the invention has been described and illustrated with reference to certain particular embodiments thereof, those skilled in the art will appreciate that various adaptations, changes, modifications, substitutions, deletions, or additions of procedures and protocols may be made without departing from the scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention.

What is claimed is:
1. A compound of structural formula I:

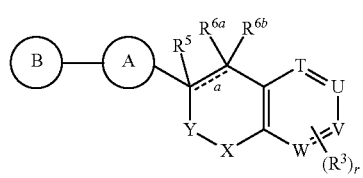

or a pharmaceutically acceptable salt thereof; wherein
"a" is a single bond or a double bond, provided that if "a" is a double bond, then $R^5$ and $R^{6b}$ are absent;
T is CH;
U is $CR^1$;
V is $CR^2$;
W is CH;
X is selected from the group consisting of:
(1) oxygen,
(2) sulfur,
(3) $S(O)_2$,
(4) —$CR^gR^g$, and
(5) C=O;
Y is selected from the group consisting of:
(1) oxygen, and
(2) —$CR^{4a}R^{4b}$,
provided that if X is oxygen, or sulfur, then Y is not oxygen, and further provided that if X is $S(O)_2$, then Y is not oxygen;
A is selected from the group consisting of:
(1) aryl, and
(2) $C_{3-5}$ cycloheteroalkyl,
wherein each aryl and cycloheteroalkyl is unsubstituted or substituted with one to five substituents independently selected from $R^a$;
B is selected from the group consisting of:
(1) aryl,
(2) aryl-$C_{1-10}$ alkyl-, and
(3) heteroaryl,
wherein each alkyl, aryl and heteroaryl is unsubstituted or substituted with one to five substituents independently selected from $R^b$;
$R^1$ and $R^2$ are each independently selected from:
(1) hydrogen, and
(2) —$C_{1-6}$alkyl, wherein one of $R^1$ and $R^2$ is —$C_{1-6}$alkyl substituted with $R^7$, and wherein alkyl is unsubstituted or further substituted with one to three substituents independently selected from $R^L$;
$R^3$ is absent or hydrogen;
$R^{4a}$ is hydrogen;
$R^{4b}$ is hydrogen;
$R^5$ is absent or hydrogen;
$R^{6a}$ is hydrogen;
$R^{6b}$ is absent or hydrogen;
$R^7$ is —$CO_2R^8$;
$R^8$ is hydrogen;
each $R^a$ is independently selected from the group consisting of:
(1) —$C_{1-6}$alkyl,
(2) halogen,
(3) —$C_{0-6}$ alkyl-$OR^e$,
(4) —$C_{0-6}$alkyl-$NR^cS(O)_nR^e$,
(5) —$C_{0-6}$ alkyl-$S(O)_nR^e$,
(6) —$C_{0-6}$alkyl-$S(O)_nNR^cR^d$,
(7) —$C_{0-6}$ alkyl-$NR^cR^d$,
(8) —$C_{0-6}$alkyl-$C(O)R^e$,
(9) —$C_{0-6}$alkyl-$OC(O)R^e$,
(10) —$C_{0-6}$alkyl-$CO_2R^e$,
(11) —$C_{0-6}$alkyl-CN,
(12) —$C_{0-6}$alkyl-$C(O)NR^cR^d$,
(13) —$C_{0-6}$alkyl-$NR^cC(O)R^e$,
(14) —$C_{0-6}$alkyl-$NR^cC(O)OR^e$,
(15) —$C_{0-6}$alkyl-$NR^cC(O)NR^cR^d$,
(16) —$CF_3$,
(17) —$OCF_3$,
(18) —$OCHF_2$,
(19) —$C_{0-6}$alkyl-aryl,
(20) —$C_{0-6}$alkyl-heteroaryl,
(21) —$C_{0-6}$alkyl-$C_{3-10}$cycloalkyl,
(22) —$C_{0-6}$alkyl-$C_{3-10}$cycloalkenyl, and
(23) —$C_{0-6}$alkyl-$C_{2-10}$cycloheteroalkyl,
wherein each alkyl, cycloalkyl, cycloalkenyl, cycloheteroalkyl, aryl and heteroaryl is unsubstituted or substituted with one to five substituents independently selected from: —$C_{1-6}$alkyl, halogen, OH, —O—$C_{1-6}$ alkyl, —CN, —$OCHF_2$, —$OCF_3$, —$CF_3$, and —$C_{0-6}$ alkyl-$NR^cR^d$;
each $R^b$ is independently selected from the group consisting of:
(1) —$C_{1-10}$alkyl,
(2) —$C_{2-10}$alkenyl,
(3) —$CF_3$,
(4) halogen,
(5) —CN,
(6) —OH,
(7) —$OC_{1-10}$alkyl,
(8) —$OC_{2-10}$alkenyl,
(9) —$O(CH_2)pOC_{1-10}$alkyl,
(10) —$O(CH_2)pC_{3-6}$cycloalkyl,
(11) —$O(CH_2)pC_{3-6}$ cycloalkyl-$C_{1-10}$alkyl,
(12) —$O(CH_2)pC_{2-5}$cycloheteroalkyl,
(13) —$O(CH_2)pC_{2-5}$cycloheteroalkyl-$C_{1-10}$alkyl,
(14) —O-aryl,
(15) —O-heteroaryl,
(16) —O-aryl-$C_{1-10}$alkyl,
(17) —O-heteroaryl-$C_{1-10}$alkyl,
(18) —$O(CH_2)pNR^cS(O)_mR^e$,
(19) —$O(CH_2)pS(O)_mR^e$,
(20) —$O(CH_2)pS(O)_mNR^cR^d$,
(21) —$O(CH_2)pNR^cR^d$,
(22) —$C(O)R^e$,

(23) —OC(O)R$^e$,
(24) —CO$_2$R$^e$,
(25) —C(O)NR$^c$R$^d$,
(26) —NR$^c$C(O)R$^e$,
(27) —NR$^c$C(O)OR$^e$,
(28) —NR$^c$C(O)NR$^c$R$^d$,
(29) —O(CH$_2$)pO—C$_{3-6}$cycloalkyl,
(30) —O(CH$_2$)pO—C$_{2-5}$cycloheteroalkyl,
(31) —OCF$_3$,
(32) —OCHF$_2$,
(33) —(CH$_2$)pC$_{3-6}$cycloalkyl,
(34) —(CH$_2$)pC$_{2-5}$cycloheteroalkyl,
(35) aryl,
(36) heteroaryl,
(37) aryl-C$_{1-10}$alkyl-, and
(38) heteroaryl-C$_{1-10}$alkyl-,
wherein each CH, CH$_2$, alkyl, alkenyl, cycloalkyl, cycloheteroalkyl, aryl and heteroaryl is unsubstituted or substituted with one to five substituents independently selected from: —C$_{1-6}$alkyl, halogen, OH, —O—C$_{1-6}$alkyl and —CF$_3$;
R$^c$ and R$^d$ are each independently selected from the group consisting of:
(1) hydrogen,
(2) C$_{1-10}$alkyl,
(3) C$_{2-10}$alkenyl,
(4) C$_{3-6}$cycloalkyl,
(5) C$_{3-6}$ cycloalkyl-C$_{1-10}$alkyl-,
(6) C$_{2-5}$cycloheteroalkyl,
(7) C$_{2-5}$cycloheteroalkyl-C$_{1-10}$alkyl-,
(8) aryl,
(9) heteroaryl,
(10) aryl-C$_{1-10}$alkyl-, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents independently selected from R$^f$,
or R$^c$ and R$^d$ together with the atom(s) to which they are attached form a C$_{2-10}$cycloheteroalkyl ring containing 0-2 additional heteroatoms independently selected from oxygen, sulfur and N—R$^g$, wherein each R$^c$ and R$^d$ is unsubstituted or substituted with one to three substituents independently selected from R$^f$;
each R$^e$ is independently selected from the group consisting of:
(1) hydrogen,
(2) —C$_{1-10}$alkyl,
(3) —C$_{2-10}$ alkenyl,
(4) —C$_{3-6}$ cycloalkyl,
(5) C$_{3-6}$ cycloalkyl-C$_{1-10}$alkyl-,
(6) —C$_{2-5}$cycloheteroalkyl,
(7) C$_{2-5}$cycloheteroalkyl-C$_{1-10}$alkyl-,
(8) aryl,
(9) aryl-C$_{1-10}$alkyl-,
(10) heteroaryl, and
(11) heteroaryl-C$_{1-10}$alkyl-,
wherein each alkyl, alkenyl, cycloalkyl, cycloheteroalkyl, aryl and heteroaryl is unsubstituted or substituted with one to three substituents independently selected from R$^h$;
each R$^f$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, C$_{1-6}$alkyl, cyano and S(O)$_2$C$_{1-6}$alkyl;
each R$^g$ is selected from the group consisting of:
(1) hydrogen,
(2) —C(O)R$^e$, and
(3) —C$_{1-10}$alkyl,
wherein each alkyl is unsubstituted or substituted with one to five halogens;
each R$^h$ is selected from the group consisting of:
(1) halogen,
(2) C$_{1-10}$alkyl,
(3) —OH,
(4) —O—C$_{1-4}$alkyl,
(5) —S(O)$_m$—C$_{1-4}$alkyl,
(6) —CN,
(7) —CF$_3$,
(8) —OCHF$_2$, and
(9) —OCF$_3$,
wherein each alkyl is unsubstituted or substituted with one to three substituents independently selected from: —OH, halogen, C$_{1-6}$alkyl, cyano and S(O)$_2$C$_{1-6}$alkyl;
each R$^L$ is independently selected from the group consisting of:
(1) —CO$_2$C$_{1-6}$alkyl,
(2) —C$_{1-10}$alkyl,
(3) —C$_{2-10}$alkenyl,
(4) —C$_{2-10}$alkynyl,
(5) —C$_{3-6}$cycloalkyl,
(6) —C$_{2-6}$cycloheteroalkyl,
(7) aryl, and
(8) heteroaryl,
wherein each alkyl, alkenyl, alkynyl, cycloalkyl, cycloheteroalkyl, aryl and heteroaryl is unsubstituted or substituted with one to four substituents independently selected from C$_{1-6}$alkyl, halogen, and —OC$_{1-6}$alkyl;
each n is independently selected from: 0, 1 or 2;
each m is independently selected from: 0, 1 or 2;
each p is independently selected from: 0, 1, 2, 3, 4, 5 or 6; and
each r is independently selected from: 0, 1, 2 or 3.

2. The compound according to claim 1 wherein X is selected from the group consisting of:
(1) oxygen,
(2) sulfur, and
(3) —CR$^g$R$^g$;
or a pharmaceutically acceptable salt thereof.

3. The compound according to claim 1 wherein A is aryl, wherein aryl is unsubstituted or substituted with one to five substituents independently selected from R$^a$; or a pharmaceutically acceptable salt thereof.

4. The compound according to claim 1 wherein B is selected from the group consisting of:
(1) aryl, and
(2) heteroaryl,
wherein each aryl and heteroaryl is unsubstituted or substituted with one to five substituents independently selected from R$^b$; or a pharmaceutically acceptable salt thereof.

5. The compound according to claim 1 wherein R$^1$ and R$^2$ are each independently selected from:
(1) hydrogen, and
(2) ethyl, wherein one of R¹ and R² is ethyl substituted with R⁷, and wherein ethyl is unsubstituted or further substituted with one to three substituents independently selected from $R^L$;

or a pharmaceutically acceptable salt thereof.

6. The compound according to claim 1 wherein
"a" is a single bond or a double bond, provided that if "a" is a double bond, then R⁵ and $R^{6b}$ are absent;
T is CH;
U is CR¹;
V is CR²;
W is CH;
X is selected from the group consisting of:
(1) oxygen,
(2) sulfur,
(3) S(O)₂,
(4) —$CR^gR^g$, and
(5) C=O;
Y is selected from the group consisting of:
(1) oxygen, and
(2) —$CR^{4a}R^{4b}$,
provided that if X is oxygen or sulfur, then Y is not oxygen, and further provided that if X is S(O)₂, then Y is not oxygen;
A is selected from the group consisting of:
(1) aryl, and
(2) C₃₋₅cycloheteroalkyl,
wherein each aryl and cycloheteroalkyl is unsubstituted or substituted with one to five substituents independently selected from $R^a$;
B is selected from the group consisting of:
(1) aryl,
(2) aryl-C₁₋₁₀ alkyl-, and
(3) heteroaryl,
wherein each alkyl, aryl and heteroaryl is unsubstituted or substituted with one to five substituents independently selected from $R^b$;
R¹ and R² are each independently selected from:
(1) hydrogen, and
(2) —C₁₋₆alkyl,
wherein one of R¹ and R² is —C₁₋₆alkyl substituted with R⁷, and wherein alkyl is unsubstituted or further substituted with one to three substituents independently selected from $R^L$;
R³ is absent or hydrogen;
$R^{4a}$ is hydrogen;
$R^{4b}$ is hydrogen;
R⁵ is absent or hydrogen;
$R^{6a}$ is hydrogen; and
$R^{6b}$ is absent or hydrogen;
R⁷ is —CO₂R⁸;
R⁸ is hydrogen;
$R^a$ is halogen;
each $R^b$ is independently selected from the group consisting of: —C₁₋₁₀alkyl, —CF₃, halogen, —OC₁₋₁₀alkyl, and —OC₃₋₆cycloalkyl;
$R^g$ is hydrogen; and
each $R^L$ is independently selected from the group consisting of: —C₁₋₁₀alkyl, and —C₃₋₆cycloalkyl;
or a pharmaceutically acceptable salt thereof.

7. The compound according to claim 1 wherein
"a" is a single bond or a double bond, provided that if "a" is a double bond, then R⁵ and $R^{6b}$ are absent;
T is CH;
U is CR¹;
V is CH;
W is CH;
X is selected from the group consisting of:
(1) oxygen,
(2) sulfur, and
(3) —$CR^gR^g$;
Y is selected from the group consisting of:
(1) oxygen, and
(2) —CH₂,
provided that if X is oxygen or sulfur, then Y is not oxygen;
A is aryl, wherein aryl is unsubstituted or substituted with one to five substituents independently selected from $R^a$;
B is selected from the group consisting of:
(1) aryl, and
(2) heteroaryl,
wherein each aryl and heteroaryl is unsubstituted or substituted with one to five substituents independently selected from $R^b$;
R¹ is ethyl, wherein ethyl is unsubstituted or substituted with one to three substituents independently selected from $R^L$, and wherein R¹ is further substituted with R⁷;
R³ is absent or hydrogen;
$R^{4a}$ is hydrogen;
$R^{4b}$ is hydrogen;
R⁵ is absent or hydrogen;
$R^{6a}$ is hydrogen; and
$R^{6b}$ is absent or hydrogen;
R⁷ is —CO₂R⁸;
R⁸ is hydrogen;
$R^a$ is halogen;
each $R^b$ is independently selected from the group consisting of: halogen, and —OC₁₋₁₀alkyl;
$R^g$ is hydrogen; and
each $R^L$ is independently selected from the group consisting of: —C₁₋₁₀alkyl, and —C₃₋₆cycloalkyl;
or a pharmaceutically acceptable salt thereof.

8. The compound according to claim 7 selected from:

-continued

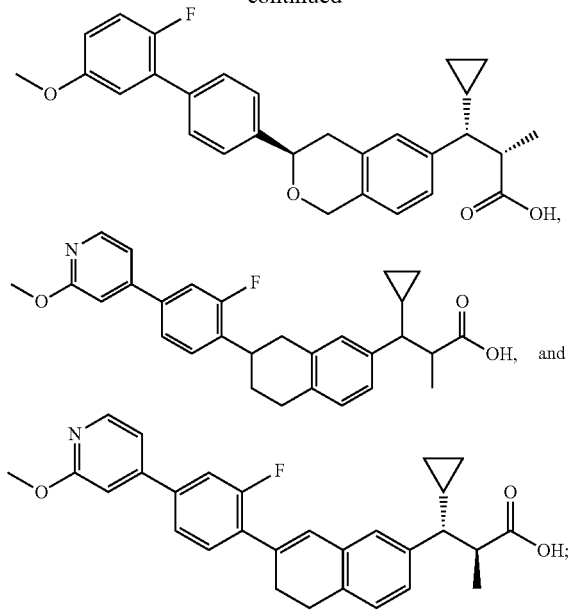

or a pharmaceutically acceptable salt thereof.

9. The compound according to claim 1 selected from:

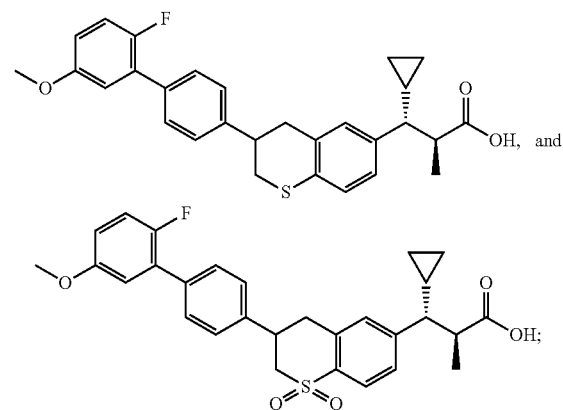

or a pharmaceutically acceptable salt thereof.

10. The compound according to claim 1 selected from:

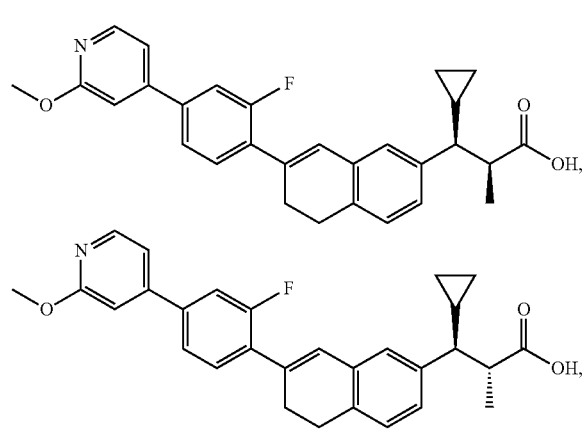

-continued

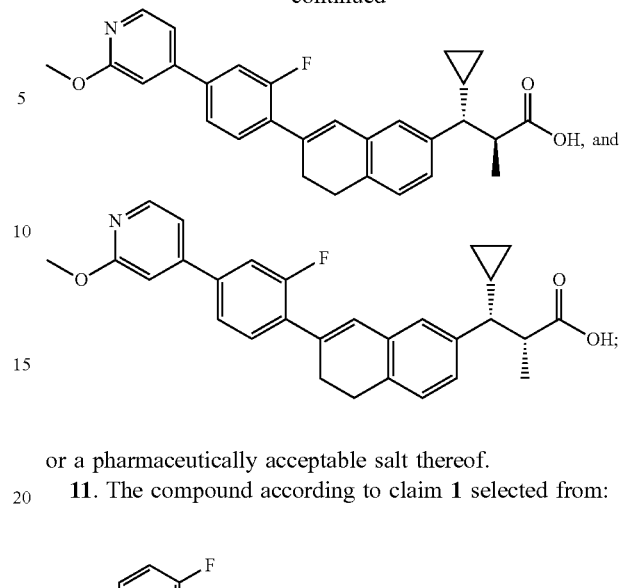

or a pharmaceutically acceptable salt thereof.

11. The compound according to claim 1 selected from:

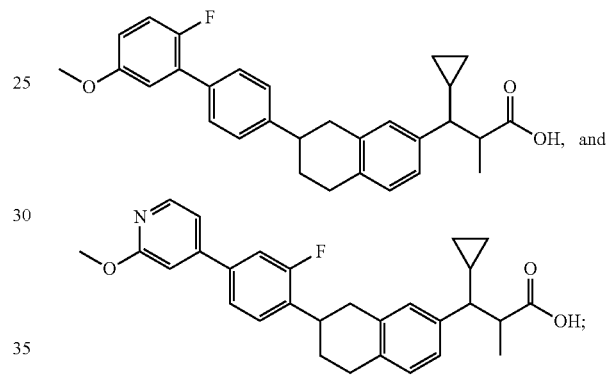

or a pharmaceutically acceptable salt thereof.

12. The compound according to claim 1 selected from:

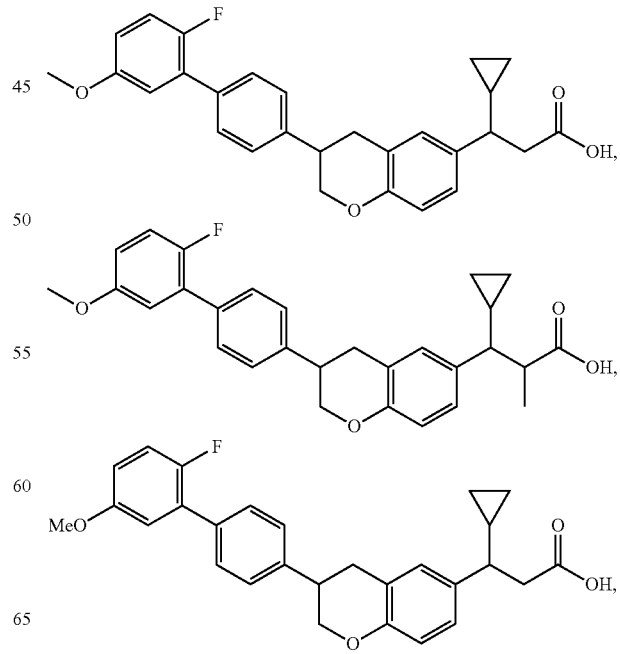

133
-continued
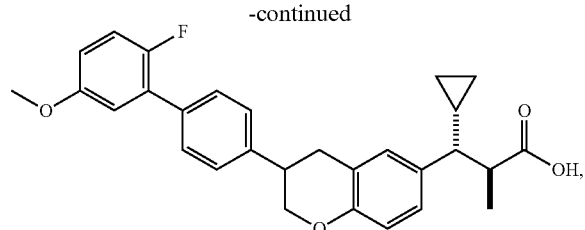
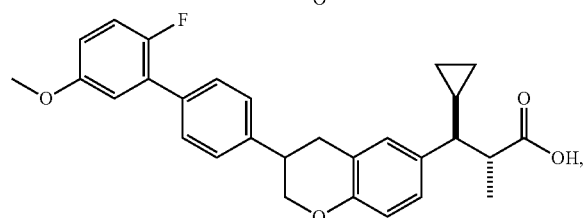
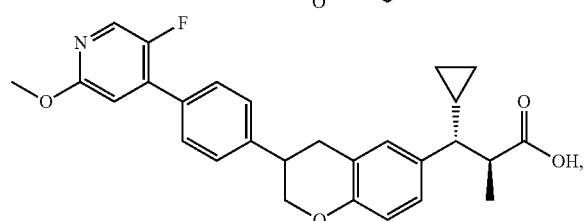
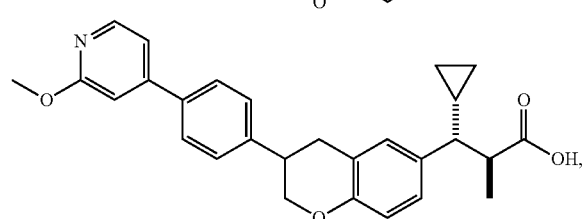
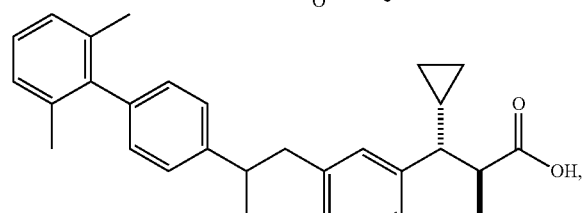
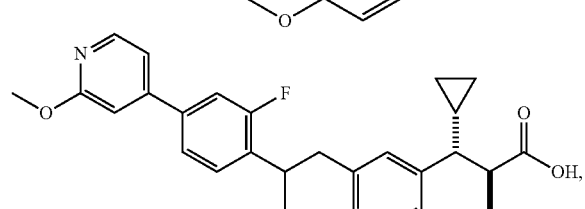
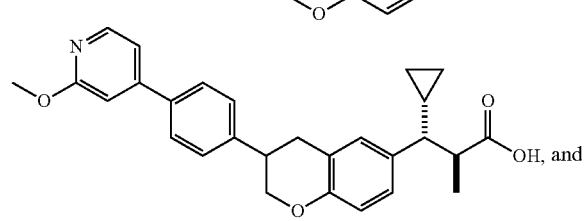
OH, and
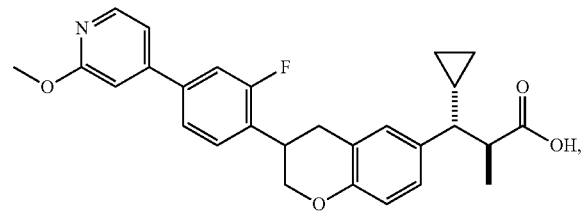
134
-continued
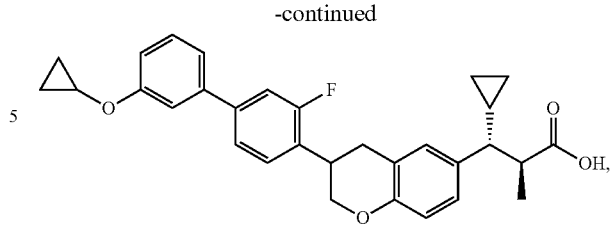
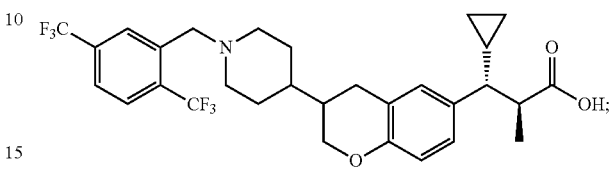
or a pharmaceutically acceptable salt thereof.
13. The compound according to claim 1 selected from:
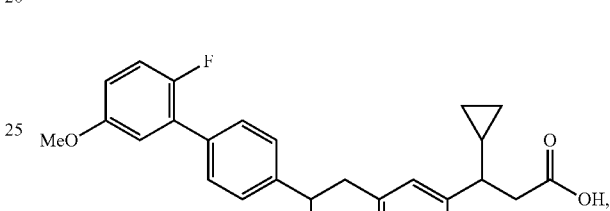
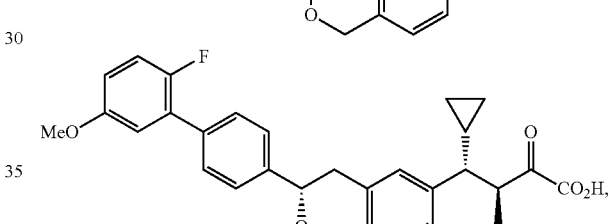
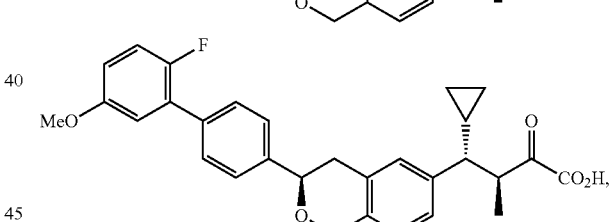
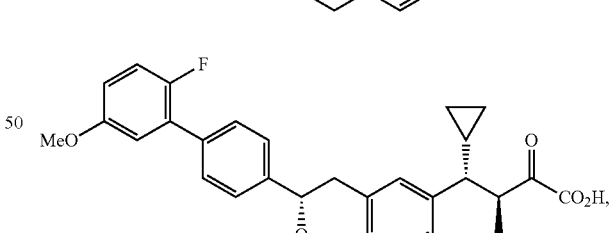
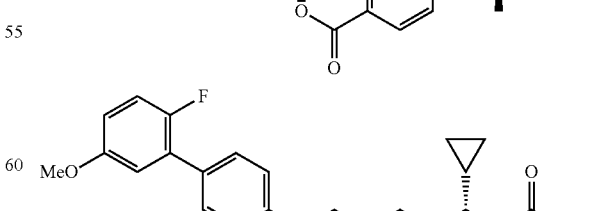
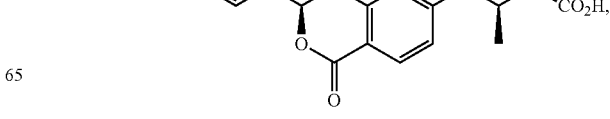

135
-continued

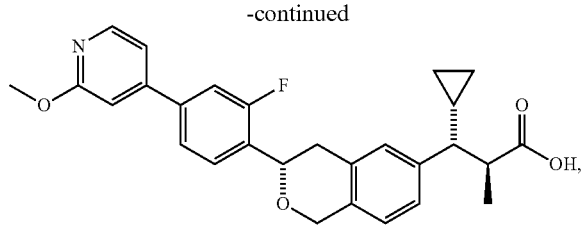

136
-continued

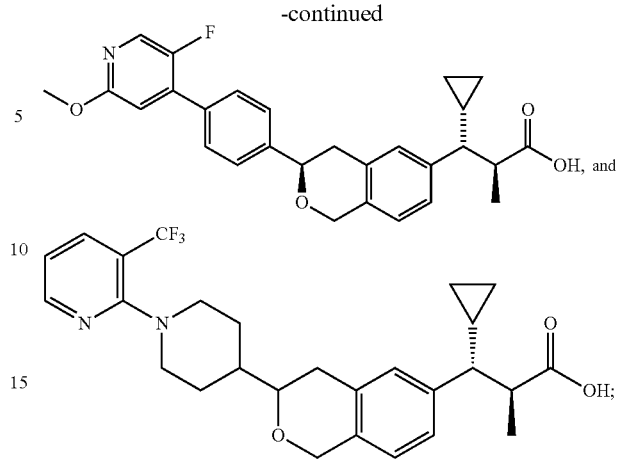

or a pharmaceutically acceptable salt thereof.

14. A pharmaceutical composition comprising a compound of claim 1, or a pharmaceutically acceptable salt thereof, and a pharmaceutically acceptable carrier.

15. A method of treating type 2 diabetes mellitus in a patient in need of treatment comprising the administration to the patient of a therapeutically effective amount of a compound of claim 1, or a pharmaceutically acceptable salt thereof.

* * * * *